(12) United States Patent
Weinberger

(10) Patent No.: US 10,106,817 B2
(45) Date of Patent: Oct. 23, 2018

(54) COMPOSITIONS AND METHODS OF USE THEREOF FOR IDENTIFYING ANTI-VIRAL AGENTS

(71) Applicant: The J. David Gladstone Institutes, San Francisco, CA (US)

(72) Inventor: Leor S. Weinberger, San Francisco, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 0 days.

(21) Appl. No.: 14/767,541

(22) PCT Filed: Feb. 13, 2014

(86) PCT No.: PCT/US2014/016296
§ 371 (c)(1),
(2) Date: Aug. 12, 2015

(87) PCT Pub. No.: WO2014/127148
PCT Pub. Date: Aug. 21, 2014

(65) Prior Publication Data
US 2016/0002668 A1    Jan. 7, 2016

Related U.S. Application Data

(60) Provisional application No. 61/764,854, filed on Feb. 14, 2013.

(51) Int. Cl.
*G01N 33/50* (2006.01)
*C12N 15/86* (2006.01)

(52) U.S. Cl.
CPC ......... *C12N 15/86* (2013.01); *G01N 33/5023* (2013.01); *C12N 2710/16122* (2013.01); *C12N 2710/16143* (2013.01); *C12N 2740/15043* (2013.01); *C12N 2830/00* (2013.01); *C12N 2830/48* (2013.01); *C12N 2830/60* (2013.01); *C12N 2840/203* (2013.01)

(58) Field of Classification Search
None
See application file for complete search history.

(56) References Cited

U.S. PATENT DOCUMENTS

| | | | | |
|---|---|---|---|---|
| 5,674,730 A | * | 10/1997 | Baim | .................. C07K 14/005 435/320.1 |
| 5,945,276 A | * | 8/1999 | Wu | .................. C12N 15/85 435/235.1 |
| 2002/0065243 A1 | * | 5/2002 | Fung | .................. A61K 38/1709 514/44 A |
| 2002/0151049 A1 | * | 10/2002 | Mueller | .................. A61K 38/47 435/320.1 |
| 2005/0003343 A1 | * | 1/2005 | Palese | .................. C12N 15/1086 435/5 |
| 2005/0266564 A1 | | 12/2005 | Yao et al. | |
| 2009/0210952 A1 | * | 8/2009 | Wu | .................. C12N 15/63 800/13 |
| 2011/0136896 A1 | * | 6/2011 | Fu | .................. C07K 14/005 514/44 R |
| 2012/0156238 A1 | | 6/2012 | Silverstein et al. | |
| 2013/0345294 A1 | * | 12/2013 | Yang | .................. C12N 15/63 514/44 R |
| 2015/0218584 A1 | * | 8/2015 | Payne | .................. C12N 15/85 435/455 |

FOREIGN PATENT DOCUMENTS

| | | |
|---|---|---|
| WO | WO 199303769 | 3/1993 |
| WO | WO 199309239 | 5/1993 |
| WO | WO 199319191 | 9/1993 |
| WO | WO 199412649 | 6/1994 |
| WO | WO 199428938 | 12/1994 |
| WO | WO 199500655 | 1/1995 |
| WO | WO 199511984 | 5/1995 |
| WO | WO 2009155535 A2 * | 12/2009 ......... A61K 31/7105 |

OTHER PUBLICATIONS

Zheng C, Brownlie R, Babiuk LA, van Drunen Littel-van den Hurk S. Characterization of the nuclear localization and nuclear export signals of bovine herpesvirus 1 VP22. J Virol. Sep. 2005;79(18):11864-72.*

Bieleski L, Talbot SL. Kaposi's sarcoma-associated herpesvirus vCyclin open reading frame contains an internal ribosome entry site. J Virol. Feb. 2001;75(4):1864-9.*

Souza AP, Haut L, Reyes-Sandoval A, Pinto AR. Recombinant viruses as vaccines against viral diseases. Braz J Med Biol Res. Apr. 2005;38(4):509-22. Epub Apr. 13, 2005.*

Teng MW, Bolovan-Fritts C, Dar RD, Womack A, Simpson ML, Shenk T, Weinberger LS. An endogenous accelerator for viral gene expression confers a fitness advantage. Cell. Dec. 21, 2012;151(7):1569-80.*

Asmar J, Wiebusch L, Truss M, Hagemeier C. The putative zinc finger of the human cytomegalovirus IE2 86-kilodalton protein is dispensable for DNA binding and autorepression, thereby demarcating a concise core domain in the C terminus of the protein. J Virol. Nov. 2004;78(21):11853-64.*

(Continued)

Primary Examiner — Catherine S Hibbert

(74) Attorney, Agent, or Firm — Michael B. Rubin; Bozicevic, Field & Francis LLP

(57) ABSTRACT

A recombinant expression vector comprising a nucleotide sequence encoding a herpesvirus transactivator, where the nucleotide sequence is operably linked to a herpesvirus control element is provided as are cell lines genetically modified to express a herpesvirus transactivator under the control of a herpesvirus control element. Also provided are methods of identifying agents that disrupt feedback regulation of a herpesvirus transcriptional control element by a herpesvirus transactivator.

24 Claims, 62 Drawing Sheets

Specification includes a Sequence Listing.

(56) References Cited

OTHER PUBLICATIONS

Sussman H. "Choosing the Best Reporter Assay." The Scientist. Jul. 2001. http://www.the-scientist.com/?articles.view/articleNo/13507/title/Choosing-the-Best-Reporter-Assay/.*

"Epitope Tags in Protein Research: Tag Selection & Immunotechniques." Sigma Life Science. Feb. 12, 2012, http://www.sigmaaldrich.com/content/dam/sigma-aldrich/docs/Sigma-Aldrich/Brochure/1/epitope-tags-in-protein-research.pdf.*

Luke G, Escuin H, De Felipe P, Ryan M. 2A to the fore—research, technology and applications. Biotechnol Genet Eng Rev. 2010;26:223-60.*

Fukui et al ("Establishment of a Cell-Based Assay for Screening of Compounds Inhibiting Very Early Events in the Cytomegalovirus Replication Cycle and Characterization of a Compound Identified Using the Assay" Antimicrobiol (Year: 2008).*

Lu, Rui et al (1998) "The herpesvirus transactivator VP16 mimics a human basic domain leucine zipper protein, luman, in its interaction with HCF"; Journal of Virology; pp. 6291-6297.

Luganini, A. et al; (2008) "New cell-based indicator assays for the detection of human cytomegalovirus infection and screening of inhibitors of viral immediate-early 2 protein activity"; Journal of Applied Microbiology 105(6); pp. 1791-1801.

Papworth, Monika et al (2003) "Inhibition of herpes simplex virus 1 gene expression by designer zinc-finger transcription factors" Proc Natl Acad Sci U S A. 100(4); pp. 1621-1626.

Ali et al; (1996) "Gene transfer into the mouse retina mediated by an adeno-associated viral vector" Hum Mol Genet 5: pp. 591 594.

Ali et al; (1998) "Adeno-Associated Virus Gene Transfer to Mouse Retina"; Human Gene Therapy 9; pp. 81 86.

Barrasa, M.I. et al; (2005) "The phosphorylation status of the serine-rich region of the human cytomegalovirus 86-kilodalton major immediate-early protein IE2/IEP86 affects temporal viral gene expression"; Journal of Virology 79, pp. 1428-1437.

Bennett et al; "Real-Time, Noninvasive in Vivo Assessment of Adeno-Associated Virus-Mediated Retinal Transduction"; *Investigative Ophthalmology & Visual Science*, vol. 38, No. 13; (Dec. 1997) pp. 2857-2863.

Black, H.S. (1999) "Stabilized feed-back amplifiers"; (Reprinted from Electrical Engineering, vol. 53, p. 114-120, 1934). *Proceedings of the IEEE 87*, pp. 379-385.

Bolovan-Fritts, C. and Wiedeman, J.A. (2001). "Human cytomegalovirus strain Toledo lacks a virus-encoded tropism factor required for infection of aortic endothelial cells", *J Infect Dis 184*, 1252-1261.

Bolovan-Fritts et al; (2004) "Human cytomegalovirusspecific CD4+-T-cell cytokine response induces fractalkine in endothelial cells", *Journal of Virology*, vol. 78, No. 23; pp. 13173-13181.

Borras et al.; (1999) "Adenoviral reporter gene transfer to the human trabecular meshwork does not alter aqueous humor outflow. Relevance for potential gene therapy of glaucoma"; *Gene Therapy 6*; pp. 515-524.

Bresnahan, W.A. and Shenk, T.E; (2000) "UL82 virion protein activates expression immediate early viral genes in human cytomegalovirus-infected cells";. *Proc Natl Acad Sci USA 97*; pp. 14506-14511.

Campbell et al; (2002) "A monomeric red fluorescent protein"; *Proc. Natl. Acad. Sci. USA* 99(12):7877-7782.

Cagatay, Tolga, et al; (2009); "Architecture-dependent noise discriminates functionally analogous differentiation circuits"; *Cell 139(3)*; pp. 512-522.

Cauwels, A., and Brouckaert, P.; (2007) "Survival of TNF toxicity: dependence on caspases and NO"; *Arch Biochem Biophys 462*; pp. 132-139.

Chen, J. et al; (1994) "Wild-type operator binding and altered cooperativity for inducer binding of lac repressor dimer mutant R3"; *J Biol Chern 269*; pp. 12482-12487.

Chiou, C.J. et al; (1993) "Identification and mapping of dimerization and DNA-binding domains in the C terminus of the IE2 regulatory protein of human cytomegalovirus"; *J Virol 67*: 6201-6214.

Choi, K.H. et al; (2005) "Activation of CMV promoter-controlled glycosyltransferase and beta—galactosidase glycogenes by butyrate, tricostatin A, and 5-aza-2'-deoxycytidine"; *Glycoconj J 22*; pp. 63-69.

Cuevas-Bennett, C., and Shenk, T.; (2008) "Dynamic histone H3 acetylation and methylation at human cytomegalovirus promoters during replication in fibroblasts"; *J Virol 82*, pp. 9525-9536.

Damania et al; (2004) "Comparison of the Rta/Orf50 transactivator proteins of gamma-2-herpesviruses.";*J Virol. 78*; pp. 5491-5499.

Deshaies, R.J., and Ferrell, J.E., Jr.; (2001) "Multisite phosphorylation and the countdown to S phase"; *Cell107*; pp. 819-822.

Dull, T. et al; (1998) "A third-generation lentivirus vector with a conditional packaging system"; *J Virol 72*; pp. 8463-8471.

Dwarakanath, R.S.et al; (2001) "The use of recombinant baculoviruses for sustained expression of human cytomegalovirus immediate early proteins in fibroblasts"; '*Virology 284*; pp. 297-307.

Everett, R.D., and Chelbi-Alix, M.K.; (2007) "PML and PML nuclear bodies: implications in antiviral defence"; *Biochimie 89*; pp. 819-830.

Fan, S. et al; (2005) "Valproic acid enhances gene expression from viral gene transfer vectors"; *J Virol Methods 125*; pp. 23-33.

Flannery et al., (1997); "Efficient photoreceptor-targeted gene expression in vivo by recombinant adeno-associated virus"; *PNAS 94*: pp. 6916-6921.

Flemington; (2001) "Herpesvirus lytic replication and the cell cycle: arresting new developments"; *J Virol. 75(10)*:4475-4481.

Flotte et al., (1993) "Stable in vivo expression of the cystic fibrosis transmembrane conductance regulator with an adeno-associated virus vector"; *PNAS 90(22)*:10613-10617.

Garcia-Pino, A. et al; (2010) "Allostery and intrinsic disorder mediate transcription regulation by conditional cooperativity"; *Cell 142*; pp. 101-111.

Gardner, T.S. et al; (2000) "Construction of a genetic toggle switch in *Escherichia coli*"; *Nature 403*; pp. 339-342.

Gautier, I., et al; (2001) "Homo-FRET microscopy in living cells to measure monomer-dimer transition of GFP-tagged proteins"; *Biophys J 80*; pp. 3000-3008.

Gebert, S. et al; (1997) "The UL84 protein of human cytomegalovirus acts as a transdominant inhibitor of immediate-early-mediated transactivation that is able to prevent viral replication"; *J Virol 71*; pp. 7048-7060.

Haase, A.T.; (2010) "Targeting early infection to prevent HIV-1 mucosal transmission"; *Nature 464*; pp. 217-223.

Hofmann, H., et al; (2000) "Covalent modification of the transactivator protein IE2-p86 of human cytomegalovirus by conjugation to the ubiquitin-homologous proteins SUMO-1 and hSMT3b"; *J Virol 74*; pp. 2510-2524.

Hooshangi, S. et al; (2005) "Ultrasensitivity and noise propagation in a synthetic transcriptional cascade"; *Proc Natl Acad Sci U S A 102*; pp. 3581-3586.

Hummel, M., and Abecassis, M.M.; (2002) "A model for reactivation of CMV from latency"; *J Clin Virol 25 Suppl 2*; pp. S123-136.

Isomura, H., et al; (2008) "A cis element between the TATA Box and the transcription start site of the major immediate-early promoter of human cytomegalovirus determines efficiency of viral replication"; *J Virol 82*; pp. 849-858.

Jomary et al.; (1997) "Rescue of photoreceptor function by AAV-mediated gene transfer in a mouse model of inherited retinal degeneration"; *Gene Ther 4*; pp. 683-690.

Kobayashi, H., et al. (2004) "Programmable cells: interfacing natural and engineered gene networks"; *Proc Natl Acad Sci U S A 101*; pp. 8414-8419.

Li and Davidson; (1995) Phenotype correction in retinal pigment epithelium in murine mucopolysaccharidosis VII by adenovirus-mediated gene transfer'; PNAS 92; pp. 7700-7704.

Li et al; (1994) "In vivo transfer of a reporter gene to the retina mediated by an adenoviral vector" *Invest Opthalmol Vis Sci 35*; pp. 2543-2549.

Liu, Bo, et al; (1991) "A cis-acting element in the major immediate-early (IE) promoter of human cytomegalovirus is required for negative regulation by IE2"; *J Virol. 65(2)* :897-903.

Liebermann et al; (1990) "The zta transactivator involved in induction of lytic cycle gene expression in Epstein-Barr virus-infected

(56) References Cited

OTHER PUBLICATIONS lymphocytes binds to both AP-1 and ZRE sites in target promoter and enhancer regions"; *J Virol.*64(3):1143-55.

Ma, W., et al; (2009) "Defining network topologies that can achieve biochemical adaptation"; *Cell 138*; pp. 760-773.

Macias, M.P., and Stinski, M.F.; (1993) "An in vitro system for human cytomegalovirus immediate early 2 protein (IE2)-mediated site-dependent repression of transcription and direct binding of IE2 to the major immediate early promoter"; *Proc Natl Acad Sci USA 90*; pp. 707-711.

Mendelson et al.; (1988) "Expression and rescue of a nonselected marker from an integrated AAV vector"; *Virol* 166(1):154-165.

Miyagishi et al; (2002) "U6 promoter-driven siRNAs with four uridine 3' overhangs efficiently suppress targeted gene expression in mammalian cells"; Nature Biotechnology 20(5); pp. 497-500.

Miyoshi et al.; (1997) "Stable and efficient gene transfer into the retina using an HIV-based lentiviral vector"; *PNAS 94*:pp. 10319-10323.

Moorman, N.J. et al; (2008) "Human cytomegalovirus protein UL38 inhibits host cell stress responses by antagonizing the tuberous sclerosis protein complex"; *Cell Host Microbe 3*; pp. 253-262.

Muzzey, D., et al; (2009) "A systems-level analysis of perfect adaptation in yeast osmoregulation"; *Cell 138*; pp. 160-171.

Nevels, M., et al; (2004) "SUMOylation of the human cytomegalovirus 72-kilodalton IE1 protein facilitates expression of the 86-kilodalton IE2 protein and promotes viral replication"; *J Virol 78*; pp. 7803-7812.

Noguchi et al; (2003) "PDX-1 protein containing its own antennapedia-like protein transduction domain can transduce pancreatic duct and islet cells"; *Diabetes* 52(7):1732-1737.

Ozbudak, E.M., et al; (2004) "Multistability in the lactose utilization network of *Escherichia coli*"; *Nature 427*; pp. 737-740.

Rolling et al.; (1999) "Evaluation of adeno-associated virus-mediated gene transfer into the rat retina by clinical fluorescence photography"; *Hum Gene Ther 10*; pp. 641 648.

Rosenfeld, N., et al (2002). "Negative autoregulation speeds the response times of transcription networks"; *J Mol Biol 323*; pp. 785-793.

Rosenke, K. And Fortunato, E.A.; (2004) "Bromodeoxyuridine-labeled viral particles as a tool for visualization of the immediate-early events of human cytomegalovirus infection"; *J Virol 78*; pp. 7818-7822.

Roth, J., et al; (2006) "Molecular aspects of fever and hyperthermia"; *Neurol Clin 24*; pp. 421-439.

Runnels, et al; (1995) "Theory and Application of Fluorescence Homotransfer to Melittin Oligomerization"; *Biophys Journ. 69*; pp. 1569-1583.

Sakamoto et al; (1998) "A vitrectomy improves the transfection efficiency of adenoviral vector-mediated gene transfer to Müller cells"; *Gene Ther* 5(8); pp. 1088-1097.

Samulski et al; (1989) "Helper-free stocks of recombinant adeno-associated viruses: normal integration does not require viral gene expression"; *J. Vir. 63*; pp. 3822-3828.

Sanders, R.L., et al; (2008) "Development of cell lines that provide tightly controlled temporal translation of the human cytomegalovirus IE2 proteins for complementation and functional analyses of growth-impaired and nonviable IE2 mutant viruses"; *J Virol 82*; pp. 7059-7077.

Shaner et al; (2005) "A guide to choosing fluorescent proteins"; *Nat. Methods* 2(12):905-909.

Shimizu, et al; (1993) "Analysis of the BZLF1 promoter of Epstein-Barr virus: identification of an anti-immunoglobulin response sequence";*J Virol.* 67(6):3240-3245.

Sourvinos, G., et al; (2007) "Recruitment of human cytomegalovirus immediate-early 2 protein onto parental viral genomes in association with ND10 in live-infected cells";*J Virol 81*; pp. 10123-10136.

Stinski, M.F., and Isomura, H. (2008) "Role of the cytomegalovirus major immediate early enhancer in acute infection and reactivation from latency"; *Med Microbiol Immunol 197*; pp. 223-231.

Stinski, M.F., and Petrik, D.T. (2008) "Functional roles of the human cytomegalovirus essential IE86 protein"; *Curr Top Microbiol Immunol 325*; pp. 133-152.

Takahashi et al; (1999) "Rescue from photoreceptor degeneration in the rd mouse by human immunodeficiency virus vector-mediated gene transfer"; *J Virol. 73*; pp. 7812-7816.

Teng et al.; "An Endogenous Accelerator for Viral Gene Expression Confers a Fitness Advantage"; *Cell, vol. 151, No. 7*; Dec. 21, 2012; pp. 1569-1580.

Trehin et al. (2004) "Cellular uptake but low permeation of human calcitonin-derived cell penetrating peptides and Tat(47-57) through well-differentiated epithelial models"; *Pharm. Research, 21*(7):1248-1256.

Waheed, I., et al; (1998) "Binding of the human cytomegalovirus 80-kDa immediate-early protein (IE2) to minor groove A/T-rich sequences bounded by CG dinucleotides is regulated by protein oligomerization and phosphorylation"; *Virology 252*; pp. 235-257.

Wang et al. (2009) "Regulation of the ORF61 promoter and ORF61 functions in varicella-zoster virus replication and pathogenesis"; *J. Virol. 83*(15):7560-7572.

Weil et al. (2010) "Making the message clear: visualizing mRNA localization"; *Trends Cell Biol.* 20(7):380-390.

Weinberger, L.S et al; (2008) "Transient-mediated fate determination in a transcriptional circuit of HIV"; *Nat Genet 40*; pp. 466-470.

Weinberger, L.S., and Shenk, T. (2007) "An HIV feedback resistor: auto-regulatory circuit deactivator and noise buffer"; *PLoS Biol 5*; e9.

Wender et al; (2000) "The design, synthesis, and evaluation of molecules that enable or enhance cellular uptake: peptoid molecular transporters"; *PNAS, vol. 97*(4):13003-13008.

Wuest et al., "The Herpes Simplex Virus-1 Transactivator Infected Cell Protein-4 Drives VEGF—A Dependent Neovascularization," *Plos Pathogens, vol. 7, Iss. 10*, Oct. 6, 2011; pp. 1-17.

Xia et al; "An enhanced U6 promoter for synthesis of short hairpin RNA"; *Nucleic Acids Res.* 31(17); Sep. 1, 2003; e100.

Yu, D. et al; (2003) "Functional map of human cytomegalovirus AD169 defined by global mutational analysis"; *Proc Natl Acad Sci U S A 100*; pp. 12396-12401.

Yu, D., et al (2002) "Construction of a self-excisable bacterial artificial chromosome containing the human cytomegalovirus genome and mutagenesis of the diploid TRL/IRL13 gene"; *J Virol 76*; pp. 2316-2328.

Zender et al; "VP22-mediated intercellular transport of p53 in hepatoma cells in vitro and in vivo"; *Cancer Gene Ther.* 9(6): (Jun. 2002) pp. 489-496.

\* cited by examiner

>LE2idw (11,771 bp)
```
   1 CTAGCATGGA GTCCTCTGCC AAGAGAAAGA TGGACCCTGA TAATCCTGAC GAGGGCCCTT
  61 CCTCCAAGGT GCCACGGCCC GAGACACCCG TGACCAAGGC CACGACGTTC CTGCAGACTA
 121 TGTTGAGGAA GGAGGTTAAC AGTCAGCTGA GTCTGGGAGA CCCGCTGTTT CCAGAGTTGG
 181 CCGAAGAATC CCTCAAAACT TTTGAACAAG TGACCGAGGA TTGCAACGAG AACCCCGAGA
 241 AAGATGTCCT GGCAGAACTC GGTGACATCC TCGCCCAGGC TGTCAATCAT GCCGGTATCG
 301 ATTCCAGTAG CACCGGCCCC ACGCTGACAA CCCACTCTTG CAGCGTTAGC AGCGCCCCTC
 361 TTAACAAGCC GACCCCCACC AGCGTCGCGG TTACTAACAC TCCTCTCCCC GGGGCATCCG
 421 CTACTCCCGA GCTCAGCCCG CGTAAGAAAC GCGCAAAAC CACGCGTCCT TTCAAGGTGA
 481 TTATTAAACC GCCCGTGCCT CCCGCGCCTA TCATGCTGCC CCTCATCAAA CAGGAAGACA
 541 TCAAGCCCGA GCCCGACTTT ACCATCCAGT ACCGCAACAA GATTATCGAT ACCGCCGGCT
 601 GTATCGTGAT CTCTGATAGC GAGGAAGAAC AGGGTGAAGA AGTCGAAACC CGCGGTGCTA
 661 CCGCGTCTTC CCCTTCCACC GGCAGCGGCA CGCCGCGAGT GACCTCTCCC ACGCACCCGC
 721 TCTCCCAGAT GAACCACCCT CCTCTTCCCG ATCCCTTGGG CCGGCCCGAT GAAGATAGTT
 781 CCTCTTCGTC TTCCTCCTCC TGCAGTTCGG CTTCGGACTC GGAGAGTGAG TCCGAGGAGA
 841 TGAAATGCAG CAGTGGCGGA GGAGCATCCG TGACCTCGAG CCACCATGGG CGCGGCGGTT
 901 TTGGTGGCGC GGCCTCCTCC TCTCTGCTGA GCTGCGGCCA TCAGAGCAGC GGCGGGGCGA
 961 GCACCGGACC CCGCAAGAAG AAGAGCAAAC GCATCTCCGA GTTGGACAAC GAGAAGGTGC
1021 GCAATATCAT GAAAGATAAG AACACCCCCT TCTGCACACC CAACGTGCAG ACTCGGCGGG
1081 GTCGCGTCAA GATTGACGAG GTGAGCCGCA TGTTCCGCAA CACCAATCGC TCTCTTGAGT
1141 ACAAGAACCT GCCCTTCACG ATTCCCAGTA TGCACCAGGT GTTAGATGAG GCCATCAAAG
1201 CCTGCAAAAC CATGCAGGTG AACAACAAGG GCATCAGAT TATCTACACC CGCAATCATG
1261 AGGTGAAGAG TGAGGTGGAT GCGGTGCGGT GTCGCCTGGG CACCATGTGC AACCTGGCCC
1321 TCTCCACTCC CTTCCTCATG GAGCACACCA TGCCCGTGAC ACATCCACCC GAAGTGGCGC
1381 AGCGCACAGC CGATGCTTGT AACGAAGGCG TCAAGGCCGC GTGGAGCCTC AAAGAATTGC
1441 ACACCCACCA ATTATGCCCC CGTTCCTCCG ATTACCGCAA CATGATCATC CACGCTGCCA
1501 CCCCCGTGGA CCTGTTGGGC GCTCTCAACC TGTGCCTGCC CCTGATGCAA AAGTTTCCCA
1561 AACAGGTCAT GGTGCGCATC TTCTCCACCA ACCAGGGTGG GTTCATGCTG CCTATCTACG
1621 AGACGGCCGC GAAGGCCTAC GCCGTGGGGC AGTTTGAGCA GCCCACCGAG ACCCCTCCCG
1681 AAGACCTGGA CACCCTGAGC CTGGCCATCG AGGCAGCCAT CCAGGACCTG AGGAACAAGT
1741 CTCAGTAAGG ATCCGCCCCT CTCCCCTCCC CCCCCCTAAC GTTACTGGCC GAAGCCGCTT
1801 GGAATAAGGC CGGTGTGCGT TTGTCTATAT GTTATTTTCC ACCATATTGC CGTCTTTTGG
1861 CAATGTGAGG GCCCGGAAAC CTGGCCCTGT CTTCTTGACG AGCATTCCTA GGGGTCTTTC
1921 CCCTCTCGCC AAAGGAATGC AAGGTCTGTT GAATGTCGTG AAGGAAGCAG TTCCTCTGGA
1981 AGCTTCTTGA AGACAAACAA CGTCTGTAGC GACCCTTTGC AGGCAGCGGA ACCCCCCACC
2041 TGGCGACAGG TGCCTCTGCG GCCAAAAGCC ACGTGTATAA GATACACCTG CAAAGGCGGC
2101 ACAACCCCAG TGCCACGTTG TGAGTTGGAT AGTTGTGGAA AGAGTCAAAT GGCTCTCCTC
2161 AAGCGTATTC AACAAGGGGC TGAAGGATGC CCAGAAGGTA CCCCATTGTA TGGGATCTGA
2221 TCTGGGGCCT CGGTGCACAT GCTTTACATG TGTTTAGTCG AGGTTAAAAA AACGTCTAGG
2281 CCCCCCGAAC CACGGGGACG TGGTTTTCCT TTGAAAAACA CGATGATAAT ATGGCCACAA
2341 CCATGCCCTC CTCCAGGGAC GTCATCAAGG AGTTCATGCG CTTCAAGGTG CGCATGGAGG
2401 GCTCCGTGAA CGGCCACGAG TTCGAGATCG AGGGCGAGGG CGAGGGCCGC CCCTACGAGG
2461 GCACCCAGAC CGCCAAGCTG AAGGTGACCA AGGGCGGCCC CCTGCCCTTC GCCTGGGACA
2521 TCCTGTCCCC CCAGTTCCAG TACGGCTCCA AGGTGTACGT GAAGCACCCC GCCGACATCC
2581 CCGACTACAA GAAGCTGTCC TTCCCCGAGG GCTTCAAGTG GGAGCGCGTG ATGAACTTCG
2641 AGGACGGCGG CGTGGTGACC GTGACCCAGG ACTCCTCCCT GCAGGACGGC TCCTTCATCT
```

FIG. 2A

```
2701 ACAAGGTGAA GTTCATCGGC GTGAACTTCC CCTCCGACGG CCCCGTAATG CAGAAGAAGA
2761 CTATGGGCTG GGAGGCCTCC ACCGAGCGCC TGTACCCCCG CGACGGCGTG CTGAAGGGCG
2821 AGATCCACAA GGCCCTGAAG CTGAAGGACG GCGGCCACTA CCTGGTGGAG TTCAAGTCCA
2881 TCTACATGGC CAAGAAGCCC GTGCAGCTGC CCGGCTACTA CTACGTGGAC TCCAAGCTGG
2941 ACATCACCTC CCACAACGAG GACTACACCA TCGTGGAGCA GTACGAGCGC GCCGAGGGCC
3001 GCCACCACCT GTTCCTGTAG GCGGCCGCAA TCAACCTCTG GATTACAAAA TTTGTGAAAG
3061 ATTGACTGGT ATTCTTAACT ATGTTGCTCC TTTTACGCTA TGTGGATACG CTGCTTTAAT
3121 GCCTTTGTAT CATGCTATTA CTTCCCGTAC GGCTTTCATT TTCTCCTCCT TGTATAAATC
3181 CTGGTTGCTG TCTCTTTATG AGGAGTTGTG GCCCGTTGTC AGGCAACGTG GCGTGGTGTG
3241 CACTGTGTTT GCTGACGCAA CCCCCACTGG TTGGGGCATT GCCACCACCT ATCAACTCCT
3301 TTCCGGGACT TTCGCTTTCC CCCTCCCTAT TGCCACGGCG GAACTCATTG CCGCCTGCCT
3361 TGCCCGCTGC TGGACAGGGG CTCGGCTGTT GGGCACTGAC AATTCCGTGG TGTTGTCGGG
3421 GAAGCTGACG TCCTTTCCAT GGCTGCTCGC CTGTGTTGCC AACTGGATTC TGCGCGGGAC
3481 GTCCTTCTGC TACGTCCCTT CGGCCCTCAA TCCAGCGGAC CTTCCTTCCC GCGGCCTGCT
3541 GCCGGTTCTG CGGCCTCTTC CGCGTCTTCG CCTTCGCCCT CAGACGAGTC GGATCTCCCT
3601 TTGGGCCGCC TCCCCGCCTG CCTGCAGGTT TGTCGAGACC TAGAAAAACA TGGAGCAATC
3661 ACAAGTAGCA ATACAGCAGC TACCAATGCT GATTGTGCCT GGCTAGAAGC ACAAGAGGAG
3721 GAGGAGGTGG GTTTTCCAGT CACACCTCAG GTACCTTTAA GACCAATGAC TTACAAGGCA
3781 GCTGTAGATC TTAGCCACTT TTTAAAAGAA AAGGGGGGAC TGGAAGGGCT AATTCACTCC
3841 CAACGAAGAC AAGATCTGCT TTTTGCTTGT ACTGGGTCTC TCTGGTTAGA CCAGATCTGA
3901 GCCTGGGAGC TCTCTGGCTA ACTAGGGAAC CCACTGCTTA AGCCTCAATA AAGCTTGCCT
3961 TGAGTGCTTC AAGTAGTGTG TGCCCGTCTG TTGTGTGACT CTGGTAACTA GAGATCCCTC
4021 AGACCCTTTT AGTCAGTGTG GAAAATCTCT AGCAGGGCCC GTTTAAACCC GCTGATCAGC
4081 CTCGACTGTG CCTTCTAGTT GCCAGCCATC TGTTGTTTGC CCCTCCCCCG TGCCTTCCTT
4141 GACCCTGGAA GGTGCCACTC CCACTGTCCT TTCCTAATAA AATGAGGAAA TTGCATCGCA
4201 TTGTCTGAGT AGGTGTCATT CTATTCTGGG GGGTGGGGTG GGCAGGACA GCAAGGGGGA
4261 GGATTGGGAA GACAATAGCA GGCATGCTGG GGATGCGGTG GGCTCTATGG CTTCTGAGGC
4321 GGAAAGAACC AGCTGGGGCT CTAGGGGGTA TCCCCACGCG CCCTGTAGCG GCGCATTAAG
4381 CGCGGCGGGT GTGGTGGTTA CGCGCAGCGT GACCGCTACA CTTGCCAGCG CCCTAGCGCC
4441 CGCTCCTTTC GCTTTCTTCC CTTCCTTTCT CGCCACGTTC GCCGGCTTTC CCCGTCAAGC
4501 TCTAAATCGG GGCATCCCTT TAGGGTTCCG ATTTAGTGCT TTACGGCACC TCGACCCCAA
4561 AAAACTTGAT TAGGGTGATG GTTCACGTAG TGGGCCATCG CCCTGATAGA CGGTTTTTCG
4621 CCCTTTGACG TTGGAGTCCA CGTTCTTTAA TAGTGGACTC TTGTTCCAAA CTGAACAAC
4681 ACTCAACCCT ATCTCGGTCT ATTCTTTTGA TTTATAAGGG ATTTTGGGGA TTTCGGCCTA
4741 TTGGTTAAAA AATGAGCTGA TTTAACAAAA ATTTAACGCG AATTAATTCT GTGGAATGTG
4801 TGTCAGTTAG GGTGTGGAAA GTCCCCAGGC TCCCCAGGCA GGCAGAAGTA TGCAAAGCAT
4861 GCATCTCAAT TAGTCAGCAA CCAGGTGTGG AAAGTCCCCA GGCTCCCCAG CAGGCAGAAG
4921 TATGCAAAGC ATGCATCTCA ATTAGTCAGC AACCATAGTC CGCCCCTAA CTCCGCCCAT
4981 CCCGCCCCTA ACTCCGCCCA GTTCCGCCCA TTCTCCGCCC CATGGCTGAC TAATTTTTTT
5041 TATTTATGCA GAGGCCGAGG CCGCCTCTGC CTCTGAGCTA TTCCAGAAGT AGTGAGGAGG
5101 CTTTTTTGGA GGCCTAGGCT TTTGCAAAAA GCTCCCGGGA GCTTGTATAT CCATTTTCGG
5161 ATCTGATCAG CACGTGTTGA CAATTAATCA TCGGCATAGT ATATCGGCAT AGTATAATAC
5221 GACAAGGTGA GGAACTAAAC CATGGCCAAG TTGACCAGTG CCGTTCCGGT GCTCACCGCG
5281 CGCGACGTCG CCGGAGCGGT CGAGTTCTGG ACCGACCGGC TCGGGTTCTC CCGGGACTTC
5341 GTGGAGGACG ACTTCGCCGG TGTGGTCCGG GACGACGTGA CCCTGTTCAT CAGCGCGGTC
```

FIG. 2B

```
5401 CAGGACCAGG TGGTGCCGGA CAACACCCTG GCCTGGGTGT GGGTGCGCGG CCTGGACGAG
5461 CTGTACGCCG AGTGGTCGGA GGTCGTGTCC ACGAACTTCC GGGACGCCTC CGGGCCGGCC
5521 ATGACCGAGA TCGGCGAGCA GCCGTGGGGG CGGGAGTTCG CCCTGCGCGA CCCGGCCGGC
5581 AACTGCGTGC ACTTCGTGGC CGAGGAGCAG GACTGACACG TGCTACGAGA TTTCGATTCC
5641 ACCGCCGCCT TCTATGAAAG GTTGGGCTTC GGAATCGTTT TCCGGGACGC CGGCTGGATG
5701 ATCCTCCAGC GCGGGGATCT CATGCTGGAG TTCTTCGCCC ACCCCAACTT GTTTATTGCA
5761 GCTTATAATG GTTACAAATA AAGCAATAGC ATCACAAATT TCACAAATAA AGCATTTTTT
5821 TCACTGCATT CTAGTTGTGG TTTGTCCAAA CTCATCAATG TATCTTATCA TGTCTGTATA
5881 CCGTCGACCT CTAGCTAGAG CTTGGCGTAA TCATGGTCAT AGCTGTTTCC TGTGTGAAAT
5941 TGTTATCCGC TCACAATTCC ACACAACATA CGAGCCGGAA GCATAAAGTG TAAAGCCTGG
6001 GGTGCCTAAT GAGTGAGCTA ACTCACATTA ATTGCGTTGC GCTCACTGCC CGCTTTCCAG
6061 TCGGGAAACC TGTCGTGCCA GCTGCATTAA TGAATCGGCC AACGCGCGGG GAGAGGCGGT
6121 TTGCGTATTG GGCGCTCTTC CGCTTCCTCG CTCACTGACT CGCTGCGCTC GGTCGTTCGG
6181 CTGCGGCGAG CGGTATCAGC TCACTCAAAG GCGGTAATAC GGTTATCCAC AGAATCAGGG
6241 GATAACGCAG GAAAGAACAT GTGAGCAAAA GGCCAGCAAA AGGCCAGGAA CCGTAAAAAG
6301 GCCGCGTTGC TGGCGTTTTT CCATAGGCTC CGCCCCCCTG ACGAGCATCA CAAAAATCGA
6361 CGCTCAAGTC AGAGGTGGCG AAACCCGACA GGACTATAAA GATACCAGGC GTTTCCCCCT
6421 GGAAGCTCCC TCGTGCGCTC TCCTGTTCCG ACCCTGCCGC TTACCGGATA CCTGTCCGCC
6481 TTTCTCCCTT CGGGAAGCGT GGCGCTTTCT CAATGCTCAC GCTGTAGGTA TCTCAGTTCG
6541 GTGTAGGTCG TTCGCTCCAA GCTGGGCTGT GTGCACGAAC CCCCCGTTCA GCCCGACCGC
6601 TGCGCCTTAT CCGGTAACTA TCGTCTTGAG TCCAACCCGG TAAGACACGA CTTATCGCCA
6661 CTGGCAGCAG CCACTGGTAA CAGGATTAGC AGAGCGAGGT ATGTAGGCGG TGCTACAGAG
6721 TTCTTGAAGT GGTGGCCTAA CTACGGCTAC ACTAGAAGGA CAGTATTTGG TATCTGCGCT
6781 CTGCTGAAGC CAGTTACCTT CGGAAAAAGA GTTGGTAGCT CTTGATCCGG CAAACAAACC
6841 ACCGCTGGTA GCGGTGGTTT TTTTGTTTGC AAGCAGCAGA TTACGCGCAG AAAAAAAGGA
6901 TCTCAAGAAG ATCCTTTGAT CTTTTCTACG GGGTCTGACG CTCAGTGGAA CGAAAACTCA
6961 CGTTAAGGGA TTTTGGTCAT GAGATTATCA AAAAGGATCT TCACCTAGAT CCTTTTAAAT
7021 TAAAAATGAA GTTTTAAATC AATCTAAAGT ATATATGAGT AAACTTGGTC TGACAGTTAC
7081 CAATGCTTAA TCAGTGAGGC ACCTATCTCA GCGATCTGTC TATTTCGTTC ATCCATAGTT
7141 GCCTGACTCC CCGTCGTGTA GATAACTACG ATACGGGAGG GCTTACCATC TGGCCCCAGT
7201 GCTGCAATGA TACCGCGAGA CCCACGCTCA CCGGCTCCAG ATTTATCAGC AATAAACCAG
7261 CCAGCCGGAA GGGCCGAGCG CAGAAGTGGT CCTGCAACTT TATCCGCCTC CATCCAGTCT
7321 ATTAATTGTT GCCGGGAAGC TAGAGTAAGT AGTTCGCCAG TTAATAGTTT GCGCAACGTT
7381 GTTGCCATTG CTACAGGCAT CGTGGTGTCA CGCTCGTCGT TTGGTATGGC TTCATTCAGC
7441 TCCGGTTCCC AACGATCAAG GCGAGTTACA TGATCCCCCA TGTTGTGCAA AAAAGCGGTT
7501 AGCTCCTTCG GTCCTCCGAT CGTTGTCAGA AGTAAGTTGG CCGCAGTGTT ATCACTCATG
7561 GTTATGGCAG CACTGCATAA TTCTCTTACT GTCATGCCAT CCGTAAGATG CTTTTCTGTG
7621 ACTGGTGAGT ACTCAACCAA GTCATTCTGA GAATAGTGTA TGCGGCGACC GAGTTGCTCT
7681 TGCCCGGCGT CAATACGGGA TAATACCGCG CCACATAGCA GAACTTTAAA AGTGCTCATC
7741 ATTGGAAAAC GTTCTTCGGG GCGAAAACTC TCAAGGATCT TACCGCTGTT GAGATCCAGT
7801 TCGATGTAAC CCACTCGTGC ACCCAACTGA TCTTCAGCAT CTTTTACTTT CACCAGCGTT
7861 TCTGGGTGAG CAAAAACAGG AAGGCAAAAT GCCGCAAAAA AGGGAATAAG GGCGACACGG
7921 AAATGTTGAA TACTCATACT CTTCCTTTTT CAATATTATT GAAGCATTTA TCAGGGTTAT
7981 TGTCTCATGA GCGGATACAT ATTTGAATGT ATTTAGAAAA ATAAACAAAT AGGGGTTCCG
8041 CGCACATTTC CCCGAAAAGT GCCACCTGAC GTCGACGGAT CGGGAGATCT CCCGATCCCC
8101 TATGGTGCAC TCTCAGTACA ATCTGCTCTG ATGCCGCATA GTTAAGCCAG TATCTGCTCC
8161 CTGCTTGTGT GTTGGAGGTC GCTGAGTAGT GCGCGAGCAA AATTTAAGCT ACAACAAGGC
8221 AAGGCTTGAC CGACAATTGC ATGAAGAATC TGCTTAGGGT TAGGCGTTTT GCGCTGCTTC
8281 GCGATGTACG GGCCAGATAT ACGCGTTGAC ATTGATTATT GACTAGTTAT TAATAGTAAT
8341 CAATTACGGG GTCATTAGTT CATAGCCCAT ATATGGAGTT CCGCGTTACA TAACTTACGG
```

FIG. 2C

```
8401 TAAATGGCCC GCCTGGCTGA CCGCCCAACG ACCCCCGCCC ATTGACGTCA ATAATGACGT
8461 ATGTTCCCAT AGTAACGCCA ATAGGGACTT TCCATTGACG TCAATGGGTG GACTATTTAC
8521 GGTAAACTGC CCACTTGGCA GTACATCAAG TGTATCATAT GCCAAGTACG CCCCCTATTG
8581 ACGTCAATGA CGGTAAATGG CCCGCCTGGC ATTATGCCCA GTACATGACC TTATGGGACT
8641 TTCCTACTTG GCAGTACATC TACGTATTAG TCATCGCTAT TACCATGGTG ATGCGGTTTT
8701 GGCAGTACAT CAATGGGCGT GGATAGCGGT TTGACTCACG GGGATTTCCA AGTCTCCACC
8761 CCATTGACGT CAATGGGAGT TTGTTTTGGC ACCAAAATCA ACGGGACTTT CCAAAATGTC
8821 GTAACAACTC CGCCCCATTG ACGCAAATGG GCGGTAGGCG TGTACGGTGG GAGGTCTATA
8881 TAAGCAGAGC TCTCTGGCTA ACTAGAGAAC CCACTGCTTA CTGGCTTATC GAAATTAATA
8941 CGACTCACTA TAGGGAGACC CAAGCTGGTT TAAACTTAAG CTTGGTACCG AGCTCACTAG
9001 TCCAGTGTGG TGGCAGATAT CCAGCACAGT GGCGGCCGCT CGAGTCTAGA GGGCCCGTTT
9061 TGCCTGTACT GGGTCTCTCT GGTTAGACCA GATCTGAGCC TGGGAGCTCT CTGGCTAACT
9121 AGGGAACCCA CTGCTTAAGC CTCAATAAAG CTTGCCTTGA GTGCTTCAAG TAGTGTGTGC
9181 CCGTCTGTTG TGTGACTCTG GTAACTAGAG ATCCCTCAGA CCCTTTTAGT CAGTGTGGAA
9241 AATCTCTAGC AGTGGCGCCC GAACAGGGAC TTGAAAGCGA AAGGGAAACC AGAGGAGCTC
9301 TCTCGACGCA GGACTCGGCT TGCTGAAGCG CGCACGGCAA GAGGCGAGGG GCGGCGACTG
9361 GTGAGTACGC CAAAAATTTT GACTAGCGGA GGCTAGAAGG AGAGAGATGG GTGCGAGAGC
9421 GTCAGTATTA AGCGGGGGAG AATTAGATCG CGATGGGAAA AAATTCGGTT AAGGCCAGGG
9481 GGAAAGAAAA AATATAAATT AAAACATATA GTATGGGCAA GCAGGGAGCT AGAACGATTC
9541 GCAGTTAATC CTGGCCTGTT AGAAACATCA GAAGGCTGTA GACAAATACT GGGACAGCTA
9601 CAACCATCCC TTCAGACAGG ATCAGAAGAA CTTAGATCAT TATATAATAC AGTAGCAACC
9661 CTCTATTGTG TGCATCAAAG GATAGAGATA AAGACACCA AGGAAGCTTT AGACAAGATA
9721 GAGGAAGAGC AAAACAAAAG TAAGACCACC GCACAGCAAG CGGCCGCTGA TCTTCAGACC
9781 TGGAGGAGGA GATATGAGGG ACAATTGGAG AAGTGAATTA TATAAATATA AAGTAGTAAA
9841 AATTGAACCA TTAGGAGTAG CACCCACCAA GGCAAAGAGA AGAGTGGTGC AGAGAGAAAA
9901 AAGAGCAGTG GAATAGGAG CTTTGTTCCT TGGGTTCTTG GGAGCAGCAG GAAGCACTAT
9961 GGGCGCAGCG TCAATGACGC TGACGGTACA GGCCAGACAA TTATTGTCTG GTATAGTGCA
10021 GCAGCAGAAC AATTTGCTGA GGGCTATTGA GGCGCAACAG CATCTGTTGC AACTCACAGT
10081 CTGGGGCATC AAGCAGCTCC AGGCAAGAAT CCTGGCTGTG GAAAGATACC TAAAGGATCA
10141 ACAGCTCCTG GGGATTTGGG GTTGCTCTGG AAAACTCATT TGCACCACTG CTGTGCCTTG
10201 GAATGCTAGT TGGAGTAATA AATCTCTGGA ACAGATTTGG AATCACACGA CCTGGATGGA
10261 GTGGGACAGA GAAATTAACA ATTACACAAG CTTAATACAC TCCTTAATTG AAGAATCGCA
10321 AAACCAGCAA GAAAAGAATG AACAAGAATT ATTGGAATTA GATAAATGGG CAAGTTTGTG
10381 GAATTGGTTT AACATAACAA ATTGGCTGTG GTATATAAAA TTATTCATAA TGATAGTAGG
10441 AGGCTTGGTA GGTTTAAGAA TAGTTTTTGC TGTACTTTCT ATAGTGAATA GAGTTAGGCA
10501 GGGATATTCA CCATTATCGT TTCAGACCCA CCTCCCAACC CCGAGGGGAC CCGACAGGCC
10561 CTTAATTAAT TGGCTCCGGT GCCCGTCAGT GGGCAGAGCG CACATCGCCC ACAGTCCCCG
10621 AGAAGTTGGG GGGAGGGGTC GGCAATTGAA CCGGTGCCTA GAGAAGGTGG CGCGGGGTAA
10681 ACTGGGAAAG TGATGTCGTG TACTGGCTCC GCCTTTTCC CGAGGGTGGG GGAGAACCGT
10741 ATATAAGTGC AGTAGTCGCC GTGAACGTTC TTTTTCGCAA CGGGTTTGCC GCCAGAACAC
10801 AGGTAAGTGC CGTGTGTGGT TCCCGCGGGC CTGGCCTCTT TACGGGTTAT GGCCCTTGCG
10861 TGCCTTGAAT TACTTCCACC TGGCTGCAGT ACGTGATTCT TGATCCCGAG CTTCGGGTTG
10921 GAAGTGGGTG GGAGAGTTCG AGGCCTTGCG CTTAAGGAGC CCCTTCGCCT CGTGCTTGAG
10981 TTGAGGCCTG GCCTGGGCGC TGGGGCCGCC GCGTGCGAAT CTGGTGGCAC CTTCGCGCCT
11041 GTCTCGCTGC TTTCGATAAG TCTCTAGCCA TTTAAATTT TGATGACCT GCTGCGACGC
11101 TTTTTTTCTG GCAAGATAGT CTTGTAAATG CGGGCCAAGA TCTGCACACT GGTATTTCGG
```

FIG. 2D

```
11161 TTTTTGGGGC CGCGGGCGGC GACGGGGCCC GTGCGTCCCA GCGCACATGT TCGGCGAGGC
11221 GGGGCCTGCG AGCGCGGCCA CCGAGAATCG GACGGGGGTA GTCTCAAGCT GGCCGGCCTG
11281 CTCTGGTGCC TGGCCTCGCG CCGCCGTGTA TCGCCCCGCC CTGGGCGGCA AGGCTGGCCC
11341 GGTCGGCACC AGTTGCGTGA GCGGAAAGAT GGCCGCTTCC CGGCCCTGCT GCAGGGAGCT
11401 CAAAATGGAG GACGCGGCGC TCGGGAGAGC GGGCGGGTGA GTCACCCACA CAAAGGAAAA
11461 GGGCCTTTCC GTCCTCAGCC GTCGCTTCAT GTGACTCCAC GGAGTACCGG GCGCCGTCCA
11521 GGCACCTCGA TTAGTTCTCG AGCTTTTGGA GTACGTCGTC TTTAGGTTGG GGGGAGGGGT
11581 TTTATGCGAT GGAGTTTCCC CACACTGAGT GGGTGGAGAC TGAAGTTAGG CCAGCTTGGC
11641 ACTTGATGTA ATTCTCCTTG GAATTTGCCC TTTTTGAGTT TGGATCTTGG TTCATTCTCA
11701 AGCCTCAGAC AGTGGTTCAA AGTTTTTTTC TTCCATTTCA GGTGTCGTGA GGAATTCGGC
11761 CATTACGGCC G
```

|  | Location | | Size (bp) |
|---|---|---|---|
|  | (start) | (end) |  |
| IE2 | 6 .. | 1748 | 1743 |
| IRES | 1755 .. | 2339 | 585 |
| Kozak consensus | 2337 .. | 2346 | 10 |
| DsRED2 | 2343 .. | 3020 | 678 |
| WPRE | 3029 .. | 3620 | 592 |
| deltaU3-3'LTR | 3820 .. | 4054 | 235 |
| BGH PolyA | 4080 .. | 4293 | 214 |
| f1 ori | 4356 .. | 4768 | 413 |
| SV40 ori | 4834 .. | 5159 | 326 |
| EM7 | 5175 .. | 5240 | 66 |
| Zeocin | 5242 .. | 5616 | 375 |
| pUC ori | 6259 .. | 6932 | 674 |
| Amp | 7077 .. | 7937 | 861 |
| bla | 7938 .. | 8035 | 98 |
| PCMV | 8282 .. | 8933 | 652 |
| T7 promoter | 8936 .. | 8955 | 20 |
| MCS | 8968 .. | 9070 | 103 |
| 5' LTR | 9071 .. | 9251 | 181 |
| PEF1-alpha | 10,570 .. | 11,743 | 1174 |

FIG. 2E

```
>LM2G (10,760 bp)
   1 TCGAGACCTA GAAAAACATG GAGCAATCAC AAGTAGCAAT ACAGCAGCTA CCAATGCTGA
  61 TTGTGCCTGG CTAGAAGCAC AAGAGGAGGA GGAGGTGGGT TTTCCAGTCA CACCTCAGGT
 121 ACCTTTAAGA CCAATGACTT ACAAGGCAGC TGTAGATCTT AGCCACTTTT TAAAAGAAAA
 181 GGGGGGACTG GAAGGGCTAA TTCACTCCCA ACGAAGACAA GATCTGCTTT TGCTTGTAC
 241 TGGGTCTCTC TGGTTAGACC AGATCTGAGC CTGGGAGCTC TCTGGCTAAC TAGGGAACCC
 301 ACTGCTTAAG CCTCAATAAA GCTTGCCTTG AGTGCTTCAA GTAGTGTGTG CCCGTCTGTT
 361 GTGTGACTCT GGTAACTAGA GATCCCTCAG ACCCTTTTAG TCAGTGTGGA AAATCTCTAG
 421 CAGGGCCCGT TTAAACCCGC TGATCAGCCT CGACTGTGCC TTCTAGTTGC CAGCCATCTG
 481 TTGTTTGCCC CTCCCCCGTG CCTTCCTTGA CCCTGGAAGG TGCCACTCCC ACTGTCCTTT
 541 CCTAATAAAA TGAGGAAATT GCATCGCATT GTCTGAGTAG GTGTCATTCT ATTCTGGGGG
 601 GTGGGGTGGG GCAGGACAGC AAGGGGGAGG ATTGGGAAGA CAATAGCAGG CATGCTGGGG
 661 ATGCGGTGGG CTCTATGGCT TCTGAGGCGG AAAGAACCAG CTGGGGCTCT AGGGGGTATC
 721 CCCACGCGCC CTGTAGCGGC GCATTAAGCG CGGCGGGTGT GGTGGTTACG CGCAGCGTGA
 781 CCGCTACACT TGCCAGCGCC CTAGCGCCCG CTCCTTTCGC TTTCTTCCCT TCCTTTCTCG
 841 CCACGTTCGC CGGCTTTCCC CGTCAAGCTC TAAATCGGGG CATCCCTTTA GGGTTCCGAT
 901 TTAGTGCTTT ACGGCACCTC GACCCCAAAA AACTTGATTA GGGTGATGGT TCACGTAGTG
 961 GGCCATCGCC CTGATAGACG GTTTTCGCC CTTTGACGTT GGAGTCCACG TTCTTTAATA
1021 GTGGACTCTT GTTCCAAACT GGAACAACAC TCAACCCTAT CTCGGTCTAT TCTTTTGATT
1081 TATAAGGGAT TTTGGGGATT TCGGCCTATT GGTTAAAAAA TGAGCTGATT TAACAAAAAT
1141 TTAACGCGAA TTAATTCTGT GGAATGTGTG TCAGTTAGGG TGTGGAAAGT CCCCAGGCTC
1201 CCCAGGCAGG CAGAAGTATG CAAAGCATGC ATCTCAATTA GTCAGCAACC AGGTGTGGAA
1261 AGTCCCCAGG CTCCCCAGCA GGCAGAAGTA TGCAAAGCAT GCATCTCAAT TAGTCAGCAA
1321 CCATAGTCCC GCCCCTAACT CCGCCCATCC CGCCCCTAAC TCCGCCCAGT TCCGCCCATT
1381 CTCCGCCCCA TGGCTGACTA ATTTTTTTTA TTTATGCAGA GGCCGAGGCC GCCTCTGCCT
1441 CTGAGCTATT CCAGAAGTAG TGAGGAGGCT TTTTTGGAGG CCTAGGCTTT TGCAAAAAGC
1501 TCCCGGGAGC TTGTATATCC ATTTTCGGAT CTGATCAGCA CGTGTTGACA ATTAATCATC
1561 GGCATAGTAT ATCGGCATAG TATAATACGA CAAGGTGAGG AACTAAACCA TGGCCAAGTT
1621 GACCAGTGCC GTTCCGGTGC TCACCGCGCG CGACGTCGCC GGAGCGGTCG AGTTCTGGAC
1681 CGACCGGCTC GGGTTCTCCC GGGACTTCGT GGAGGACGAC TTCGCCGGTG TGGTCCGGGA
1741 CGACGTGACC CTGTTCATCA GCGCGGTCCA GGACCAGGTG GTGCCGGACA ACACCCTGGC
1801 CTGGGTGTGG GTGCGCGGCC TGGACGAGCT GTACGCCGAG TGGTCGGAGG TCGTGTCCAC
1861 GAACTTCCGG GACGCCTCCG GCCGGCCAT GACCGAGATC GGCGAGCAGC CGTGGGGGCG
1921 GGAGTTCGCC CTGCGCGACC CGGCCGGCAA CTGCGTGCAC TTCGTGGCCG AGGAGCAGGA
1981 CTGACACGTG CTACGAGATT TCGATTCCAC CGCCGCCTTC TATGAAAGGT TGGGCTTCGG
2041 AATCGTTTTC CGGGACGCCG GCTGGATGAT CCTCCAGCGC GGGGATCTCA TGCTGGAGTT
2101 CTTCGCCCAC CCCAACTTGT TTATTGCAGC TTATAATGGT TACAAATAAA GCAATAGCAT
2161 CACAAATTTC ACAAATAAAG CATTTTTTTC ACTGCATTCT AGTTGTGGTT TGTCCAAACT
2221 CATCAATGTA TCTTATCATG TCTGTATACC GTCGACCTCT AGCTAGAGCT TGGCGTAATC
2281 ATGGTCATAG CTGTTTCCTG TGTGAAATTG TTATCCGCTC ACAATTCCAC ACAACATACG
2341 AGCCGGAAGC ATAAAGTGTA AAGCCTGGGG TGCCTAATGA GTGAGCTAAC TCACATTAAT
2401 TGCGTTGCGC TCACTGCCCG CTTTCCAGTC GGGAAACCTG TCGTGCCAGC TGCATTAATG
2461 AATCGGCCAA CGCGCGGGA GAGGCGGTTT GCGTATTGGG CGCTCTTCCG CTTCCTCGCT
2521 CACTGACTCG CTGCGCTCGG TCGTTCGGCT GCGGCGAGCG GTATCAGCTC ACTCAAAGGC
2581 GGTAATACGG TTATCCACAG AATCAGGGGA TAACGCAGGA AGAACATGT GAGCAAAAGG
2641 CCAGCAAAAG GCCAGGAACC GTAAAAAGGC CGCGTTGCTG GCGTTTTTCC ATAGGCTCCG
```

FIG. 4A

```
2701 CCCCCCTGAC GAGCATCACA AAAATCGACG CTCAAGTCAG AGGTGGCGAA ACCCGACAGG
2761 ACTATAAAGA TACCAGGCGT TTCCCCCTGG AAGCTCCCTC GTGCGCTCTC CTGTTCCGAC
2821 CCTGCCGCTT ACCGGATACC TGTCCGCCTT TCTCCCTTCG GGAAGCGTGG CGCTTTCTCA
2881 ATGCTCACGC TGTAGGTATC TCAGTTCGGT GTAGGTCGTT CGCTCCAAGC TGGGCTGTGT
2941 GCACGAACCC CCCGTTCAGC CCGACCGCTG CGCCTTATCC GGTAACTATC GTCTTGAGTC
3001 CAACCCGGTA AGACACGACT TATCGCCACT GGCAGCAGCC ACTGGTAACA GGATTAGCAG
3061 AGCGAGGTAT GTAGGCGGTG CTACAGAGTT CTTGAAGTGG TGGCCTAACT ACGGCTACAC
3121 TAGAAGGACA GTATTTGGTA TCTGCGCTCT GCTGAAGCCA GTTACCTTCG GAAAAAGAGT
3181 TGGTAGCTCT TGATCCGGCA AACAAACCAC CGCTGGTAGC GGTGGTTTTT TTGTTTGCAA
3241 GCAGCAGATT ACGCGCAGAA AAAAGGATC TCAAGAAGAT CCTTTGATCT TTTCTACGGG
3301 GTCTGACGCT CAGTGGAACG AAAACTCACG TTAAGGGATT TTGGTCATGA GATTATCAAA
3361 AAGGATCTTC ACCTAGATCC TTTTAAATTA AAAATGAAGT TTTAAATCAA TCTAAAGTAT
3421 ATATGAGTAA ACTTGGTCTG ACAGTTACCA ATGCTTAATC AGTGAGGCAC CTATCTCAGC
3481 GATCTGTCTA TTTCGTTCAT CCATAGTTGC CTGACTCCCC GTCGTGTAGA TAACTACGAT
3541 ACGGGAGGGC TTACCATCTG GCCCCAGTGC TGCAATGATA CCGCGAGACC CACGCTCACC
3601 GGCTCCAGAT TTATCAGCAA TAAACCAGCC AGCCGGAAGG GCCGAGCGCA GAAGTGGTCC
3661 TGCAACTTTA TCCGCCTCCA TCCAGTCTAT TAATTGTTGC CGGGAAGCTA GAGTAAGTAG
3721 TTCGCCAGTT AATAGTTTGC GCAACGTTGT TGCCATTGCT ACAGGCATCG TGGTGTCACG
3781 CTCGTCGTTT GGTATGGCTT CATTCAGCTC CGGTTCCCAA CGATCAAGGC GAGTTACATG
3841 ATCCCCCATG TTGTGCAAAA AAGCGGTTAG CTCCTTCGGT CCTCCGATCG TTGTCAGAAG
3901 TAAGTTGGCC GCAGTGTTAT CACTCATGGT TATGGCAGCA CTGCATAATT CTCTTACTGT
3961 CATGCCATCC GTAAGATGCT TTTCTGTGAC TGGTGAGTAC TCAACCAAGT CATTCTGAGA
4021 ATAGTGTATG CGGCGACCGA GTTGCTCTTG CCCGGCGTCA ATACGGGATA ATACCGCGCC
4081 ACATAGCAGA ACTTTAAAAG TGCTCATCAT TGGAAAACGT TCTTCGGGGC GAAAACTCTC
4141 AAGGATCTTA CCGCTGTTGA GATCCAGTTC GATGTAACCC ACTCGTGCAC CCAACTGATC
4201 TTCAGCATCT TTTACTTTCA CCAGCGTTTC TGGGTGAGCA AAAACAGGAA GGCAAAATGC
4261 CGCAAAAAAG GGAATAAGGG CGACACGGAA ATGTTGAATA CTCATACTCT TCCTTTTTCA
4321 ATATTATTGA AGCATTTATC AGGGTTATTG TCTCATGAGC GGATACATAT TTGAATGTAT
4381 TTAGAAAAAT AAACAAATAG GGGTTCCGCG CACATTTCCC CGAAAAGTGC CACCTGACGT
4441 CGACGGATCG GGAGATCTCC CGATCCCCTA TGGTGCACTC TCAGTACAAT CTGCTCTGAT
4501 GCCGCATAGT TAAGCCAGTA TCTGCTCCCT GCTTGTGTGT TGGAGGTCGC TGAGTAGTGC
4561 GCGAGCAAAA TTTAAGCTAC AACAAGGCAA GGCTTGACCG ACAATTGCAT GAAGAATCTG
4621 CTTAGGGTTA GGCGTTTTGC GCTGCTTCGC GATGTACGGG CCAGATATAC GCGTTGACAT
4681 TGATTATTGA CTAGTTATTA ATAGTAATCA ATTACGGGGT CATTAGTTCA TAGCCCATAT
4741 ATGGAGTTCC GCGTTACATA ACTTACGGTA AATGGCCCGC CTGGCTGACC GCCCAACGAC
4801 CCCCGCCCAT TGACGTCAAT AATGACGTAT GTTCCCATAG TAACGCCAAT AGGGACTTTC
4861 CATTGACGTC AATGGGTGGA CTATTTACGG TAAACTGCCC ACTTGGCAGT ACATCAAGTG
4921 TATCATATGC CAAGTACGCC CCCTATTGAC GTCAATGACG GTAAATGGCC CGCCTGGCAT
4981 TATGCCCAGT ACATGACCTT ATGGGACTTT CCTACTTGGC AGTACATCTA CGTATTAGTC
5041 ATCGCTATTA CCATGGTGAT GCGGTTTTGG CAGTACATCA ATGGGCGTGG ATAGCGGTTT
5101 GACTCACGGG GATTTCCAAG TCTCCACCCC ATTGACGTCA ATGGGAGTTT GTTTTGGCAC
5161 CAAAATCAAC GGGACTTTCC AAAATGTCGT AACAACTCCG CCCCATTGAC GCAAATGGGC
5221 GGTAGGCGTG TACGGTGGGA GGTCTATATA AGCAGAGCTC TCTGGCTAAC TAGAGAACCC
5281 ACTGCTTACT GGCTTATCGA AATTAATACG ACTCACTATA GGGAGACCCA AGCTGGTTTA
5341 AACTTAAGCT TGGTACCGAG CTCACTAGTC CAGTGTGGTG GCAGATATCC AGCACAGTGG
5401 CGGCCGCTCG AGTCTAGAGG GCCCGTTTTG CCTGTACTGG GTCTCTCTGG TTAGACCAGA
5461 TCTGAGCCTG GGAGCTCTCT GGCTAACTAG GAACCCACT GCTTAAGCCT CAATAAAGCT
5521 TGCCTTGAGT GCTTCAAGTA GTGTGTGCCC GTCTGTTGTG TGACTCTGGT AACTAGAGAT
5581 CCCTCAGACC CTTTTAGTCA GTGTGGAAAA TCTCTAGCAG TGGCGCCCGA ACAGGGACTT
```

FIG. 4B

```
5641 GAAAGCGAAA GGGAAACCAG AGGAGCTCTC TCGACGCAGG ACTCGGCTTG CTGAAGCGCG
5701 CACGGCAAGA GGCGAGGGGC GGCGACTGGT GAGTACGCCA AAAATTTTGA CTAGCGGAGG
5761 CTAGAAGGAG AGAGATGGGT GCGAGAGCGT CAGTATTAAG CGGGGGAGAA TTAGATCGCG
5821 ATGGGAAAAA ATTCGGTTAA GGCCAGGGGG AAAGAAAAAA TATAAATTAA AACATATAGT
5881 ATGGGCAAGC AGGGAGCTAG AACGATTCGC AGTTAATCCT GGCCTGTTAG AAACATCAGA
5941 AGGCTGTAGA CAAATACTGG GACAGCTACA ACCATCCCTT CAGACAGGAT CAGAAGAACT
6001 TAGATCATTA TATAATACAG TAGCAACCCT CTATTGTGTG CATTTAATTA ACTGGAATAC
6061 GACAAGATAA CCCGGATCGT GGGCCTGGAT CAGTACCTGG AGAGCGTTAA AAAACACAAA
6121 CGGCTGGATG TGTGCCGCGC TAAAATGGGC TATATGCTGC AGTGAATAAT AAAATGTGTG
6181 TTTGTCCGAA ATACGCGTTT TGAGATTTCT GTCGCCGACT AAATTCATGT CGCGCGATAG
6241 TGGTGTTTAT CGCCGATAGA GATGGCGATA TTGGAAAAAT CGATATTTGA AAATATGGCA
6301 TATTGAAAAT GTCGCCGATG TGAGTTTCTG TGTAACTGAT ATCGCCATTT TTCCAAAAGT
6361 GATTTTTGGG CATACGCGAT ATCTGGCGAT AGCGCTTATA TCGTTTACGG GGGATGGCGA
6421 TAGACGACTT TGGTGACTTG GGCGATTCTG TGTGTCGCAA ATATCGCAGT TTCGATATAG
6481 GTGACAGACG ATATGAGGCT ATATCGCCGA TAGAGGCGAC ATCAAGCTGG CACATGGCCA
6541 ATGCATATCG ATCTATACAT TGAATCAATA TTGGCCATTA GCCATATTAT TCATTGGTTA
6601 TATAGCATAA ATCAATATTG GCTATTGGCC ATTGCATACG TTGTATCCAT ATCATAATAT
6661 GTACATTTAT ATTGGCTCAT GTCCAACATT ACCGCCATGT TGACATTGAT TATTGACTAG
6721 TTATTAATAG TAATCAATTA CGGGGTCATT AGTTCATAGC CCATATATGG AGTTCCGCGT
6781 TACATAACTT ACGGTAAATG GCCCGCCTGG CTGACCGCCC AACGACCCCC GCCCATTGAC
6841 GTCAATAATG ACGTATGTTC CCATAGTAAC GCCAATAGGG ACTTTCCATT GACGTCAATG
6901 GGTGGAGTAT TTACGGTAAA CTGCCCACTT GGCAGTACAT CAAGTGTATC ATATGCCAAG
6961 TACGCCCCCT ATTGACGTCA ATGACGGTAA ATGGCCCGCC TGGCATTATG CCCAGTACAT
7021 GACCTTATGG GACTTTCCTA CTTGGCAGTA CATCTACGTA TTAGTCATCG CTATTACCAT
7081 GGTGATGCGG TTTTGGCAGT ACATCAATGG GCGTGGATAG CGGTTTGACT CACGGGGATT
7141 TCCAAGTCTC CACCCCATTG ACGTCAATGG GAGTTTGTTT TGGCACCAAA ATCAACGGGA
7201 CTTTCCAAAA TGTCGTAACA ACTCCGCCCC ATTGACGCAA ATGGGCGGTA GGCGTGTACG
7261 GTGGGAGGTC TATATAAGCA GAGCTCGTTT AGTGAACCGT CAGATCGCCT GGAGACGCCA
7321 TCCACGCTGT TTTGACCTCC ATAGAAGACA CCGGGACCGA TCCAGCCTCC GCGGCCGGGA
7381 ACGGTGCATT GGAACGCGGA TTCCCCGTGC CAAGAGTGAC GTAAGTACCG CCTATAGAGT
7441 CTATAGGCCC ACCCCCTTGG CTTCTTATGC ATGCTATACT GTTTTTGGCT TGGGGTCTAT
7501 ACACCCCGCC TTCCTCATGT TATAGGTGAT GGTATAGCTT AGCCTATAGG TGTGGGTTAT
7561 TGACCATTAT TGACCACTCC CCTATTGGTG ACGATACTTT CCATTACTAA TCCATAACAT
7621 GGCTCTTTGC CACAACTCTC TTTATTGGCT ATATGCCAAT ACACTGTCCT TCAGAGACTG
7681 ACACGGACTC TGTATTTTTA CAGGATGGGG TCTCATTTAT TATTTACAAA TTCACATATA
7741 CAACACCACC GTCCCCAGTG CCCGCAGTTT TTATTAAACA TAACGTGGGA TCTCCACGCG
7801 AATCTCGGGT ACGTGTTCCG GACATGGGCT CTTCTCCGGT AGCGGCGGAG CTTCTACATC
7861 CGAGCCCTGC TCCCATGCCT CCAGCGACTC ATGGTCGCTC GGCAGCTCCT TGCTCCTAAC
7921 AGTGGAGGCC AGACTTAGGC ACAGCACGAT GCCCACCACC ACCAGTGTGC CGCACAAGGC
7981 CGTGGCGGTA GGGTATGTGT CTGAAAATGA GCTCGGGGAG CGGGCTTGCA CCGCTGACGC
8041 ATTTGGAAGA CTTAAGGCAG CGGCAGAAGA AGATGCAGGC AGCTGAGTTG TTGTGTTCTG
8101 ATAAGAGTCA GAGGTAACTC CCGTTGCGGT GCTGTTAACG GTGGAGGGCA GTGTAGTCTG
8161 AGCAGTACTC GTTGCTGCCG CGCGCGCCAC CAGACATAAT AGCTGACAGA CTAACAGACT
8221 GTTCCTTTCC ATGGGTCTTT TCTGCAGTCA CCGTCCTTGA CACGGCTAGC ATGGAGTCCT
8281 CTGCCAAGAG AAAGATGGAC CCTGATAATC CTGACGAGGG CCCTTCCTCC AAGGTGCCAC
8341 GGCCCGAGAC ACCCGTGACC AAGGCACGA CGTTCCTGCA GACTATGTTG AGGAAGGAGG
8401 TTAACAGTCA GCTGAGTCTG GGAGACCCGC TGTTTCCAGA GTTGGCCGAA GAATCCCTCA
8461 AAACTTTTGA CAAGTGACC GAGGATTGCA ACGAGAACCC CGAGAAAGAT GTCCTGGCAG
8521 AACTCGGTGA CATCCTCGCC CAGGCTGTCA ATCATGCCGG TATCGATTCC AGTAGCACCG
```

FIG. 4C

```
 8581 GCCCCACGCT GACAACCCAC TCTTGCAGCG TTAGCAGCGC CCCTCTTAAC AAGCCGACCC
 8641 CCACCAGCGT CGCGGTTACT AACACTCCTC TCCCCGGGGC ATCCGCTACT CCCGAGCTCA
 8701 GCCCGCGTAA GAAACCGCGC AAAACCACGC GTCCTTTCAA GGTGATTATT AAACCGCCCG
 8761 TGCCTCCCGC GCCTATCATG CTGCCCCTCA TCAAACAGGA AGACATCAAG CCCGAGCCCG
 8821 ACTTTACCAT CCAGTACCGC AACAAGATTA TCGATACCGC CGGCTGTATC GTGATCTCTG
 8881 ATAGCGAGGA AGAACAGGGT GAAGAAGTCG AAACCCGCGG TGCTACCGCG TCTTCCCCTT
 8941 CCACCGGCAG CGGCACGCCG CGAGTGACCT CTCCCACGCA CCCGCTCTCC CAGATGAACC
 9001 ACCCTCCTCT TCCCGATCCC TTGGGCCGGC CCGATGAAGA TAGTTCCTCT TCGTCTTCCT
 9061 CCTCCTGCAG TTCGGCTTCG GACTCGGAGA GTGAGTCCGA GGAGATGAAA TGCAGCAGTG
 9121 GCGGAGGAGC ATCCGTGACC TCGAGCCACC ATGGGCGCGG CGGTTTTGGT GGCGCGGCCT
 9181 CCTCCTCTCT GCTGAGCTGC GGCCATCAGA GCAGCGGCGG GGCGAGCACC GGACCCCGCA
 9241 AGAAGAAGAG CAAACGCATC TCCGAGTTGG ACAACGAGAA GGTGCGCAAT ATCATGAAAG
 9301 ATAAGAACAC CCCCTTCTGC ACACCCAACG TGCAGACTCG GCGGGGTCGC GTCAAGATTG
 9361 ACGAGGTGAG CCGCATGTTC CGCAACACCA ATCGCTCTCT TGAGTACAAG AACCTGCCCT
 9421 TCACGATTCC CAGTATGCAC CAGGTGTTAG ATGAGGCCAT CAAAGCCTGC AAAACCATGC
 9481 AGGTGAACAA CAAGGGCATC CAGATTATCT ACACCCGCAA TCATGAGGTG AAGAGTGAGG
 9541 TGGATGCGGT GCGGTGTCGC CTGGGCACCA TGTGCAACCT GGCCTCTCC ACTCCCTTCC
 9601 TCATGGAGCA CACCATGCCC GTGACACATC CACCCGAAGT GGCGCAGCGC ACAGCCGATG
 9661 CTTGTAACGA AGGCGTCAAG GCCGCGTGGA GCCTCAAAGA ATTGCACACC CACCAATTAT
 9721 GCCCCCGTTC CTCCGATTAC CGCAACATGA TCATCCACGC TGCCACCCCC GTGGACCTGT
 9781 TGGGCGCTCT CAACCTGTGC CTGCCCCTGA TGCAAAAGTT TCCCAAACAG GTCATGGTGC
 9841 GCATCTTCTC CACCAACCAG GGTGGGTTCA TGCTGCCTAT CTACGAGACG GCCGCGAAGG
 9901 CCTACGCCGT GGGGCAGTTT GAGCAGCCCA CCGAGACCCC TCCCGAAGAC CTGGACACCC
 9961 TGAGCCTGGC CATCGAGGCA GCCATCCAGG ACCTGAGGAA CAAGTCTCAG TAAGGTGCTG
10021 GTGCTGGTGC TGGTGCTGGT GCTGTGAGCA AGGGCGAGGA GCTGTTCACC GGGGTGGTGC
10081 CCATCCTGGT CGAGCTGGAC GGCGACGTAA ACGGCCACAA GTTCAGCGTG TCCGGCGAGG
10141 GCGAGGGCGA TGCCACCTAC GGCAAGCTGA CCCTGAAGTT CATCTGCACC ACCGGCAAGC
10201 TGCCCGTGCC CTGGCCCACC CTCGTGACCA CCCTGACCTA CGGCGTGCAG TGCTTCAGCC
10261 GCTACCCCGA CCACATGAAG CAGCACGACT TCTTCAAGTC CGCCATGCCC GAAGGCTACG
10321 TCCAGGAGCG CACCATCTTC TTCAAGGACG ACGGCAACTA CAAGACCCGC GCCGAGGTGA
10381 AGTTCGAGGG CGACACCCTG GTGAACCGCA TCGAGCTGAA GGGCATCGAC TTCAAGGAGG
10441 ACGGCAACAT CCTGGGGCAC AAGCTGGAGT ACAACTACAA CAGCCACAAC GTCTATATCA
10501 TGGCCGACAA GCAGAAGAAC GGCATCAAGG TGAACTTCAA GATCCGCCAC AACATCGAGG
10561 ACGGCAGCGT GCAGCTCGCC GACCACTACC AGCAGAACAC CCCCATCGGC GACGGCCCCG
10621 TGCTGCTGCC CGACAACCAC TACCTGAGCA CCCAGTCCGC CCTGAGCAAA GACCCCAACG
10681 AGAAGCGCGA TCACATGGTC CTGCTGGAGT TCGTGACCGC CGCCGGGATC ACTCTCGGCA
10741 TGGACGAGCT GTACAAGTAA
```

|  | Location |  | Size (bp) |
|---|---|---|---|
|  | (start) | (end) |  |
| 3' LTR | 188 .. | 422 | 235 |
| 5' LTR | 5439 .. | 5619 | 181 |
| MIE Modulator/Unique | 6052 .. | 6562 | 511 |
| MIE promoter/Enhancer | 6563 .. | 7306 | 744 |
| IE2 | 8271 .. | 10,013 | 1743 |
| GFP | 10,044 .. | 10,760 | 717 |

FIG. 4D

```
>LM2ich (11,362 bp)
    1 GGTTTGTCGA GACCTAGAAA AACATGGAGC AATCACAAGT AGCAATACAG CAGCTACCAA
   61 TGCTGATTGT GCCTGGCTAG AAGCACAAGA GGAGGAGGAG GTGGGTTTTC CAGTCACACC
  121 TCAGGTACCT TTAAGACCAA TGACTTACAA GGCAGCTGTA GATCTTAGCC ACTTTTTAAA
  181 AGAAAAGGGG GGACTGGAAG GGCTAATTCA CTCCCAACGA AGACAAGATC TGCTTTTTGC
  241 TTGTACTGGG TCTCTCTGGT TAGACCAGAT CTGAGCCTGG GAGCTCTCTG GCTAACTAGG
  301 GAACCCACTG CTTAAGCCTC AATAAAGCTT GCCTTGAGTG CTTCAAGTAG TGTGTGCCCG
  361 TCTGTTGTGT GACTCTGGTA ACTAGAGATC CCTCAGACCC TTTTAGTCAG TGTGGAAAAT
  421 CTCTAGCAGG GCCCGTTTAA ACCCGCTGAT CAGCCTCGAC TGTGCCTTCT AGTTGCCAGC
  481 CATCTGTTGT TTGCCCCTCC CCCGTGCCTT CCTTGACCCT GGAAGGTGCC ACTCCCACTG
  541 TCCTTTCCTA ATAAAATGAG GAAATTGCAT CGCATTGTCT GAGTAGGTGT CATTCTATTC
  601 TGGGGGGTGG GGTGGGGCAG GACAGCAAGG GGGAGGATTG GGAAGACAAT AGCAGGCATG
  661 CTGGGGATGC GGTGGGCTCT ATGGCTTCTG AGGCGGAAAG AACCAGCTGG GGCTCTAGGG
  721 GGTATCCCCA CGCGCCCTGT AGCGGCGCAT TAAGCGCGGC GGGTGTGGTG GTTACGCGCA
  781 GCGTGACCGC TACACTTGCC AGCGCCCTAG CGCCCGCTCC TTTCGCTTTC TTCCCTTCCT
  841 TTCTCGCCAC GTTCGCCGGC TTTCCCCGTC AAGCTCTAAA TCGGGGCATC CCTTTAGGGT
  901 TCCGATTTAG TGCTTTACGG CACCTCGACC CCAAAAAACT TGATTAGGGT GATGGTTCAC
  961 GTAGTGGGCC ATCGCCCTGA TAGACGGTTT TTCGCCCTTT GACGTTGGAG TCCACGTTCT
 1021 TTAATAGTGG ACTCTTGTTC CAAACTGGAA CAACACTCAA CCCTATCTCG GTCTATTCTT
 1081 TTGATTTATA AGGGATTTTG GGGATTTCGG CCTATTGGTT AAAAAATGAG CTGATTTAAC
 1141 AAAAATTTAA CGCGAATTAA TTCTGTGGAA TGTGTGTCAG TTAGGGTGTG GAAAGTCCCC
 1201 AGGCTCCCCA GGCAGGCAGA AGTATGCAAA GCATGCATCT CAATTAGTCA GCAACCAGGT
 1261 GTGGAAAGTC CCCAGGCTCC CCAGCAGGCA GAAGTATGCA AAGCATGCAT CTCAATTAGT
 1321 CAGCAACCAT AGTCCCGCCC CTAACTCCGC CCATCCCGCC CTAACTCCG CCCAGTTCCG
 1381 CCCATTCTCC GCCCCATGGC TGACTAATTT TTTTTATTTA TGCAGAGGCC GAGGCCGCCT
 1441 CTGCCTCTGA GCTATTCCAG AAGTAGTGAG GAGGCTTTTT TGGAGGCCTA GGCTTTTGCA
 1501 AAAAGCTCCC GGGAGCTTGT ATATCCATTT TCGGATCTGA TCAGCACGTG TTGACAATTA
 1561 ATCATCGGCA TAGTATATCG GCATAGTATA ATACGACAAG GTGAGGAACT AAACCATGGC
 1621 CAAGTTGACC AGTGCCGTTC CGGTGCTCAC CGCGCGCGAC GTCGCCGGAG CGGTCGAGTT
 1681 CTGGACCGAC CGGCTCGGGT TCTCCCGGGA CTTCGTGGAG GACGACTTCG CCGGTGTGGT
 1741 CCGGGACGAC GTGACCCTGT TCATCAGCGC GGTCCAGGAC CAGGTGGTGC CGGACAACAC
 1801 CCTGGCCTGG GTGTGGGTGC GCGGCCTGGA CGAGCTGTAC GCCGAGTGGT CGGAGGTCGT
 1861 GTCCACGAAC TTCCGGGACG CCTCCGGGCC GGCCATGACC GAGATCGGCG AGCAGCCGTG
 1921 GGGGCGGGAG TTCGCCCTGC GCGACCCGGC CGGCAACTGC GTGCACTTCG TGGCCGAGGA
 1981 GCAGGACTGA CACGTGCTAC GAGATTTCGA TTCCACCGCC GCCTTCTATG AAAGGTTGGG
 2041 CTTCGGAATC GTTTTCCGGG ACGCCGGCTG GATGATCCTC CAGCGCGGGG ATCTCATGCT
 2101 GGAGTTCTTC GCCCACCCCA ACTTGTTTAT TGCAGCTTAT AATGGTTACA AATAAAGCAA
 2161 TAGCATCACA AATTTCACAA ATAAAGCATT TTTTTCACTG CATTCTAGTT GTGGTTTGTC
 2221 CAAACTCATC AATGTATCTT ATCATGTCTG TATACCGTCG ACCTCTAGCT AGAGCTTGGC
 2281 GTAATCATGG TCATAGCTGT TTCCTGTGTG AAATTGTTAT CCGCTCACAA TTCCACACAA
 2341 CATACGAGCC GGAAGCATAA AGTGTAAAGC CTGGGGTGCC TAATGAGTGA GCTAACTCAC
 2401 ATTAATTGCG TTGCGCTCAC TGCCCGCTTT CCAGTCGGGA AACCTGTCGT GCCAGCTGCA
 2461 TTAATGAATC GGCCAACGCG CGGGGAGAGG CGGTTTGCGT ATTGGGCGCT CTTCCGCTTC
 2521 CTCGCTCACT GACTCGCTGC GCTCGGTCGT TCGGCTGCGG CGAGCGGTAT CAGCTCACTC
 2581 AAAGGCGGTA ATACGGTTAT CCACAGAATC AGGGGATAAC GCAGGAAAGA ACATGTGAGC
 2641 AAAAGGCCAG CAAAAGGCCA GGAACCGTAA AAAGGCCGCG TTGCTGGCGT TTTTCCATAG
 2701 GCTCCGCCCC CCTGACGAGC ATCACAAAAA TCGACGCTCA AGTCAGAGGT GGCGAAACCC
```

FIG. 6A

```
2761 GACAGGACTA TAAAGATACC AGGCGTTTCC CCCTGGAAGC TCCCTCGTGC GCTCTCCTGT
2821 TCCGACCCTG CCGCTTACCG GATACCTGTC CGCCTTTCTC CCTTCGGGAA GCGTGGCGCT
2881 TTCTCAATGC TCACGCTGTA GGTATCTCAG TTCGTGTAG GTCGTTCGCT CCAAGCTGGG
2941 CTGTGTGCAC GAACCCCCCG TTCAGCCCGA CCGCTGCGCC TTATCCGGTA ACTATCGTCT
3001 TGAGTCCAAC CCGGTAAGAC ACGACTTATC GCCACTGGCA GCAGCCACTG GTAACAGGAT
3061 TAGCAGAGCG AGGTATGTAG GCGGTGCTAC AGAGTTCTTG AAGTGGTGGC CTAACTACGG
3121 CTACACTAGA AGGACAGTAT TTGGTATCTG CGCTCTGCTG AAGCCAGTTA CCTTCGGAAA
3181 AAGAGTTGGT AGCTCTTGAT CCGGCAAACA AACCACCGCT GGTAGCGGTG GTTTTTTTGT
3241 TTGCAAGCAG CAGATTACGC GCAGAAAAAA AGGATCTCAA GAAGATCCTT TGATCTTTTC
3301 TACGGGGTCT GACGCTCAGT GGAACGAAAA CTCACGTTAA GGGATTTTGG TCATGAGATT
3361 ATCAAAAAGG ATCTTCACCT AGATCCTTTT AAATTAAAAA TGAAGTTTTA AATCAATCTA
3421 AAGTATATAT GAGTAAACTT GGTCTGACAG TTACCAATGC TTAATCAGTG AGGCACCTAT
3481 CTCAGCGATC TGTCTATTTC GTTCATCCAT AGTTGCCTGA CTCCCCGTCG TGTAGATAAC
3541 TACGATACGG GAGGGCTTAC CATCTGGCCC CAGTGCTGCA ATGATACCGC GAGACCCACG
3601 CTCACCGGCT CCAGATTTAT CAGCAATAAA CCAGCCAGCC GGAAGGGCCG AGCGCAGAAG
3661 TGGTCCTGCA ACTTTATCCG CCTCCATCCA GTCTATTAAT TGTTGCCGGG AAGCTAGAGT
3721 AAGTAGTTCG CCAGTTAATA GTTTGCGCAA CGTTGTTGCC ATTGCTACAG GCATCGTGGT
3781 GTCACGCTCG TCGTTTGGTA TGGCTTCATT CAGCTCCGGT TCCCAACGAT CAAGGCGAGT
3841 TACATGATCC CCCATGTTGT GCAAAAAAGC GGTTAGCTCC TTCGGTCCTC CGATCGTTGT
3901 CAGAAGTAAG TTGGCCGCAG TGTTATCACT CATGGTTATG GCAGCACTGC ATAATTCTCT
3961 TACTGTCATG CCATCCGTAA GATGCTTTTC TGTGACTGGT GAGTACTCAA CCAAGTCATT
4021 CTGAGAATAG TGTATGCGGC GACCGAGTTG CTCTTGCCCG GCGTCAATAC GGGATAATAC
4081 CGCGCCACAT AGCAGAACTT TAAAAGTGCT CATCATTGGA AAACGTTCTT CGGGGCGAAA
4141 ACTCTCAAGG ATCTTACCGC TGTTGAGATC CAGTTCGATG TAACCCACTC GTGCACCCAA
4201 CTGATCTTCA GCATCTTTTA CTTTCACCAG CGTTTCTGGG TGAGCAAAAA CAGGAAGGCA
4261 AAATGCCGCA AAAAAGGGAA TAAGGGCGAC ACGGAAATGT TGAATACTCA TACTCTTCCT
4321 TTTTCAATAT TATTGAAGCA TTTATCAGGG TTATTGTCTC ATGAGCGGAT ACATATTTGA
4381 ATGTATTTAG AAAAATAAAC AAATAGGGGT TCCGCGCACA TTTCCCCGAA AAGTGCCACC
4441 TGACGTCGAC GGATCGGGAG ATCTCCCGAT CCCCTATGGT GCACTCTCAG TACAATCTGC
4501 TCTGATGCCG CATAGTTAAG CCAGTATCTG CTCCCTGCTT GTGTGTTGGA GGTCGCTGAG
4561 TAGTGCGCGA GCAAAATTTA AGCTACAACA AGGCAAGGCT TGACCGACAA TTGCATGAAG
4621 AATCTGCTTA GGGTTAGGCG TTTTGCGCTG CTTCGCGATG TACGGGCCAG ATATACGCGT
4681 TGACATTGAT TATTGACTAG TTATTAATAG TAATCAATTA CGGGGTCATT AGTTCATAGC
4741 CCATATATGG AGTTCCGCGT TACATAACTT ACGGTAAATG GCCCGCCTGG CTGACCGCCC
4801 AACGACCCCC GCCCATTGAC GTCAATAATG ACGTATGTTC CCATAGTAAC GCCAATAGGG
4861 ACTTTCCATT GACGTCAATG GGTGGACTAT TTACGGTAAA CTGCCCACTT GGCAGTACAT
4921 CAAGTGTATC ATATGCCAAG TACGCCCCCT ATTGACGTCA ATGACGGTAA ATGGCCCGCC
4981 TGGCATTATG CCCAGTACAT GACCTTATGG GACTTTCCTA CTTGGCAGTA CATCTACGTA
5041 TTAGTCATCG CTATTACCAT GGTGATGCGG TTTTGGCAGT ACATCAATGG GCGTGGATAG
5101 CGGTTTGACT CACGGGGATT TCCAAGTCTC CACCCCATTG ACGTCAATGG GAGTTTGTTT
5161 TGGCACCAAA ATCAACGGGA CTTTCCAAAA TGTCGTAACA ACTCCGCCCC ATTGACGCAA
5221 ATGGGCGGTA GGCGTGTACG GTGGGAGGTC TATATAAGCA GAGCTCTCTG GCTAACTAGA
5281 GAACCCACTG CTTACTGGCT TATCGAAATT AATACGACTC ACTATAGGGA GACCCAAGCT
5341 GGTTTAAACT TAAGCTTGGT ACCGAGCTCA CTAGTCCAGT GTGGTGGCAG ATATCCAGCA
5401 CAGTGGCGGC CGCTCGAGTC TAGAGGGCCC GTTTTGCCTG TACTGGGTCT CTCTGGTTAG
5461 ACCAGATCTG AGCCTGGGAG CTCTCTGGCT AACTAGGGAA CCCACTGCTT AAGCCTCAAT
```

FIG. 6B

```
5521 AAAGCTTGCC TTGAGTGCTT CAAGTAGTGT GTGCCCGTCT GTTGTGTGAC TCTGGTAACT
5581 AGAGATCCCT CAGACCCTTT TAGTCAGTGT GGAAAATCTC TAGCAGTGGC GCCCGAACAG
5641 GGACTTGAAA GCGAAAGGGA AACCAGAGGA GCTCTCTCGA CGCAGGACTC GGCTTGCTGA
5701 AGCGCGCACG GCAAGAGGCG AGGGGCGGCG ACTGGTGAGT ACGCCAAAAA TTTTGACTAG
5761 CGGAGGCTAG AAGGAGAGAG ATGGGTGCGA GAGCGTCAGT ATTAAGCGGG GGAGAATTAG
5821 ATCGCGATGG GAAAAAATTC GGTTAAGGCC AGGGGGAAAG AAAAAATATA AATTAAAACA
5881 TATAGTATGG GCAAGCAGGG AGCTAGAACG ATTCGCAGTT AATCCTGGCC TGTTAGAAAC
5941 ATCAGAAGGC TGTAGACAAA TACTGGGACA GCTACAACCA TCCCTTCAGA CAGGATCAGA
6001 AGAACTTAGA TCATTATATA ATACAGTAGC AACCCTCTAT TGTGTGCATT TAATTAACTG
6061 GAATACGACA AGATAACCCG GATCGTGGGC CTGGATCAGT ACCTGGAGAG CGTTAAAAAA
6121 CACAAACGGC TGGATGTGTG CCGCGCTAAA ATGGGCTATA TGCTGCAGTG AATAATAAAA
6181 TGTGTGTTTG TCCGAAATAC GCGTTTTGAG ATTTCTGTCG CCGACTAAAT TCATGTCGCG
6241 CGATAGTGGT GTTTATCGCC GATAGAGATG GCGATATTGG AAAAATCGAT ATTTGAAAAT
6301 ATGGCATATT GAAAATGTCG CCGATGTGAG TTTCTGTGTA ACTGATATCG CCATTTTTCC
6361 AAAAGTGATT TTTGGGCATA CGCGATATCT GGCGATAGCG CTTATATCGT TTACGGGGGA
6421 TGGCGATAGA CGACTTTGGT GACTTGGGCG ATTCTGTGTG TCGCAAATAT CGCAGTTTCG
6481 ATATAGGTGA CAGACGATAT GAGGCTATAT CGCCGATAGA GGCGACATCA AGCTGGCACA
6541 TGGCCAATGC ATATCGATCT ATACATTGAA TCAATATTGG CCATTAGCCA TATTATTCAT
6601 TGGTTATATA GCATAAATCA ATATTGGCTA TTGGCCATTG CATACGTTGT ATCCATATCA
6661 TAATATGTAC ATTTATATTG GCTCATGTCC AACATTACCG CCATGTTGAC ATTGATTATT
6721 GACTAGTTAT TAATAGTAAT CAATTACGGG GTCATTAGTT CATAGCCCAT ATATGGAGTT
6781 CCGCGTTACA TAACTTACGG TAAATGGCCC GCCTGGCTGA CCGCCCAACG ACCCCGCCC
6841 ATTGACGTCA ATAATGACGT ATGTTCCCAT AGTAACGCCA ATAGGGACTT TCCATTGACG
6901 TCAATGGGTG GAGTATTTAC GGTAAACTGC CCACTTGGCA GTACATCAAG TGTATCATAT
6961 GCCAAGTACG CCCCCTATTG ACGTCAATGA CGGTAAATGG CCCGCCTGGC ATTATGCCCA
7021 GTACATGACC TTATGGGACT TTCCTACTTG GCAGTACATC TACGTATTAG TCATCGCTAT
7081 TACCATGGTG ATGCGGTTTT GGCAGTACAT CAATGGGCGT GGATAGCGGT TTGACTCACG
7141 GGGATTTCCA AGTCTCCACC CCATTGACGT CAATGGGAGT TTGTTTTGGC ACCAAAATCA
7201 ACGGGACTTT CCAAAATGTC GTAACAACTC CGCCCCATTG ACGCAAATGG GCGGTAGGCG
7261 TGTACGGTGG GAGGTCTATA TAAGCAGAGC TCGTTTAGTG AACCGTCAGA TCGCCTGGAG
7321 ACGCCATCCA CGCTGTTTTG ACCTCCATAG AAGACACCGG GACCGATCCA GCCTCCGCGG
7381 CCGGGAACGG TGCATTGGAA CGCGGATTCC CCGTGCCAAG AGTGACGTAA GTACCGCCTA
7441 TAGAGTCTAT AGGCCCACCC CCTTGGCTTC TTATGCATGC TATACTGTTT TTGGCTTGGG
7501 GTCTATACAC CCCCGCTTCC TCATGTTATA GGTGATGGTA TAGCTTAGCC TATAGGTGTG
7561 GGTTATTGAC CATTATTGAC CACTCCCCTA TTGGTGACGA TACTTTCCAT TACTAATCCA
7621 TAACATGGCT CTTTGCCACA ACTCTCTTTA TTGGCTATAT GCCAATACAC TGTCCTTCAG
7681 AGACTGACAC GGACTCTGTA TTTTTACAGG ATGGGGTCTC ATTTATTATT TACAAATTCA
7741 CATATACAAC ACCACCGTCC CCAGTGCCCG CAGTTTTTAT TAAACATAAC GTGGGATCTC
7801 CACGCGAATC TCGGGTACGT GTTCCGGACA TGGGCTCTTC TCCGGTAGCG GCGGAGCTTC
7861 TACATCCGAG CCCTGCTCCC ATGCCTCCAG CGACTCATGG TCGCTCGGCA GCTCCTTGCT
7921 CCTAACAGTG GAGGCCAGAC TTAGGCACAG CACGATGCCC ACCACCACCA GTGTGCCGCA
7981 CAAGGCCGTG GCGGTAGGGT ATGTGTCTGA AAATGAGCTC GGGGAGCGGG CTTGCACCGC
8041 TGACGCATTT GGAAGACTTA AGGCAGCGGC AGAAGAAGAT GCAGGCAGCT GAGTTGTTGT
8101 GTTCTGATAA GAGTCAGAGG TAACTCCGTT GCGGTGCTG TTAACGGTGG AGGGCAGTGT
8161 AGTCTGAGCA GTACTCGTTG CTGCCGCGCG CGCCACCAGA CATAATAGCT GACAGACTAA
8221 CAGACTGTTC CTTTCCATGG GTCTTTTCTG CAGTCACCGT CCTTGACACG GCTAGCATGG
8281 AGTCCTCTGC CAAGAGAAAG ATGGACCCTG ATAATCCTGA CGAGGGCCCT TCCTCCAAGG
```

FIG. 6C

```
8341 TGCCACGGCC CGAGACACCC GTGACCAAGG CCACGACGTT CCTGCAGACT ATGTTGAGGA
8401 AGGAGGTTAA CAGTCAGCTG AGTCTGGGAG ACCCGCTGTT TCCAGAGTTG GCCGAAGAAT
8461 CCCTCAAAAC TTTTGAACGA GTGACCGAGG ATTGCAACGA GAACCCCGAG AAAGATGTCC
8521 TGGCAGAACT CGGTGACATC CTCGCCCAGG CTGTCAATCA TGCCGGTATC GATTCCAGTA
8581 GCACCGGCCC CACGCTGACA ACCCACTCTT GCAGCGTTAG CAGCGCCCCT CTTAACAAGC
8641 CGACCCCCAC CAGCGTCGCG GTTACTAACA CTCCTCTCCC CGGGGCATCC GCTACTCCCG
8701 AGCTCAGCCC GCGTAAGAAA CCGCGCAAAA CCACGCGTCC TTTCAAGGTG ATTATTAAAC
8761 CGCCCGTGCC TCCCGCGCCT ATCATGCTGC CCCTCATCAA ACAGGAAGAC ATCAAGCCCG
8821 AGCCCGACTT TACCATCCAG TACCGCAACA AGATTATCGA TACCGCCGGC TGTATCGTGA
8881 TCTCTGATAG CGAGGAAGAA CAGGGTGAAG AAGTCGAAAC CCGCGGTGCT ACCGCGTCTT
8941 CCCCTTCCAC CGGCAGCGGC ACGCCGCGAG TGACCTCTCC CACGCACCCG CTCTCCCAGA
9001 TAAACCACCC TCCTCTTCCC GATCCCTTGG GCCGGCCCGA TGAAGATAGT TCCTCTTCGT
9061 CTTCCTCCTG CAGTTCGGCT TCGGACTCGG AGAGTGAGTC CGAGGAGATG AAATGCAGCA
9121 GTGGCGGAGG AGCATCCGTG ACCTCGAGCC ACCATGGGCG CGGCGGTTTT GGTGGCGCGG
9181 CCTCCTCCTC TCTGCTGAGC TGCGGCCATC AGAGCAGCGG CGGGGCGAGC ACCGGACCCC
9241 GCAAGAAGAA GAGCAAACGC ATCTCCGAGT TGGACAACGA GAAGGTGCGC AATATCATGA
9301 AAGATAAGAA CACCCCCTTC TGCACACCCA ACGTGCAGAC TCGGCGGGGT CGCGTCAAGA
9361 TTGACGAGGT GAGCCGCATG TTCCGCAACA CCAATCGCTC TCTTGAGTAC AAGAACCTGC
9421 CCTTCACGAT TCCCAGTATG CACCAGGTGT TAGATGAGGC CATCAAAGCC TGCAAAACCA
9481 TGCAGGTGAA CAACAAGGGC ATCCAGATTA TCTACACCCG CAATCATGAG GTGAAGAGTG
9541 AGGTGGATGC GGTGCGGTGT CGCCTGGGCA CCATGTGCAA CCTGGCCCTC TCCACTCCCT
9601 TCCTCATGGA GCACACCATG CCCGTGACAC ATCCACCCGA AGTGGCGCAG CGCACAGCCG
9661 ATACTTGTAA CGAAGGCGTC AAGGCCGCGT GGAGCCTCAA AGAATTGCAC ACCCACCAAT
9721 TATGCCCCCG TTCCTCCGAT TACCGCAACA TGATCATCCA CGCTGCCACC CCCGTGGACC
9781 TGTTGGGCGC TCTCAACCTG TGCCTGCCCC TGATGCAAAA GTTTCCCAAA CAGGTCATGG
9841 TGCGCATCTT CTCCACCAAC CAGGGTGGGT TCATGCTGCC TATCTACGAG ACGGCCGCGA
9901 AGGCCTACGC CGTGGGGCAG TTTGAGCAGC CCACCGAGAC CCCTCCCGAA GACCTGGACA
9961 CCCTGAGCCT GGCCATCGAG GCAGCCATCC AGGACCTGAG GAACAAGTCT CAGTAAGGAT
10021 CCGCCCCTCT CCCTCCCCCC CCCTAACGT TACTGGCCGA AGCCGCTTGG AATAAGGCCG
10081 GTGTGCGTTT GTCTATATGT TATTTTCCAC CATATTGCCG TCTTTTGGCA ATGTGAGGGC
10141 CCGGAAACCT GGCCCTGTCT TCTTGACGAG CATTCCTAGG GGTCTTTCCC CTCTCGCCAA
10201 AGGAATGCAA GGTCTGTTGA ATGTCGTGAA GGAAGCAGTT CCTCTGGAAG CTTCTTGAAG
10261 ACAAACAACG TCTGTAGCGA CCCTTTGCAG GCAGCGGAAC CCCCCACCTG GCGACAGGTG
10321 CCTCTGCGGC CAAAAGCCAC GTGTATAAGA TACACCTGCA AAGGCGGCAC AACCCCAGTG
10381 CCACGTTGTG AGTTGGATAG TTGTGGAAAG AGTCAAATGG CTCTCCTCAA GCGTATTCAA
10441 CAAGGGGCTG AAGGATGCCC AGAAGGTACC CCATTGTATG GGATCTGATC TGGGGCCTCG
10501 GTACACATGC TTTACATGTG TTTAGTCGAG GTTAAAAAAA CGTCTAGGCC CCCCGAACCA
10561 CGGGGACGTG GTTTTCCTTT GAAAAACACG ATGATAATAT GGCCACAACC ATGGTGAGCA
10621 AGGGCGAGGA GGATAACATG GCCATCATCA AGGAGTTCAT GCGCTTCAAG GTGCACATGG
10681 AGGGCTCCGT GAACGGCCAC GAGTTCGAGA TCGAGGGCGA GGGCGAGGGC CGCCCCTACG
10741 AGGGCACCCA GACCGCCAAG CTGAAGGTGA CCAAGGGTGG CCCCCTGCCC TTCGCCTGGG
10801 ACATCCTGTC CCCTCAGTTC ATGTACGGCT CCAAGGCCTA CGTGAAGCAC CCCGCCGACA
10861 TCCCCGACTA CTTGAAGCTG TCCTTCCCCG AGGGCTTCAA GTGGGAGCGC GTGATGAACT
10921 TCGAGGACGG CGGCGTGGTG ACCGTGACCC AGGACTCCTC CCTGCAGGAC GGCGAGTTCA
```

FIG. 6D

```
10981 TCTACAAGGT GAAGCTGCGC GGCACCAACT TCCCCTCCGA CGGCCCCGTA ATGCAGAAGA
11041 AGACCATGGG CTGGGAGGCC TCCTCCGAGC GGATGTACCC CGAGGACGGC GCCCTGAAGG
11101 GCGAGATCAA GCAGAGGCTG AAGCTGAAGG ACGGCGGCCA CTACGACGCT GAGGTCAAGA
11161 CCACCTACAA GGCCAAGAAG CCCGTGCAGC TGCCCGGCGC CTACAACGTC AACATCAAGT
11221 TGGACATCAC CTCCCACAAC GAGGACTACA CCATCGTGGA ACAGTACGAA CGCGCCGAGG
11281 GCCGCCACTC CACCGGCGGC ATGGACGAGC TGTACAAGAG CAGCCTGAGG CCTCCTAAGA
11341 AGAAGAGGAA GGTTTGAATG CA
```

|  | Location | | Size (bp) |
|---|---|---|---|
|  | (start) | (end) |  |
| deltaU3-3'LTR | 194 .. | 428 | 235 |
| BGH PolyA | 454 .. | 667 | 214 |
| f1 ori | 730 .. | 1142 | 413 |
| SV40 ori | 1208 .. | 1533 | 326 |
| EM7 | 1549 .. | 1614 | 66 |
| Zeocin | 1616 .. | 1990 | 375 |
| pUC ori | 2633 .. | 3306 | 674 |
| Amp | 3451 .. | 4311 | 861 |
| bla | 4312 .. | 4409 | 98 |
| PCMV | 4656 .. | 5307 | 652 |
| T7 promoter | 5310 .. | 5329 | 20 |
| MCS | 5342 .. | 5444 | 103 |
| 5' LTR | 5445 .. | 5625 | 181 |
| MIE Modular/Unique | 6058 .. | 6568 | 511 |
| UL128 [Split] | 6058 .. | 6171 | 114 |
| MIEP modulator 5' primer | 6058 .. | 6080 | 23 |
| UL127 | 6146 .. | 6583 | 438 |
| UL127 | 6146 .. | 6541 | 396 |
| MIE Promoter/Enhancer | 6569 .. | 7312 | 744 |
| UL126 [Split] | 7127 .. | 7531 | 405 |
| UL125 | 7617 .. | 7925 | 309 |
| UL124 | 7780 .. | 8253 | 474 |
| Exon 2/1 primer | 8250 .. | 8270 | 21 |
| IE2 | 8277 .. | 10,016 | 1740 |
| IRES | 10,023 .. | 10,610 | 588 |
| mCherry | 10,611 .. | 11,318 | 708 |
| SV40NLS | 11,319 .. | 11,357 | 39 |

FIG. 6E

>LM2ig (11,375 bp)
```
   1 GATCCGCCCC TCTCCCTCCC CCCCCCCTAA CGTTACTGGC CGAAGCCGCT TGGAATAAGG
  61 CCGGTGTGCG TTTGTCTATA TGTTATTTTC CACCATATTG CCGTCTTTTG GCAATGTGAG
 121 GGCCCGGAAA CCTGGCCCTG TCTTCTTGAC GAGCATTCCT AGGGGTCTTT CCCCTCTCGC
 181 CAAAGGAATG CAAGGTCTGT TGAATGTCGT GAAGGAAGCA GTTCCTCTGG AAGCTTCTTG
 241 AAGACAAACA ACGTCTGTAG CGACCCTTTG CAGGCAGCGG AACCCCCAC CTGGCGACAG
 301 GTGCCTCTGC GGCCAAAAGC CACGTGTATA AGATACACCT GCAAAGGCGG CACAACCCCA
 361 GTGCCACGTT GTGAGTTGGA TAGTTGTGGA AAGAGTCAAA TGGCTCTCCT CAAGCGTATT
 421 CAACAAGGGG CTGAAGGATG CCCAGAAGGT ACCCCATTGT ATGGGATCTG ATCTGGGGCC
 481 TCGGTGCACA TGCTTTACAT GTGTTTAGTC GAGGTTAAAA AAACGTCTAG GCCCCCCGAA
 541 CCACGGGGAC GTGGTTTTCC TTTGAAAAAC ACGATGATAA TATGGCCACA ACCATGGTGA
 601 GCAAGGGCGA GGAGCTGTTC ACCGGGGTGG TGCCCATCCT GGTCGAGCTG GACGGCGACG
 661 TAAACGGCCA CAAGTTCAGC GTGTCCGGCG AGGGCGAGGG CGATGCCACC TACGGCAAGC
 721 TGACCCTGAA GTTCATCTGC ACCACCGGCA AGCTGCCCGT GCCCTGGCCC ACCCTCGTGA
 781 CCACCCTGAC CTACGGCGTG CAGTGCTTCA GCCGCTACCC CGACCACATG AAGCAGCACG
 841 ACTTCTTCAA GTCCGCCATG CCCGAAGGCT ACGTCCAGGA GCGCACCATC TTCTTCAAGG
 901 ACGACGGCAA CTACAAGACC CGCGCCGAGG TGAAGTTCGA GGGCGACACC CTGGTGAACC
 961 GCATCGAGCT GAAGGGCATC GACTTCAAGG AGGACGGCAA CATCCTGGGG CACAAGCTGG
1021 AGTACAACTA CAACAGCCAC AACGTCTATA TCATGGCCGA CAAGCAGAAG AACGGCATCA
1081 AGGTGAACTT CAAGATCCGC CACAACATCG AGGACGGCAG CGTGCAGCTC GCCGACCACT
1141 ACCAGCAGAA CACCCCCATC GGCGACGGCC CCGTGCTGCT GCCCGACAAC CACTACCTGA
1201 GCACCCAGTC CGCCCTGAGC AAAGACCCCA ACGAGAAGCG CGATCACATG GTCCTGCTGG
1261 AGTTCGTGAC CGCCGCCGGG ATCACTCTCG GCATGGACGA GCTGTACAAG AGCAGCCTGA
1321 GGCCTCCTAA GAAGAAGAGG AAGGTTTGAC CTGCAGGTTT GTCGAGACCT AGAAAAACAT
1381 GGAGCAATCA CAAGTAGCAA TACAGCAGCT ACCAATGCTG ATTGTGCCTG GCTAGAAGCA
1441 CAAGAGGAGG AGGAGGTGGG TTTTCCAGTC ACACCTCAGG TACCTTTAAG ACCAATGACT
1501 TACAAGGCAG CTGTAGATCT TAGCCACTTT TTAAAAGAAA AGGGGGGACT GGAAGGGCTA
1561 ATTCACTCCC AACGAAGACA AGATCTGCTT TTTGCTTGTA CTGGGTCTCT CTGGTTAGAC
1621 CAGATCTGAG CCTGGGAGCT CTCTGGCTAA CTAGGGAACC CACTGCTTAA GCCTCAATAA
1681 AGCTTGCCTT GAGTGCTTCA AGTAGTGTGT GCCCGTCTGT TGTGTGACTC TGGTAACTAG
1741 AGATCCCTCA GACCCTTTTA GTCAGTGTGG AAAATCTCTA GCAGGGCCCG TTTAAACCCG
1801 CTGATCAGCC TCGACTGTGC CTTCTAGTTG CCAGCCATCT GTTGTTTGCC CCTCCCCCGT
1861 GCCTTCCTTG ACCCTGGAAG GTGCCACTCC CACTGTCCTT TCCTAATAAA ATGAGGAAAT
1921 TGCATCGCAT TGTCTGAGTA GGTGTCATTC TATTCTGGGG GGTGGGGTGG GGCAGGACAG
1981 CAAGGGGGAG GATTGGGAAG ACAATAGCAG GCATGCTGGG GATGCGGTGG GCTCTATGGC
2041 TTCTGAGGCG GAAAGAACCA GCTGGGGCTC TAGGGGGTAT CCCCACGCGC CCTGTAGCGG
2101 CGCATTAAGC GCGGCGGGTG TGGTGGTTAC GCGCAGCGTG ACCGCTACAC TTGCCAGCGC
2161 CCTAGCGCCC GCTCCTTTCG CTTTCTTCCC TTCCTTTCTC GCCACGTTCG CCGGCTTTCC
2221 CCGTCAAGCT CTAAATCGGG GCATCCCTTT AGGGTTCCGA TTTAGTGCTT TACGGCACCT
2281 CGACCCCAAA AAACTTGATT AGGGTGATGG TTCACGTAGT GGGCCATCGC CCTGATAGAC
2341 GGTTTTTCGC CCTTTGACGT TGGAGTCCAC GTTCTTTAAT AGTGGACTCT TGTTCCAAAC
2401 TGGAACAACA CTCAACCCTA TCTCGGTCTA TTCTTTTGAT TTATAAGGGA TTTTGGGGAT
2461 TTCGGCCTAT TGGTTAAAAA ATGAGCTGAT TTAACAAAAA TTTAACGCGA ATTAATTCTG
2521 TGGAATGTGT GTCAGTTAGG GTGTGGAAAG TCCCCAGGCT CCCCAGGCAG CAGAAGTAT
2581 GCAAAGCATG CATCTCAATT AGTCAGCAAC CAGGTGTGGA AAGTCCCCAG GCTCCCCAGC
2641 AGGCAGAAGT ATGCAAAGCA TGCATCTCAA TTAGTCAGCA ACCATAGTCC CGCCCCTAAC
2701 TCCGCCCATC CCGCCCCTAA CTCCGCCCAG TTCCGCCCAT TCTCCGCCCC ATGGCTGACT
2761 AATTTTTTTT ATTTATGCAG AGGCCGAGGC CGCCTCTGCC TCTGAGCTAT TCCAGAAGTA
```

FIG. 8A

```
2821 GTGAGGAGGC TTTTTTGGAG GCCTAGGCTT TTGCAAAAAG CTCCCGGGAG CTTGTATATC
2881 CATTTTCGGA TCTGATCAGC ACGTGTTGAC AATTAATCAT CGGCATAGTA TATCGGCATA
2941 GTATAATACG ACAAGGTGAG GAACTAAACC ATGGCCAAGT TGACCAGTGC CGTTCCGGTG
3001 CTCACCGCGC GCGACGTCGC CGGAGCGGTC GAGTTCTGGA CCGACCGGCT CGGGTTCTCC
3061 CGGGACTTCG TGGAGGACGA CTTCGCCGGT GTGGTCCGGG ACGACGTGAC CCTGTTCATC
3121 AGCGCGGTCC AGGACCAGGT GGTGCCGGAC AACACCCTGG CCTGGGTGTG GGTGCGCGGC
3181 CTGGACGAGC TGTACGCCGA GTGGTCGGAG GTCGTGTCCA CGAACTTCCG GGACGCCTCC
3241 GGGCCGGCCA TGACCGAGAT CGGCGAGCAG CCGTGGGGGC GGGAGTTCGC CCTGCGCGAC
3301 CCGGCCGGCA ACTGCGTGCA CTTCGTGGCC GAGGAGCAGG ACTGACACGT GCTACGAGAT
3361 TTCGATTCCA CCGCCGCCTT CTATGAAAGG TTGGGCTTCG GAATCGTTTT CCGGGACGCC
3421 GGCTGGATGA TCCTCCAGCG CGGGGATCTC ATGCTGGAGT TCTTCGCCCA CCCCAACTTG
3481 TTTATTGCAG CTTATAATGG TTACAAATAA AGCAATAGCA TCACAAATTT CACAAATAAA
3541 GCATTTTTTT CACTGCATTC TAGTTGTGGT TTGTCCAAAC TCATCAATGT ATCTTATCAT
3601 GTCTGTATAC CGTCGACCTC TAGCTAGAGC TTGGCGTAAT CATGGTCATA GCTGTTTCCT
3661 GTGTGAAATT GTTATCCGCT CACAATTCCA CACAACATAC GAGCCGGAAG CATAAAGTGT
3721 AAAGCCTGGG GTGCCTAATG AGTGAGCTAA CTCACATTAA TTGCGTTGCG CTCACTGCCC
3781 GCTTTCCAGT CGGGAAACCT GTCGTGCCAG CTGCATTAAT GAATCGGCCA ACGCGCGGGG
3841 AGAGGCGGTT TGCGTATTGG GCGCTCTTCC GCTTCCTCGC TCACTGACTC GCTGCGCTCG
3901 GTCGTTCGGC TGCGGCGAGC GGTATCAGCT CACTCAAAGG CGGTAATACG GTTATCCACA
3961 GAATCAGGGG ATAACGCAGG AAAGAACATG TGAGCAAAAG GCCAGCAAAA GGCCAGGAAC
4021 CGTAAAAAGG CCGCGTTGCT GGCGTTTTTC CATAGGCTCC GCCCCCTGA CGAGCATCAC
4081 AAAAATCGAC GCTCAAGTCA GAGGTGGCGA AACCCGACAG GACTATAAAG ATACCAGGCG
4141 TTTCCCCCTG GAAGCTCCCT CGTGCGCTCT CCTGTTCCGA CCCTGCCGCT TACCGGATAC
4201 CTGTCCGCCT TTCTCCCTTC GGGAAGCGTG GCGCTTTCTC AATGCTCACG CTGTAGGTAT
4261 CTCAGTTCGG TGTAGGTCGT TCGCTCCAAG CTGGGCTGTG TGCACGAACC CCCCGTTCAG
4321 CCCGACCGCT GCGCCTTATC CGGTAACTAT CGTCTTGAGT CCAACCCGGT AAGACACGAC
4381 TTATCGCCAC TGGCAGCAGC CACTGGTAAC AGGATTAGCA GAGCGAGGTA TGTAGGCGGT
4441 GCTACAGAGT TCTTGAAGTG GTGGCCTAAC TACGGCTACA CTAGAAGGAC AGTATTTGGT
4501 ATCTGCGCTC TGCTGAAGCC AGTTACCTTC GGAAAAAGAG TTGGTAGCTC TTGATCCGGC
4561 AAACAAACCA CCGCTGGTAG CGGTGGTTTT TTTGTTTGCA AGCAGCAGAT TACGCGCAGA
4621 AAAAAAGGAT CTCAAGAAGA TCCTTTGATC TTTTCTACGG GGTCTGACGC TCAGTGGAAC
4681 GAAAACTCAC GTTAAGGGAT TTTGGTCATG AGATTATCAA AAAGGATCTT CACCTAGATC
4741 CTTTTAAATT AAAAATGAAG TTTTAAATCA ATCTAAAGTA TATATGAGTA AACTTGGTCT
4801 GACAGTTACC AATGCTTAAT CAGTGAGGCA CCTATCTCAG CGATCTGTCT ATTTCGTTCA
4861 TCCATAGTTG CCTGACTCCC CGTCGTGTAG ATAACTACGA TACGGGAGGG CTTACCATCT
4921 GGCCCCAGTG CTGCAATGAT ACCGCGAGAC CCACGCTCAC CGGCTCCAGA TTTATCAGCA
4981 ATAAACCAGC CAGCCGGAAG GGCCGAGCGC AGAAGTGGTC CTGCAACTTT ATCCGCCTCC
5041 ATCCAGTCTA TTAATTGTTG CCGGGAAGCT AGAGTAAGTA GTTCGCCAGT TAATAGTTTG
5101 CGCAACGTTG TTGCCATTGC TACAGGCATC GTGGTGTCAC GCTCGTCGTT TGGTATGGCT
5161 TCATTCAGCT CCGGTTCCCA ACGATCAAGG CGAGTTACAT GATCCCCCAT GTTGTGCAAA
5221 AAAGCGGTTA GCTCCTTCGG TCCTCCGATC GTTGTCAGAA GTAAGTTGGC CGCAGTGTTA
5281 TCACTCATGG TTATGGCAGC ACTGCATAAT TCTCTTACTG TCATGCCATC CGTAAGATGC
5341 TTTTCTGTGA CTGGTGAGTA CTCAACCAAG TCATTCTGAG AATAGTGTAT GCGGCGACCG
5401 AGTTGCTCTT GCCCGGCGTC AATACGGGAT AATACCGCGC CACATAGCAG AACTTTAAAA
5461 GTGCTCATCA TTGGAAAACG TTCTTCGGGG CGAAAACTCT CAAGGATCTT ACCGCTGTTG
5521 AGATCCAGTT CGATGTAACC CACTCGTGCA CCCAACTGAT CTTCAGCATC TTTTACTTTC
5581 ACCAGCGTTT CTGGGTGAGC AAAAACAGGA AGGCAAAATG CCGCAAAAAA GGGAATAAGG
5641 GCGACACGGA AATGTTGAAT ACTCATACTC TTCCTTTTTC AATATTATTG AAGCATTTAT
```

FIG. 8B

```
5701 CAGGGTTATT GTCTCATGAG CGGATACATA TTTGAATGTA TTTAGAAAAA TAAACAAATA
5761 GGGGTTCCGC GCACATTTCC CCGAAAAGTG CCACCTGACG TCGACGGATC GGGAGATCTC
5821 CCGATCCCCT ATGGTGCACT CTCAGTACAA TCTGCTCTGA TGCCGCATAG TTAAGCCAGT
5881 ATCTGCTCCC TGCTTGTGTG TTGGAGGTCG CTGAGTAGTG CGCGAGCAAA ATTTAAGCTA
5941 CAACAAGGCA AGGCTTGACC GACAATTGCA TGAAGAATCT GCTTAGGGTT AGGCGTTTTG
6001 CGCTGCTTCG CGATGTACGG GCCAGATATA CGCGTTGACA TTGATTATTG ACTAGTTATT
6061 AATAGTAATC AATTACGGGG TCATTAGTTC ATAGCCCATA TATGGAGTTC CGCGTTACAT
6121 AACTTACGGT AAATGCCCG CCTGGCTGAC CGCCCAACGA CCCCCGCCCA TTGACGTCAA
6181 TAATGACGTA TGTTCCCATA GTAACGCCAA TAGGGACTTT CCATTGACGT CAATGGGTGG
6241 ACTATTTACG GTAAACTGCC CACTTGGCAG TACATCAAGT GTATCATATG CCAAGTACGC
6301 CCCCTATTGA CGTCAATGAC GGTAAATGGC CCGCCTGGCA TTATGCCCAG TACATGACCT
6361 TATGGGACTT TCCTACTTGG CAGTACATCT ACGTATTAGT CATCGCTATT ACCATGGTGA
6421 TGCGGTTTTG GCAGTACATC AATGGGCGTG GATAGCGGTT TGACTCACGG GGATTTCCAA
6481 GTCTCCACCC CATTGACGTC AATGGGAGTT TGTTTTGGCA CCAAAATCAA CGGGACTTTC
6541 CAAAATGTCG TAACAACTCC GCCCCATTGA CGCAAATGGG CGGTAGGCGT GTACGGTGGG
6601 AGGTCTATAT AAGCAGAGCT CTCTGGCTAA CTAGAGAACC CACTGCTTAC TGGCTTATCG
6661 AAATTAATAC GACTCACTAT AGGGAGACCC AAGCTGGTTT AAACTTAAGC TTGGTACCGA
6721 GCTCACTAGT CCAGTGTGGT GGCAGATATC CAGCACAGTG GCGGCCGCTC GAGTCTAGAG
6781 GGCCCGTTTT GCCTGTACTG GGTCTCTCTG GTTAGACCAG ATCTGAGCCT GGGAGCTCTC
6841 TGGCTAACTA GGGAACCCAC TGCTTAAGCC TCAATAAAGC TTGCCTTGAG TGCTTCAAGT
6901 AGTGTGTGCC CGTCTGTTGT GTGACTCTGG TAACTAGAGA TCCCTCAGAC CCTTTTAGTC
6961 AGTGTGGAAA ATCTCTAGCA GTGGCGCCCG AACAGGGACT TGAAAGCGAA AGGGAAACCA
7021 GAGGAGCTCT CTCGACGCAG GACTCGGCTT GCTGAAGCGC GCACGGCAAG AGGCGAGGGG
7081 CGGCGACTGG TGAGTACGCC AAAAATTTTG ACTAGCGGAG GCTAGAAGGA GAGAGATGGG
7141 TGCGAGAGCG TCAGTATTAA GCGGGGGAGA ATTAGATCGC GATGGGAAAA AATTCGGTTA
7201 AGGCCAGGGG GAAAGAAAAA ATATAAATTA AAACATATAG TATGGGCAAG CAGGGAGCTA
7261 GAACGATTCG CAGTTAATCC TGGCCTGTTA GAAACATCAG AAGGCTGTAG ACAAATACTG
7321 GGACAGCTAC AACCATCCCT TCAGACAGGA TCAGAAGAAC TTAGATCATT ATATAATACA
7381 GTAGCAACCC TCTATTGTGT GCATTTAATT AACTGGAATA CGACAAGATA ACCCGGATCG
7441 TGGGCCTGGA TCAGTACCTG GAGAGCGTTA AAAAACACAA ACGGCTGGAT GTGTGCCGCG
7501 CTAAAATGGG CTATATGCTG CAGTGAATAA TAAAATGTGT GTTTGTCCGA AATACGCGTT
7561 TTGAGATTTC TGTCGCCGAC TAAATTCATG TCGCGCGATA GTGGTGTTTA TCGCCGATAG
7621 AGATGCGAT ATTGGAAAAA TCGATATTTG AAAATATGGC ATATTGAAAA TGTCGCCGAT
7681 GTGAGTTTCT GTGTAACTGA TATCGCCATT TTTCCAAAAG TGATTTTGG GCATACGCGA
7741 TATCTGGCGA TAGCGCTTAT ATCGTTTACG GGGATGGCG ATAGACGACT TGGTGACTT
7801 GGGCGATTCT GTGTGTCGCA AATATCGCAG TTTCGATATA GGTGACAGAC GATATGAGGC
7861 TATATCGCCG ATAGAGGCGA CATCAAGCTG GCACATGGCC AATGCATATC GATCTATACA
7921 TTGAATCAAT ATTGGCCATT AGCCATATTA TTCATTGGTT ATATAGCATA AATCAATATT
7981 GGCTATTGGC CATTGCATAC GTTGTATCCA TATCATAATA TGTACATTTA TATTGGCTCA
8041 TGTCCAACAT TACCGCCATG TTGACATTGA TTATTGACTA GTTATTAATA GTAATCAATT
8101 ACGGGGTCAT TAGTTCATAG CCCATATATG GAGTTCCGCG TTACATAACT TACGGTAAAT
8161 GGCCCGCCTG GCTGACCGCC CAACGACCCC CGCCCATTGA CGTCAATAAT GACGTATGTT
8221 CCCATAGTAA CGCCAATAGG GACTTTCCAT TGACGTCAAT GGGTGGAGTA TTTACGGTAA
8281 ACTGCCCACT TGGCAGTACA TCAAGTGTAT CATATGCCAA GTACGCCCCC TATTGACGTC
8341 AATGACGGTA AATGGCCCGC CTGGCATTAT GCCCAGTACA TGACCTTATG GACTTTCCT
8401 ACTTGGCAGT ACATCTACGT ATTAGTCATC GCTATTACCA TGGTGATGCG GTTTTGGCAG
8461 TACATCAATG GGCGTGGATA GCGGTTTGAC TCACGGGGAT TTCCAAGTCT CCACCCCATT
```

FIG. 8C

```
 8521 GACGTCAATG GGAGTTTGTT TTGGCACCAA AATCAACGGG ACTTTCCAAA ATGTCGTAAC
 8581 AACTCCGCCC CATTGACGCA AATGGGCGGT AGGCGTGTAC GGTGGGAGGT CTATATAAGC
 8641 AGAGCTCGTT TAGTGAACCG TCAGATCGCC TGGAGACGCC ATCCACGCTG TTTTGACCTC
 8701 CATAGAAGAC ACCGGGACCG ATCCAGCCTC CGCGGCCGGG AACGGTGCAT TGGAACGCGG
 8761 ATTCCCCGTG CCAAGAGTGA CGTAAGTACC GCCTATAGAG TCTATAGGCC CACCCCCTTG
 8821 GCTTCTTATG CATGCTATAC TGTTTTTGGC TTGGGGTCTA TACACCCCCG CTTCCTCATG
 8881 TTATAGGTGA TGGTATAGCT TAGCCTATAG GTGTGGGTTA TTGACCATTA TTGACCACTC
 8941 CCCTATTGGT GACGATACTT TCCATTACTA ATCCATAACA TGGCTCTTTG CCACAACTCT
 9001 CTTTATTGGC TATATGCCAA TACACTGTCC TTCAGAGACT GACACGGACT CTGTATTTTT
 9061 ACAGGATGGG GTCTCATTTA TTATTTACAA ATTCACATAT ACAACACCAC CGTCCCCAGT
 9121 GCCCGCAGTT TTTATTAAAC ATAACGTGGG ATCTCCACGC GAATCTCGGG TACGTGTTCC
 9181 GGACATGGGC TCTTCTCCGG TAGCGGCGGA GCTTCTACAT CCGAGCCCTG CTCCCATGCC
 9241 TCCAGCGACT CATGGTCGCT CGGCAGCTCC TTGCTCCTAA CAGTGGAGGC CAGACTTAGG
 9301 CACAGCACGA TGCCCACCAC CACCAGTGTG CCGCACAAGG CCGTGGCGGT AGGGTATGTG
 9361 TCTGAAAATG AGCTCGGGGA GCGGGCTTGC ACCGCTGACG CATTTGGAAG ACTTAAGGCA
 9421 GCGGCAGAAG AAGATGCAGG CAGCTGAGTT GTTGTGTTCT GATAAGAGTC AGAGGTAACT
 9481 CCCGTTGCGG TGCTGTTAAC GGTGGAGGGC AGTGTAGTCT GAGCAGTACT CGTTGCTGCC
 9541 GCGCGCGCCA CCAGACATAA TAGCTGACAG ACTAACAGAC TGTTCCTTTC CATGGGTCTT
 9601 TTCTGCAGTC ACCGTCCTTG ACACGGCTAG CATGGAGTCC TCTGCCAAGA GAAAGATGGA
 9661 CCCTGATAAT CCTGACGAGG GCCCTTCCTC CAAGGTGCCA CGGCCCGAGA CACCCGTGAC
 9721 CAAGGCCACG ACGTTCCTGC AGACTATGTT GAGGAAGGAG GTTAACAGTC AGCTGAGTCT
 9781 GGGAGACCCG CTGTTTCCAG AGTTGGCCGA AGAATCCCTC AAAACTTTTG AACAAGTGAC
 9841 CGAGGATTGC AACGAGAACC CCGAGAAAGA TGTCCTGGCA GAACTCGGTG ACATCCTCGC
 9901 CCAGGCTGTC AATCATGCCG GTATCGATTC CAGTAGCACC GGCCCCACGC TGACAACCCA
 9961 CTCTTGCAGC GTTAGCAGCG CCCCTCTTAA CAAGCCGACC CCCACCAGCG TCGCGGTTAC
10021 TAACACTCCT CTCCCCGGGG CATCCGCTAC TCCCGAGCTC AGCCCGCGTA AGAAACCGCG
10081 CAAAACCACG CGTCCTTTCA AGGTGATTAT TAAACCGCCC GTGCCTCCCG CGCCTATCAT
10141 GCTGCCCCTC ATCAAACAGG AAGACATCAA GCCCGAGCCC GACTTTACCA TCCAGTACCG
10201 CAACAAGATT ATCGATACCG CCGGCTGTAT CGTGATCTCT GATAGCGAGG AAGAACAGGG
10261 TGAAGAAGTC GAAACCCGCG GTGCTACCGC GTCTTCCCCT TCCACCGGCA GCGGCACGCC
10321 GCGAGTGACC TCTCCCACGC ACCCGCTCTC CCAGATGAAC CACCCTCCTC TTCCCGATCC
10381 CTTGGGCCGG CCCGATGAAG ATAGTTCCTC TTCGTCTTCC TCCTCCTGCA GTTCGGCTTC
10441 GGACTCGGAG AGTGAGTCCG AGGAGATGAA ATGCAGCAGT GGCGGAGGAG CATCCGTGAC
10501 CTCGAGCCAC CATGGGCGCG GCGGTTTTGG TGGCGCGGCC TCCTCCTCTC TGCTGAGCTG
10561 CGGCCATCAG AGCAGCGGCG GGCGAGCAC CGGACCCCGC AAGAAGAAGA GCAAACGCAT
10621 CTCCGAGTTG GACAACGAGA AGGTGCGCAA TATCATGAAA GATAAGAACA CCCCCTTCTG
10681 CACACCCAAC GTGCAGACTC GGCGGGGTCG CGTCAAGATT GACGAGGTGA GCCGCATGTT
10741 CCGCAACACC AATCGCTCTC TTGAGTACAA GAACCTGCCC TTCACGATTC CCAGTATGCA
10801 CCAGGTGTTA GATGAGGCCA TCAAAGCCTG CAAAACCATG CAGGTGAACA ACAAGGGCAT
10861 CCAGATTATC TACACCCGCA ATCATGAGGT GAAGAGTGAG GTGGATGCGG TGCGGTGTCG
10921 CCTGGGCACC ATGTGCAACC TGGCCCTCTC CACTCCCTTC CTCATGGAGC ACACCATGCC
10981 CGTGACACAT CCACCCGAAG TGGCGCAGCG CACAGCCGAT GCTTGTAACG AAGGCGTCAA
11041 GGCCGCGTGG AGCCTCAAAG AATTGCACAC CCACCAATTA TGCCCCGTT CCTCCGATTA
11101 CCGCAACATG ATCATCCACG CTGCCACCCC CGTGGACCTG TTGGGCGCTC TCAACCTGTG
```

FIG. 8D

```
11161 CCTGCCCCTG ATGCAAAAGT TTCCCAAACA GGTCATGGTG CGCATCTTCT CCACCAACCA
11221 GGGTGGGTTC ATGCTGCCTA TCTACGAGAC GGCCGCGAAG GCCTACGCCG TGGGGCAGTT
11281 TGAGCAGCCC ACCGAGACCC CTCCCGAAGA CCTGGACACC CTGAGCCTGG CCATCGAGGC
11341 AGCCATCCAG GACCTGAGGA ACAAGTCTCA GTAAG
```

|  | Location | | Size (bp) |
|---|---|---|---|
|  | (start) | (end) |  |
| IRES | 6 .. | 590 | 585 |
| Kozak consensus | 587 .. | 597 | 11 |
| EGFP | 594 .. | 1310 | 717 |
| SV40 NLS | 1311 .. | 1349 | 39 |
| deltaU3-3'LTR | 1549 .. | 1783 | 235 |
| BGH PolyA | 1809 .. | 2022 | 214 |
| f1 ori | 2085 .. | 2497 | 413 |
| SV40 ori | 2563 .. | 2888 | 326 |
| EM7 | 2904 .. | 2969 | 66 |
| Zeocin | 2971 .. | 3345 | 375 |
| pUC ori | 3988 .. | 4661 | 674 |
| Amp | 4806 .. | 5666 | 861 |
| bla | 5667 .. | 5764 | 98 |
| PCMV | 6011 .. | 6662 | 652 |
| T7 promoter | 6665 .. | 6684 | 20 |
| MCS | 6697 .. | 6799 | 103 |
| 5' LTR | 6800 .. | 6980 | 181 |
| MIE Modular/Unique | 7413 .. | 7923 | 511 |
| UL128 [Split] | 7413 .. | 7526 | 114 |
| MIEP modulator 5' primer | 7413 .. | 7435 | 23 |
| UL127 | 7501 .. | 7938 | 438 |
| UL127 | 7501 .. | 7896 | 396 |
| MIE Promoter/Enhancer | 7924 .. | 8667 | 744 |
| UL126 [Split] | 8482 .. | 8886 | 405 |
| UL125 | 8972 .. | 9280 | 309 |
| UL124 | 9135 .. | 9608 | 474 |
| Exon 2/1 primer | 9605 .. | 9625 | 21 |
| IE2 | 9632 .. | 11,374 | 1743 |

FIG. 8E

>LM2igw (11,939 bp)
```
    1 GATCCGCCCC TCTCCCTCCC CCCCCCCTAA CGTTACTGGC CGAAGCCGCT TGGAATAAGG
   61 CCGGTGTGCG TTTGTCTATA TGTTATTTTC CACCATATTG CCGTCTTTTG GCAATGTGAG
  121 GGCCCGGAAA CCTGGCCCTG TCTTCTTGAC GAGCATTCCT AGGGGTCTTT CCCCTCTCGC
  181 CAAAGGAATG CAAGGTCTGT TGAATGTCGT GAAGGAAGCA GTTCCTCTGG AAGCTTCTTG
  241 AAGACAAACA ACGTCTGTAG CGACCCTTTG CAGGCAGCGG AACCCCCAC CTGGCGACAG
  301 GTGCCTCTGC GGCCAAAAGC CACGTGTATA AGATACACCT GCAAAGGCGG CACAACCCCA
  361 GTGCCACGTT GTGAGTTGGA TAGTTGTGGA AAGAGTCAAA TGGCTCTCCT CAAGCGTATT
  421 CAACAAGGGG CTGAAGGATG CCCAGAAGGT ACCCCATTGT ATGGGATCTG ATCTGGGGCC
  481 TCGGTGCACA TGCTTTACAT GTGTTTAGTC GAGGTTAAAA AAACGTCTAG GCCCCCCGAA
  541 CCACGGGGAC GTGGTTTTCC TTTGAAAAAC ACGATGATAA TATGGCCACA ACCATGGTGA
  601 GCAAGGGCGA GGAGCTGTTC ACCGGGGTGG TGCCCATCCT GGTCGAGCTG GACGGCGACG
  661 TAAACGGCCA CAAGTTCAGC GTGTCCGGCG AGGGCGAGGG CGATGCCACC TACGGCAAGC
  721 TGACCCTGAA GTTCATCTGC ACCACCGGCA AGCTGCCCGT GCCCTGGCCC ACCCTCGTGA
  781 CCACCCTGAC CTACGGCGTG CAGTGCTTCA GCCGCTACCC CGACCACATG AAGCAGCACG
  841 ACTTCTTCAA GTCCGCCATG CCCGAAGGCT ACGTCCAGGA GCGCACCATC TTCTTCAAGG
  901 ACGACGGCAA CTACAAGACC CGCGCCGAGG TGAAGTTCGA GGGCGACACC CTGGTGAACC
  961 GCATCGAGCT GAAGGGCATC GACTTCAAGG AGGACGGCAA CATCCTGGGG CACAAGCTGG
 1021 AGTACAACTA CAACAGCCAC AACGTCTATA TCATGGCCGA CAAGCAGAAG AACGGCATCA
 1081 AGGTGAACTT CAAGATCCGC CACAACATCG AGGACGGCAG CGTGCAGCTC GCCGACCACT
 1141 ACCAGCAGAA CACCCCCATC GGCGACGGCC CCGTGCTGCT GCCCGACAAC CACTACCTGA
 1201 GCACCCAGTC CGCCCTGAGC AAAGACCCCA ACGAGAAGCG CGATCACATG GTCCTGCTGG
 1261 AGTTCGTGAC CGCCGCCGGG ATCACTCTCG GCATGGACGA GCTGTACAAG TAAGCGGCCG
 1321 CAATCAACCT CTGGATTACA AAATTTGTGA AAGATTGACT GGTATTCTTA ACTATGTTGC
 1381 TCCTTTTACG CTATGTGGAT ACGCTGCTTT AATGCCTTTG TATCATGCTA TTACTTCCCG
 1441 TACGGCTTTC ATTTTCTCCT CCTTGTATAA ATCCTGGTTG CTGTCTCTTT ATGAGGAGTT
 1501 GTGGCCCGTT GTCAGGCAAC GTGGCGTGGT GTGCACTGTG TTTGCTGACG CAACCCCCAC
 1561 TGGTTGGGGC ATTGCCACCA CCTATCAACT CCTTTCCGGG ACTTTCGCTT TCCCCCTCCC
 1621 TATTGCCACG GCGGAACTCA TTGCCGCCTG CCTTGCCCGC TGCTGGACAG GGGCTCGGCT
 1681 GTTGGGCACT GACAATTCCG TGGTGTTGTC GGGGAAGCTG ACGTCCTTTC CATGGCTGCT
 1741 CGCCTGTGTT GCCAACTGGA TTCTGCGCGG GACGTCCTTC TGCTACGTCC CTTCGGCCCT
 1801 CAATCCAGCG GACCTTCCTT CCCGCGGCCT GCTGCCGGTT CTGCGGCCTC TTCCGCGTCT
 1861 TCGCCTTCGC CCTCAGACGA GTCGGATCTC CCTTTGGGCC GCCTCCCCGC CTGCCTGCAG
 1921 GTTTGTCGAG ACCTAGAAAA ACATGGAGCA ATCACAAGTA GCAATACAGC AGCTACCAAT
 1981 GCTGATTGTG CCTGGCTAGA AGCACAAGGA GAGGAGGAGG TGGGTTTTCC AGTCACACCT
 2041 CAGGTACCTT TAAGACCAAT GACTTACAAG GCAGCTGTAG ATCTTAGCCA CTTTTTAAAA
 2101 GAAAAGGGGG GACTGGAAGG GCTAATTCAC TCCCAACGAA GACAAGATCT GCTTTTTGCT
 2161 TGTACTGGGT CTCTCTGGTT AGACCAGATC TGAGCCTGGG AGCTCTCTGG CTAACTAGGG
 2221 AACCCACTGC TTAAGCCTCA ATAAAGCTTG CCTTGAGTGC TTCAAGTAGT GTGTGCCCGT
 2281 CTGTTGTGTG ACTCTGGTAA CTAGAGATCC CTCAGACCCT TTTAGTCAGT GTGGAAAATC
 2341 TCTAGCAGGG CCCGTTTAAA CCCGCTGATC AGCCTCGACT GTGCCTTCTA GTTGCCAGCC
 2401 ATCTGTTGTT TGCCCCTCCC CCGTGCCTTC CTTGACCCTG GAAGGTGCCA CTCCCACTGT
 2461 CCTTTCCTAA TAAAATGAGG AAATTGCATC GCATTGTCTG AGTAGGTGTC ATTCTATTCT
 2521 GGGGGGTGGG GTGGGCAGG ACAGCAAGGG GGAGGATTGG GAAGACAATA GCAGGCATGC
 2581 TGGGGATGCG GTGGGCTCTA TGGCTTCTGA GGCGGAAAGA ACCAGCTGGG GCTCTAGGGG
 2641 GTATCCCCAC GCGCCCTGTA GCGGCGCATT AAGCGCGGCG GGTGTGGTGG TTACGCGCAG
 2701 CGTGACCGCT ACACTTGCCA GCGCCCTAGC GCCCGCTCCT TTCGCTTTCT TCCCTTCCTT
 2761 TCTCGCCACG TTCGCCGGCT TTCCCCGTCA AGCTCTAAAT CGGGGCATCC CTTTAGGGTT
```

FIG. 10A

```
2821 CCGATTTAGT GCTTTACGGC ACCTCGACCC CAAAAAACTT GATTAGGGTG ATGGTTCACG
2881 TAGTGGGCCA TCGCCCTGAT AGACGGTTTT TCGCCCTTTG ACGTTGGAGT CCACGTTCTT
2941 TAATAGTGGA CTCTTGTTCC AAACTGGAAC AACACTCAAC CCTATCTCGG TCTATTCTTT
3001 TGATTTATAA GGGATTTTGG GGATTTCGGC CTATTGGTTA AAAAATGAGC TGATTTAACA
3061 AAAATTTAAC GCGAATTAAT TCTGTGGAAT GTGTGTCAGT TAGGGTGTGG AAAGTCCCCA
3121 GGCTCCCCAG GCAGGCAGAA GTATGCAAAG CATGCATCTC AATTAGTCAG CAACCAGGTG
3181 TGGAAAGTCC CCAGGCTCCC CAGCAGGCAG AAGTATGCAA AGCATGCATC TCAATTAGTC
3241 AGCAACCATA GTCCCGCCCC TAACTCCGCC CATCCCGCCC CTAACTCCGC CCAGTTCCGC
3301 CCATTCTCCG CCCCATGGCT GACTAATTTT TTTTATTTAT GCAGAGGCCG AGGCCGCCTC
3361 TGCCTCTGAG CTATTCCAGA AGTAGTGAGG AGGCTTTTTT GGAGGCCTAG GCTTTTGCAA
3421 AAAGCTCCCG GGAGCTTGTA TATCCATTTT CGGATCTGAT CAGCACGTGT TGACAATTAA
3481 TCATCGGCAT AGTATATCGG CATAGTATAA TACGACAAGG TGAGGAACTA AACCATGGCC
3541 AAGTTGACCA GTGCCGTTCC GGTGCTCACC GCGCGCGACG TCGCCGGAGC GGTCGAGTTC
3601 TGGACCGACC GGCTCGGGTT CTCCCGGGAC TTCGTGGAGG ACGACTTCGC CGGTGTGGTC
3661 CGGGACGACG TGACCCTGTT CATCAGCGCG GTCCAGGACC AGGTGGTGCC GGACAACACC
3721 CTGGCCTGGG TGTGGGTGCG CGGCCTGGAC GAGCTGTACG CCGAGTGGTC GGAGGTCGTG
3781 TCCACGAACT TCCGGGACGC CTCCGGGCCG GCCATGACCG AGATCGGCGA GCAGCCGTGG
3841 GGGCGGGAGT TCGCCCTGCG CGACCCGGCC GGCAACTGCG TGCACTTCGT GGCCGAGGAG
3901 CAGGACTGAC ACGTGCTACG AGATTTCGAT TCCACCGCCG CCTTCTATGA AAGGTTGGGC
3961 TTCGGAATCG TTTTCCGGGA CGCCGGCTGG ATGATCCTCC AGCGCGGGGA TCTCATGCTG
4021 GAGTTCTTCG CCCACCCCAA CTTGTTTATT GCAGCTTATA ATGGTTACAA ATAAAGCAAT
4081 AGCATCACAA ATTTCACAAA TAAAGCATTT TTTTCACTGC ATTCTAGTTG TGGTTTGTCC
4141 AAACTCATCA ATGTATCTTA TCATGTCTGT ATACCGTCGA CCTCTAGCTA GAGCTTGGCG
4201 TAATCATGGT CATAGCTGTT TCCTGTGTGA AATTGTTATC CGCTCACAAT TCCACACAAC
4261 ATACGAGCCG GAAGCATAAA GTGTAAAGCC TGGGGTGCCT AATGAGTGAG CTAACTCACA
4321 TTAATTGCGT TGCGCTCACT GCCCGCTTTC CAGTCGGGAA ACCTGTCGTG CCAGCTGCAT
4381 TAATGAATCG GCCAACGCGC GGGGAGAGGC GGTTTGCGTA TTGGGCGCTC TTCCGCTTCC
4441 TCGCTCACTG ACTCGCTGCG CTCGGTCGTT CGGCTGCGGC GAGCGGTATC AGCTCACTCA
4501 AAGGCGGTAA TACGGTTATC CACAGAATCA GGGGATAACG CAGGAAAGAA CATGTGAGCA
4561 AAAGGCCAGC AAAAGGCCAG GAACCGTAAA AAGGCCGCGT TGCTGGCGTT TTTCCATAGG
4621 CTCCGCCCCC CTGACGAGCA TCACAAAAAT CGACGCTCAA GTCAGAGGTG GCGAAACCCG
4681 ACAGGACTAT AAAGATACCA GGCGTTTCCC CCTGGAAGCT CCCTCGTGCG CTCTCCTGTT
4741 CCGACCCTGC CGCTTACCGG ATACCTGTCC GCCTTTCTCC CTTCGGAAG CGTGGCGCTT
4801 TCTCAATGCT CACGCTGTAG GTATCTCAGT TCGGTGTAGG TCGTTCGCTC CAAGCTGGGC
4861 TGTGTGCACG AACCCCCCGT TCAGCCCGAC CGCTGCGCCT TATCCGGTAA CTATCGTCTT
4921 GAGTCCAACC CGGTAAGACA CGACTTATCG CCACTGGCAG CAGCCACTGG TAACAGGATT
4981 AGCAGAGCCA GGTATGTAGG CGGTGCTACA GAGTTCTTGA AGTGGTGGCC TAACTACGGC
5041 TACACTAGAA GGACAGTATT TGGTATCTGC GCTCTGCTGA AGCCAGTTAC CTTCGGAAAA
5101 AGAGTTGGTA GCTCTTGATC CGGCAAACAA ACCACCGCTG GTAGCGGTGG TTTTTTTGTT
5161 TGCAAGCAGC AGATTACGCG CAGAAAAAAA GGATCTCAAG AAGATCCTTT GATCTTTTCT
5221 ACGGGGTCTG ACGCTCAGTG AACGAAAAC TCACGTTAAG GGATTTTGGT CATGAGATTA
5281 TCAAAAGGA TCTTCACCTA GATCCTTTTA AATTAAAAAT GAAGTTTTAA ATCAATCTAA
5341 AGTATATATG AGTAAACTTG GTCTGACAGT TACCAATGCT TAATCAGTGA GGCACCTATC
5401 TCAGCGATCT GTCTATTTCG TTCATCCATA GTTGCCTGAC TCCCCGTCGT GTAGATAACT
5461 ACGATACGGG AGGGCTTACC ATCTGGCCCC AGTGCTGCAA TGATACCGCG AGACCACGC
5521 TCACCGGCTC CAGATTTATC AGCAATAAAC CAGCCAGCCG GAAGGGCCGA GCGCAGAAGT
5581 GGTCCTGCAA CTTTATCCGC CTCCATCCAG TCTATTAATT GTTGCCGGGA AGCTAGAGTA
```

FIG. 10B

```
5641 AGTAGTTCGC CAGTTAATAG TTTGCGCAAC GTTGTTGCCA TTGCTACAGG CATCGTGGTG
5701 TCACGCTCGT CGTTTGGTAT GGCTTCATTC AGCTCCGGTT CCCAACGATC AAGGCGAGTT
5761 ACATGATCCC CCATGTTGTG CAAAAAGCG GTTAGCTCCT TCGGTCCTCC GATCGTTGTC
5821 AGAAGTAAGT TGGCCGCAGT GTTATCACTC ATGGTTATGG CAGCACTGCA TAATTCTCTT
5881 ACTGTCATGC CATCCGTAAG ATGCTTTTCT GTGACTGGTG AGTACTCAAC CAAGTCATTC
5941 TGAGAATAGT GTATGCGGCG ACCGAGTTGC TCTTGCCCGG CGTCAATACG GGATAATACC
6001 GCGCCACATA GCAGAACTTT AAAAGTGCTC ATCATTGGAA AACGTTCTTC GGGGCGAAAA
6061 CTCTCAAGGA TCTTACCGCT GTTGAGATCC AGTTCGATGT AACCCACTCG TGCACCCAAC
6121 TGATCTTCAG CATCTTTTAC TTTCACCAGC GTTTCTGGGT GAGCAAAAAC AGGAAGGCAA
6181 AATGCCGCAA AAAAGGGAAT AAGGGCGACA CGGAAATGTT GAATACTCAT ACTCTTCCTT
6241 TTTCAATATT ATTGAAGCAT TTATCAGGGT TATTGTCTCA TGAGCGGATA CATATTTGAA
6301 TGTATTTAGA AAAATAAACA AATAGGGGTT CCGCGCACAT TTCCCCGAAA AGTGCCACCT
6361 GACGTCGACG GATCGGGAGA TCTCCCGATC CCCTATGGTG CACTCTCAGT ACAATCTGCT
6421 CTGATGCCGC ATAGTTAAGC CAGTATCTGC TCCCTGCTTG TGTGTTGGAG GTCGCTGAGT
6481 AGTGCGCGAG CAAAATTTAA GCTACAACAA GGCAAGGCTT GACCGACAAT TGCATGAAGA
6541 ATCTGCTTAG GGTTAGGCGT TTTGCGCTGC TTCGCGATGT ACGGGCCAGA TATACGCGTT
6601 GACATTGATT ATTGACTAGT TATTAATAGT AATCAATTAC GGGGTCATTA GTTCATAGCC
6661 CATATATGGA GTTCCGCGTT ACATAACTTA CGGTAAATGG CCCGCCTGGC TGACCGCCCA
6721 ACGACCCCCG CCCATTGACG TCAATAATGA CGTATGTTCC CATAGTAACG CCAATAGGGA
6781 CTTTCCATTG ACGTCAATGG GTGGACTATT TACGGTAAAC TGCCCACTTG GCAGTACATC
6841 AAGTGTATCA TATGCCAAGT ACGCCCCCTA TTGACGTCAA TGACGGTAAA TGGCCCGCCT
6901 GGCATTATGC CCAGTACATG ACCTTATGGG ACTTTCCTAC TTGGCAGTAC ATCTACGTAT
6961 TAGTCATCGC TATTACCATG GTGATGCGGT TTTGGCAGTA CATCAATGGG CGTGGATAGC
7021 GGTTTGACTC ACGGGGATTT CCAAGTCTCC ACCCCATTGA CGTCAATGGG AGTTTGTTTT
7081 GGCACCAAAA TCAACGGGAC TTTCCAAAAT GTCGTAACAA CTCCGCCCCA TTGACGCAAA
7141 TGGGCGGTAG GCGTGTACGG TGGGAGGTCT ATATAAGCAG AGCTCTCTGG CTAACTAGAG
7201 AACCCACTGC TTACTGGCTT ATCGAAATTA ATACGACTCA CTATAGGGAG ACCCAAGCTG
7261 GTTTAAACTT AAGCTTGGTA CCGAGCTCAC TAGTCCAGTG TGGTGGCAGA TATCCAGCAC
7321 AGTGGCGGCC GCTCGAGTCT AGAGGGCCCG TTTTGCCTGT ACTGGGTCTC TCTGGTTAGA
7381 CCAGATCTGA GCCTGGGAGC TCTCTGGCTA ACTAGGGAAC CCACTGCTTA AGCCTCAATA
7441 AAGCTTGCCT TGAGTGCTTC AAGTAGTGTG TGCCCGTCTG TTGTGTGACT CTGGTAACTA
7501 GAGATCCCTC AGACCCTTTT AGTCAGTGTG GAAAATCTCT AGCAGTGGCG CCCGAACAGG
7561 GACTTGAAAG CGAAAGGGAA ACCAGAGGAG CTCTCTCGAC GCAGGACTCG GCTTGCTGAA
7621 GCGCGCACGG CAAGAGGCGA GGGGCGGCGA CTGGTGAGTA CGCCAAAAAT TTTGACTAGC
7681 GGAGGCTAGA AGGAGAGAGA TGGGTGCGAG AGCGTCAGTA TTAAGCGGGG GAGAATTAGA
7741 TCGCGATGGG AAAAAATTCG GTTAAGGCCA GGGGAAAGA AAAATATAA ATTAAAACAT
7801 ATAGTATGGG CAAGCAGGGA GCTAGAACGA TTCGCAGTTA ATCCTGGCCT GTTAGAAACA
7861 TCAGAAGGCT GTAGACAAAT ACTGGGACAG CTACAACCAT CCCTTCAGAC AGGATCAGAA
7921 GAACTTAGAT CATTATATAA TACAGTAGCA ACCCTCTATT GTGTGCATTT AATTAACTGG
7981 AATACGACAA GATAACCCGG ATCGTGGGCC TGGATCAGTA CCTGGAGAGC GTTAAAAAAC
8041 ACAAACGGCT GGATGTGTGC CGCGCTAAAA TGGGCTATAT GCTGCAGTGA ATAATAAAT
8101 GTGTGTTTGT CCGAAATACG CGTTTTGAGA TTTCTGTCGC CGACTAAATT CATGTCGCGC
8161 GATAGTGGTG TTTATCGCCG ATAGAGATGG CGATATTGGA AAAATCGATA TTTGAAAATA
8221 TGGCATATTG AAAATGTCGC CGATGTGAGT TTCTGTGTAA CTGATATCGC CATTTTTCCA
8281 AAAGTGATTT TTGGGCATAC GCGATATCTG GCGATAGCGC TTATATCGTT TACGGGGGAT
8341 GGCGATAGAC GACTTTGGTG ACTTGGGCGA TTCTGTGTGT CGCAAATATC GCAGTTTCGA
8401 TATAGGTGAC AGACGATATG AGGCTATATC GCCGATAGAG GCGACATCAA GCTGGCACAT
8461 GGCCAATGCA TATCGATCTA TACATTGAAT CAATATTGGC CATTAGCCAT ATTATTCATT
8521 GGTTATATAG CATAAATCAA TATTGGCTAT TGGCCATTGC ATACGTTGTA TCCATATCAT
8581 AATATGTACA TTTATATTGG CTCATGTCCA ACATTACCGC CATGTTGACA TTGATTATTG
```

FIG. 10C

```
8641 ACTAGTTATT AATAGTAATC AATTACGGGG TCATTAGTTC ATAGCCCATA TATGGAGTTC
8701 CGCGTTACAT AACTTACGGT AAATGGCCCG CCTGGCTGAC CGCCCAACGA CCCCCGCCCA
8761 TTGACGTCAA TAATGACGTA TGTTCCCATA GTAACGCCAA TAGGGACTTT CCATTGACGT
8821 CAATGGGTGG AGTATTTACG GTAAACTGCC CACTTGGCAG TACATCAAGT GTATCATATG
8881 CCAAGTACGC CCCCTATTGA CGTCAATGAC GGTAAATGGC CCGCCTGGCA TTATGCCCAG
8941 TACATGACCT TATGGGACTT TCCTACTTGG CAGTACATCT ACGTATTAGT CATCGCTATT
9001 ACCATGGTGA TGCGGTTTTG GCAGTACATC AATGGGCGTG GATAGCGGTT TGACTCACGG
9061 GGATTTCCAA GTCTCCACCC CATTGACGTC AATGGGAGTT TGTTTTGGCA CCAAAATCAA
9121 CGGGACTTTC CAAAATGTCG TAACAACTCC GCCCCATTGA CGCAAATGGG CGGTAGGCGT
9181 GTACGGTGGG AGGTCTATAT AAGCAGAGCT CGTTTAGTGA ACCGTCAGAT CGCCTGGAGA
9241 CGCCATCCAC GCTGTTTTGA CCTCCATAGA AGACACCGGG ACCGATCCAG CCTCCGCGGC
9301 CGGGAACGGT GCATTGGAAC GCGGATTCCC CGTGCCAAGA GTGACGTAAG TACCGCCTAT
9361 AGAGTCTATA GGCCCACCCC CTTGGCTTCT TATGCATGCT ATACTGTTTT TGGCTTGGGG
9421 TCTATACACC CCCGCTTCCT CATGTTATAG GTGATGGTAT AGCTTAGCCT ATAGGTGTGG
9481 GTTATTGACC ATTATTGACC ACTCCCCTAT TGGTGACGAT ACTTTCCATT ACTAATCCAT
9541 AACATGGCTC TTTGCCACAA CTCTCTTTAT TGGCTATATG CCAATACACT GTCCTTCAGA
9601 GACTGACACG GACTCTGTAT TTTTACAGGA TGGGGTCTCA TTTATTATTT ACAAATTCAC
9661 ATATACAACA CCACCGTCCC CAGTGCCCGC AGTTTTTATT AAACATAACG TGGGATCTCC
9721 ACGCGAATCT CGGGTACGTG TTCCGGACAT GGGCTCTTCT CCGGTAGCGG CGGAGCTTCT
9781 ACATCCGAGC CCTGCTCCCA TGCCTCCAGC GACTCATGGT CGCTCGGCAG CTCCTTGCTC
9841 CTAACAGTGG AGGCCAGACT TAGGCACAGC ACGATGCCCA CCACCACCAG TGTGCCGCAC
9901 AAGGCCGTGG CGGTAGGGTA TGTGTCTGAA AATGAGCTCG GGAGCGGGC TTGCACCGCT
9961 GACGCATTTG GAAGACTTAA GGCAGCGGCA GAAGAAGATG CAGGCAGCTG AGTTGTTGTG
10021 TTCTGATAAG AGTCAGAGGT AACTCCCGTT GCGGTGCTGT TAACGGTGGA GGGCAGTGTA
10081 GTCTGAGCAG TACTCGTTGC TGCCGCGCGC GCCACCAGAC ATAATAGCTG ACAGACTAAC
10141 AGACTGTTCC TTTCCATGGG TCTTTTCTGC AGTCACCGTC CTTGACACGG CTAGCATGGA
10201 GTCCTCTGCC AAGAAGAAGA TGGACCCTGA TAATCCTGAC GAGGGCCCTT CCTCCAAGGT
10261 GCCACGGCCC GAGACACCCG TGACCAAGGC CACGACGTTC CTGCAGACTA TGTTGAGGAA
10321 GGAGGTTAAC AGTCAGCTGA GTCTGGGAGA CCCGCTGTTT CCAGAGTTGG CCGAAGAATC
10381 CCTCAAAACT TTTGAACAAG TGACCGAGGA TTGCAACGAG AACCCCGAGA AGATGTCCT
10441 GGCAGAACTC GGTGACATCC TCGCCCAGGC TGTCAATCAT GCCGGTATCG ATTCCAGTAG
10501 CACCGGCCCC ACGCTGACAA CCCACTCTTG CAGCGTTAGC AGCGCCCCTC TTAACAAGCC
10561 GACCCCCACC AGCGTCGCGG TTACTAACAC TCCTCTCCCC GGGGCATCCG CTACTCCCGA
10621 GCTCAGCCCG CGTAAGAAAC GCGCAAAAC CACGCGTCCT TCAAGGTGA TTATTAAACC
10681 GCCCGTGCCT CCCGCGCCTA TCATGCTGCC CCTCATCAAA CAGGAAGACA TCAAGCCCGA
10741 GCCCGACTTT ACCATCCAGT ACCGCAACAA GATTATCGAT ACCGCCGGCT GTATCGTGAT
10801 CTCTGATAGC GAGGAAGAAC AGGGTGAAGA AGTCGAAACC CGCGGTGCTA CCGCGTCTTC
10861 CCCTTCCACC GGCAGCGGCA CGCCGCGAGT GACCTCTCCC ACGCACCCGC TCTCCCAGAT
10921 GAACCACCCT CCTCTTCCCG ATCCCTTGGG CCGGCCCGAT GAAGATAGTT CCTCTTCGTC
10981 TTCCTCCTCC TGCAGTTCGG CTTCGGACTC GGAGAGTGAG TCCGAGGAGA TGAAATGCAG
11041 CAGTGGCGGA GGAGCATCCG TGACCTCGAG CCACCATGGG CGCGGCGGTT TTGGTGGCGC
11101 GGCCTCCTCC TCTCTGCTGA GCTGCGGCCA TCAGAGCAGC GGCGGGGCGA GCACCGGACC
11161 CCGCAAGAAG AAGAGCAAAC GCATCTCCGA GTTGGACAAC GAGAAGGTGC GCAATATCAT
11221 GAAAGATAAG AACACCCCCT TCTGCACACC CAACGTGCAG ACTCGGCGGG GTCGCGTCAA
11281 GATTGACGAG GTGAGCCGCA TGTTCCGCAA CACCAATCGC TCTCTTGAGT ACAAGAACCT
11341 GCCCTTCACG ATTCCCAGTA TGCACCAGGT GTTAGATGAG GCCATCAAAG CCTGCAAAAC
11401 CATGCAGGTG AACAACAAGG GCATCCAGAT TATCTACACC CGCAATCATG AGGTGAAGAG
11461 TGAGGTGGAT GCGGTGCGGT GTCGCCTGGG CACCATGTGC AACCTGGCCC TCTCCACTCC
11521 CTTCCTCATG GAGCACACCA TGCCCGTGAC ACATCCACCC GAAGTGGCGC AGCGCACAGC
11581 CGATGCTTGT AACGAAGGCG TCAAGGCCGC GTGGAGCCTC AAAGAATTGC ACACCCACCA
```

FIG. 10D

```
11641 ATTATGCCCC CGTTCCTCCG ATTACCGCAA CATGATCATC CACGCTGCCA CCCCCGTGGA
11701 CCTGTTGGGC GCTCTCAACC TGTGCCTGCC CCTGATGCAA AAGTTTCCCA AACAGGTCAT
11761 GGTGCGCATC TTCTCCACCA ACCAGGGTGG GTTCATGCTG CCTATCTACG AGACGGCCGC
11821 GAAGGCCTAC GCCGTGGGGC AGTTTGAGCA GCCCACCGAG ACCCCTCCCG AAGACCTGGA
11881 CACCCTGAGC CTGGCCATCG AGGCAGCCAT CCAGGACCTG AGGAACAAGT CTCAGTAAG
```

|  | Location | | Size (bp) |
|---|---|---|---|
|  | (start) | (end) |  |
| IRES | 6 .. | 590 | 585 |
| Kozak consensus | 587 .. | 597 | 11 |
| EGFP | 594 .. | 1313 | 720 |
| WPRE | 1322 .. | 1913 | 592 |
| deltaU3-3'LTR | 2113 .. | 2347 | 235 |
| BGH PolyA | 2373 .. | 2586 | 214 |
| f1 ori | 2649 .. | 3061 | 413 |
| SV40 ori | 3127 .. | 3452 | 326 |
| EM7 | 3468 .. | 3533 | 66 |
| Zeocin | 3535 .. | 3909 | 375 |
| pUC ori | 4552 .. | 5225 | 674 |
| Amp | 5370 .. | 6230 | 861 |
| bla | 6231 .. | 6328 | 98 |
| PCMV | 6575 .. | 7226 | 652 |
| T7 promoter | 7229 .. | 7248 | 20 |
| MCS | 7261 .. | 7363 | 103 |
| 5' LTR | 7364 .. | 7544 | 181 |
| MIE Modular/Unique | 7977 .. | 8487 | 511 |
| UL128 [Split] | 7977 .. | 8090 | 114 |
| MIEP modulator 5' primer | 7977 .. | 7999 | 23 |
| UL127 | 8065 .. | 8502 | 438 |
| UL127 | 8065 .. | 8460 | 396 |
| MIE Promoter/Enhancer | 8488 .. | 9231 | 744 |
| UL126 [Split] | 9046 .. | 9450 | 405 |
| UL125 | 9536 .. | 9844 | 309 |
| UL124 | 9699 .. | 10,172 | 474 |
| Exon 2/1 primer | 10,169 .. | 10,189 | 21 |
| IE2 | 10,196 .. | 11,938 | 1743 |

FIG. 10E

>LMChIG (10,343 bp)
```
   1 TTAATTAACT GGAATACGAC AAGATAACCC GGATCGTGGG CCTGGATCAG TACCTGGAGA
  61 GCGTTAAAAA ACACAAACGG CTGGATGTGT GCCGCGCTAA AATGGGCTAT ATGCTGCAGT
 121 GAATAATAAA ATGTGTGTTT GTCCGAAATA CGCGTTTTGA GATTTCTGTC GCCGACTAAA
 181 TTCATGTCGC GCGATAGTGG TGTTTATCGC CGATAGAGAT GGCGATATTG GAAAAATCGA
 241 TATTTGAAAA TATGGCATAT TGAAAATGTC GCCGATGTGA GTTTCTGTGT AACTGATATC
 301 GCCATTTTTC CAAAAGTGAT TTTTGGGCAT ACGCGATATC TGGCGATAGC GCTTATATCG
 361 TTTACGGGGG ATGGCGATAG ACGACTTTGG TGACTTGGGC GATTCTGTGT GTCGCAAATA
 421 TCGCAGTTTC GATATAGGTG ACAGACGATA TGAGGCTATA TCGCCGATAG AGGCGACATC
 481 AAGCTGGCAC ATGGCCAATG CATATCGATC TATACATTGA ATCAATATTG GCCATTAGCC
 541 ATATTATTCA TTGGTTATAT AGCATAAATC AATATTGGCT ATTGGCCATT GCATACGTTG
 601 TATCCATATC ATAATATGTA CATTTATATT GGCTCATGTC CAACATTACC GCCATGTTGA
 661 CATTGATTAT TGACTAGTTA TTAATAGTAA TCAATTACGG GGTCATTAGT TCATAGCCCA
 721 TATATGGAGT TCCGCGTTAC ATAACTTACG GTAAATGGCC CGCCTGGCTG ACCGCCCAAC
 781 GACCCCCGCC CATTGACGTC AATAATGACG TATGTTCCCA TAGTAACGCC AATAGGGACT
 841 TTCCATTGAC GTCAATGGGT GGAGTATTTA CGGTAAACTG CCCACTTGGC AGTACATCAA
 901 GTGTATCATA TGCCAAGTAC GCCCCCTATT GACGTCAATG ACGGTAAATG GCCCGCCTGG
 961 CATTATGCCC AGTACATGAC CTTATGGGAC TTTCCTACTT GGCAGTACAT CTACGTATTA
1021 GTCATCGCTA TTACCATGGT GATGCGGTTT TGGCAGTACA TCAATGGGCG TGGATAGCGG
1081 TTTGACTCAC GGGGATTTCC AAGTCTCCAC CCCATTGACG TCAATGGGAG TTTGTTTTGG
1141 CACCAAAATC AACGGGACTT TCCAAAATGT CGTAACAACT CCGCCCCATT GACGCAAATG
1201 GGCGGTAGGC GTGTACGGTG GGAGGTCTAT ATAAGCAGAG CTCGTTTAGT GAACCGTCAG
1261 ATCGCCTGGA GACGCCATCC ACGCTGTTTT GACCTCCATA GAAGACACCG GGACCGATCC
1321 AGCCTCCGCG GCCGGGAACG GTGCATTGGA ACGCGGATTC CCCGTGCCAA GAGTGACGTA
1381 AGTACCGCCT ATAGAGTCTA TAGGCCCACC CCCTTGGCTT CTTATGCATG CTATACTGTT
1441 TTTGGCTTGG GGTCTATACA CCCCCGCTTC CTCATGTTAT AGGTGATGGT ATAGCTTAGC
1501 CTATAGGTGT GGGTTATTGA CCATTATTGA CCACTCCCCT ATTGGTGACG ATACTTTCCA
1561 TTACTAATCC ATAACATGGC TCTTTGCCAC AACTCTCTTT ATTGGCTATA TGCCAATACA
1621 CTGTCCTTCA GAGACTGACA CGGACTCTGT ATTTTTACAG GATGGGGTCT CATTTATTAT
1681 TTACAAATTC ACATATACAA CACCACCGTC CCCAGTGCCC GCAGTTTTTA TTAAACATAA
1741 CGTGGGATCT CCACGCGAAT CTCGGGTACG TGTTCCGGAC ATGGGCTCTT CTCCGGTAGC
1801 GGCGGAGCTT CTACATCCGA GCCCTGCTCC CATGCCTCCA GCGACTCATG GTCGCTCGGC
1861 AGCTCCTTGC TCCTAACAGT GGAGGCCAGA CTTAGGCACA GCACGATGCC CACCACCACC
1921 AGTGTGCCGC ACAAGGCCGT GGCGGTAGGG TATGTGTCTG AAAATGAGCT CGGGGAGCGG
1981 GCTTGCACCG CTGACGCATT TGGAAGACTT AAGGCAGCGG CAGAAGAAGA TGCAGGCAGC
2041 TGAGTTGTTG TGTTCTGATA AGAGTCAGAG GTAACTCCCG TTGCGGTGCT GTTAACGGTG
2101 GAGGGCAGTG TAGTCTGAGC AGTACTCGTT GCTGCCGCGC GCGCCACCAG ACATAATAGC
2161 TGACAGACTA ACAGACTGTT CCTTTCCATG GGTCTTTTCT GCAGTCACCG TCCTTGACAC
2221 GGCTAGCATG GTGAGCAAGG GCGAGGAGGA TAACATGGCC ATCATCAAGG AGTTCATGCG
2281 CTTCAAGGTG CACATGGAGG GCTCCGTGAA CGGCCACGAG TTCGAGATCG AGGGCGAGGG
2341 CGAGGGCCGC CCCTACGAGG GCACCCAGAC CGCCAAGCTG AAGGTGACCA AGGGTGGCCC
2401 CCTGCCCTTC GCCTGGGACA TCCTGTCCCC TCAGTTCATG TACGGCTCCA AGGCCTACGT
2461 GAAGCACCCC GCCGACATCC CCGACTACTT GAAGCTGTCC TTCCCCGAGG GCTTCAAGTG
2521 GGAGCGCGTG ATGAACTTCG AGGACGGCGG CGTGGTGACC GTGACCCAGG ACTCCTCCCT
2581 GCAGGACGGC GAGTTCATCT ACAAGGTGAA GCTGCGCGGC ACCAACTTCC CCTCCGACGG
2641 CCCCGTAATG CAGAAGAAGA CCATGGGCTG GGAGGCCTCC TCCGAGCGGA TGTACCCCGA
2701 GGACGGCGCC CTGAAGGGCG AGATCAAGCA GAGGCTGAAG CTGAAGGACG GCGGCCACTA
2761 CGACGCTGAG GTCAAGACCA CCTACAAGGC CAAGAAGCCC GTGCAGCTGC CGGGCGCCTA
2821 CAACGTCAAC ATCAAGTTGG ACATCACCTC CCACAACGAG GACTACACCA TCGTGGAACA
```

FIG. 12A

```
2881 GTACGAACGC GCCGAGGGCC GCCACTCCAC CGGCGGCATG GACGAGCTGT ACAAGTAAGG
2941 ATCCGCCCCT CTCCCTCCCC CCCCCCTAAC GTTACTGGCC GAAGCCGCTT GGAATAAGGC
3001 CGGTGTGCGT TTGTCTATAT GTTATTTTCC ACCATATTGC CGTCTTTTGG CAATGTGAGG
3061 GCCCGGAAAC CTGGCCCTGT CTTCTTGACG AGCATTCCTA GGGGTCTTTC CCCTCTCGCC
3121 AAAGGAATGC AAGGTCTGTT GAATGTCGTG AAGGAAGCAG TTCCTCTGGA AGCTTCTTGA
3181 AGACAAACAA CGTCTGTAGC GACCCTTTGC AGGCAGCGGA ACCCCCCACC TGGCGACAGG
3241 TGCCTCTGCG GCCAAAAGCC ACGTGTATAA GATACACCTG CAAAGGCGGC ACAACCCCAG
3301 TGCCACGTTG TGAGTTGGAT AGTTGTGGAA AGAGTCAAAT GGCTCTCCTC AAGCGTATTC
3361 AACAAGGGGC TGAAGGATGC CCAGAAGGTA CCCCATTGTA TGGGATCTGA TCTGGGGCCT
3421 CGGTGCACAT GCTTTACATG TGTTTAGTCG AGGTTAAAAA AACGTCTAGG CCCCCCGAAC
3481 CACGGGGACG TGGTTTTCCT TTGAAAAACA CGATGATAAT ATGGCCACAA CCATGGTGAG
3541 CAAGGGCGAG GAGCTGTTCA CCGGGGTGGT GCCCATCCTG GTCGAGCTGG ACGGCGACGT
3601 AAACGGCCAC AAGTTCAGCG TGTCCGGCGA GGGCGAGGGC GATGCCACCT ACGGCAAGCT
3661 GACCCTGAAG TTCATCTGCA CCACCGGCAA GCTGCCCGTG CCCTGGCCCA CCCTCGTGAC
3721 CACCCTGACC TACGGCGTGC AGTGCTTCAG CCGCTACCCC GACCACATGA AGCAGCACGA
3781 CTTCTTCAAG TCCGCCATGC CCGAAGGCTA CGTCCAGGAG CGCACCATCT TCTTCAAGGA
3841 CGACGGCAAC TACAAGACCC GCGCCGAGGT GAAGTTCGAG GGCGACACCC TGGTGAACCG
3901 CATCGAGCTG AAGGGCATCG ACTTCAAGGA GGACGGCAAC ATCCTGGGGC ACAAGCTGGA
3961 GTACAACTAC AACAGCCACA ACGTCTATAT CATGGCCGAC AAGCAGAAGA ACGGCATCAA
4021 GGTGAACTTC AAGATCCGCC ACAACATCGA GGACGGCAGC GTGCAGCTCG CCGACCACTA
4081 CCAGCAGAAC ACCCCCATCG GCGACGGCCC CGTGCTGCTG CCCGACAACC ACTACCTGAG
4141 CACCCAGTCC GCCCTGAGCA AAGACCCCAA CGAGAAGCGC GATCACATGG TCCTGCTGGA
4201 GTTCGTGACC GCCGCCGGGA TCACTCTCGG CATGGACGAG CTGTACAAGA GCAGCCTGAG
4261 GCCTCCTAAG AAGAAGAGGA AGGTTTGACC TGCAGGTTTG TCGAGACCTA GAAAAACATG
4321 GAGCAATCAC AAGTAGCAAT ACAGCAGCTA CCAATGCTGA TTGTGCCTGG CTAGAAGCAC
4381 AAGAGGAGGA GGAGGTGGGT TTTCCAGTCA CACCTCAGGT ACCTTTAAGA CCAATGACTT
4441 ACAAGGCAGC TGTAGATCTT AGCCACTTTT TAAAAGAAAA GGGGGGACTG GAAGGGCTAA
4501 TTCACTCCCA ACGAAGACAA GATCTGCTTT TTGCTTGTAC TGGGTCTCTC TGGTTAGACC
4561 AGATCTGAGC CTGGGAGCTC TCTGGCTAAC TAGGGAACCC ACTGCTTAAG CCTCAATAAA
4621 GCTTGCCTTG AGTGCTTCAA GTAGTGTGTG CCCGTCTGTT GTGTGACTCT GGTAACTAGA
4681 GATCCCTCAG ACCCTTTTAG TCAGTGTGGA AAATCTCTAG CAGGGCCCGT TTAAACCCGC
4741 TGATCAGCCT CGACTGTGCC TTCTAGTTGC CAGCCATCTG TTGTTTGCCC CTCCCCCGTG
4801 CCTTCCTTGA CCCTGGAAGG TGCCACTCCC ACTGTCCTTT CCTAATAAAA TGAGGAAATT
4861 GCATCGCATT GTCTGAGTAG GTGTCATTCT ATTCTGGGGG GTGGGGTGGG GCAGGACAGC
4921 AAGGGGGAGG ATTGGGAAGA CAATAGCAGG CATGCTGGGG ATGCGGTGGG CTCTATGGCT
4981 TCTGAGGCGG AAAGAACCAG CTGGGGCTCT AGGGGGTATC CCCACGCGCC CTGTAGCGGC
5041 GCATTAAGCG CGGCGGGTGT GGTGGTTACG CGCAGCGTGA CCGCTACACT TGCCAGCGCC
5101 CTAGCGCCCG CTCCTTTCGC TTTCTTCCCT TCCTTTCTCG CCACGTTCGC CGGCTTTCCC
5161 CGTCAAGCTC TAAATCGGGG CATCCCTTTA GGGTTCCGAT TTAGTGCTTT ACGGCACCTC
5221 GACCCCAAAA AACTTGATTA GGGTGATGGT TCACGTAGTG GGCCATCGCC CTGATAGACG
5281 GTTTTTCGCC CTTTGACGTT GGAGTCCACG TTCTTTAATA GTGGACTCTT GTTCCAAACT
5341 GGAACAACAC TCAACCCTAT CTCGGTCTAT TCTTTTGATT TATAAGGGAT TTTGGGGATT
5401 TCGGCCTATT GGTTAAAAAA TGAGCTGATT TAACAAAAAT TTAACGCGAA TTAATTCTGT
5461 GGAATGTGTG TCAGTTAGGG TGTGGAAAGT CCCCAGGCTC CCCAGGCAGG CAGAAGTATG
5521 CAAAGCATGC ATCTCAATTA GTCAGCAACC AGGTGTGGAA AGTCCCCAGG CTCCCCAGCA
5581 GGCAGAAGTA TGCAAAGCAT GCATCTCAAT TAGTCAGCAA CCATAGTCCC GCCCCTAACT
5641 CCGCCCATCC CGCCCCTAAC TCCGCCCAGT TCCGCCCATT CTCCGCCCCA TGGCTGACTA
5701 ATTTTTTTTA TTTATGCAGA GGCCGAGGCC GCCTCTGCCT CTGAGCTATT CCAGAAGTAG
5761 TGAGGAGGCT TTTTTGGAGG CCTAGGCTTT TGCAAAAAGC TCCCGGGAGC TTGTATATCC
5821 ATTTTCGGAT CTGATCAGCA CGTGTTGACA ATTAATCATC GGCATAGTAT ATCGGCATAG
```

FIG. 12B

```
5881 TATAATACGA CAAGGTGAGG AACTAAACCA TGGCCAAGTT GACCAGTGCC GTTCCGGTGC
5941 TCACCGCGCG CGACGTCGCC GGAGCGGTCG AGTTCTGGAC CGACCGGCTC GGGTTCTCCC
6001 GGGACTTCGT GGAGGACGAC TTCGCCGGTG TGGTCCGGGA CGACGTGACC CTGTTCATCA
6061 GCGCGGTCCA GGACCAGGTG GTGCCGGACA ACACCCTGGC CTGGGTGTGG GTGCGCGGCC
6121 TGGACGAGCT GTACGCCGAG TGGTCGGAGG TCGTGTCCAC GAACTTCCGG GACGCCTCCG
6181 GGCCGGCCAT GACCGAGATC GGCGAGCAGC CGTGGGGGCG GGAGTTCGCC CTGCGCGACC
6241 CGGCCGGCAA CTGCGTGCAC TTCGTGGCCG AGGAGCAGGA CTGACACGTG CTACGAGATT
6301 TCGATTCCAC CGCCGCCTTC TATGAAAGGT TGGGCTTCGG AATCGTTTTC CGGGACGCCG
6361 GCTGGATGAT CCTCCAGCGC GGGGATCTCA TGCTGGAGTT CTTCGCCCAC CCCAACTTGT
6421 TTATTGCAGC TTATAATGGT TACAAATAAA GCAATAGCAT CACAAATTTC ACAAATAAAG
6481 CATTTTTTTC ACTGCATTCT AGTTGTGGTT TGTCCAAACT CATCAATGTA TCTTATCATG
6541 TCTGTATACC GTCGACCTCT AGCTAGAGCT TGGCGTAATC ATGGTCATAG CTGTTTCCTG
6601 TGTGAAATTG TTATCCGCTC ACAATTCCAC ACAACATACG AGCCGGAAGC ATAAAGTGTA
6661 AAGCCTGGGG TGCCTAATGA GTGAGCTAAC TCACATTAAT TGCGTTGCGC TCACTGCCCG
6721 CTTTCCAGTC GGGAAACCTG TCGTGCCAGC TGCATTAATG AATCGGCCAA CGCGCGGGA
6781 GAGGCGGTTT GCGTATTGGG CGCTCTTCCG CTTCCTCGCT CACTGACTCG CTGCGCTCGG
6841 TCGTTCGGCT GCGGCGAGCG GTATCAGCTC ACTCAAAGGC GGTAATACGG TTATCCACAG
6901 AATCAGGGGA TAACGCAGGA AAGAACATGT GAGCAAAAGG CCAGCAAAAG GCCAGGAACC
6961 GTAAAAAGGC CGCGTTGCTG GCGTTTTTCC ATAGGCTCCG CCCCCCTGAC GAGCATCACA
7021 AAAATCGACG CTCAAGTCAG AGGTGGCGAA ACCCGACAGG ACTATAAAGA TACCAGGCGT
7081 TTCCCCCTGG AAGCTCCCTC GTGCGCTCTC CTGTTCCGAC CCTGCCGCTT ACCGGATACC
7141 TGTCCGCCTT TCTCCCTTCG GGAAGCGTGG CGCTTTCTCA ATGCTCACGC TGTAGGTATC
7201 TCAGTTCGGT GTAGGTCGTT CGCTCCAAGC TGGGCTGTGT GCACGAACCC CCCGTTCAGC
7261 CCGACCGCTG CGCCTTATCC GGTAACTATC GTCTTGAGTC AACCCGGTA AGACACGACT
7321 TATCGCCACT GGCAGCAGCC ACTGGTAACA GGATTAGCAG AGCGAGGTAT GTAGGCGGTG
7381 CTACAGAGTT CTTGAAGTGG TGGCCTAACT ACGGCTACAC TAGAAGGACA GTATTTGGTA
7441 TCTGCGCTCT GCTGAAGCCA GTTACCTTCG GAAAAAGAGT TGGTAGCTCT TGATCCGGCA
7501 AACAAACCAC CGCTGGTAGC GGTGGTTTTT TTGTTTGCAA GCAGCAGATT ACGCGCAGAA
7561 AAAAAGGATC TCAAGAAGAT CCTTTGATCT TTTCTACGGG GTCTGACGCT CAGTGGAACG
7621 AAAACTCACG TTAAGGGATT TTGGTCATGA GATTATCAAA AAGGATCTTC ACCTAGATCC
7681 TTTTAAATTA AAAATGAAGT TTTAAATCAA TCTAAAGTAT ATATGAGTAA ACTTGGTCTG
7741 ACAGTTACCA ATGCTTAATC AGTGAGGCAC CTATCTCAGC GATCTGTCTA TTTCGTTCAT
7801 CCATAGTTGC CTGACTCCCC GTCGTGTAGA TAACTACGAT ACGGGAGGGC TTACCATCTG
7861 GCCCCAGTGC TGCAATGATA CCGCGAGACC CACGCTCACC GGCTCCAGAT TTATCAGCAA
7921 TAAACCAGCC AGCCGGAAGG GCCGAGCGCA GAAGTGGTCC TGCAACTTTA TCCGCCTCCA
7981 TCCAGTCTAT TAATTGTTGC CGGGAAGCTA GAGTAAGTAG TTCGCCAGTT AATAGTTTGC
8041 GCAACGTTGT TGCCATTGCT ACAGGCATCG TGGTGTCACG CTCGTCGTTT GGTATGGCTT
8101 CATTCAGCTC CGGTTCCCAA CGATCAAGGC GAGTTACATG ATCCCCCATG TTGTGCAAAA
8161 AAGCGGTTAG CTCCTTCGGT CCTCCGATCG TTGTCAGAAG TAAGTTGGCC GCAGTGTTAT
8221 CACTCATGGT TATGGCAGCA CTGCATAATT CTCTTACTGT CATGCCATCC GTAAGATGCT
8281 TTTCTGTGAC TGGTGAGTAC TCAACCAAGT CATTCTGAGA ATAGTGTATG CGGCGACCGA
8341 GTTGCTCTTG CCCGGCGTCA ATACGGGATA ATACCGCGCC ACATAGCAGA ACTTTAAAAG
8401 TGCTCATCAT TGGAAAACGT TCTTCGGGGC GAAAACTCTC AAGGATCTTA CCGCTGTTGA
8461 GATCCAGTTC GATGTAACCC ACTCGTGCAC CCAACTGATC TTCAGCATCT TTTACTTTCA
8521 CCAGCGTTTC TGGGTGAGCA AAAACAGGAA GGCAAAATGC CGCAAAAAAG GGAATAAGGG
8581 CGACACGGAA ATGTTGAATA CTCATACTCT TCCTTTTTCA ATATTATTGA AGCATTTATC
8641 AGGGTTATTG TCTCATGAGC GGATACATAT TTGAATGTAT TTAGAAAAAT AAACAAATAG
8701 GGGTTCCGCG CACATTTCCC CGAAAAGTGC CACCTGACGT CGACGGATCG GGAGATCTCC
8761 CGATCCCCTA TGGTGCACTC TCAGTACAAT CTGCTCTGAT GCCGCATAGT TAAGCCAGTA
8821 TCTGCTCCCT GCTTGTGTGT TGGAGGTCGC TGAGTAGTGC GCGAGCAAAA TTTAAGCTAC
```

FIG. 12C

```
8881  AACAAGGCAA GGCTTGACCG ACAATTGCAT GAAGAATCTG CTTAGGGTTA GGCGTTTTGC
8941  GCTGCTTCGC GATGTACGGG CCAGATATAC GCGTTGACAT TGATTATTGA CTAGTTATTA
9001  ATAGTAATCA ATTACGGGGT CATTAGTTCA TAGCCCATAT ATGGAGTTCC GCGTTACATA
9061  ACTTACGGTA AATGGCCCGC CTGGCTGACC GCCCAACGAC CCCCGCCCAT TGACGTCAAT
9121  AATGACGTAT GTTCCCATAG TAACGCCAAT AGGGACTTTC CATTGACGTC AATGGGTGGA
9181  CTATTTACGG TAAACTGCCC ACTTGGCAGT ACATCAAGTG TATCATATGC CAAGTACGCC
9241  CCCTATTGAC GTCAATGACG GTAAATGGCC CGCCTGGCAT TATGCCCAGT ACATGACCTT
9301  ATGGGACTTT CCTACTTGGC AGTACATCTA CGTATTAGTC ATCGCTATTA CCATGGTGAT
9361  GCGGTTTTGG CAGTACATCA ATGGGCGTGG ATAGCGGTTT GACTCACGGG GATTTCCAAG
9421  TCTCCACCCC ATTGACGTCA ATGGGAGTTT GTTTTGGCAC CAAAATCAAC GGGACTTTCC
9481  AAAATGTCGT AACAACTCCG CCCCATTGAC GCAAATGGGC GGTAGGCGTG TACGGTGGGA
9541  GGTCTATATA AGCAGAGCTC TCTGGCTAAC TAGAGAACCC ACTGCTTACT GGCTTATCGA
9601  AATTAATACG ACTCACTATA GGGAGACCCA AGCTGGTTTA AACTTAAGCT TGGTACCGAG
9661  CTCACTAGTC CAGTGTGGTG GCAGATATCC AGCACAGTGG CGGCCGCTCG AGTCTAGAGG
9721  GCCCGTTTTG CCTGTACTGG GTCTCTCTGG TTAGACCAGA TCTGAGCCTG GGAGCTCTCT
9781  GGCTAACTAG GAACCCACT GCTTAAGCCT CAATAAAGCT TGCCTTGAGT GCTTCAAGTA
9841  GTGTGTGCCC GTCTGTTGTG TGACTCTGGT AACTAGAGAT CCCTCAGACC CTTTTAGTCA
9901  GTGTGGAAAA TCTCTAGCAG TGGCGCCCGA ACAGGGACTT GAAAGCGAAA GGGAAACCAG
9961  AGGAGCTCTC TCGACGCAGG ACTCGGCTTG CTGAAGCGCG CACGGCAAGA GGCGAGGGGC
10021 GGCGACTGGT GAGTACGCCA AAAATTTTGA CTAGCGGAGG CTAGAAGGAG AGAGATGGGT
10081 GCGAGAGCGT CAGTATTAAG CGGGGGAGAA TTAGATCGCG ATGGGAAAAA ATTCGGTTAA
10141 GGCCAGGGGG AAAGAAAAAA TATAAATTAA AACATATAGT ATGGGCAAGC AGGGAGCTAG
10201 AACGATTCGC AGTTAATCCT GGCCTGTTAG AAACATCAGA AGGCTGTAGA CAAATACTGG
10261 GACAGCTACA ACCATCCCTT CAGACAGGAT CAGAAGAACT TAGATCATTA TATAATACAG
10321 TAGCAACCCT CTATTGTGTG CAT
```

FIG. 12D

|  | Location | | Size (bp) |
|---|---|---|---|
|  | (start) | (end) |  |
| MIE Modular /Unique | 9 .. | 519 | 511 |
| UL128 [Split] | 9 .. | 122 | 114 |
| MIEP modulator 5' primer | 9 .. | 31 | 23 |
| UL127 | 97 .. | 534 | 438 |
| UL127 | 97 .. | 492 | 396 |
| MIE Promoter /Enhancer | 520 .. | 1263 | 744 |
| UL126 [Split] | 1078 .. | 1482 | 405 |
| UL125 | 1568 .. | 1876 | 309 |
| UL124 | 1731 .. | 2204 | 474 |
| Exon 2/1 primer | 2201 .. | 2221 | 21 |
| mCherry | 2228 .. | 2938 | 711 |
| IRES | 2945 .. | 3529 | 585 |
| Kozak consensus | 3526 .. | 3536 | 11 |
| EGFP | 3533 .. | 4249 | 717 |
| SV40 NLS | 4250 .. | 4288 | 39 |
| deltaU3-3'LTR | 4488 .. | 4722 | 235 |
| BGH PolyA | 4748 .. | 4961 | 214 |
| f1 ori | 5024 .. | 5436 | 413 |
| SV40 ori | 5502 .. | 5827 | 326 |
| EM7 | 5843 .. | 5908 | 66 |
| Zeocin | 5910 .. | 6284 | 375 |
| pUC ori | 6927 .. | 7600 | 674 |
| Amp | 7745 .. | 8605 | 861 |
| bla | 8606 .. | 8703 | 98 |
| PCMV | 8950 .. | 9601 | 652 |
| T7 promoter | 9604 .. | 9623 | 20 |
| MCS | 9636 .. | 9738 | 103 |
| 5' LTR | 9739 .. | 9919 | 181 |

FIG. 12E

>pLMChi2 (11,369 hb)
```
   1 GATCCAGCAG CCTGAGGCCT CCTAAGAAGA AGAGGAAGGT TTGAGAATTC GCCCCTCTCC
  61 CTCCCCCCCC CCTAACGTTA CTGGCCGAAG CCGCTTGGAA TAAGGCCGGT GTGCGTTTGT
 121 CTATATGTTA TTTTCCACCA TATTGCCGTC TTTTGGCAAT GTGAGGGCCC GGAAACCTGG
 181 CCCTGTCTTC TTGACGAGCA TTCCTAGGGG TCTTTCCCCT CTCGCCAAAG GAATGCAAGG
 241 TCTGTTGAAT GTCGTGAAGG AAGCAGTTCC TCTGGAAGCT TCTTGAAGAC AAACAACGTC
 301 TGTAGCGACC CTTTGCAGGC AGCGGAACCC CCCACCTGGC GACAGGTGCC TCTGCGGCCA
 361 AAAGCCACGT GTATAAGATA CACCTGCAAA GGCGGCACAA CCCCAGTGCC ACGTTGTGAG
 421 TTGGATAGTT GTGGAAAGAG TCAAATGGCT CTCCTCAAGC GTATTCAACA AGGGGCTGAA
 481 GGATGCCCAG AAGGTACCCC ATTGTATGGG ATCTGATCTG GGGCCTCGGT ACACATGCTT
 541 TACATGTGTT TAGTCGAGGT TAAAAAAACG TCTAGGCCCC CCGAACCACG GGACGTGGT
 601 TTTCCTTTGA AAAACACGAT GATAATATGG CCACAACCAT GGAGTCCTCT GCCAAGAGAA
 661 AGATGGACCC TGATAATCCT GACGAGGGCC CTTCCTCCAA GGTGCCACGG CCCGAGACAC
 721 CCGTGACCAA GGCCACGACG TTCCTGCAGA CTATGTTGAG GAAGGAGGTT AACAGTCAGC
 781 TGAGTCTGGG AGACCCGCTG TTTCCAGAGT TGGCCGAAGA ATCCCTCAAA ACTTTTGAAC
 841 GAGTGACCGA GGATTGCAAC GAGAACCCCG AGAAAGATGT CCTGGCAGAA CTCGGTGACA
 901 TCCTCGCCCA GGCTGTCAAT CATGCCGGTA TCGATTCCAG TAGCACCGGC CCCACGCTGA
 961 CAACCCACTC TTGCAGCGTT AGCAGCGCCC CTCTTAACAA GCCGACCCCC ACCAGCGTCG
1021 CGGTTACTAA CACTCCTCTC CCCGGGGCAT CCGCTACTCC CGAGCTCAGC CCGCGTAAGA
1081 AACCGCGCAA AACCACGCGT CCTTTCAAGG TGATTATTAA ACCGCCGTG CCTCCCGCGC
1141 CTATCATGCT GCCCCTCATC AAACAGGAAG ACATCAAGCC CGAGCCCGAC TTTACCATCC
1201 AGTACCGCAA CAAGATTATC GATACCGCCG GCTGTATCGT GATCTCTGAT AGCGAGGAAG
1261 AACAGGGTGA AGAAGTCGAA ACCCGCGGTG CTACCGCGTC TTCCCCTTCC ACCGGCAGCG
1321 GCACGCCGCG AGTGACCTCT CCCACGCACC CGCTCTCCCA GATAAACCAC CCTCCTCTTC
1381 CCGATCCCTT GGGCCGGCCC GATGAAGATA GTTCCTCTTC GTCTTCCTCC TGCAGTTCGG
1441 CTTCGGACTC GGAGAGTGAG TCCGAGGAGA TGAAATGCAG CAGTGGCGGA GGAGCATCCG
1501 TGACCTCGAG CCACCATGGG CGCGGCGGTT TTGGTGGCGC GGCCTCCTCC TCTCTGCTGA
1561 GCTGCGGCCA TCAGAGCAGC GGCGGGGCGA GCACCGGACC CCGCAAGAAG AAGAGCAAAC
1621 GCATCTCCGA GTTGGACAAC GAGAAGGTGC GCAATATCAT GAAAGATAAG AACACCCCCT
1681 TCTGCACACC CAACGTGCAG ACTCGGCGGG TCGCGTCAA GATTGACGAG GTGAGCCGCA
1741 TGTTCCGCAA CACCAATCGC TCTCTTGAGT ACAAGAACCT GCCCTTCACG ATTCCCAGTA
1801 TGCACCAGGT GTTAGATGAG GCCATCAAAG CCTGCAAAAC CATGCAGGTG AACAACAAGG
1861 GCATCCAGAT TATCTACACC CGCAATCATG AGGTGAAGAG TGAGGTGGAT GCGGTGCGGT
1921 GTCGCCTGGG CACCATGTGC AACCTGGCCC TCTCCACTCC CTTCCTCATG GAGCACACCA
1981 TGCCCGTGAC ACATCCACCC GAAGTGGCGC AGCGCACAGC CGATACTTGT AACGAAGGCG
2041 TCAAGGCCGC GTGGAGCCTC AAAGAATTGC ACACCCACCA ATTATGCCCC CGTTCCTCCG
2101 ATTACCGCAA CATGATCATC CACGCTGCCA CCCCGTGGA CCTGTTGGGC GCTCTCAACC
2161 TGTGCCTGCC CCTGATGCAA AAGTTTCCCA ACAGGTCAT GGTGCGCATC TTCTCCACCA
2221 ACCAGGGTGG GTTCATGCTG CCTATCTACG AGACGGCCGC GAAGGCCTAC GCCGTGGGGC
2281 AGTTTGAGCA GCCCACCGAG ACCCCTCCCG AAGACCTGGA CACCCTGAGC CTGGCCATCG
2341 AGGCAGCCAT CCAGGACCTG AGGAACAAGT CTCAGTAACC TGCAGGTTTG TCGAGACCTA
2401 GAAAAACATG GAGCAATCAC AAGTAGCAAT ACAGCAGCTA CCAATGCTGA TTGTGCCTGG
2461 CTAGAAGCAC AAGAGGAGGA GGAGGTGGGT TTTCCAGTCA CACCTCAGGT ACCTTTAAGA
2521 CCAATGACTT ACAAGGCAGC TGTAGATCTT AGCCACTTTT TAAAAGAAAA GGGGGGACTG
2581 GAAGGGCTAA TTCACTCCCA ACGAAGACAA GATCTGCTTT TTGCTTGTAC TGGGTCTCTC
2641 TGGTTAGACC AGATCTGAGC CTGGGAGCTC TCTGGCTAAC TAGGGAACCC ACTGCTTAAG
2701 CCTCAATAAA GCTTGCCTTG AGTGCTTCAA GTAGTGTGTG CCCGTCTGTT GTGTGACTCT
2761 GGTAACTAGA GATCCCTCAG ACCCTTTTAG TCAGTGTGGA AAATCTCTAG CAGGGCCCGT
```

FIG. 14A

```
2821 TTAAACCCGC TGATCAGCCT CGACTGTGCC TTCTAGTTGC CAGCCATCTG TTGTTTGCCC
2881 CTCCCCCGTG CCTTCCTTGA CCCTGGAAGG TGCCACTCCC ACTGTCCTTT CCTAATAAAA
2941 TGAGGAAATT GCATCGCATT GTCTGAGTAG GTGTCATTCT ATTCTGGGGG GTGGGGTGGG
3001 GCAGGACAGC AAGGGGGAGG ATTGGGAAGA CAATAGCAGG CATGCTGGGG ATGCGGTGGG
3061 CTCTATGGCT TCTGAGGCGG AAAGAACCAG CTGGGGCTCT AGGGGGTATC CCCACGCGCC
3121 CTGTAGCGGC GCATTAAGCG CGGCGGGTGT GGTGGTTACG CGCAGCGTGA CCGCTACACT
3181 TGCCAGCGCC CTAGCGCCCG CTCCTTTCGC TTTCTTCCCT TCCTTTCTCG CCACGTTCGC
3241 CGGCTTTCCC CGTCAAGCTC TAAATCGGGG CATCCCTTTA GGGTTCCGAT TTAGTGCTTT
3301 ACGGCACCTC GACCCCAAAA AACTTGATTA GGGTGATGGT TCACGTAGTG GGCCATCGCC
3361 CTGATAGACG GTTTTTCGCC CTTTGACGTT GGAGTCCACG TTCTTTAATA GTGGACTCTT
3421 GTTCCAAACT GGAACAACAC TCAACCCTAT CTCGGTCTAT TCTTTTGATT TATAAGGGAT
3481 TTTGGGGATT TCGGCCTATT GGTTAAAAAA TGAGCTGATT TAACAAAAAT TTAACGCGAA
3541 TTAATTCTGT GGAATGTGTG TCAGTTAGGG TGTGGAAAGT CCCCAGGCTC CCCAGGCAGG
3601 CAGAAGTATG CAAAGCATGC ATCTCAATTA GTCAGCAACC AGGTGTGGAA AGTCCCCAGG
3661 CTCCCCAGCA GGCAGAAGTA TGCAAAGCAT GCATCTCAAT TAGTCAGCAA CCATAGTCCC
3721 GCCCCTAACT CCGCCCATCC CGCCCCTAAC TCCGCCCAGT TCCGCCCATT CTCCGCCCCA
3781 TGGCTGACTA ATTTTTTTTA TTTATGCAGA GGCCGAGGCC GCCTCTGCCT CTGAGCTATT
3841 CCAGAAGTAG TGAGGAGGCT TTTTTGGAGG CCTAGGCTTT TGCAAAAAGC TCCCGGGAGC
3901 TTGTATATCC ATTTTCGGAT CTGATCAGCA CGTGTTGACA ATTAATCATC GGCATAGTAT
3961 ATCGGCATAG TATAATACGA CAAGGTGAGG AACTAAACCA TGGCCAAGTT GACCAGTGCC
4021 GTTCCGGTGC TCACCGCGCG CGACGTCGCC GGAGCGGTCG AGTTCTGGAC CGACCGGCTC
4081 GGGTTCTCCC GGGACTTCGT GGAGGACGAC TTCGCCGGTG TGGTCCGGGA CGACGTGACC
4141 CTGTTCATCA GCGCGGTCCA GGACCAGGTG GTGCCGGACA ACACCCTGGC CTGGGTGTGG
4201 GTGCGCGGCC TGGACGAGCT GTACGCCGAG TGGTCGGAGG TCGTGTCCAC GAACTTCCGG
4261 GACGCCTCCG GCCCGGCCAT GACCGAGATC GGCGAGCAGC CGTGGGGGCG GGAGTTCGCC
4321 CTGCGCGACC CGGCCGGCAA CTGCGTGCAC TTCGTGGCCG AGGAGCAGGA CTGACACGTG
4381 CTACGAGATT TCGATTCCAC CGCCGCCTTC TATGAAAGGT TGGGCTTCGG AATCGTTTTC
4441 CGGGACGCCG GCTGGATGAT CCTCCAGCGC GGGGATCTCA TGCTGGAGTT CTTCGCCCAC
4501 CCCAACTTGT TTATTGCAGC TTATAATGGT TACAAATAAA GCAATAGCAT CACAAATTTC
4561 ACAAATAAAG CATTTTTTTC ACTGCATTCT AGTTGTGGTT TGTCCAAACT CATCAATGTA
4621 TCTTATCATG TCTGTATACC GTCGACCTCT AGCTAGAGCT TGGCGTAATC ATGGTCATAG
4681 CTGTTTCCTG TGTGAAATTG TTATCCGCTC ACAATTCCAC ACAACATACG AGCCGGAAGC
4741 ATAAAGTGTA AAGCCTGGGG TGCCTAATGA GTGAGCTAAC TCACATTAAT TGCGTTGCGC
4801 TCACTGCCCG CTTTCCAGTC GGGAAACCTG TCGTGCCAGC TGCATTAATG AATCGGCCAA
4861 CGCGCGGGGA GAGGCGGTTT GCGTATTGGG CGCTCTTCCG CTTCCTCGCT CACTGACTCG
4921 CTGCGCTCGG TCGTTCGGCT GCGGCGAGCG GTATCAGCTC ACTCAAAGGC GGTAATACGG
4981 TTATCCACAG AATCAGGGGA TAACGCAGGA AGAACATGT GAGCAAAAGG CCAGCAAAAG
5041 GCCAGGAACC GTAAAAAGGC CGCGTTGCTG GCGTTTTTCC ATAGGCTCCG CCCCCCTGAC
5101 GAGCATCACA AAAATCGACG CTCAAGTCAG AGGTGGCGAA ACCCGACAGG ACTATAAAGA
5161 TACCAGGCGT TTCCCCCTGG AAGCTCCCTC GTGCGCTCTC CTGTTCCGAC CCTGCCGCTT
5221 ACCGGATACC TGTCCGCCTT TCTCCCTTCG GAAGCGTGG CGCTTTCTCA ATGCTCACGC
5281 TGTAGGTATC TCAGTTCGGT GTAGGTCGTT CGCTCCAAGC TGGGCTGTGT GCACGAACCC
5341 CCCGTTCAGC CCGACCGCTG CGCCTTATCC GGTAACTATC GTCTTGAGTC CAACCCGGTA
5401 AGACACGACT TATCGCCACT GGCAGCAGCC ACTGGTAACA GGATTAGCAG AGCGAGGTAT
5461 GTAGGCGGTG CTACAGAGTT CTTGAAGTGG TGGCCTAACT ACGGCTACAC TAGAAGGACA
5521 GTATTTGGTA TCTGCGCTCT GCTGAAGCCA GTTACCTTCG GAAAAGAGT TGGTAGCTCT
5581 TGATCCGGCA ACAAACCAC CGCTGGTAGC GGTGGTTTTT TGTTTGCAA GCAGCAGATT
5641 ACGCGCAGAA AAAAAGGATC TCAAGAAGAT CCTTTGATCT TTTCTACGGG GTCTGACGCT
5701 CAGTGGAACG AAAACTCACG TTAAGGGATT TTGGTCATGA GATTATCAAA AAGGATCTTC
```

FIG. 14B

5761 ACCTAGATCC TTTTAAATTA AAAATGAAGT TTTAAATCAA TCTAAAGTAT ATATGAGTAA
5821 ACTTGGTCTG ACAGTTACCA ATGCTTAATC AGTGAGGCAC CTATCTCAGC GATCTGTCTA
5881 TTTCGTTCAT CCATAGTTGC CTGACTCCCC GTCGTGTAGA TAACTACGAT ACGGGAGGGC
5941 TTACCATCTG GCCCCAGTGC TGCAATGATA CCGCGAGACC CACGCTCACC GGCTCCAGAT
6001 TTATCAGCAA TAAACCAGCC AGCCGGAAGG GCCGAGCGCA GAAGTGGTCC TGCAACTTTA
6061 TCCGCCTCCA TCCAGTCTAT TAATTGTTGC CGGGAAGCTA GAGTAAGTAG TTCGCCAGTT
6121 AATAGTTTGC GCAACGTTGT TGCCATTGCT ACAGGCATCG TGGTGTCACG CTCGTCGTTT
6181 GGTATGGCTT CATTCAGCTC CGGTTCCCAA CGATCAAGGC GAGTTACATG ATCCCCCATG
6241 TTGTGCAAAA AAGCGGTTAG CTCCTTCGGT CCTCCGATCG TTGTCAGAAG TAAGTTGGCC
6301 GCAGTGTTAT CACTCATGGT TATGGCAGCA CTGCATAATT CTCTTACTGT CATGCCATCC
6361 GTAAGATGCT TTTCTGTGAC TGGTGAGTAC TCAACCAAGT CATTCTGAGA ATAGTGTATG
6421 CGGCGACCGA GTTGCTCTTG CCCGGCGTCA ATACGGGATA ATACCGCGCC ACATAGCAGA
6481 ACTTTAAAAG TGCTCATCAT TGGAAAACGT TCTTCGGGGC GAAAACTCTC AAGGATCTTA
6541 CCGCTGTTGA GATCCAGTTC GATGTAACCC ACTCGTGCAC CCAACTGATC TTCAGCATCT
6601 TTTACTTTCA CCAGCGTTTC TGGGTGAGCA AAAACAGGAA GGCAAAATGC CGCAAAAAAG
6661 GGAATAAGGG CGACACGGAA ATGTTGAATA CTCATACTCT TCCTTTTTCA ATATTATTGA
6721 AGCATTTATC AGGGTTATTG TCTCATGAGC GGATACATAT TTGAATGTAT TTAGAAAAAT
6781 AAACAAATAG GGGTTCCGCG CACATTTCCC CGAAAAGTGC CACCTGACGT CGACGGATCG
6841 GGAGATCTCC CGATCCCCTA TGGTGCACTC TCAGTACAAT CTGCTCTGAT GCCGCATAGT
6901 TAAGCCAGTA TCTGCTCCCT GCTTGTGTGT TGGAGGTCGC TGAGTAGTGC GCGAGCAAAA
6961 TTTAAGCTAC AACAAGGCAA GGCTTGACCG ACAATTGCAT GAAGAATCTG CTTAGGGTTA
7021 GGCGTTTTGC GCTGCTTCGC GATGTACGGG CCAGATATAC GCGTTGACAT TGATTATTGA
7081 CTAGTTATTA ATAGTAATCA ATTACGGGGT CATTAGTTCA TAGCCCATAT ATGGAGTTCC
7141 GCGTTACATA ACTTACGGTA ATGGCCCGC CTGGCTGACC GCCCAACGAC CCCCGCCCAT
7201 TGACGTCAAT AATGACGTAT GTTCCCATAG TAACGCCAAT AGGGACTTTC CATTGACGTC
7261 AATGGGTGGA CTATTTACGG TAAACTGCCC ACTTGGCAGT ACATCAAGTG TATCATATGC
7321 CAAGTACGCC CCCTATTGAC GTCAATGACG GTAAATGGCC CGCCTGGCAT TATGCCCAGT
7381 ACATGACCTT ATGGGACTTT CCTACTTGGC AGTACATCTA CGTATTAGTC ATCGCTATTA
7441 CCATGGTGAT GCGGTTTTGG CAGTACATCA ATGGGCGTGG ATAGCGGTTT GACTCACGGG
7501 GATTTCCAAG TCTCCACCCC ATTGACGTCA ATGGGAGTTT GTTTTGGCAC CAAAATCAAC
7561 GGGACTTTCC AAAATGTCGT AACAACTCCG CCCCATTGAC GCAAATGGGC GGTAGGCGTG
7621 TACGGTGGGA GGTCTATATA AGCAGAGCTC TCTGGCTAAC TAGAGAACCC ACTGCTTACT
7681 GGCTTATCGA AATTAATACG ACTCACTATA GGGAGACCCA AGCTGGTTTA AACTTAAGCT
7741 TGGTACCGAG CTCACTAGTC CAGTGTGGTG GCAGATATCC AGCACAGTGG CGGCCGCTCG
7801 AGTCTAGAGG GCCCGTTTTG CCTGTACTGG GTCTCTCTGG TTAGACCAGA TCTGAGCCTG
7861 GGAGCTCTCT GGCTAACTAG GGAACCCACT GCTTAAGCCT CAATAAAGCT TGCCTTGAGT
7921 GCTTCAAGTA GTGTGTGCCC GTCTGTTGTG TGACTCTGGT AACTAGAGAT CCCTCAGACC
7981 CTTTTAGTCA GTGTGGAAAA TCTCTAGCAG TGGCGCCCGA ACAGGGACTT GAAAGCGAAA
8041 GGGAAACCAG AGGAGCTCTC TCGACGCAGG ACTCGGCTTG CTGAAGCGCG CACGGCAAGA
8101 GGCGAGGGGC GGCGACTGGT GAGTACGCCA AAATTTTGA CTAGCGGAGG CTAGAAGGAG
8161 AGAGATGGGT GCGAGAGCGT CAGTATTAAG CGGGGGAGAA TTAGATCGCG ATGGGAAAAA
8221 ATTCGGTTAA GGCCAGGGGG AAAGAAAAAA TATAAATTAA AACATATAGT ATGGGCAAGC
8281 AGGGAGCTAG AACGATTCGC AGTTAATCCT GGCCTGTTAG AAACATCAGA AGGCTGTAGA
8341 CAAATACTGG GACAGCTACA ACCATCCCTT CAGACAGGAT CAGAAGAACT TAGATCATTA
8401 TATAATACAG TAGCAACCCT CTATTGTGTG CATTTAATTA ACTGGAATAC GACAAGATAA
8461 CCCGGATCGT GGGCCTGGAT CAGTACCTGG AGAGCGTTAA AAAACACAAA CGGCTGGATG

FIG. 14C

```
8521 TGTGCCGCGC TAAAATGGGC TATATGCTGC AGTGAATAAT AAAATGTGTG TTTGTCCGAA
8581 ATACGCGTTT TGAGATTTCT GTCGCCGACT AAATTCATGT CGCGCGATAG TGGTGTTTAT
8641 CGCCGATAGA GATGGCGATA TTGGAAAAAT CGATATTTGA AAATATGGCA TATTGAAAAT
8701 GTCGCCGATG TGAGTTTCTG TGTAACTGAT ATCGCCATTT TTCCAAAAGT GATTTTTGGG
8761 CATACGCGAT ATCTGGCGAT AGCGCTTATA TCGTTACGG GGGATGGCGA TAGACGACTT
8821 TGGTGACTTG GGCGATTCTG TGTGTCGCAA ATATCGCAGT TTCGATATAG GTGACAGACG
8881 ATATGAGGCT ATATCGCCGA TAGAGGCGAC ATCAAGCTGG CACATGGCCA ATGCATATCG
8941 ATCTATACAT TGAATCAATA TTGGCCATTA GCCATATTAT TCATTGGTTA TATAGCATAA
9001 ATCAATATTG GCTATTGGCC ATTGCATACG TTGTATCCAT ATCATAATAT GTACATTTAT
9061 ATTGGCTCAT GTCCAACATT ACCGCCATGT TGACATTGAT TATTGACTAG TTATTAATAG
9121 TAATCAATTA CGGGGTCATT AGTTCATAGC CCATATATGG AGTTCCGCGT TACATAACTT
9181 ACGGTAAATG GCCCGCCTGG CTGACCGCCC AACGACCCCC GCCCATTGAC GTCAATAATG
9241 ACGTATGTTC CCATAGTAAC GCCAATAGGG ACTTTCCATT GACGTCAATG GGTGGAGTAT
9301 TTACGGTAAA CTGCCCACTT GGCAGTACAT CAAGTGTATC ATATGCCAAG TACGCCCCCT
9361 ATTGACGTCA ATGACGGTAA ATGGCCCGCC TGGCATTATG CCCAGTACAT GACCTTATGG
9421 GACTTTCCTA CTTGGCAGTA CATCTACGTA TTAGTCATCG CTATTACCAT GGTGATGCGG
9481 TTTTGGCAGT ACATCAATGG GCGTGGATAG CGGTTTGACT CACGGGGATT TCCAAGTCTC
9541 CACCCCATTG ACGTCAATGG GAGTTTGTTT TGGCACCAAA ATCAACGGGA CTTTCCAAAA
9601 TGTCGTAACA ACTCCGCCCC ATTGACGCAA ATGGGCGGTA GGCGTGTACG GTGGGAGGTC
9661 TATATAAGCA GAGCTCGTTT AGTGAACCGT CAGATCGCCT GGAGACGCCA TCCACGCTGT
9721 TTTGACCTCC ATAGAAGACA CCGGGACCGA TCCAGCCTCC GCGGCCGGGA ACGGTGCATT
9781 GGAACGCGGA TTCCCCGTGC CAAGAGTGAC GTAAGTACCG CCTATAGAGT CTATAGGCCC
9841 ACCCCCTTGG CTTCTTATGC ATGCTATACT GTTTTTGGCT TGGGGTCTAT ACACCCCCGC
9901 TTCCTCATGT TATAGGTGAT GGTATAGCTT AGCCTATAGG TGTGGGTTAT TGACCATTAT
9961 TGACCACTCC CCTATTGGTG ACGATACTTT CCATTACTAA TCCATAACAT GGCTCTTTGC
10021 CACAACTCTC TTTATTGGCT ATATGCCAAT ACACTGTCCT TCAGAGACTG ACACGGACTC
10081 TGTATTTTTA CAGGATGGGG TCTCATTTAT TATTTACAAA TTCACATATA CAACACCACC
10141 GTCCCAGTG CCCGCAGTTT TTATTAAACA TAACGTGGGA TCTCCACGCG AATCTCGGGT
10201 ACGTGTTCCG GACATGGGCT CTTCTCCGGT AGCGGCGGAG CTTCTACATC CGAGCCCTGC
10261 TCCCATGCCT CCAGCGACTC ATGGTCGCTC GGCAGCTCCT TGCTCCTAAC AGTGGAGGCC
10321 AGACTTAGGC ACAGCACGAT GCCCACCACC ACCAGTGTGC CGCACAAGGC CGTGGCGGTA
10381 GGGTATGTGT CTGAAAATGA GCTCGGGGAG CGGGCTTGCA CCGCTGACGC ATTTGGAAGA
10441 CTTAAGGCAG CGGCAGAAGA AGATGCAGGC AGCTGAGTTG TTGTGTTCTG ATAAGAGTCA
10501 GAGGTAACTC CCGTTGCGGT GCTGTTAACG GTGGAGGGCA GTGTAGTCTG AGCAGTACTC
10561 GTTGCTGCCG CGCGCGCCAC CAGACATAAT AGCTGACAGA CTAACAGACT GTTCCTTTCC
10621 ATGGGTCTTT TCTGCAGTCA CCGTCCTTGA CACGGCTAGC ATGGTGAGCA AGGGCGAGGA
10681 GGATAACATG GCCATCATCA AGGAGTTCAT GCGCTTCAAG GTGCACATGG AGGGCTCCGT
10741 GAACGGCCAC GAGTTCGAGA TCGAGGGCGA GGGCGAGGGC CGCCCCTACG AGGGCACCCA
10801 GACCGCCAAG CTGAAGGTGA CCAAGGGTGG CCCCCTGCCC TTCGCCTGGG ACATCCTGTC
10861 CCCTCAGTTC ATGTACGGCT CCAAGGCCTA CGTGAAGCAC CCCGCCGACA TCCCCGACTA
10921 CTTGAAGCTG TCCTTCCCCG AGGGCTTCAA GTGGGAGCGC GTGATGAACT TCGAGGACGG
10981 CGGCGTGGTG ACCGTGACCC AGGACTCCTC CCTGCAGGAC GGCGAGTTCA TCTACAAGGT
11041 GAAGCTGCGC GGCACCAACT TCCCCTCCGA CGGCCCCGTA ATGCAGAAGA AGACCATGGG
11101 CTGGGAGGCC TCCTCCGAGC GGATGTACCC CGAGGACGGC GCCCTGAAGG GCGAGATCAA
```

FIG. 14D

```
11161 GCAGAGGCTG AAGCTGAAGG ACGGCGGCCA CTACGACGCT GAGGTCAAGA CCACCTACAA
11221 GGCCAAGAAG CCCGTGCAGC TGCCCGGCGC CTACAACGTC AACATCAAGT TGGACATCAC
11281 CTCCCACAAC GAGGACTACA CCATCGTGGA ACAGTACGAA CGCGCCGAGG GCCGCCACTC
11341 CACCGGCGGC ATGGACGAGC TGTACAAGG
```

|  | Location | | Size (bp) |
|---|---|---|---|
|  | (start) | (end) |  |
| SV40NLS | 6 .. | 44 | 39 |
| IRES | 51 .. | 638 | 588 |
| IE2 | 639 .. | 2378 | 1740 |
| deltaU3-3'LTR | 2578 .. | 2812 | 235 |
| BGH PolyA | 2838 .. | 3051 | 214 |
| f1 ori | 3114 .. | 3526 | 413 |
| SV40 ori | 3592 .. | 3917 | 326 |
| EM7 | 3933 .. | 3998 | 66 |
| Zeocin | 4000 .. | 4374 | 375 |
| pUC ori | 5017 .. | 5690 | 674 |
| Amp | 5835 .. | 6695 | 861 |
| bla | 6696 .. | 6793 | 98 |
| PCMV | 7040 .. | 7691 | 652 |
| T7 promoter | 7694 .. | 7713 | 20 |
| MCS | 7726 .. | 7828 | 103 |
| 5' LTR | 7829 .. | 8009 | 181 |
| MIE Modular/Unique | 8442 .. | 8952 | 511 |
| UL128 [Split] | 8442 .. | 8555 | 114 |
| MIEP modulator 5' primer | 8442 .. | 8464 | 23 |
| UL127 | 8530 .. | 8967 | 438 |
| UL127 | 8530 .. | 8925 | 396 |
| MIE Promoter/Enhancer | 8953 .. | 9696 | 744 |
| UL126 [Split] | 9511 .. | 9915 | 405 |
| UL125 | 10,001 .. | 10,309 | 309 |
| UL124 | 10,164 .. | 10,637 | 474 |
| Exon 2/1 primer | 10,634 .. | 10,654 | 21 |
| mCherry | 10,661 .. | 11,368 | 708 |

FIG. 14E

>IE2
MESSAKRKMDPDNPDEGPSSKVPRPETPVTKATTFLQTMLRKEVNSQLSLGDPL
FPELAEESLKTFEQVTEDCNENPEKDVLAELGDILAQAVNHAGIDSSSTGPTLTTH
SCSVSSAPLNKPTPTSV A VTNTPLPGASATPELSPRKKPRKTTRPFKVIIKPPVPPA
PIMLPLIKQEDIKPEPDFTIQYRNKIIDTAGCIVISDSEEEQGEEVETRGAT ASSPSTG
SGTPRVTSPTHPLSQMNHPPLPDPLGRPDEDSSSSSSSSCSSASDSESESEEMKCSS
GGGASVTSSHHGRGGFGGAASSSLLSCGHQSSGGASTGPRKKKSKRISELDNEK
VRNIMKDKNTPFCTPNVQTRRGRVKIDEVSRMFRNTNRSLEYKNLPFTIPSMHQV
LDEAIKACKTMQVNNKGIQIIYTRNHEVKSEVDAVRCRLGTMCNLALSTPFLME
HTMPVTHPPEV AQRT ADACNEGV KAAWSLKELHTHQLCPRSSDYRNMIIHAATP
VDLLGALNLCLPLMQKFPKQVMVRIFSTNQGGFMLPIYETAAKAY A VGQFEQPT
ETPPEDLDTLSLAIEAAIQDLRNKSQ

>UL127
MCQLDV ASIGDIASYRLSPISKLRYLRHTESPKSPKSSIAIPRKRYKRYRQISRMPK
NHFWKNGDISYTETHIGDIFNMPYFQISIFPISPSLSAINTTIARHEFSRRQKSQNAY
FGQTHILLFTAA YSPF

>Zeocin(r)
MAKLTSA VPVLT ARD V AGA VEFWTDRLGFSRDFVEDDFAGVVRDDVTLFISA V
QDQVVPDNTLAWVWVRGLDEL Y AEWSEVVSTNFRDASGPAMTEIGEQPWGRE
FALRDP AGNCVHFV AEEQD >Amp(r)
MSIQHFRV ALIPFF AAFCLPVFAHPETL VKVKDAEDQLGARVGYIELDLNSGKILE
SFRPEERFPMMSTFKVLLCGA VLSRIDAGQEQLGRRIHYSQNDLVEYSPVTEKHL
TDGMTVRELCSAAITMSDNTAANLLL TTIGGPKEL TAFLHNMGDHVTRLDRWEP
ELNEAIPNDERDTTMPV AMATTLRKLL TGELL TLASRQQLIDWMEADKV AGPLL
RSALPAGWFIADKSGAGERGSRGIIAALGPDGKPSRIVVIYTTGSQA TMDERNRQI
AEIGASLIKHW

FIG. 15

>DsRed
MASSEDVIKEFMRFKVRMEGSVNGHEFEIEGEGEGRPYEGTQTAKLKVTKGGPL
PF AWDILSPQFQYGSKVYVKHP ADIPDYKKLSFPEGFKWERVMNFEDGGVVTVT
QDSSLQDGSFIYKVKFIGVNFPSDGPVMQKKTMGWEASTERLYPRDGVLKGEIH
KALKLKDGGHYLVEFKSIYMAKKPVQLPGYYYVDSKLDITSHNEDYTIVEQYER
AEGRHHLFL

>mCherry
MVSKGEEDNMAIIKEFMRFKVHMEGSVNGHEFEIEGEGEGRPYEGTQTAKLKVT
KGGPLPF A WDILSPQFMYGSKA YVKHPADIPDYLKLSFPEGFKWERVMNFEDGG
VVTVTQDSSLQDGEFIYKVKLRGTNFPSDGPVMQKKTMGWEASSERMYPEDGA
LKGEIKQRLKLKDGGHYDAEVKTTYKAKKPVQLPGAYNVNIKLDITSHNEDYTI
VEQYERAEGRHSTGGMDELYK >EGFP
MVSKGEELFTGVVPILVELDGDVNGHKFSVSGEGEGDA TYGKLTLKFICTTGKLP
VPWPTL VTTLTYGVQCFSR YPDHMKQHDFFKSAMPEGYVQERTIFFKDDGNYK
TRAEVKFEGDTLVNRIELKGIDFKEDGNILGHKLEYNYNSHNVYIMADKQKNGI
KVNFKIRHNIEDGSVQLADHYQQNTPIGDGPVLLPDNHYLSTQSALSKDPNEKRD
HMVLLEFVTAAGITLGMDEL YK

FIG. 16

```
GenBank AAR31391
CMV IE2
580 aa 1 messakrkmd pdnpdegpss kvprpetpvt kattflqtml rkevnsqlsl gdplfpelae
 61 eslktfeqvt edcnenpekd vlaelgdila qavnhagids sstgptltth scsvssapln
121 kptptsvavt ntplpgasat pelsprkkpr kttrpfkvii kppvppapim lplikqedik
181 pepdftiqyr nkiidtagci visdseeeqg eevetrgata sspstgsgtp rvtspthpls
241 qmnhpplpdp lgrpdedsss ssssscssas dseseseemk cssgggasvt sshhgrggfg
301 gaasssllsc ghqssggast gprkkkskri seldnekvrn imkdkntpfc tpnvqtrrgr
361 vkidevsrmf rntnrsleyk nlpftipsmh qvldeaikac ktmqvnnkgi qiiytrnhev
421 ksevdavrcr lgtmcnlals tpflmehtmp vthppevaqr tadacnegvk aawslkelht
481 hqlcprssdy rnmiihaatp vdllgalnlc lplmqkfpkq vmvrifstnq ggfmlpiyet
541 aakayavgqf eqptetpped ldtlslaiea aiqdlrnksq (SEQ ID NO:1)
```

FIG. 17A

```
From GenBank JQ394986
CMV MIEP
Nt 2289-2790 (502 nt)

cg cgttacataa cttacggtaa atggcccgcc tggctgaccg cccaacgacc
2341 cccgcccatt gacgtcaata atgacgtatg ttcccatagt aacgccaata gggactttcc
2401 attgacgtca atgggtggac tatttacggt aaactgccca cttggcagta catcaagtgt
2461 atcatatgcc aagtacgccc cctattgacg tcaatgacgg taaatggccc gcctggcatt
2521 atgcccagta catgacctta tgggactttc ctacttggca gtacatctac gtattagtca
2581 tcgctattac catggtgatg cggttttggc agtacatcaa tgggcgtgga tagcggtttg
2641 actcacgggg atttccaagt ctccacccca ttgacgtcaa tgggagtttg ttttggcacc
2701 aaaatcaacg ggactttcca aaatgtcgta acaactccgc cccattgacg caaatgggcg
2761 gtaggcgtgt acggtgggag gtctatataa (SEQ ID NO:2)
```

FIG. 17B

```
HSV ICP0
GenBank AFE62827
776 amino acids 1 meprpgastr rpegrpqrep apdvwvfpcd rdlpdssdse aetevggrgd adhhdddsas
 61 eadstdtelf etgllgpqgv dggavsggsp preedpgscg gappredggs degdvcavct
121 deiaphlrcd tfpcmhrfci pcmktwmqlr ntcplcnakl vylivgvtps gsfstipivn
181 dpqtrmeaee avragtavdf iwtgnqrfap ryltlgghtv ralspthpep ttdedddld
241 dadyvppapr rtprapprrg aaappvtgga shaapqpaaa rtappsapig phgssntntt
301 tnssggggsr qsraavprga sgpsggvgvv eaeagrprgr tgplvnrpap lannrdpivi
361 sdsppasphr ppaapmpgsa prpgppasaa asgparpraa vapcvrappp gpgprapapg
421 aepaarpada rrvpqshssl aqaanqeqsl craratvarg sggpgveggh gpsrgaapsg
481 aapsgapplp saasveqeaa vrprkrrgsg qenpspqstr pplapagakr aathppsdsg
541 pggrgqggpg tpltssaasa ssssasssa ptpagatssa tgaasssasa ssggavgalg
601 grqeetslgp raasgprgpr kcarktrhae tsgavpaggl trylpisgvs svvalspyvn
661 ktitgdclpi ldmetgniga yvvlvdqtgn matrlraavp gwsrrtllpe tagnhvtppe
721 yptapasewn slwmtpvgnm lfdqgtlvga ldfrslrsrh pwsgeqgast rdegkq (SEQ ID NO:3)
```

FIG. 18A

```
GenBank J02209
HSV-1 α0 (ICP0) gene promoter
499 nt 1 cctggggttc cgggtatggt aatgagtttc ttcgggaagg cgggaagccc cggggcaccg
 61 acgcaggcca agcccctgtt gcgtcggtgg gaggggcatg ctaatggggt tctttggggg
121 acaccgggtt ggtcccccaa atcggggggcc gggccgtgca tgctaatgat attctttggg
181 ggcgccgggt tggtccccgg ggacgggccc gccccgcggt gggcctgcct cccctgggac
241 gcgcggccat tgggggaatc gtcactgccg ccccctttggg gaggggaaag gcgtggggta
301 taagttagcc ctggcccgac agtctggtcg catttgcacc tcggcactcg gagcgagacg
361 cagcagccag gcagactcgg gccgccccct ctccgcatca ccacagaagc cccgcctacg
421 ttgcgacccc cagggaccct ccgtccgcga ccctccagcc gcatacgacc cccatggagc
481 cccgccccgg agcgggtac (SEQ ID NO:4)
```

FIG. 18B

GenBank YP_401673
245 aa
EBV BZLF1 (Zta)

1 mmdpnstsed vkftpdpyqv pfvqafdqat rvyqdlggps qaplpcvlwp vlpeplpqgq
 61 ltayhvstap tgswfsapqp apenayqaya apqlfpvsdi tqnqqtnqag geapqpgdns
121 tvqtaaavvf acpganqgqq ladigvpqpa pvaaparrtr kpqqpeslee cdseleikry
181 knrvasrkcr akfkqllqhy revaaaksse ndrlrlllkq mcpsldvdsi iprtpdvlhe
241 dllnf (SEQ ID NO:5)

FIG. 19A

GenBank FJ756536
EBV Zta promoter region
222 nt 1 gcatatttca actgggctgt ctatttttga caccagctta ttttagacac ttctgaaaac
 61 tgcctcctcc tcttttggaa actatgcatg agccacaggc attgctaatg tgcctcagag
121 acacacctaa atttagcacg tcccaaacca tgacatcaca gaggaggctg gtgccttggc
181 tttaaagggg agatgttaga caggtaactc actaaacatt gc (SEQ ID NO:6)

Region II = underlined
Region III = bold

FIG. 19B

```
HHV-8 RTA (ORF50)
GenBank ABD28900
691 aa 1 maqddkgkkl rrscvesfvg lsdelkaqly qcvllinday etiydpsdln rvvedvciri
 61 mkecsklgal cglftdinmf nlfcffrasr mrtkgaagyn vpcaeasqgi irilterilf
121 ctekafltaa csgvslppai ckllheiyte mkakclgawr rlvcnrrpim iltssllkly
181 ntydtaglls eqsralcllv fqpvylprim apleimtkgq lapenfysit gsaekrrpit
241 tgkvtglsyp gsglmpesli lpilepgllp asmvdlsdvl akpavilsap alsqfviskp
301 hpnmphtvsi ipfnpsgtdp afistwqaas qnmvyntsta plkpatgssq tvsvkavaqg
361 avitattvpq ampargtgge lpvmsastpa rdqvaacfva entgdspdnp ssfltschpc
421 dpntvivaqq fqppqcvtll qvtcapsstp ppdstvrapv vqlptvvplp asaflpalaq
481 peasgeelpg ghdgdqgvpc rdstaaataa eattpkrkqr skersskkrk altvpeadtt
541 pstttpgtsl gsittpqdvh atdvatsegp seaqppllsl pppldvdqsl falldeagpe
601 twdvgsplsp tddallssil qglyqldtpp plrspspasf gpespadips psggeytqlq
661 pvratsatpa nevqesgtly qlhqwrnyfr d (SEQ ID NO:7)
```

FIG. 20A

```
GenBank NC_009333 NC_003409
HHSV-8 RTA (ORF50) promoter 71481                    gttcagtcac atgtacgcta gggtctcccc acccaacccc
71521 cataggaccc agctacagct tatcctccac taaataccag gcagctaccg gcgactcatt
71581 aagcccccgcc cagaaaccag tagctgggtg gcaatgacac gtcccctttta aaaagtcaac
71641 cttactccgc aaggggtagt ctgttgtgag aatactgtcc aggcagccac aaaaatg (SEQ ID NO:8)
```

FIG. 20B

```
GenBank AFV60003
mCherry 236 aa 1 mvskgeednm aiikefmrfk vhmegsvngh efeiegegeg rpyegtqtak lkvtkggplp
 61 fawdilspqf mygskayvkh padipdylkl sfpegfkwer vmnfedggvv tvtqdsslqd
121 gefiykvklr gtnfpsdgpv mqkktmgwea ssermypedg alkgeikqrl klkdgghyda
181 evkttykakk pvqlpgaynv nikldithn edytiveqye raegrhstgg mdelyk (SEQ ID NO:9)
```

FIG. 21

```
GenBank P08392
1298 aa
HSV ICP4

1 masenkqrpg spgptdgppp tpspdrderg algwgaetee ggddpdhdpd hphdlddarr
  61 dgrapaagtd agedagdavs prqlallasm veeavrtipt pdpaaspprt pafraddddg
 121 deyddaadaa gdrapargre reaplrgayp dptdrlsprp paqpprrrrh grwrpsasst
 181 ssdsgsssss sassssssd ededdgnda adharearav grgpssaapa apgrtppppg
 241 ppplseaapk praaartpaa sagrierrra raavagrdat grftagqprr veldadatsg
 301 afyaryrdgy vsgepwpgag ppppgrvlyg glgdsrpglw gapeaeearr rfeasgapaa
 361 vwapelgdaa qqyalitrll ytpdaeamgw lqnprvvpgd valdqacfri sgaarnsssf
 421 itgsvaravp hlgyamaagr fgwglahaaa avamsrrydr aqkgflltsl rrayapllar
 481 enaaltgaag spgagaddeg vaavaaaapg eravpagyga agilaalgrl saapaspagg
 541 ddpdaarhad adddagrraq agrvavecla acrgileala egfdgdlaav pglagarpas
 601 pprpegpagp asppphada prlrawlrel rfvrdalvlm rlrgdlrvag gseaavaavr
 661 avslvagalg palprdprlp ssaaaaaadl lfdnqslrpl laaaasapda adalaaaaas
 721 aapregrkrk spgparppgg ggprppktkk sgadapgsda raplpapapp stppgpepap
 781 aqpaapraaa aqarprpvav srrpaegpdp lggwrrqppg pshtaapaaa aleaycspra
 841 vaeltdhplf pvpwrpalmf dpralasiaa rcagpapaaq aacgggdddd nphphgaagg
 901 rlfgplrasg plrrmaawmr qipdpedvrv vvlysplpge dlagggasgg ppewsaergg
 961 lscllaalan rlcgpdtaaw agnwtgapdv salgaqgvll lstrdlafag aveflgllas
1021 agdrrlivvn tvracdwpad gpavsrqhay lacellpavq cavrwpaard lrrtvlasgr
1081 vfgpgvfarv eaaharlypd applrlcrgg nvryrvrtrf gpdtpvpmsp reyrravlpa
1141 ldgraaasgt tdamapgapd fceeeahsha acarwglgap lrpvyvalgr eavragparw
1201 rgprrdfcar allepdddap plvlrgdddg pgalppappg irwasatgrs gtvlaaagav
1261 evlgaeagla tpprrevvdw egawdeddgg afegdgvl (SEQ ID NO:10)
```

FIG. 22

Figure 23
GenBank AEL30876
VZV ORF61
467 aa

```
  1 mdtilaggsg tsdasdntct icmstvsdlg ktmpclhdfc fvcirawtst svqcplcrcp
 61 vqsilhkivs dtsykeyevh psdddgfsep sfedsidilp gdvidllpps pgpsresiqq
121 ptsrssrepi qspnpgplqs sareptaesp sdsqqdsiqp ptrdsspgvt ktcstasflr
181 kvffkdqpav rsatpvvygs iesaqqprtg gqdyrdrpvs vginqdprtm drlpfratdr
241 gtegnarfpc ymqpllgwld dqlaelyqpe iveptkmlil nyigiygrde aglktslrcl
301 lhdstgpfvt nmlflldrct dptrltmqtw twkdtaiqli tgpivrpett stgetsrgde
361 rdtrlvntpq kvrlfsvlpg ikpgsargak rrlfhtgrdv krcltidlts esdsackgsk
421 trkvaspqge sntpstsgst sgslkhltkk ssagkagkgi pnkmkks (SEQ ID NO:11)
```

Figure 24
GenBank AAY57671
VZV ORF62
1310 aa

```
   1 mdtppmqrst pqragspdtl elmdlldaaa aaaehrarvv tssqpddllf gengvmvgre
  61 heivsipsvs glqpeprted vgeeltqddy vcedgqdlxg spviplaevf htrfseagar
 121 eptgadrsle tvslgtklar spkppmndge tgrgttppfp qafspvspas pvgdaagndq
 181 redqrsiprq ttrgnspglp svvhrdrqtq sisgkkpgde qaghahasgd gvvlqktqrp
 241 aqgkspkkkt lkvkvplpar kpggpvpgpv eqlyhvlsds vpakgakadl pfetddtrpr
 301 khdargitpr vpgrssggkp raflalpgrs hapdpiedds pvekkpksre fvsssssss
 361 wgsssededd eprrvsvgse ttgsrsgreh apspsnsdds dsndggstkq niqpgyrsis
 421 gpdprirktk rlagepgrqr qksfslprsr tpiippvsgp lmmpdgspwp gsaplpsnrv
 481 rfgpsgetre ghwedeavra araryeaste pxplyvpelg dparqyrali nliycpdrdp
 541 iawlqnpklt gvnsalnqfy qkllppgrag tavtgsvasp vphvgeamat gealwalpha
 601 aaavamsrry draqkhfilq slrrafagma ypeatgsspa arisrghpsp ttpatqtpdp
 661 qpsaaarsls vcppddrlrt prkrksqpve srslldkire tpvadarvad dhvvskakrr
 721 vsepvtitsg pvvdppavit mpldgpapng gfrriprgal htpvpsdqar kayctpetia
 781 rlvddplfpt awrpalsfdp galaeiaarr pgggdrrfgp psgvealrrr cawmrqipdp
 841 edvrlliiyd plpgedingp lestlatdpg pswpsrggl svvlaalsnr lclpsthawa
 901 gnwtgppdvs alnargvlll strdlafaga veylgsrlas arrrllvlda valerwpgdg
 961 palsqyhvyv raparpdaqa vvrwpdsavt eglaravfas srtfgpasfa rietafanly
1021 pgeqplclcr ggnvaytvct ragpktrvpl spreyrqyvl pgfdgckdla rqsrglglga
1081 adfvdeaahs hraanrwglg aalrpvflpe grrpgaagpe agdvptwarv fcrhallepd
1141 paaeplvlpp vagrsvalya sadearnalp piprvmwppg fgaaetvleg sdgtrfafgh
1201 hggserpaet qagrqrrtad drehalepdd wevgcedawd seegggddgd apgssfgvsv
1261 vsvapgvlrd rrvgxrpavk vellsssss ededdvwggr ggrsppqsrg
```
(SEQ ID NO:12)

Figure 25
VZV ORF61 promoter region
acattttatacccacgttttagtgggtgggacttaaaagaaatgggtggagggatatagggtgtgtcttcgttggtaccaat
tataaaaatgtactcgccacaactcacaatttagaacgcatggcagttctgctacgtgtttggatgcccggacattagaatac
agccagttgttacc (SEQ ID NO:13)

US 10,106,817 B2

COMPOSITIONS AND METHODS OF USE THEREOF FOR IDENTIFYING ANTI-VIRAL AGENTS

CROSS-REFERENCE

This application claims the benefit of U.S. Provisional Patent Application No. 61/764,854, filed Feb. 14, 2013, which application is incorporated herein by reference in its entirety.

STATEMENT REGARDING FEDERALLY SPONSORED RESEARCH

This invention was made with government support under Grant No. K25GM083395 awarded by the National Institutes of Health. The government has certain rights in the invention.

INCORPORATION BY REFERENCE OF SEQUENCE LISTING PROVIDED AS A TEXT FILE

A Sequence Listing is provided herewith as a text file, "GLAD-406WO_SeqList_ST25.txt" created on Feb. 12, 2014 and having a size of 172 KB. The contents of the text file are incorporated by reference herein in their entirety.

INTRODUCTION

Cytomegalovirus (CMV) infects a majority of the world's population, is a leading cause of birth defects, and is a major cause of morbidity and mortality in the immunocompromised population. The virus initiates an infectious program within the cell by expressing its 86-kDa viral transactivator protein Immediate-Early 2 (IE2), which is a promiscuous transactivator of viral promoters and is essential for viral replication, but also highly cytotoxic. CMV must quickly express IE2 to establish a replication-favorable environment but also limit IE2 levels to avoid prematurely compromising the cell's ability to produce viral progeny. IE2, along with IE1, is encoded by a precursor mRNA expressed from the CMV Major Immediate-Early (MIE) promoter, which directs all subsequent viral gene expression and is considered to be the chief regulator of the lytic cycle. The MIE promoter (MIEP) is exceptionally strong and contains multiple transcription factor-binding sites within its ~500-nucleotide enhancer. The MIEP is also auto-repressed by IE2 via direct DNA binding to a 12-nucleotide cis repression sequence (crs) located between positions −13 and +1 relative to the transcriptional start site. The impact of IE2 autoregulation upon the virus life cycle is largely unknown.

LITERATURE

Teng et al. (2012) *Cell* 151:1569; Sanders et al. (2008) *J. Virol.* 82:7059.

SUMMARY

The present disclosure provides a recombinant expression vector comprising a nucleotide sequence encoding a herpesvirus transactivator, where the nucleotide sequence is operably linked to a herpesvirus control element. The present disclosure provides cell lines genetically modified to express a herpesvirus transactivator under the control of a herpesvirus control element. The present disclosure provides methods of identifying agents that disrupt feedback regulation of a herpesvirus transcriptional control element by a herpesvirus transactivator.

BRIEF DESCRIPTION OF THE DRAWINGS

FIGS. 2A-E provide the sequence of vector LE2idw and a legend describing the location and size of various features (SEQ ID NO: 14).

FIGS. 4A-D provide the sequence of vector LM2G and a legend describing the location and size of various features (SEQ ID NO: 15).

FIGS. 6A-E provide the sequence of vector LM2iCh and a legend describing the location and size of various features (SEQ ID NO: 16).

FIGS. 8A-E provide the sequence of vector LM2ig and a legend describing the location and size of various features (SEQ ID NO: 17).

FIGS. 10A-E provide the sequence of vector LM2igw and a legend describing the location and size of various features (SEQ ID NO: 18).

FIGS. 12A-E provide the sequence of vector LMChIG and a legend describing the location and size of various features (SEQ ID NO: 19).

FIGS. 14A-E provide the sequence of vector pLMChi2 and a legend describing the location and size of various features (SEQ ID NO: 20).

FIG. 15 provides translations of various features described in FIGS. 1-14. IE2 (SEQ ID NO:30); UL127 (SEQ ID NO:31); Zeocin(r) (SEQ ID NO:32); and Amp(r) (SEQ ID NO:33).

FIG. 16 provides translations of various features described in FIGS. 1-14. DsRed (SEQ ID NO:34); mCherry (SEQ ID NO:9); and EGFP (SEQ ID NO:35).

FIGS. 17A and 17B provide an amino acid sequence (FIG. 17A) of CMV IE2, and a nucleotide sequence (FIG. 17B) of a MIEP.

FIGS. 18A and 18B provide an amino acid sequence (FIG. 18A) of herpes simplex virus-1 (HSV-1) infected cell protein 0 (ICP0) and a nucleotide sequence (FIG. 18B) of an HSV-1 ICP0 gene promoter.

FIGS. 19A and 19B provide an amino acid sequence (FIG. 19A) of an Epstein-Barr Virus (EBV) Zta polypeptide, and a nucleotide sequence (FIG. 19B) of an EBV Zta gene promoter.

FIGS. 20A and 20B provide an amino acid sequence (FIG. 20A) of a Human Herpesvirus-8 (HHV-8) ORF50 (RTA) polypeptide, and a nucleotide sequence (FIG. 20B) of an HHV-8 ORF50 gene promoter.

FIG. 21 provides an amino acid sequence of a fluorescent protein.

FIG. 22 provides an amino acid sequence of HSV-1 ICP4.

FIG. 23 provides an amino acid sequence of varicella zoster virus (VZV) ORF61.

FIG. 24 provides an amino acid sequence of (VZV) ORF62.

FIG. 25 provides a nucleotide sequence of a (VZV) ORF61 gene promoter.

DEFINITIONS

Figure 1:
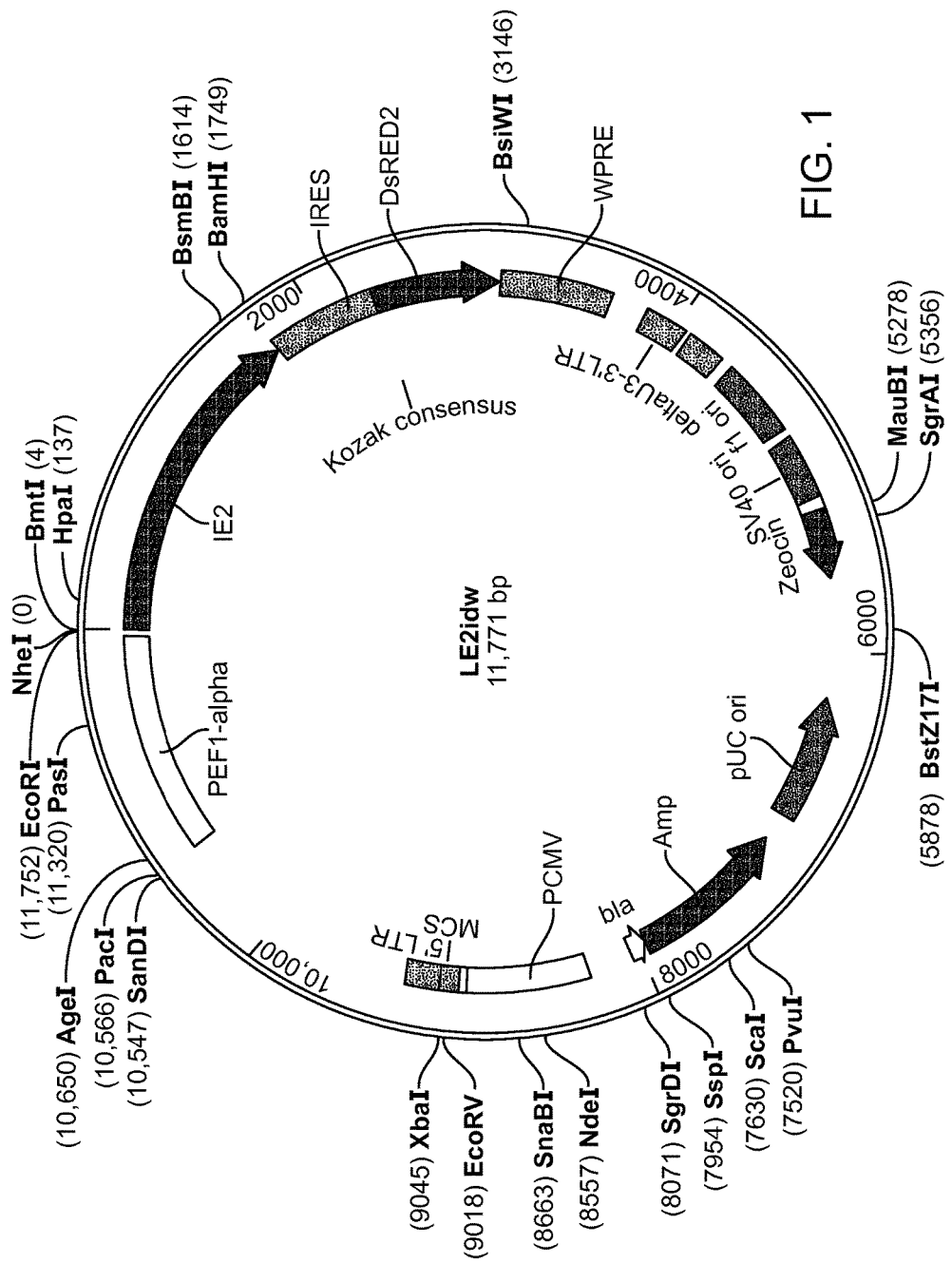
FIG. 1 provides a map of vector LE2idw.
Figure 3:
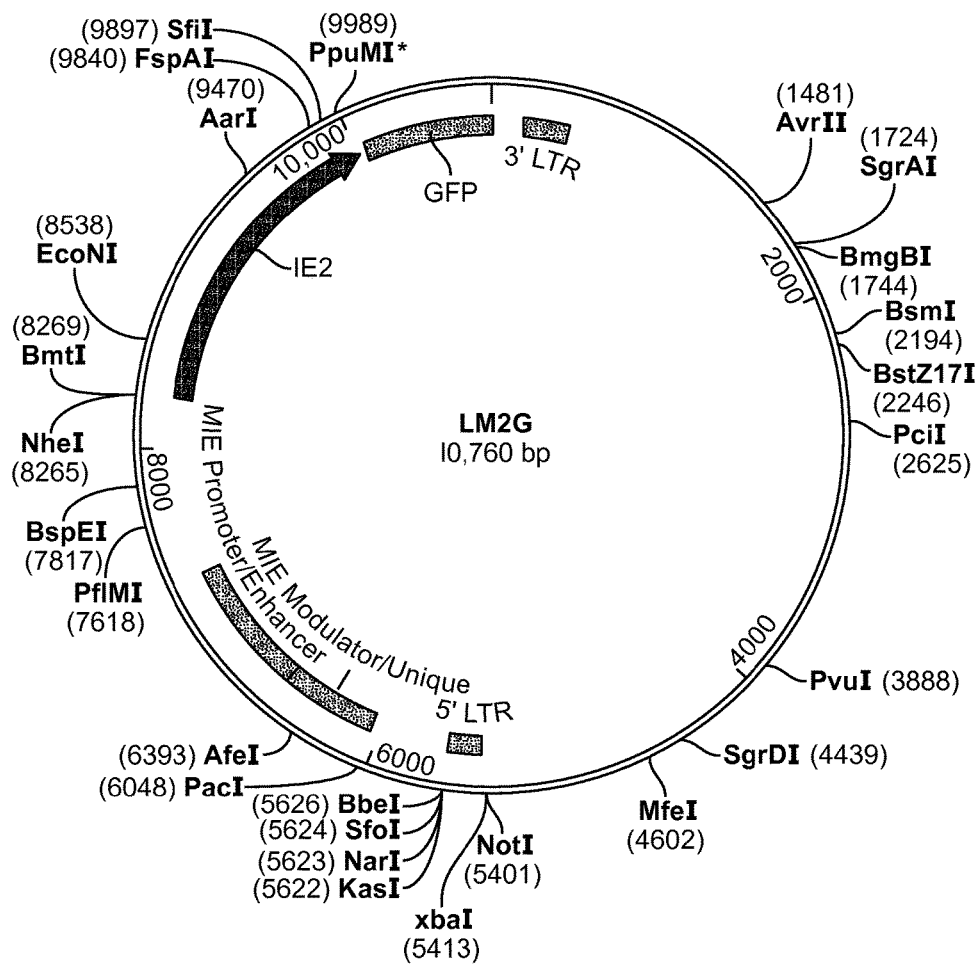
FIG. 3 provides a map of vector LM2G.
Figure 5:
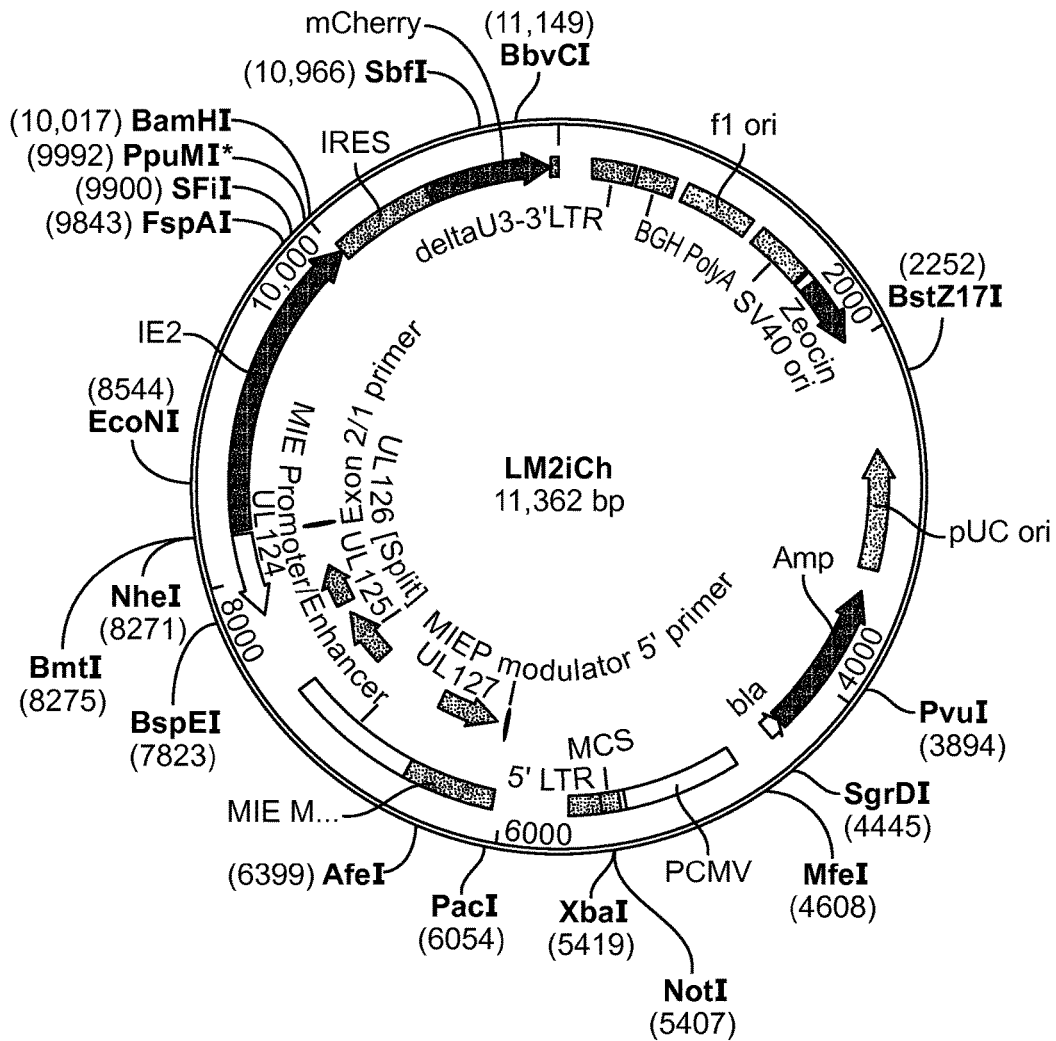
FIG. 5 provides a map of vector LM2iCh.
Figure 7:
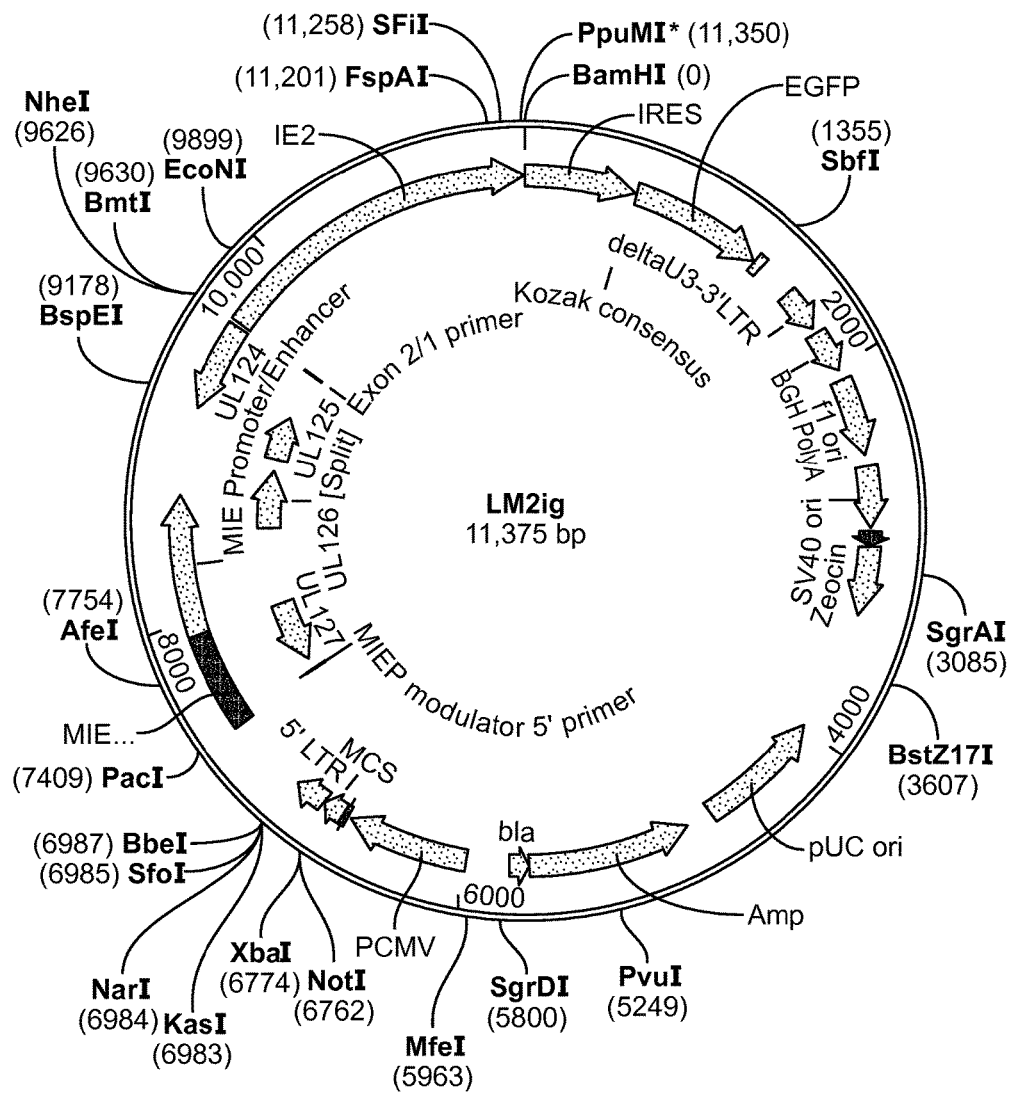
FIG. 7 provides a map of vector LM2ig.
Figure 9:
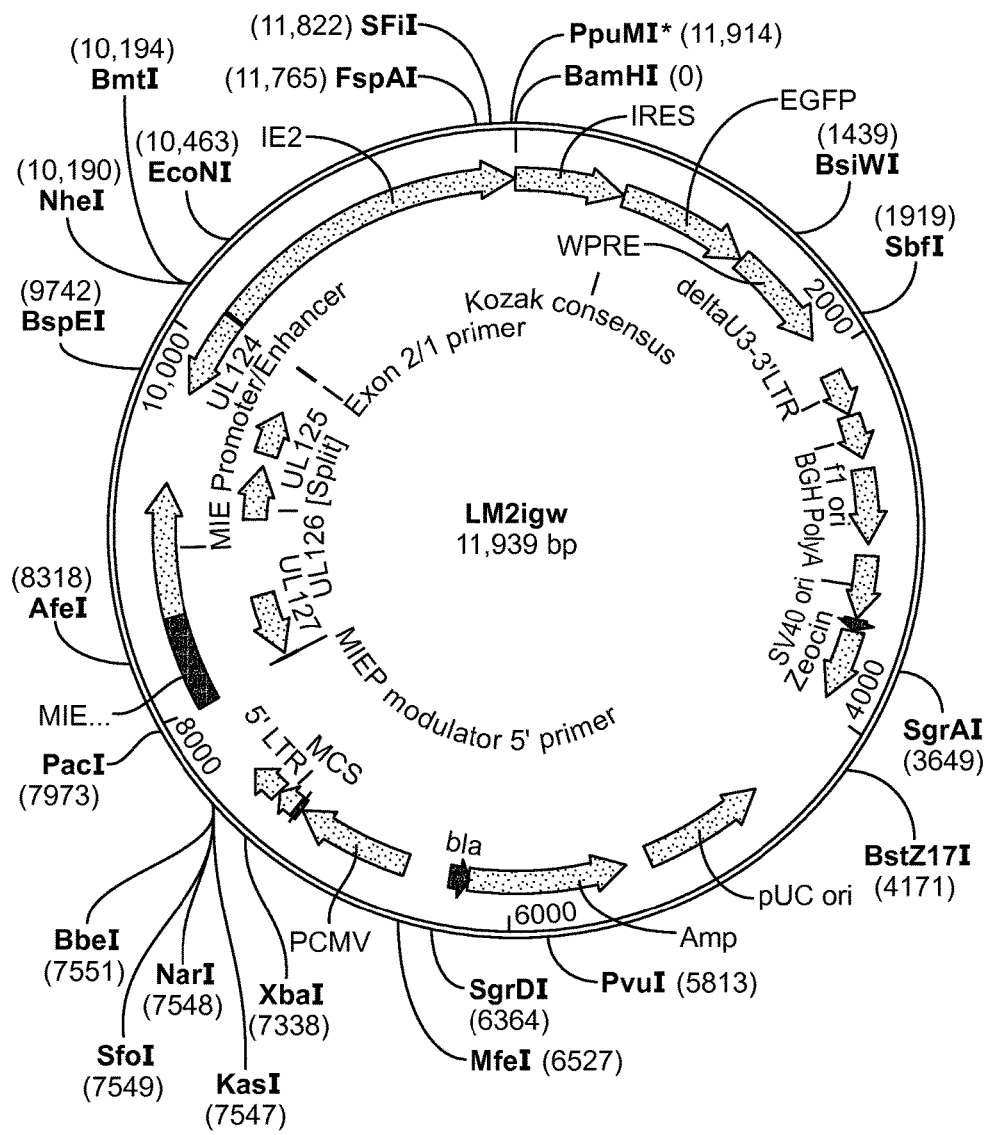
FIG. 9 provides a map of vector LM2igw.
Figure 11:
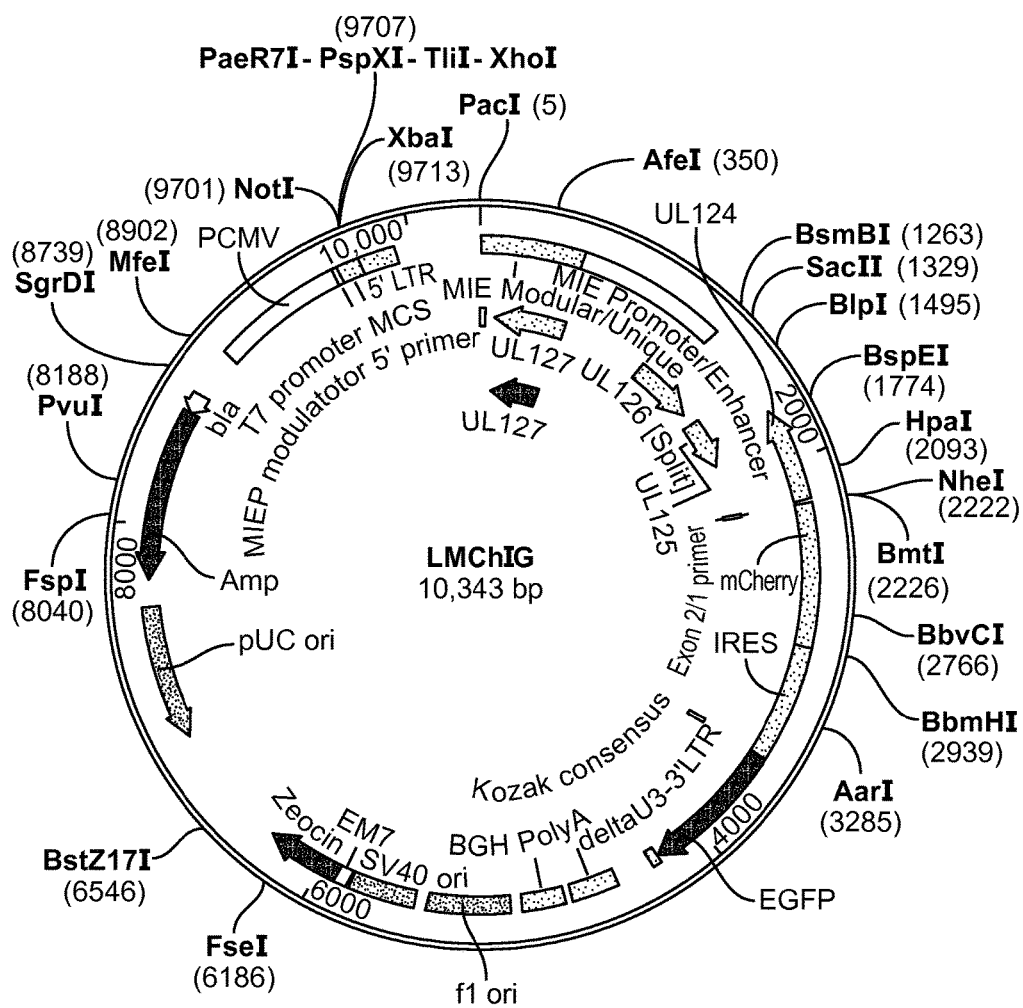
FIG. 11 provides a map of vector LMChIG.
Figure 13:
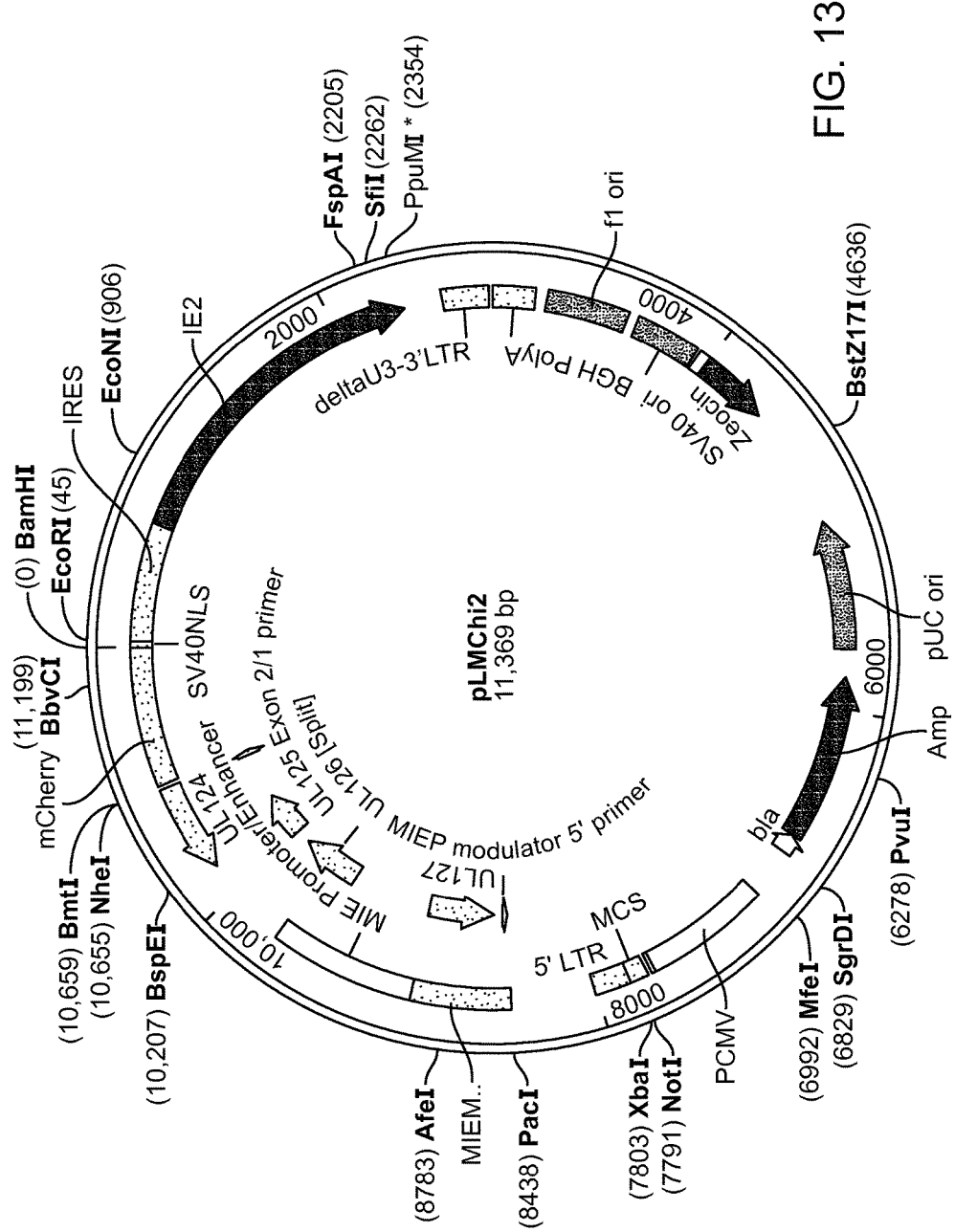
FIG. 13 provides a map of vector pLMChi2.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Operably linked" refers to a juxtaposition wherein the components so described are in a relationship permitting them to function in their intended manner. For instance, a promoter is operably linked to a coding nucleotide sequence if the promoter affects transcription or expression of the coding nucleotide sequence.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

The terms "recombinant expression vector," or "DNA construct" are used interchangeably herein to refer to a DNA molecule comprising a vector and at least one insert. Recombinant expression vectors are usually generated for the purpose of expressing and/or propagating the insert(s), or for the construction of other recombinant nucleotide sequences. The insert(s) may or may not be operably linked to a transcriptional control element (e.g., a promoter sequence and/or an enhancer sequence).

The term "herpesvirus" is well understood in the art, and refers to any member of the family Herpesviridae. Herpesviruses include, e.g., cytomegalovirus (CMV), herpes simplex virus-1 (HSV-1), herpes simplex virus-2 (HSV-2), varicella zoster virus, Epstein-Ban virus (EBV), and Kaposi's sarcoma-associated herpesvirus (KSHV; also known as human herpesvirus-8 or HHV-8).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a cytomegalovirus transactivator" includes a plurality of such transactivators and reference to "the cell line" includes reference to one or more cell lines and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a recombinant expression vector comprising a nucleotide sequence encoding a herpesvirus transactivator, where the nucleotide sequence is operably linked to a herpesvirus control element. The present disclosure provides cell lines genetically modified to express a herpesvirus transactivator under the control of a herpesvirus control element. The present disclosure provides methods of identifying agents that disrupt feedback regulation of a herpesvirus transcriptional control element by a herpesvirus transactivator.

Recombinant Expression Vectors and Systems

The present disclosure provides recombinant expression vectors, and systems comprising two recombinant expression vectors. The recombinant expression vectors and systems are useful for generating genetically modified mammalian host cells, which in turn can be used to identify candidate anti-viral agents.

Recombinant Expression Vectors

The present disclosure provides a recombinant expression vector comprising: a) a nucleotide sequence encoding a herpesvirus transactivator; and b) a herpesvirus transcriptional control element operably linked to the nucleotide sequence encoding the herpesvirus transactivator. The herpesvirus transcriptional control element is derived from a naturally occurring herpesvirus transcriptional control element that regulates transcription of the transactivator in a wild-type herpesvirus. As used herein, a herpesvirus transcriptional control element that is "derived from" a naturally-occurring herpesvirus transcriptional control element can include: a) all or a portion of a naturally-occurring herpesvirus transcriptional control element; b) a chimeric transcriptional control element that includes a portion of a naturally-occurring herpesvirus transcriptional control element linked to or embedded within a non-herpesvirus promoter; and the like.

For example, the present disclosure provides a recombinant expression vector comprising: a) a nucleotide sequence encoding a CMV transactivator; and b) a CMV transcriptional control element operably linked to the nucleotide sequence encoding the CMV transactivator. The CMV transcriptional control element is derived from a naturally occurring CMV transcriptional control element that regulates transcription of the transactivator in a wild-type CMV.

The herpesvirus transactivator binds to and regulates the herpesvirus transcriptional control element in the vector. "Regulate" as used herein, includes repressing (decreasing transcription) and activating (increasing transcription).

In some cases, a subject recombinant expression vector further comprises a nucleotide sequence encoding a reporter, where the reporter can be: i) a polypeptide that produces a detectable signal; or ii) a reporter mRNA that can be detected. The nucleotide sequence encoding the reporter will in some cases be operably linked to the herpesvirus transcriptional control element.

For example, in some cases, a subject recombinant expression vector further comprises a nucleotide sequence encoding a reporter polypeptide that provides a detectable signal, where the nucleotide sequence encoding the reporter polypeptide is operably linked to the herpesvirus transcriptional control element. In some cases, the reporter polypeptide is fused to the carboxyl terminus of the herpesvirus transactivator. In other cases, the reporter polypeptide is translated as a separate polypeptide from the herpesvirus transactivator. In some cases, the nucleotide sequence encoding the reporter polypeptide is 5' of the nucleotide sequence encoding the transactivator. In other cases, the nucleotide sequence encoding the reporter polypeptide is 3' of the nucleotide sequence encoding the transactivator. In some cases, an internal ribosome entry site (IRES) or a p2A element is interposed between the nucleotide sequence encoding the reporter polypeptide and the nucleotide sequence encoding the transactivator.

As another example, in some cases, a subject recombinant expression vector further comprises a nucleotide sequence encoding a reporter mRNA, where the nucleotide sequence encoding the reporter mRNA is operably linked to the herpesvirus transcriptional control element. In some cases, the reporter mRNA is transcribed as a separate mRNA from the mRNA encoding the herpesvirus transactivator. In some cases, the nucleotide sequence encoding the reporter mRNA is 5' of the nucleotide sequence encoding the transactivator. In other cases, the nucleotide sequence encoding the reporter mRNA is 3' of the nucleotide sequence encoding the transactivator. In some cases, an internal ribosome entry site (IRES) or a p2A element is interposed between the nucleotide sequence encoding the reporter mRNA and the nucleotide sequence encoding the transactivator.

For example, the present disclosure provides a recombinant expression vector comprising, in order from 5' to 3' and in operable linkage: a) a herpesvirus transcriptional control element; b) a nucleotide sequence encoding a herpesvirus transactivator that binds to and regulates the herpesvirus transcriptional control element; and c) a nucleotide sequence encoding a reporter. For example, the present disclosure provides a recombinant expression vector comprising, in order from 5' to 3' and in operable linkage: a) a herpesvirus transcriptional control element; b) a nucleotide sequence encoding a herpesvirus transactivator that binds to and regulates the herpesvirus transcriptional control element; and c) a nucleotide sequence encoding a reporter polypeptide. For example, the present disclosure provides a recombinant expression vector comprising, in order from 5' to 3' and in operable linkage: a) a herpesvirus transcriptional control element; b) a nucleotide sequence encoding a herpesvirus transactivator that binds to and regulates the herpesvirus transcriptional control element; and c) a nucleotide sequence encoding a reporter mRNA. For example, the present disclosure provides a recombinant expression vector comprising, in order from 5' to 3' and in operable linkage: a) a herpesvirus transcriptional control element; b) a nucleotide sequence encoding a herpesvirus transactivator that binds to and regulates the herpesvirus transcriptional control element; and c) a nucleotide sequence encoding a reporter polypeptide, where herpesvirus transactivator and the reporter polypeptide are translated as a fusion polypeptide.

As another example, the present disclosure provides a recombinant expression vector comprising, in order from 5' to 3' and in operable linkage: a) a herpesvirus transcriptional control element; b) a nucleotide sequence encoding a herpesvirus transactivator that binds to and regulates the herpesvirus transcriptional control element; c) an IRES or another element that provides for a bicistronic message; and d) a nucleotide sequence encoding a reporter, where the reporter is a reporter polypeptide or a reporter mRNA.

For example, the present disclosure provides a recombinant expression vector comprising, in order from 5' to 3' and in operable linkage: a) a CMV transcriptional control element; b) a nucleotide sequence encoding a CMV transactivator that binds to and regulates the herpesvirus transcriptional control element; and c) a nucleotide sequence encoding a reporter. For example, the present disclosure provides a recombinant expression vector comprising, in order from 5' to 3' and in operable linkage: a) a CMV transcriptional control element; b) a nucleotide sequence encoding a CMV transactivator that binds to and regulates the CMV transcriptional control element; and c) a nucleotide sequence encoding a reporter polypeptide. For example, the present disclosure provides a recombinant expression vector comprising, in order from 5' to 3' and in operable linkage: a) a CMV transcriptional control element; b) a nucleotide sequence encoding a CMV transactivator that binds to and regulates the herpesvirus transcriptional control element; and c) a nucleotide sequence encoding a reporter mRNA. For example, the present disclosure provides a recombinant expression vector comprising, in order from 5' to 3' and in operable linkage: a) a CMV transcriptional control element; b) a nucleotide sequence encoding a CMV transactivator that binds to and regulates the CMV transcriptional control element; and c) a nucleotide sequence encoding a reporter polypeptide, where CMV transactivator and the reporter polypeptide are translated as a fusion polypeptide.

As another example, the present disclosure provides a recombinant expression vector comprising, in order from 5' to 3' and in operable linkage: a) a CMV transcriptional control element; b) a nucleotide sequence encoding a CMV transactivator that binds to and regulates the CMV transcriptional control element; c) an IRES or another element that provides for a bicistronic message; and d) a nucleotide sequence encoding a reporter, where the reporter is a reporter polypeptide or a reporter mRNA.

A recombinant expression vector of the present disclosure can further include one or more additional elements, such as a nuclear localization signal (NLS); a Kozak consensus sequence; an origin of replication that is functional in a eukaryotic cell; a polyadenylation signal; a multiple cloning site; a nucleotide sequence encoding a selectable marker suitable for use in a prokaryotic cell; and a nucleotide sequence encoding a selectable marker suitable for use in a eukaryotic cell. Selectable markers include, e.g., antibiotic or antimycotic resistance factors, which are well known in the art, and include, e.g., neomycin resistance; zeocin resistance; ampicillin resistance; and the like.

The following are non-limiting examples of configurations of a recombinant expression vector of the present disclosure. Exemplary vectors are depicted in FIGS. 1-14.

1) In some embodiments, a recombinant expression vector of the present disclosure comprises, in order from 5' to 3' and in operable linkage: a) a herpesvirus transcriptional control element; b) a nucleotide sequence encoding a reporter polypeptide that produces a detectable signal; c) a nucleotide sequence encoding a nuclear localization signal; d) an IRES or other sequence that provides for a bicistronic message; and e) a nucleotide sequence encoding a herpesvirus transactivator that can bind to and regulate the herpesvirus transcriptional control element. In other embodiments, a recombinant expression vector of the present disclosure comprises, in order from 5' to 3' and in operable linkage: a) a herpesvirus transcriptional control element; b) a nucleotide sequence encoding a reporter mRNA; c) a nucleotide sequence encoding a nuclear localization signal; d) an IRES or other sequence that provides for a bicistronic message; and e) a nucleotide sequence encoding a herpesvirus transactivator that can bind to and regulate the herpesvirus transcriptional control element.

For example, a recombinant expression vector of the present disclosure can comprise, in order from 5' to 3' and in operable linkage: a) a CMV transcriptional control element; b) a nucleotide sequence encoding a reporter polypeptide that produces a detectable signal; c) a nucleotide sequence encoding a nuclear localization signal; d) an IRES or other sequence that provides for a bicistronic message; and e) a nucleotide sequence encoding a CMV transactivator that can bind to and regulate the CMV transcriptional control element. As another example, a recombinant expression vector of the present disclosure can comprise, in order from 5' to 3' and in operable linkage: a) a CMV transcriptional control element; b) a nucleotide sequence encoding a reporter mRNA; c) a nucleotide sequence encoding a nuclear localization signal; d) an IRES or other sequence that provides for a bicistronic message; and e) a nucleotide sequence encoding a CMV transactivator that can bind to and regulate the CMV transcriptional control element.

2) In some embodiments, a recombinant expression vector of the present disclosure comprises, in order from 5' to 3' and in operable linkage: a) a herpesvirus transcriptional control element; b) a nucleotide sequence encoding a herpesvirus transactivator that can bind to and regulate the herpesvirus transcriptional control element; c) an IRES or other sequence that provides for a bicistronic message; d) a Kozak consensus sequence; and e) a nucleotide sequence encoding a reporter polypeptide that produces a detectable signal. In other embodiments, a recombinant expression vector of the present disclosure comprises, in order from 5' to 3' and in operable linkage: a) a herpesvirus transcriptional control element; b) a nucleotide sequence encoding a herpesvirus transactivator that can bind to and regulate the herpesvirus transcriptional control element; c) an IRES or other sequence that provides for a bicistronic message; d) a Kozak consensus sequence; and e) a nucleotide sequence encoding a reporter mRNA.

As an example, a recombinant expression vector of the present disclosure can comprise, in order from 5' to 3' and in operable linkage: a) a CMV transcriptional control element; b) a nucleotide sequence encoding a CMV transactivator that can bind to and regulate the CMV transcriptional control element; c) an IRES or other sequence that provides for a bicistronic message; d) a Kozak consensus sequence; and e) a nucleotide sequence encoding a reporter polypeptide that produces a detectable signal. As another example, a recombinant expression vector of the present disclosure can comprise, in order from 5' to 3' and in operable linkage: a) a CMV transcriptional control element; b) a nucleotide sequence encoding a CMV transactivator that can bind to and regulate the CMV transcriptional control element; c) an IRES or other sequence that provides for a bicistronic message; d) a Kozak consensus sequence; and e) a nucleotide sequence encoding a reporter mRNA.

3) In some embodiments, a recombinant expression vector of the present disclosure comprises, in order from 5' to 3' and in operable linkage: a) a herpesvirus transcriptional control element; b) a nucleotide sequence encoding a herpesvirus transactivator that can bind to and regulate the herpesvirus transcriptional control element; c) an IRES or other sequence that provides for a bicistronic message; and d) a nucleotide sequence encoding a polypeptide that produces a detectable signal.

As an example, a recombinant expression vector of the present disclosure can comprise, in order from 5' to 3' and in operable linkage: a) a CMV transcriptional control element; b) a nucleotide sequence encoding a CMV transactivator that can bind to and regulate the CMV transcriptional control element; c) an IRES or other sequence that provides for a bicistronic message; and d) a nucleotide sequence encoding a polypeptide that produces a detectable signal.

4) In some embodiments, a recombinant expression vector of the present disclosure comprises, in order from 5' to 3' and in operable linkage: a) a CMV transcriptional control element; b) a nucleotide sequence encoding a CMV transactivator that can bind to and regulate the CMV transcriptional control element; and c) a nucleotide sequence encoding a polypeptide that produces a detectable signal, where (b) and (c) are in frame, such that the CMV transactivator and the polypeptide that produces a detectable signal are translated as a fusion polypeptide. In other embodiments, a recombinant expression vector of the present disclosure comprises, in order from 5' to 3' and in operable linkage: a) a CMV transcriptional control element; b) a nucleotide sequence encoding a CMV transactivator that can bind to and regulate the CMV transcriptional control element; and c) a nucleotide sequence encoding a reporter mRNA.

As an example, a recombinant expression vector of the present disclosure can comprise, in order from 5' to 3' and in operable linkage: a) a CMV transcriptional control element; b) a nucleotide sequence encoding a CMV transactivator that can bind to and regulate the CMV transcriptional control element; and c) a nucleotide sequence encoding a polypeptide that produces a detectable signal, where (b) and (c) are in frame, such that the CMV transactivator and the polypeptide that produces a detectable signal are translated as a fusion polypeptide. As an example, a recombinant expression vector of the present disclosure can comprise, in order from 5' to 3' and in operable linkage: a) a CMV transcriptional control element; b) a nucleotide sequence encoding a CMV transactivator that can bind to and regulate the CMV transcriptional control element; and c) a nucleotide sequence encoding a reporter mRNA.

5) In some embodiments, a recombinant expression vector of the present disclosure comprises, in order from 5' to 3' and in operable linkage: a) a herpesvirus transcriptional control element; b) a nucleotide sequence encoding a herpesvirus transactivator that can bind to and regulate the herpesvirus transcriptional control element; c) an IRES or other sequence that provides for a bicistronic message; d) a Kozak consensus sequence; e) a nucleotide sequence encoding a reporter polypeptide that produces a detectable signal; and f) a nucleotide sequence encoding a nuclear localization signal. In some embodiments, a recombinant expression vector of the present disclosure comprises, in order from 5' to 3' and in operable linkage: a) a herpesvirus transcriptional control element; b) a nucleotide sequence encoding a herpesvirus transactivator that can bind to and regulate the herpesvirus transcriptional control element; c) an IRES or other sequence that provides for a bicistronic message; d) a Kozak consensus sequence; e) a nucleotide sequence encoding a reporter mRNA; and f) a nucleotide sequence encoding a nuclear localization signal.

As an example, a recombinant expression vector of the present disclosure can comprise, in order from 5' to 3' and in operable linkage: a) a CMV transcriptional control element; b) a nucleotide sequence encoding a CMV transactivator that can bind to and regulate the CMV transcriptional control element; c) an IRES or other sequence that provides for a bicistronic message; d) a Kozak consensus sequence; e) a nucleotide sequence encoding a reporter polypeptide that produces a detectable signal; and f) a nucleotide sequence encoding a nuclear localization signal. As an example, a recombinant expression vector of the present disclosure can comprise, in order from 5' to 3' and in operable linkage: a) a CMV transcriptional control element; b) a nucleotide sequence encoding a CMV transactivator that can bind to and regulate the CMV transcriptional control element; c) an IRES or other sequence that provides for a bicistronic message; d) a Kozak consensus sequence; e) a nucleotide sequence encoding a reporter mRNA; and f) a nucleotide sequence encoding a nuclear localization signal.

Transactivators and Transcriptional Control Elements

Herpesvirus transactivators, and corresponding transcriptional control elements, that are suitable for use in a recombinant nucleic acid include, e.g., cytomegalovirus (CMV) Immediate Early-2 (IE2) polypeptide, and the herpesvirus transcriptional control element is derived from a CMV Major Immediate Early Promoter (MIEP); herpes simplex virus (HSV) immediate early transcription factors Infected Cell Polypeptide 0 (ICP0) and Infected Cell Polypeptide 4 (ICP4) and their cognate promoters in HSV; Kaposi's sarcoma-associated herpesvirus (KSHV; also known as human herpesvirus-8 or HHV-8) RTA polypeptide, and the RTA binding element (RTE); varicella zoster virus (VZV) ORF61 and ORF62 and their cognate promoters; Epstein-Barr Virus (EBV) transactivator Zta, and the cognate Zta promoter; and the like.

CMV

A CMV transactivator that is suitable for use is a CMV Immediate Early-2 (IE2) polypeptide; the corresponding CMV transcriptional control element is derived from a CMV Major Immediate Early Promoter (MIEP).

As noted above, a recombinant nucleic acid that is used to generate a genetically modified host cell of the present disclosure can comprise a nucleotide sequence encoding a CMV IE2 polypeptide, and can comprise a MIEP operably linked to the nucleotide sequence encoding the CMV IE2 polypeptide. Thus, in some embodiments, a recombinant nucleic acid comprises, in order from 5' to 3', a MIEP, and a nucleotide sequence encoding a CMV IE2 polypeptide.

CMV IE2 Polypeptides

A suitable IE2 polypeptide comprises an amino acid sequence having at least about 75%, at least about 80%, at least about 85%, at least about 90%, at least about 95%, at least about 98%, at least about 99%, or 100%, amino acid sequence identity to a contiguous stretch of from about 400 amino acids (aa) to about 450 aa, from about 450 aa to about 500 aa, from about 500 aa to about 550 aa, or from 550 aa to 580 aa, of the amino acid sequence set forth in SEQ ID NO:1 and depicted in FIG. 17A.

A suitable IE2 polypeptide comprises an amino acid sequence having at least about 75%, at least about 80%, at least about 85%, at least about 90%, at least about 95%, at least about 98%, at least about 99%, or 100%, amino acid sequence identity to a polypeptide consisting of: a) an amino acid sequence from the carboxyl-terminal domain of IE2, e.g., comprising from about amino acids 428 through 452 of the amino acid sequence set forth in SEQ ID NO:1 and depicted in FIG. 17A; and b) the carboxyl-terminal 29 residues of IE2. Thus, e.g., in some cases, a suitable IE2 polypeptide comprises an amino acid sequence having at least about 75%, at least about 80%, at least about 85%, at least about 90%, at least about 95%, at least about 98%, at least about 99%, or 100%, amino acid sequence identity to the following amino acid sequence: rcr lgtmcnlals tpflmehtmp vt qptetpped ldtlslaiea aiqdlrnksq.

MIEP

A suitable MIEP comprises the nucleotide sequence CG(n)$_8$CG, where n is any nucleotide. The nucleotide sequence CG(n)$_8$CG as a "crs sequence." A MIEP can comprise a crs sequence embedded within any promoter element. A MIEP can comprise a crs sequence linked to a synthetic promoter; see, e.g., Liu et al. (1991) *J. Virol.* 65:897.

A suitable MIEP comprises a nucleotide sequence having at least about 75%, at least about 80%, at least about 85%, at least about 90%, at least about 95%, at least about 98%, at least about 99%, or 100%, nucleotide sequence identity to a contiguous stretch of from about 300 nucleotides (nt) to about 350 nt, from about 350 nt to about 400 nt, from about 400 nt to about 450 nt, or from about 450 nt to about 502 nt, of the nucleotide sequence set forth in SEQ ID NO:2 and depicted in FIG. 17B.

A suitable MIEP comprises a nucleotide sequence having at least about 75%, at least about 80%, at least about 85%, at least about 90%, at least about 95%, at least about 98%, at least about 99%, or 100%, nucleotide sequence identity to a contiguous stretch of from about 300 nucleotides (nt) to about 400 nt, from about 400 nt to about 500 nt, from about 500 nt to about 600 nt, from about 600 nt to about 700 nt, from about 700 nt to about 800 nt, from about 800 nt to about 900 nt, from about 900 nt to about 1000 nt, from about 1000 nt to about 1200 nt, from about 1200 nt to about 1400 nt, or from about 1400 nt to about 1647 nt of nucleotides 8953 to 10600 of the nucleotide sequence depicted in FIG. 1.

HSV

As noted above, a recombinant nucleic acid that is used to generate a genetically modified host cell of the present disclosure can comprise a nucleotide sequence encoding an HSV ICP0 polypeptide or an ICP4 polypeptide, and can comprise an ICP0 or an ICP4 gene promoter operably linked to the nucleotide sequence encoding the HSV ICP0 polypeptide or the ICP4 polypeptide. Thus, in some embodiments, a recombinant nucleic acid comprises, in order from 5' to 3', an ICP0 gene promoter, and a nucleotide sequence encoding a HSV ICP0 polypeptide. In other embodiments, a recombinant nucleic acid comprises, in order from 5' to 3', an ICP4 gene promoter, and a nucleotide sequence encoding a HSV ICP4 polypeptide.

A suitable HSV ICP0 polypeptide comprises an amino acid sequence having at least about 75%, at least about 80%, at least about 85%, at least about 90%, at least about 95%, at least about 98%, at least about 99%, or 100%, amino acid sequence identity to a contiguous stretch of from about 500 amino acids (aa) to about 550 aa, from about 550 aa to about 600 aa, from about 600 aa to about 650 aa, from about 650 aa to about 700 aa, from about 700 aa to about 750 aa, or from 750 aa to about 776 aa, of the amino acid sequence set forth in SEQ ID NO:3 and depicted in FIG. 18A.

A suitable HSV ICP4 polypeptide comprises an amino acid sequence having at least about 75%, at least about 80%, at least about 85%, at least about 90%, at least about 95%, at least about 98%, at least about 99%, or 100%, amino acid sequence identity to a contiguous stretch of from about 800 amino acids (aa) to about 900 aa, from about 900 aa to about 1000 aa, from about 1000 aa to about 1100 aa, from about 1100 aa to about 1200 aa, or from about 1200 aa to 1298 aa, of the amino acid sequence set forth in SEQ ID NO:10 and depicted in FIG. 22.

A suitable HSV ICP0 promoter comprises a nucleotide sequence having at least about 75%, at least about 80%, at least about 85%, at least about 90%, at least about 95%, at least about 98%, at least about 99%, or 100%, nucleotide sequence identity to a contiguous stretch of from about 300 nucleotides (nt) to about 350 nt, from about 350 nt to about 400 nt, from about 400 nt to about 450 nt, or from about 450 nt to 499 nt, of the nucleotide sequence set forth in SEQ ID NO:4 and depicted in FIG. 18B. See, e.g., Mackem and Roizman (1982) *J. Virol.* 44:939.

EBV

As noted above, a recombinant nucleic acid that is used to generate a genetically modified host cell of the present disclosure can comprise a nucleotide sequence encoding an EBV Zta polypeptide, and can comprise a Zta gene promoter operably linked to the nucleotide sequence encoding the EBV Zta polypeptide. Thus, in some embodiments, a recombinant nucleic acid comprises, in order from 5' to 3', a Zta gene promoter, and a nucleotide sequence encoding an EBV Zta polypeptide. Zta is also referred to in the art as BZLF1; see, e.g., Lieberman et al. (1990) *J. Virol.* 64:1143.

A suitable EBV Zta polypeptide comprises an amino acid sequence having at least about 75%, at least about 80%, at least about 85%, at least about 90%, at least about 95%, at least about 98%, at least about 99%, or 100%, amino acid sequence identity to a contiguous stretch of from about 175 amino acids (aa) to about 200 aa, from about 200 aa to about 225 aa, or from about 225 aa to 245 aa, of the amino acid sequence set forth in SEQ ID NO:5 and depicted in FIG. 19A.

A suitable Zta promoter comprises a nucleotide sequence having at least about 75%, at least about 80%, at least about 85%, at least about 90%, at least about 95%, at least about 98%, at least about 99%, or 100%, nucleotide sequence identity to a contiguous stretch of from about 20 nucleotides (nt) to about 50 nt, from about 50 nt to about 75 nt, from about 75 nt to about 100 nt, from about 100 nt to about 150 nt, from about 150 nt to about 200 nt, or from about 200 nt to 222 nt, of the nucleotide sequence set forth in SEQ ID NO:6 and depicted in FIG. 19B.

A suitable Zta promoter can include the nucleotide sequence 5'-TGCATGAGCCACAGGCATT-3' (SEQ ID NO:44), corresponding to −134 to −116 of the Zta promoter. A suitable Zta promoter can further include the nucleotide sequence 5'-GCTGTCTATTTTTGACACCAGCTTATT-3' (SEQ ID NO:45), corresponding to −203 to −177 of the Zta promoter.

HHV-8

As noted above, a recombinant nucleic acid that is used to generate a genetically modified host cell of the present disclosure can comprise a nucleotide sequence encoding an HHV-8 RTA polypeptide, and can comprise an RTA gene promoter operably linked to the nucleotide sequence encoding the HHV-8 RTA polypeptide. Thus, in some embodiments, a recombinant nucleic acid comprises, in order from 5' to 3', an RTA gene promoter, and a nucleotide sequence encoding an HHV-8 RTA polypeptide.

A suitable HHV-8 RTA polypeptide comprises an amino acid sequence having at least about 75%, at least about 80%, at least about 85%, at least about 90%, at least about 95%, at least about 98%, at least about 99%, or 100%, amino acid sequence identity to a contiguous stretch of from about 500 amino acids (aa) to about 550 aa, from about 550 aa to about 600 aa, from about 600 aa to about 650 aa, or from about 650 aa to about 691 aa, of the amino acid sequence set forth in SEQ ID NO:7 and depicted in FIG. 20A. HHV-8 RTA is also known as Open Reading Frame 50 (ORF50). See, e.g., Damania et al. (2004) *J. Virol.* 78:5491.

A suitable RTA promoter comprises a nucleotide sequence having at least about 75%, at least about 80%, at least about 85%, at least about 90%, at least about 95%, at least about 98%, at least about 99%, or 100%, nucleotide sequence identity to a contiguous stretch of from about 100 nucleotides (nt) to about 150 nt, from about 150 nt to about 200 nt, or from about 200 nt to 215 nt, of the nucleotide sequence set forth in SEQ ID NO:8 and as depicted in FIG. 20B. For a discussion of an RTA promoter; see, e.g., Deng et al. (2000) *J. Gen. Virol.* 57:629.

VZV

As noted above, a recombinant nucleic acid that is used to generate a genetically modified host cell of the present disclosure can comprise a nucleotide sequence encoding a (VZV) ORF61 and/or ORF62 polypeptide, and can comprise an ORF61 gene promoter operably linked to the nucleotide sequence encoding the ORF61 and/or ORF62 polypeptide. Thus, in some embodiments, a recombinant nucleic acid comprises, in order from 5' to 3', an ORF61 gene promoter, and a nucleotide sequence encoding an ORF61 and/or ORF62 polypeptide.

A suitable (VZV) ORF61 polypeptide comprises an amino acid sequence having at least about 75%, at least about 80%, at least about 85%, at least about 90%, at least about 95%, at least about 98%, at least about 99%, or 100%, amino acid sequence identity to a contiguous stretch of from about 300 amino acids (aa) to about 350 aa, from 350 aa to about 400 aa, from about 400 aa to about 450 aa, or from about 450 aa to 467 aa, of the amino acid sequence set forth in SEQ ID NO:11 and depicted in FIG. 23.

A suitable (VZV) ORF62 polypeptide comprises an amino acid sequence having at least about 75%, at least about 80%, at least about 85%, at least about 90%, at least about 95%, at least about 98%, at least about 99%, or 100%, amino acid sequence identity to a contiguous stretch of from about 800 amino acids (aa) to about 900 aa, from about 900 aa to about 1000 aa, from about 1000 aa to about 1100 aa, from about 1100 aa to about 1200 aa, or from about 1200 aa to about 1310 aa, of the amino acid sequence set forth in SEQ ID NO:12 and depicted in FIG. 24.

A suitable (VZV) ORF61 promoter comprises a nucleotide sequence having at least about 75%, at least about 80%, at least about 85%, at least about 90%, at least about 95%, at least about 98%, at least about 99%, or 100%, nucleotide sequence identity to a contiguous stretch of from about 50 nucleotides (nt) to about 100 nt, from about 100 nt to about 125 nt, from about 125 nt to about 150 nt, from about 150 nt to about 175 nt, or from about 175 nt to about 180 nt, of the nucleotide sequence set forth in SEQ ID NO:13 and depicted in FIG. 25.

A suitable (VZV) ORF61 promoter can comprise the sequence:

agtgggtgggacttaaaagaaatgggtggagggatataggggtgtgtctt (SEQ ID NO:46), e.g., from about −95 to about −45 relative to the transcription start site of the ORF1 gene. See, e.g., Wang et al. (2009) *J. Virol.* 83:7560.

Reporter Polypeptides

As noted above, a recombinant expression vector of the present disclosure can include a nucleotide sequence that encodes a reporter polypeptide that produces a detectable signal. The polypeptide that produces a detectable signal can be translated as a separate translation product; or, the polypeptide that produces a detectable signal can be fused to a CMV transactivator in a single translation product. Suitable detectable signal-producing polypeptides include, e.g., fluorescent proteins; enzymes that catalyze a reaction that generates a detectable signal as a product; and the like. Detectable signals include, e.g., fluorescent signals (fluorescence), colorimetric signals (color), luminescent signals (luminescence), and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use. A Discosoma Red (DsRed) polypeptide as described in, e.g., Campbell et al. ((2002) *Proc. Natl. Acad. Sci. USA* 99:7877) is suitable for use.

As one non-limiting example, a suitable fluorescent protein can comprise an amino acid sequence having at least about 75%, at least about 80%, at least about 85%, at least about 90%, at least about 95%, at least about 98%, at least about 99%, or 100%, amino acid sequence identity with a contiguous stretch of from about 150 amino acids to about 200 amino acids, or from about 200 amino acids to 236 amino acids, of the amino acid sequence set forth in SEQ ID NO:8 and depicted in FIG. 21.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, luciferase, glucose oxidase (GO), and the like.

Reporter mRNAs

As noted above, a subject recombinant expression vector can include a nucleotide sequence encoding a reporter mRNA that can be detected. See, e.g., Weil et al. (2010) *Trends Cell Biol.* 20:380, for various methods of detecting a reporter mRNA.

For example, a nucleotide sequence can encode a reporter mRNA that includes one or more binding sites for a polypeptide, where the polypeptide can be fused with a polypeptide that provides a detectable signal. For example, a nucleotide sequence can encode a reporter mRNA that includes one or more MS2 binding sites (MS2 stem-loop motifs). Such an mRNA can be detected using MS2 coat protein (MCP) fused to a fluorescent polypeptide.

As another example, a reporter mRNA encoded by a subject recombinant expression vector can be detected by hybridization with a detectably-labeled nucleic acid. For example, a fluorescence in situ hybridization (FISH) probe can be used to detect a reporter mRNA.

IRES

As noted above, a subject recombinant nucleic acid can include an internal ribosome binding entry site (IRES). Suitable IRES sequences include, e.g., a picornavirus IRES; a hepatitis C virus IRES; a Kaposi's sarcoma-associate herpesvirus IRES: and the like. Suitable IRES sequence can be found at, e.g., on the internet at http(colon)//iresite(dot) org.

For example, a suitable IRES can comprise a nucleotide sequence having at least about 75%, at least about 80%, at least about 85%, at least about 90%, at least about 95%, at least about 98%, at least about 99%, or 100%, nucleotide sequence identity with a contiguous stretch of from about 300 nucleotides (nt) to about 350 nt, from about 350 nt to about 400 nt, from about 400 nt to about 450 nt, from about 450 nt to about 500 nt, from about 500 nt to about 550 nt, or from about 550 nt to 588 nt, of nucleotides 51 to 638 of the nucleotide sequence depicted in FIG. 1.

Nuclear Localization Signals

As noted above, a subject recombinant nucleic acid can include a nucleotide sequence encoding a nuclear localization signal (NLS). NLS are known in the art; any known NLS can be included. Suitable NLS include, but are not limited to: PKKKRKV (SEQ ID NO:36) (an SV40 NLS); KRPAATKKAGQAKKKK (SEQ ID NO:37) (the NLS of nucleoplasmin); SVGRATSTAELLVQGEEEVPAKKTK-TIVSTAQISESRQTR (SEQ ID NO:38), VQGEEEVPAK-KTKTIV (SEQ ID NO:39), VPAKKTKTIV (SEQ ID NO:40), or PAKKTKT (SEQ ID NO:41) (NLS of titin); a bipartite motif consisting of two basic domains separated by a variable number of spacer amino acids and exemplified by the *Xenopus* nucleoplasmin NLS (KR) OCXXXXXXXXKKKL) (SEQ ID NO:47); SSLRPPKKKRKV (SEQ ID NO:42); and SSLRPPKKRGRF (SEQ ID NO:43).

Vectors

A recombinant expression vector of the present disclosure can be based on a variety of vectors, e.g., a viral vector, a plasmid, a cosmid, a minicircle, a phage, etc. In some cases, a subject recombinant expression vector is a lentiviral vector. In some cases, a subject recombinant expression vector is a retroviral vector. In some cases, a subject recombinant expression vector is a plasmid vector.

Suitable viral vectors include, e.g. viral vectors based on vaccinia virus; poliovirus; adenovirus (see, e.g., Li et al., *Invest Opthalmol Vis Sci* 35:2543 2549, 1994; Borras et al., *Gene Ther* 6:515 524, 1999; Li and Davidson, *PNAS* 92:7700 7704, 1995; Sakamoto et al., *H Gene Ther* 5:1088 1097, 1999; WO 94/12649, WO 93/03769; WO 93/19191; WO 94/28938; WO 95/11984 and WO 95/00655); adeno-associated virus (see, e.g., Ali et al., *Hum Gene Ther* 9:81 86, 1998, Flannery et al., *PNAS* 94:6916 6921, 1997; Bennett et al., *Invest Opthalmol Vis Sci* 38:2857 2863, 1997; Jomary et al., *Gene Ther* 4:683 690, 1997, Rolling et al., *Hum Gene Ther* 10:641 648, 1999; Ali et al., *Hum Mol Genet* 5:591 594, 1996; Srivastava in WO 93/09239, Samulski et al., *J. Vir.* (1989) 63:3822-3828; Mendelson et al., *Virol.* (1988) 166:154-165; and Flotte et al., *PNAS* (1993) 90:10613-10617); SV40; herpes simplex virus; human immunodeficiency virus (see, e.g., Miyoshi et al., *PNAS* 94:10319 23, 1997; Takahashi et al., *J Virol* 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

System

The present disclosure provides a system comprising: a) a first recombinant expression vector, where the first recombinant expression vector comprises: i) a nucleotide sequence encoding a CMV transactivator; ii) a transcriptional control element operably linked to the nucleotide sequence encoding the CMV transactivator; and iii) a nucleotide sequence encoding a first reporter (e.g., a first reporter polypeptide that provides a detectable signal; a first reporter mRNA), where the nucleotide sequence encoding the first reporter is operably linked to the transcriptional control element; and b) a second recombinant expression vector, where the second recombinant expression vector comprises a nucleotide sequence encoding a second reporter (e.g., a second polypeptide that provides a detectable signal; a second reporter mRNA), where the nucleotide sequence is operably linked to a CMV transcriptional control element that is derived from a naturally occurring CMV transcriptional control element that regulates transcription of the transactivator in a wild-type CMV.

The CMV transactivator encoded by the first recombinant expression vector can bind to and regulate the CMV transcriptional control element present in the second recombinant expression vector.

In some cases, the first and the second reporter polypeptide that produces a detectable signal are different from one another, such that the signal produced by the first reporter polypeptide is readily distinguishable from the signal produced by the second reporter polypeptide. As non-limiting examples, the first polypeptide can be mCherry, and the second polypeptide can be DsRed; the first polypeptide can be a GFP, and the second polypeptide can be a YFP; etc.

The first and/or the second recombinant expression vector can further include one or more additional elements, such as an NLS; a Kozak consensus sequence; an origin of replication that is functional in a eukaryotic cell; a polyadenylation signal; a multiple cloning site; a nucleotide sequence encoding a selectable marker suitable for use in a prokaryotic cell; and a nucleotide sequence encoding a selectable marker suitable for use in a eukaryotic cell.

Elements included in the first and second recombinant expression vectors are described above.

In the first recombinant expression vector, the transcriptional control element (e.g., promoter) can be any promoter that is functional in a mammalian cell. Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, an Ef1a promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

In some embodiments, the first recombinant expression vector comprises, in order from 5' to 3' and in operable linkage: i) a transcriptional control element; ii) a nucleotide sequence encoding a CMV transactivator; and iii) a nucleotide sequence encoding a first reporter polypeptide that provides a detectable signal, where the nucleotide sequence encoding the CMV transactivator is in frame with the nucleotide sequence encoding the first reporter polypeptide that provides a detectable signal, such that the translation product is a fusion polypeptide comprising the transactivator and the first reporter polypeptide that provides a detectable signal. In some cases, the first recombinant expression vector comprises, in order from 5' to 3' and in operable linkage: i) a transcriptional control element; ii) a nucleotide sequence encoding a CMV transactivator; and iii) a nucleotide sequence encoding a first reporter mRNA.

In some embodiments, the first recombinant expression vector comprises, in order from 5' to 3' and in operable linkage: i) a transcriptional control element; ii) a nucleotide sequence encoding a CMV transactivator; iii) an IRES or other nucleotide sequence that provides for a bicistronic message; and iii) a nucleotide sequence encoding a first reporter polypeptide that provides a detectable signal.

In some embodiments, the second recombinant expression vector comprises, in order from 5' to 3' and in operable linkage: i) a CMV transcriptional control element that is derived from a naturally occurring CMV transcriptional control element that regulates transcription of a CMV transactivator in a wild-type CMV; and ii) a nucleotide sequence encoding a second reporter polypeptide that provides a detectable signal. In some embodiments, the second recombinant expression vector comprises, in order from 5' to 3' and in operable linkage: i) a CMV transcriptional control element that is derived from a naturally occurring CMV transcriptional control element that regulates transcription of a CMV transactivator in a wild-type CMV; and ii) a nucleotide sequence encoding a second reporter mRNA.

In some embodiments, the second recombinant expression vector comprises, in order from 5' to 3' and in operable linkage: i) a CMV transcriptional control element that is derived from a naturally occurring CMV transcriptional control element that regulates transcription of a CMV transactivator in a wild-type CMV; ii) a nucleotide sequence encoding a second reporter polypeptide that provides a detectable signal; iii) an IRES or other nucleotide sequence that provides for a bicistronic message; and iv) a nucleotide sequence encoding a third reporter polypeptide that provides a detectable signal.

Genetically Modified Host Cells

The present disclosure provides a genetically modified mammalian host cell, where the mammalian host cell is genetically modified with: a) a recombinant expression vector as described above; b) a system comprising two recombinant expression vectors, as described above; or c) a recombinant expression vector comprising a CMV transcriptional control element operably linked to a reporter (e.g., a reporter polypeptide that generates a detectable signal; a reporter mRNA). A subject genetically modified mammalian host cell is an isolated in vitro cell. A genetically modified host cell of the present disclosure can be used in a screening method to identify candidate anti-viral agents.

A mammalian host cell that is suitable for genetic modification with a) a recombinant expression vector as described above; b) a system comprising two recombinant expression vectors, as described above; or c) a recombinant expression vector comprising a CMV transcriptional control element operably linked to a reporter (e.g., a reporter polypeptide that generates a detectable signal; a reporter mRNA) can be a transformed (immortalized) cell line, or a primary cell (e.g., a primary, non-cancerous cell).

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), HLHepG2 cells, and the like.

A genetically transformed mammalian cell of the present disclosure is useful for carrying out a screening method, which screening method is described in more detail below, for identifying candidate anti-viral agents.

As noted above, in some cases, a subject genetically modified mammalian host cell is genetically modified with a subject recombinant expression vector comprising a CMV transcriptional control element operably linked to a reporter (e.g., a reporter polypeptide that generates a detectable signal; a reporter mRNA). In these embodiments, a CMV transactivator per se can be introduced into the mammalian host cell. For example, a CMV transactivator polypeptide can include a protein transduction domain; and the transactivator with the PTD can be introduced into a mammalian host cell. As a non-limiting example, a CMV transactivator is linked, covalently or non-covalently, to a protein transduction domain.

"Protein Transduction Domain" or PTD refers to a polypeptide, polynucleotide, carbohydrate, or organic or inorganic compound that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of a CMV transactivator. In some embodiments, a PTD is covalently linked to the carboxyl terminus of a CMV transactivator.

Exemplary protein transduction domains include but are not limited to a minimal undecapeptide protein transduction domain (corresponding to residues 47-57 of HIV-1 TAT comprising YGRKKRRQRRR; SEQ ID NO:21); a polyarginine sequence comprising a number of arginines sufficient to direct entry into a cell (e.g., 3, 4, 5, 6, 7, 8, 9, 10, or 10-50 arginines); a VP22 domain (Zender et al., Cancer Gene Ther. 2002 June; 9(6):489-96); an Drosophila Antennapedia protein transduction domain (Noguchi et al., Diabetes 2003; 52(7):1732-1737); a truncated human calcitonin peptide (Trehin et al. Pharm. Research, 21:1248-1256, 2004); polylysine (Wender et al., PNAS, Vol. 97:13003-13008); RRQRRTSKLMKR (SEQ ID NO:22); Transportan GWTLNSAGYLLGKINLKALAALAKKIL (SEQ ID NO:23); KALAWEAKLAKALAKALAKHLAKALAKA-LKCEA (SEQ ID NO:24); and RQIKIWFQNRRMKWKK (SEQ ID NO:25). Exemplary PTDs include but are not limited to, YGRKKRRQRRR (SEQ ID NO:21), RKKRRQRRR (SEQ ID NO:26); an arginine homopolymer of from 3 arginine residues to 50 arginine residues; YARAAARQARA (SEQ ID NO:27); THRLPRRRRRR (SEQ ID NO:28); and GGRRARRRRRR (SEQ ID NO:29).

As noted above, in some cases, a subject genetically modified mammalian host cell is genetically modified with a subject recombinant expression vector comprising a CMV transcriptional control element operably linked to a reporter (e.g., a reporter polypeptide that generates a detectable signal; a reporter mRNA). In these embodiments, in vitro-transcribed mRNA comprising nucleotide sequence encoding a CMV transactivator can be introduced into the mammalian host cell.

Screening Methods

The present disclosure provides methods of identifying agents that disrupt feedback regulation of a herpesvirus transcriptional control element by a herpesvirus transactivator. The present disclosure provides a method of identifying a candidate anti-viral agent, the method comprising: a) contacting a test agent with a genetically modified mammalian host cell of the present disclosure; and b) determining the effect, if any, of the test agent on transcription of the nucleotide sequence encoding the CMV transactivator. In some cases, an agent that increases transcription of the nucleotide sequence encoding the CMV transactivator, compared to a control, is considered a candidate anti-viral agent. In some cases, an agent that reduces transcription of the nucleotide sequence encoding the CMV transactivator, compared to a control, is considered a candidate anti-viral agent.

Whether a test agent increases or reduces transcription of the nucleotide sequence encoding the CMV transactivator can be determined by: a) measuring the level of a reporter encoded by a nucleotide sequence that is operably linked to a CMV transcriptional control element controlled by the CMV transactivator in the presence of the test agent; and b) measuring the level of a reporter encoded by a nucleotide sequence that is operably linked to a CMV transcriptional control element controlled by the CMV transactivator in the absence of the test agent.

Where the reporter is a polypeptide that produces a detectable signal, measuring the level of the reporter can involve detecting the signal produced by the reporter polypeptide; e.g., detecting fluorescence, luminescence, color, etc., produced by the reporter polypeptide. Where the reporter polypeptide that produces a detectable signal is an enzyme that produces a detectably labeled product upon action on a substrate, measuring the level of the reporter can involve detecting the signal produced the product; e.g., detecting fluorescence, chemiluminescence, color, etc., produced by the product of the enzymatic reaction. Methods for detecting color, fluorescence, luminescence, etc., are well known in the art.

Where the reporter is an mRNA, the level of the reporter can be measured using any of a variety of assays. For example, as described above, the level of a reporter mRNA can be detected using FISH. As another example, the level of a reporter mRNA can be detected by detecting binding to the mRNA of a fusion polypeptide that comprises: a) a polypeptide that binds to the reporter mRNA; and b) a polypeptide that produces a detectable signal (e.g., a fluorescent polypeptide).

In some cases, a test agent that reduces transcription of the nucleotide sequence encoding the CMV transactivator, compared to a control, is considered a candidate anti-viral agent. For example, a test agent that reduces transcription of nucleotide sequence encoding the CMV transactivator by at least about 10%, at least about 15%, at least about 20%, at least about 25%, at least about 30%, at least about 40%, at least about 50%, or more than 50%, compared to a control, is considered a candidate anti-viral agent.

In some cases, a test agent that increases transcription of the nucleotide sequence encoding the CMV transactivator, compared to a control, is considered a candidate anti-viral agent. For example, a test agent that increases transcription of nucleotide sequence encoding the CMV transactivator by at least about 10%, at least about 15%, at least about 20%, at least about 25%, at least about 30%, at least about 40%, at least about 50%, at least about 75%, at least about 100% (or 2-fold), at least about 2.5-fold, at least about 5-fold, at least about 10-fold, at least about 25-fold, at least about 50-fold, or at least about 100-fold, or more, compared to a control, is considered a candidate anti-viral agent.

As used herein, the term "determining" refers to both quantitative and qualitative determinations and as such, the term "determining" is used interchangeably herein with "assaying," "measuring," and the like.

The terms "test agent," "agent," "substance," and "compound" are used interchangeably herein. Test agents encompass numerous chemical classes, typically synthetic, semi-synthetic, or naturally-occurring inorganic or organic molecules. Test agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

Test agents can be small organic or inorganic compounds having a molecular weight of more than 50 and less than about 10,000 daltons, e.g., a test agent may have a molecular weight of from about 50 daltons to about 100 daltons, from about 100 daltons to about 150 daltons, from about 150 daltons to about 200 daltons, from about 200 daltons to about 500 daltons, from about 500 daltons to about 1000 daltons, from about 1,000 daltons to about 2500 daltons, from about 2500 daltons to about 5000 daltons, from about 5000 daltons to about 7500 daltons, or from about 7500 daltons to about 10,000 daltons. Test agents may comprise functional groups necessary for structural interaction with proteins, e.g., hydrogen bonding, and may include at least an amine, carbonyl, hydroxyl or carboxyl group, and may contain at least two of the functional chemical groups. The test agents may comprise cyclical carbon or heterocyclic structures and/or aromatic or polyaromatic structures substituted with one or more of the above functional groups. Test agents are also found among biomolecules including peptides, saccharides, fatty acids, steroids, purines, pyrimidines, derivatives, structural analogs or combinations thereof.

Assays of the invention include controls, where suitable controls include a sample (e.g., a sample comprising a subject genetically modified mammalian cell in the absence of the test agent). Generally a plurality of assay mixtures is run in parallel with different test agent concentrations to obtain a differential response to the various concentrations. Typically, one of these concentrations serves as a negative control, i.e., where the test agent is present at zero concentration or below the level of detection.

A variety of other reagents may be included in the screening assay. These include reagents like salts, neutral proteins, e.g. albumin, detergents, etc., including agents that are used to facilitate optimal enzyme activity and/or reduce non-specific or background activity. Reagents that improve the efficiency of the assay, such as protease inhibitors, anti-microbial agents, etc. may be used. The components of the assay mixture are added in any order that provides for the requisite activity. Incubations are performed at any suitable temperature, typically between 4° C. and 40° C. Incubation periods are selected for optimum activity, but may also be optimized to facilitate rapid high-throughput screening. Typically between 0.1 hour and 1 hour will be sufficient.

A test agent that is deemed a candidate anti-viral agent can be chemically modified, e.g., to increase solubility, to increase bioavailability, etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Using an integrated approach that couples mathematical modeling with quantitative time-lapse microscopy, it is shown that IE2 negative feedback is highly cooperative, which allows the virus to overcome the rate-versus-level tradeoff (FIG. 26A) by accelerating IE2 gene expression without any measurable increase in the steady-state expression level.

Methods

Cloning of Recombinant Viruses

The CMV IE2-YFP virus was constructed by inserting EYFP (Clontech) to the 3' end of IE2 exon 5 in the parent AD169 as described (Moorman et al., 2008; Yu et al., 2002).

The CMV GFP control virus (Yu et al., 2003) encodes an SV40 promoter-EGFP cassette. The CMV 0.4 I crs IE2-YFP virus was constructed from the CMV IE2-YFP background as described (Cuevas-Bennett and Shenk, 2008). Viral stocks were titered by $TCID_{50}$ (Nevels et al., 2004). To verify the integrity of the CMV Δcrs IE2-YFP virus, a rescue virus, CMV ΔcrsREVERT IE2-YFP, was constructed by homologous recombination, whereby CMV Δcrs IE2-YFP BAC DNA (20 μg) and a ~2.5 kb wild-type MIEP DNA fragment (2.5 μg) were co-transfected by electroporation into $10^6$ MRC5 cells, and subjected to two rounds of plaque purification.

Cell-culture Conditions and Drug Perturbations

MRC5 fibroblasts and life-extended human foreskin fibroblasts (HFFs) (Bresnahan and Shenk, 2000) were maintained in Dulbecco's Modified Eagle's Medium (DMEM) supplemented with 10% fetal bovine serum (FBS) and 50 U/ml penicillin-streptomycin at 37° C. and 5% $CO_2$ in a humidified incubator. ARPE-19 cells were maintained in a 1:1 mixture of DMEM/F-12 (Mediatech Inc.) with 10% FBS (HyClone) and 50 U/ml Penicillin-Streptomycin (Mediatech Inc.). Cells were pretreated in a final concentration of 1 mM VPA (Calbiochem).

Quantitative Western Blot Analysis

MRC5s at ~60% confluency were infected at MOI=1. To synchronize viral entry, adsorption was done at 4° C. for 30 min., cells washed once in PBS (Mediatech, Inc.), fresh media added, and cells placed at a 37° C. in a humidified $CO_2$ incubator. Time points were collected every 1-2 hrs for 20-24 hrs as indicated. Sample collection, protein transfer, and blot preparation were as previously described (Bolovan-Fritts et al., 2004) and samples were loaded and separated on precast SDS PAGE 10% or 7.5% bisacrylamide gels (Bio-Rad).

For quantitative IE2 detection, the 1° antibody MAB810 (Millipore) was used at 1:100 and 2° antibody 926-32212 (LI-COR™) was used at a dilution of 1:20,000. For normalization, anti-beta tubulin antibody 26-42211 (LI-COR™) used at a dilution of 1:2000 followed by 2' antibody 926-68073 (LI-COR™) at a dilution of 1:20,000. Blots were scanned and quantified on a LI-COR™ Odyssey™ according to manufacturer's protocols.

Time-lapse Fluorescence Microscopy Measurements

Life-extended HFFs and PML knockdown HFFs (a gift from Roger Everett) were passed onto a 96-well glass-bottom plate (Thermo Fisher Scientific) and grown to confluency to hold cells in the G0. Cells were synchronously infected on ice for 30 mins at MOI=1 (infection with mutant was done at room temperature). Live cells were imaged using a 20× oil objective on a spinning-disk confocal microscope (Olympus DSU™) equipped with a 37° C., humidified, 5% $CO_2$ live-cell chamber. Image collection began when YFP signal was first detected and frames were captured every 10 minutes for 16-24 hours using an exposure time between 200 and 800 msec. Single-cell tracking and segmentation were performed with custom-written code in MatLab™ (Mathworks) as previously described (Weinberger et al., 2008). Homo-FRET imaging was performed as previously described (Weinberger and Shenk, 2007).

Mathematical Modeling to Estimate H from Time-lapse Microscopy Data and Closed-loop Analysis to Measure H from Flow Cytometry Data Numerical simulations and fitting of an ODE model were performed in Berkeley Madonna™ (www(dot)berkeleymadonna(dot)com).

Mathematica™ (Wolfram Research) was used for closed-loop analysis. Standard lentiviral cloning was used to create minimal MIE circuits (Dull et al., 1998). The minimal MIEP-IE2-GFP and MIEP-GFP circuits are driven by a full-length ~2.5 kb MIE promoter-enhancer (MIEP) that spans the sequence from the MIEP modulator at the 5' edge to the junction of IE exons 1 and 2. The MIEP was PCR-cloned from AD169 into pLEIGW (a gift from Thor Lemishka) in place of the EF1a promoter. This full-length MIEP drives an IE2-IRES-GFP or mCherry-IRES-GFP cassette. IE2 was cloned from pRSV-IE86 (a gift from Jay Nelson). ARPE-19 cells were infected and FACS sorted for GFP to create stably expressing cell lines. Cells were treated with TSA for 17 hours, and GFP expression was quantified by flow cytometry. Live cells were gated by forward-versus-side scattering on a FacsCalibur™ cytometer (BD Biosciences) and mean fluorescence intensity recorded. At least 20,000 live cells were recorded for each experiment and data was analyzed in FlowJo™ (Treestar Inc.).

Replication Kinetics

Confluent MRC5 monolayers at ~5×$10^4$ cells per well were infected at indicated MOIs using 0.45 μm pre-filtered virus inoculum stocks diluted in culture media. Inoculums were calculated based on plaque-assay titrations (Bolovan-Fritts and Wiedeman, 2001), shown as time point 0 in each figure. Inoculum was then removed and replaced with 1 mL fresh media. Infected wells were collected in triplicate at indicated time points and stored at −80° C. To measure replication, samples were thawed and prepared as a 10-fold serial-dilution series in culture media, analyzed by $TCID_{50}$, then converted to PFU/ml. Error ranges were calculated by standard deviation.

Minimal Synthetic Circuit Experiments

MIEPΔcrs-IE2-GFP was constructed by PCR cloning MIEPΔcrs from the CMV Δcrs IE2-YFP bacmid and inserted into MIEP-IE2-GFP. ARPE-19 cells were transduced with the MIEP-IE2-GFP and MIEPΔcrs-IE2-GFP vectors and FACS sorted for GFP. The transduced cell lines were allowed to recover for 24 hours before the percentage of GFP-expressing cells for each cell line was quantified. Live cells were gated by forward versus side scattering on a FacsCalibur cytometer. On the first day after recovery, 2,500 GFP events were recorded. Subsequently, at least 10,000 GFP events were recorded for each experiment and analyzed using FlowJo™. For genomic PCR, genomic DNA was purified using a NucleoSpin Tissue kit (Clontech).

Immunofluorescence and Brdu-labeled Virus Detection

Brdu-labeled virus was grown and detected by adapting a previously published method (Rosenke and Fortunato, 2004). Cells were grown on 16-well chamber slides (Lab-Tek) and infected with either CMV IE2-YFP or Δcrs IE2-YFP virus on ice and with 1% FCS media to synchronize infection. After 3 hours, cells were washed, fixed, and permeabilized (Rosenke and Fortunato, 2004). PML was detected by a polyclonal PML rabbit antibody (Santa Cruz) at a 1:500 dilution, with secondary goat anti-rabbit Alexa 488 antibody (Invitrogen) at 1:500. After PML detection, the cells were stained with DAPI (Invitrogen) for 15 minutes before a second fixation with 3% formaldehyde. Brdu-labeled viral genomes were detected using a monoclonal rat Brdu antibody (Accurate Chemical Scientific Corp.) at 1:250, followed by secondary donkey anti-rat antibody conjugated with Alexa Fluor 568 (Invitrogen) at 1:500. Cells were mounted with ProLong Gold mounting media (Invitrogen) and a #1.5 cover slip (Nunc). Cover slips were imaged on a Zeiss Observer Z1 spinning-disk confocal microscope with a Plan-FLUAR 100x/1.45 oil objective. Co-localization analysis was performed in Slidebook™ 5.0 (Imaging Innovations, Inc.).

Results

Transcriptional Acceleration-Without-Amplification in CMV

Figure 26:
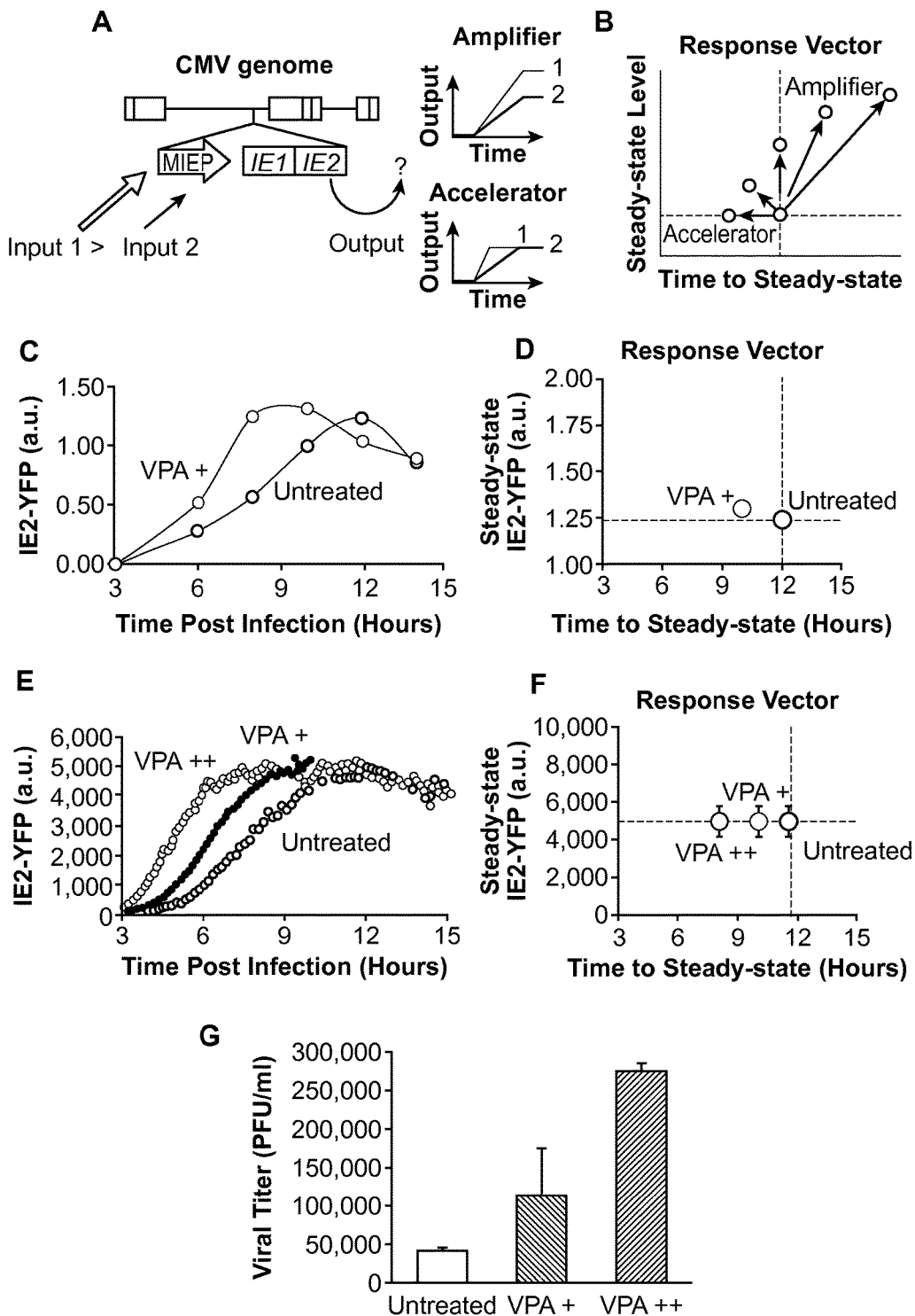
FIGS. 26A-G depict data showing that CMV encodes an endogenous accelerator of gene expression and acceleration provides a viral replication advantage.

We examined MIE gene-expression levels after increasing MIEP activity using transcriptional activators known to upregulate MIEP activity (Choi et al., 2005; Fan et al., 2005; Hummel and Abecassis, 2002). These transcriptional activators, Valproic Acid (VPA), Trichostatin A (TSA), or Tumor Necrosis Factor Alpha (TNF-α), appear to accelerate IE2 expression but do not amplify IE2 protein levels, as measured by quantitative Western blot (FIG. 26C-D). To test whether IE2 was being accelerated (but not amplified) within single cells, quantitative live time-lapse microscopy was used to track single cells undergoing infection by a recombinant CMV encoding yellow fluorescent protein (YFP) fused to the IE2 open reading frame. This recombinant CMV IE2-YFP virus replicates with wild-type kinetics and IE2-YFP levels are equivalent to wild-type IE2 levels. In agreement with previously reported IE2 fusion viruses, the IE2-YFP fusion protein correctly localizes to ND10 domains during infection (Sourvinos et al., 2007). Strikingly, increasing the activity of the MIEP by VPA pretreatment significantly accelerates IE2 expression in single cells but does not amplify steady-state IE2 levels in these single cells (FIG. 26E-F)—a result also observed under TSA or TNF-α treatment. Flow cytometry analysis confirms that acceleration without amplification is not an artifact of image processing.

To rule out the possibility that these results were caused by changes in cell physiology induced by pre-treatment with VPA (or TSA or TNF-α), we also generated an IE2-YFP virus that carried increased levels of the viral transactivator pp71 (Bresnahan and Shenk, 2000) and confirmed that this pp71+ virus, with high levels of packaged pp71 tegument factor, accelerates IE2 expression in the absence of pretreatment. As an additional control, a generalized transcriptional activator that does not specifically activate the MIE promoter during active infection was used, and it fails to accelerate IE2 expression in single cells. These controls argue that accelerated rates of MIE expression result specifically from increased activation of the MIE promoter and not from generalized activation of the target cell. Thus, the MIE circuit appears to act as an 'accelerator' that allows only the rate of IE2 expression to change without allowing significant change in the steady-state levels of IE2.

Acceleration Provides a Fitness Advantage for the Virus

Previous studies in RNA viruses have noted that small increases in a single round of replication are sufficient to allow a viral strain to competitively exclude other 'less fit' strains in resource-limited environments; in other words, the strain with the highest basic reproductive number ($R_0$), which is measured during a single round of infection, wins and excludes all other competing strains, even if that strain's $R_0$ is only marginally greater than the closest competitor (Nowak and May, 2000).

To test if acceleration of IE2 expression provides any functional advantage for the virus, we analyzed viral replication kinetics after the first round of viral maturation (~96 hours) from cells infected with CMV IE2-YFP virus (FIG. 26G). The results show that incremental increases in transcriptional activation, and the resulting acceleration in MIE kinetics, generate correlated increases in viral replication fitness with a 72-hour VPA pre-treatment, yielding an approximately five-fold increase in viral replication compared to the untreated control. IE2 acceleration and enhanced replication are also observed in the low-passage clinical CMV isolate TB40-E, which exhibits a nine-fold increase in titer.

FIGS. 26A-G: CMV encodes an endogenous accelerator of gene expression and acceleration provides a viral replication advantage. A, Schematic of the CMV genome (~230 kb), with the MIE regulatory circuit (~5 kb) magnified. Increased inputs (transcriptional activation) to the MIE promoter could result in either increased output of protein levels (amplifier) or acceleration of gene expression without amplification of level (accelerator). B, The "response-vector" allows convenient comparison between output time-lapse trajectories (i.e. white versus red points) in terms of steady-state level versus the time to steady state. Circuits that act as amplifiers respond to increased input by shifting vertically or diagonally to the upper right, while circuits that act as 'accelerators' respond by shifting horizontally left. C, Quantitative Western-blot analysis of IE2 expression levels during CMV infection from 3 hours post-infection (h.p.i.), showing acceleration in presence of VPA (pink) but no amplification in IE2 levels compared to the untreated control (white). D, Response-vector map of Western blot data. VPA pre-treatment (pink) decreases time to steady-state without increasing steady-state IE2-YFP levels when compared to the untreated control (open circles). Error bars (gray)=±one standard error. E, Single-cell time-lapse microscopy of IE2-YFP levels for an untreated infection (open circles) and infection in the presence of increasing exposure to the histone-deacetylase inhibitor VPA (72-hour VPA pre-treatment in red, 24-hour VPA pre-treatment in pink). Each trajectory is an average of 20 cells with ±one standard error in lighter background color. F, Response-vector map of single-cell microscopy data, showing that increasing VPA pre-treatment (pink, red) decreases time to steady-state without increasing steady-state IE2-YFP levels when compared to the untreated control (open circles). Error bars (gray)=±one standard error. G, Acceleration produces a significant fitness advantage for the virus as measured by CMV wild-type viral titers after a single round of infection (measured by plaque forming units, PFU/ml) on the peak day of viral production (day 4) after infection at MOI=1. Average viral titers are shown in the absence of VPA (white) and for increasing VPA exposure (red, pink); Error bars=±one standard deviation.

Acceleration-Without-Amplification Requires Highly Self-Cooperative Negative Feedback, and IE2 Exhibits a Hill Coefficient (H) of H≈7

Next, we set out to identify the mechanisms driving acceleration in the CMV MIE circuit. Based on previous studies showing that negative feedback speeds a circuit's "response time", i.e., the time required for a circuit to approach to its respective steady-state level (Black, 1999; Gardner et al., 2000; Kobayashi et al., 2004; Rosenfeld et al., 2002; Savageau, 1976), we hypothesized that acceleration-without-amplification would likely utilize negative feedback. By employing a rate-balance analysis, we find that negative feedback encoding a high 'Hill' coefficient (H) is theoretically sufficient to generate acceleration without amplification (FIG. 27A), while alternate simple models cannot generate acceleration without amplification, in agreement with previous studies (Black, 1999; Rosenfeld et al., 2002; Savageau, 1976). Based on this analysis, we constructed a nonlinear ordinary differential equation (ODE) model of the CMV MIE circuit and performed nonlinear least-squares regression of the model using the single-cell microscopy data to estimate the H value of the IE2 negative feedback. H≈7 generates the best fit to the single-cell time-lapse microscopy data (FIG. 27B), and sensitivity analysis demonstrates that H<6 and H>8 cannot generate good fits to the data even when all other parameters are allowed to vary across all physiological parameter space. These simulation results demonstrate that a negative-feedback model with a high H is sufficient to generate acceleration without amplification and predict that the IE2 circuit requires negative feedback with H>>1 in order to function as an accelerator.

Figure 27:
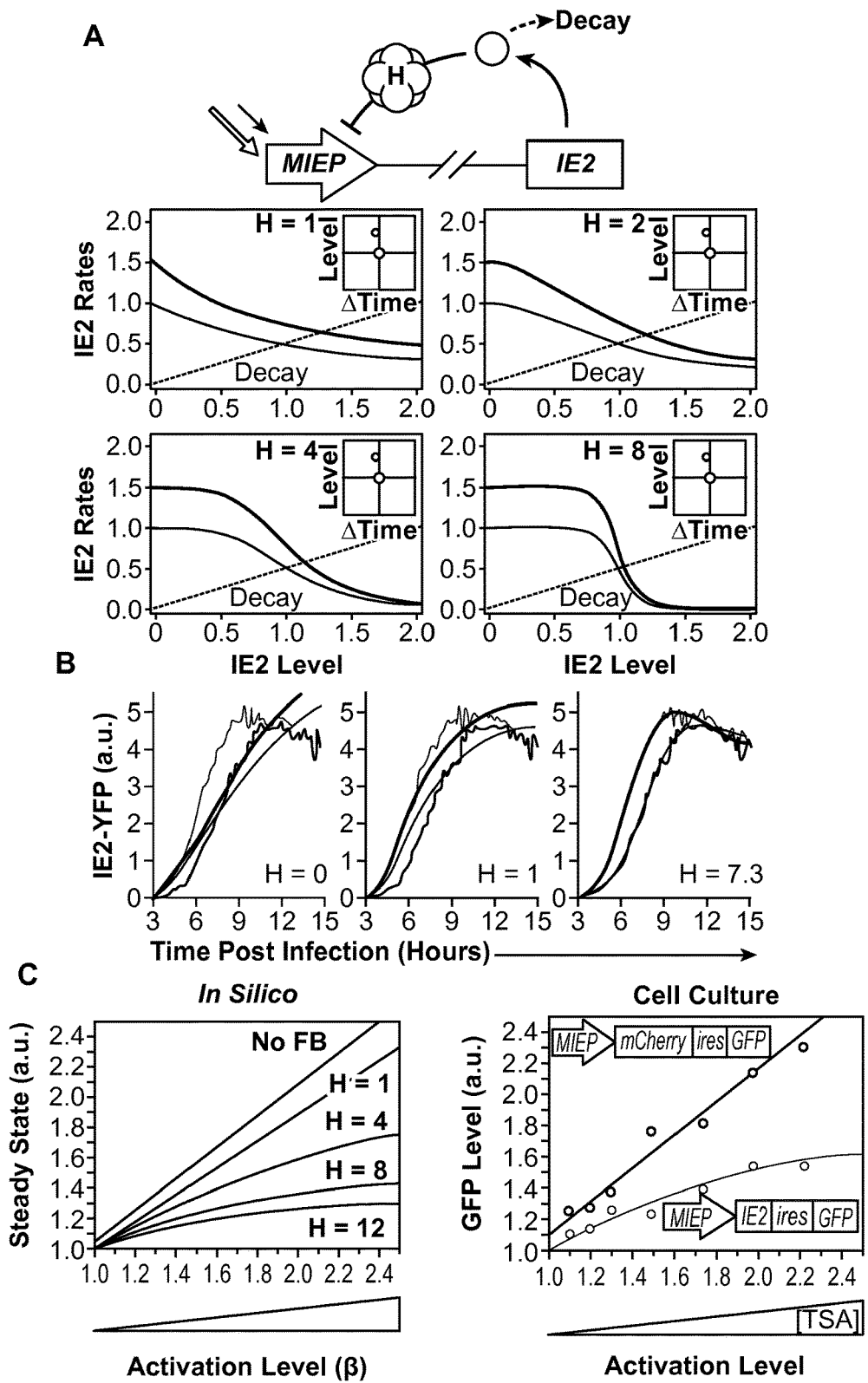
FIGS. 27A-C depict data showing that highly self-cooperative negative feedback is needed to generate an accelerator circuit and IE2 encodes negative feedback with a high Hill coefficient.

H is traditionally measured by dose-response approaches, which are 'open-loop' (i.e., whereby feedback is removed from the system). However, for transactivators that are cytotoxic at high doses, such as IE2, the dose-response method destroys the cell before the response can be measured. To circumvent this cytotoxicity problem, we developed a 'closed-loop' single-cell analysis method to analyze how a circuit's output (steady-state protein levels) saturates as a function of increasing promoter activation and varying H values (FIG. 27C). This method essentially measures the change in steady-state levels as a function of increasing promoter strength.

To measure H via this closed-loop method, flow-cytometry measurements of steady-state GFP levels were collected for a minimal negative-feedback circuit encoding the full-length MIEP driving IE2 and GFP (MIEP-IE2-IRES-GFP), and compared to a minimal non-feedback circuit encoding the full-length MIEP driving GFP (MIEP-mCherry-IRES-GFP), which acts as the non-feedback control circuit. By increasing the MIEP activity using transcriptional activators (e.g. TSA or VPA) the response of each circuit can be measured (FIG. 27C) and these responses can then be compared to theoretically predicted responses for varying H levels (FIG. 27C). As expected for the non-feedback circuit, a linear increase in activator resulted in a linear increase in GFP steady-state levels (black). However, for the MIEP-IE2-IRES-GFP negative-feedback circuit (red), the equivalent linear increase in activator input results in a significant saturation in GFP steady state. This saturation in the GFP steady-state values is consistent with the regression analysis indicating H≈7 for IE2 negative feedback. These results indicate that IE2 negative feedback acts early during CMV infection (i.e., during the first 12 hours), which has not previously been reported. Taken together, the results demonstrate that the IE2 circuit encodes a highly self-cooperative negative feedback with an H value sufficient to generate an accelerator that effectively abolishes IE2 amplification under different inputs.

FIGS. 27A-C: Highly self-cooperative negative feedback is needed to generate an accelerator circuit and IE2 encodes negative feedback with a high Hill coefficient (H≈7). A, Schematic and rate-balance analysis of a simplified negative-feedback model:

$$\frac{dx}{dt} = \frac{\beta}{(k^H + x^H)} - \delta \cdot x$$

for different values of the Hill coefficient (H). The dashed gray line represents the decay rate while solid lines (black and pink) represent synthesis rates for increasing values of β (1.0 and 1.5, respectively), which accounts for induction by a transcriptional activator that increases basal promoter activity by 1.5-fold. The points at which solid and dashed lines meet represents the steady-state and the distance separating the solid and dashed lines represents the rate of expression. Rate-balance analysis is shown for four values of H. High values of H allow expression rate to increase without amplification in the steady-state level. Insets: response vectors showing the change in steady-state level and the change in time to steady-state for each H value. B, Nonlinear least-squares regression of single-cell time-lapse microscopy data from FIG. 26E to a mathematical model of the CMV MIE circuit showing best-fit curve of H=7.3 (right panel). Gray data points are untreated trajectories from FIG. 26D while pink data points are VPA+ trajectories from FIG. 26D. Poor data fits are generated when H is fixed at H=1 or H=0 (no feedback) despite letting all other free parameters in the model vary (middle and left panels, respectively); sensitivity analysis shows that setting H<6 or H>8 generates poor fits to the data. C, Closed-loop dose-response analysis to measure H for the IE2 circuit. Left panel: steady-state solutions for the minimal negative-feedback ODE model (from panel A) as a function of increasing basal promoter strength β for different H values. Right panel: live-cell flow cytometry measurements of a non-feedback CMV MIEP-mCherry-IRES-GFP control circuit (black) and a minimal negative-feedback CMV MIEP-IE2-IRES-GFP circuit (red) induced to different levels of activation by TSA treatment. CMV MIEP-mCherry-IRES-GFP shows a linear increase in final level while CMV MIEP-IE2-IRES-GFP shows saturation in steady-state level consistent with H≈7.

Highly Self-Cooperative IE2 Feedback Results from IE2 Homo-Multimerization

We suspected that the high H value might be due to IE2 homo-multimerization, based on (i) in vitro biochemical studies reporting that IE2 peptide fragments can homo-multimerize when binding to DNA (Chiou et al., 1993; Waheed et al., 1998), and (ii) well-characterized mechanisms in other negative-regulation circuits encoding H>1 (Chen et al., 1994; Hooshangi et al., 2005). To assay for IE2 homo-multimerization in real time during CMV infection, we utilized polarization anisotropy Förster Resonance Energy Transfer (FRET) imaging, which can differentiate between monomers and higher-order homo-multimers (Gautier et al., 2001). During the first 16 hours of infection, IE2-YFP exhibits a strong homo-FRET anisotropy (r) signal corresponding to high-order IE2 homo-multimerization (FIG. 28A).

We next used an established theoretical model (Runnels and Scarlata, 1995) to estimate the number of individual IE2 monomers that might be interacting within an IE2 homo-multimer to generate the measured polarization anisotropy signal. While the model cannot precisely calculate the number of monomers making up the homo-multimer—since the distance between individual IE2 monomers is not known—a lower limit on the number of IE2 monomers within the homo-multimer can be estimated with confidence, under the most conservative assumption that the distance between each IE2-YFP monomer is the diameter of the YFP molecule (24 Å). Under this maximally conservative assumption, the measured anisotropy shift (r≥0.5→r≈0.1) is consistent with an IE2 homo-multimer composed of at least five to six IE2 monomers (FIG. 28B). Importantly, the IE2-YFP monomers are likely separated by >24 Å, and the results of FIG. 28B show that the measured anisotropy shift is well within the theoretical range of IE2 forming a homo-heptamer or higher order homo-multimer at the ND10 foci. Measurements of IE2 diffusion kinetics, from fluorescence recovery after photobleaching (FRAP), support the assertion that IE2 aggregates at ND10 domains in infected cells. Despite these direct measurements of IE2 homo-multimerization in live cells during active infection, structural studies would definitively establish the presence of a high-order IE2 homo-multimer bound to DNA.

In summary, results from three independent measurements, namely (i) regression fitting of a minimal ODE model to single-cell CMV IE2-YFP trajectories, (ii) the 'closed-loop' analysis of the isolated IE2 feedback circuit, and (iii) homo-FRET imaging of IE2-YFP, all point toward the IE2 negative-feedback circuit as operating with a high Hill coefficient (H≈7). These data argue that IE2 homo-multimerization is a core factor in establishing the high Hill coefficient of this transcriptional negative-feedback circuit, and that homo-multimerization underlies the circuit's ability to act as an accelerator.

Figure 28:
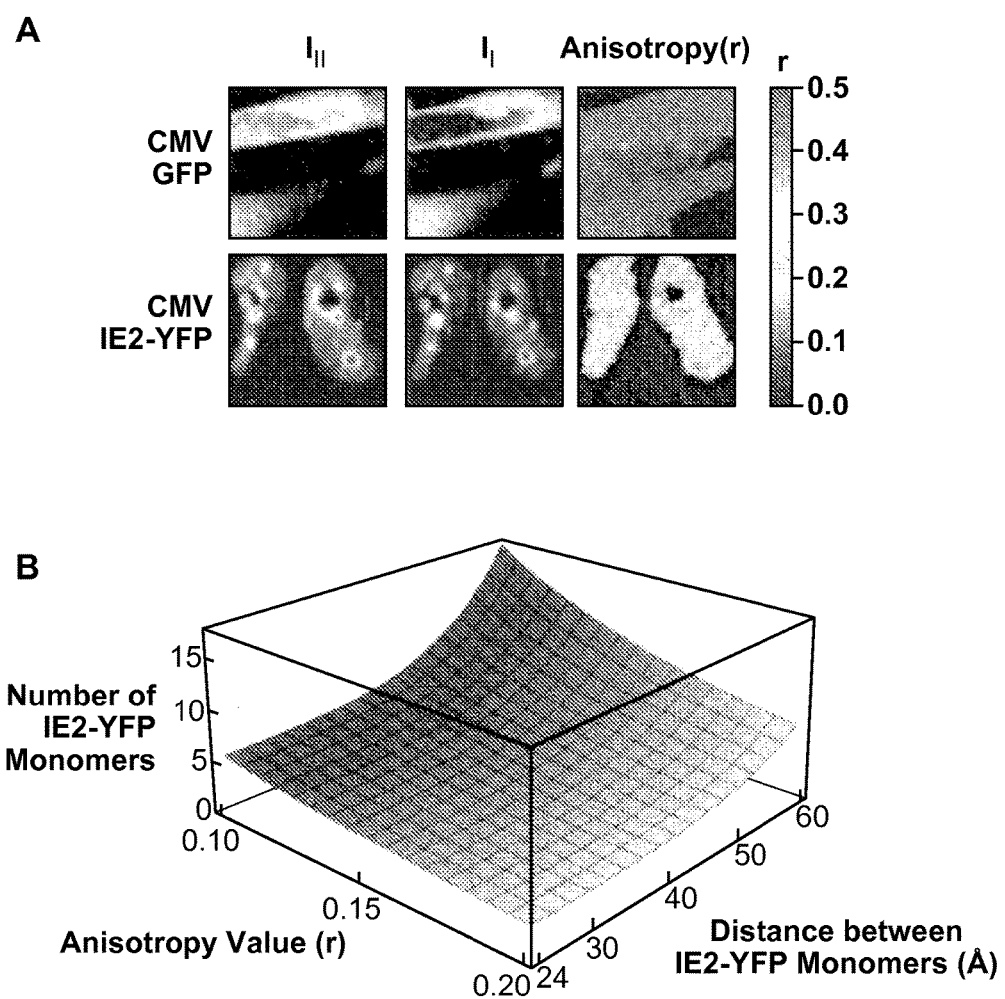
FIGS. 28A and 28B depict data showing that IE2 forms a high-order homo-multimer that can account for a high H value.

FIGS. 28A and 28B: IE2 forms a high-order homo-multimer that can account for a high H value. A, Direct measurement of IE2 homo-multimerization by two-photon steady-state homo-FRET in live cells during CMV infection. CMV IE2-YFP infected cells were imaged to determine fluorescence polarization anisotropy (r) at 15 hours post-infection and compared to cells infected with a control CMV GFP virus. An r≈0.5 represents no FRET exchange and is the two-photon theoretical maximum anisotropy for a GFP or YFP monomer. IE2-YFP exhibits significant homo-FRET exchange in the nucleus and especially at sub-nuclear foci, indicating the presence of a high-order IE2 homo-multimer. B, Calculation of number of IE2 monomers present in the IE2 multimer based on measured anisotropy values. Plotted surface is the solution to the theoretical formula which accounts for the number of IE2-YFP monomers (N) in a complex participating in FRET exchange that could account for a given value of r based on the distance between each monomer (R). The formula estimates a lower limit for YFP monomers in a homo-multimer that could generate a given r. Under the maximally-conservative assumption that all YFP monomers are as tightly packed as physically possible (R=24 Å), the minimum number of IE2-YFP monomers participating in homo-FRET exchange that could generate an anisotropy value of r=0.1 is approximately 6.

Figure 29:
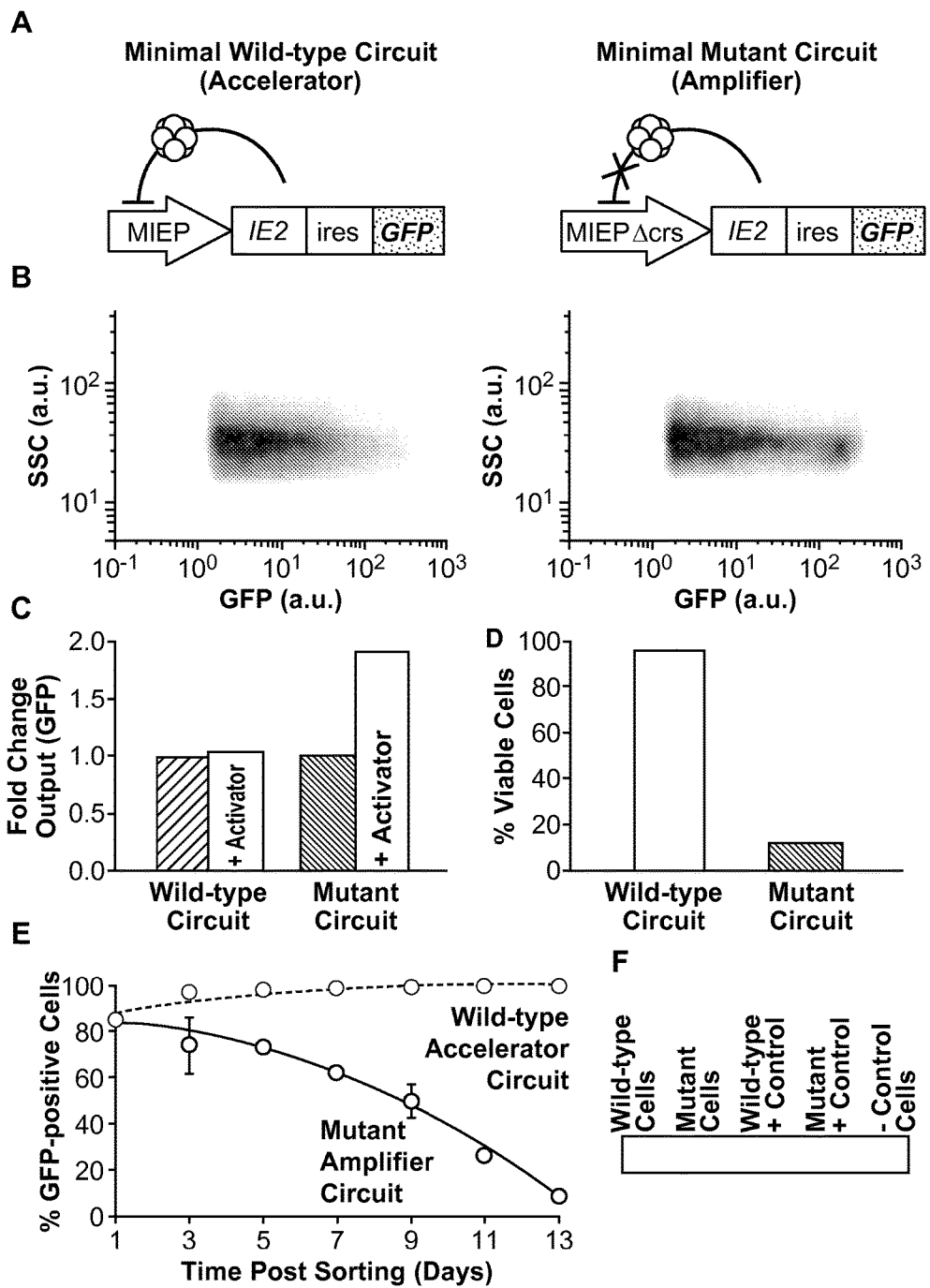
FIGS. 29A-F depict data showing that a minimal IE2 accelerator circuit provides a fitness advantage outside the context of viral infection.

A Minimal-Accelerator Circuit Provides a Fitness Advantage Outside the Infection Setting To verify that highly self-cooperative negative feedback is sufficient to generate an accelerator, we reconstructed a minimal IE2 feedback circuit lacking all other viral elements and analyzed it completely outside the virus infection setting. The minimal IE2 feedback circuit was constructed using a lentiviral vector expressing only IE2 and GFP from either the full-length wild-type MIEP or a mutant version of the MIEP where three nucleotides in the crs binding site are mutated to eliminate IE2 binding (Macias and Stinski, 1993) (FIG. 29A). Both wild-type and mutant Δcrs lentiviral circuits were stably integrated into the cellular genome. The minimal wild-type circuit stably expresses IE2, and two-color imaging confirms that the MIEP exhibits comparable kinetics both within the context of the virus and stably integrated in host-genome DNA. As predicted from the model, the minimal mutant circuit exhibits substantially increased mean GFP fluorescence intensity (FIG. 29B). The minimal mutant circuit fails to generate acceleration, instead acting as an amplifier (FIG. 29C), while the wild-type feedback circuit generates acceleration, even in the absence of all other viral elements. Cells carrying the wild-type accelerator circuit also exhibit a profound viability advantage over cells carrying mutant amplifier circuit (FIG. 29D). Dramatically, cell populations carrying the minimal wild-type accelerator circuit maintain IE2 and GFP expression while cell populations carrying the minimal mutant circuit exhibit a rapid loss of IE2 and GFP expression that increases over time (FIG. 29E). Genomic PCR (FIG. 29F) confirms that loss of IE2 and GFP expression is due to a loss of cells carrying the stably integrated mutant circuit, not from silencing of the integrated MIEP. These data argue that cells carrying the mutant circuit express higher IE2 levels and undergo increased cell death, leading to these cells being outcompeted from the population. Thus, a minimal IE2 accelerator circuit provides cells with a dramatic fitness advantage over a comparable IE2 amplifier circuit, even in the absence of all other viral factors.

FIGS. 29A-F: A minimal IE2 accelerator circuit provides a fitness advantage outside the context of viral infection. A, Schematics of the minimal wild-type accelerator circuit MIEP-IE2-IRES-GFP (left) and minimal mutant amplifier circuit MIEPΔcrs-IE2-IRES-GFP (right). Both circuits are lentiviral vectors and encode an IRES element between IE2 and GFP. B, Flow cytometry density plot of cells stably expressing the wild-type accelerator (left) or the mutant amplifier (right) circuit that exhibits ~8-fold higher mean GFP. C, Fold increase in GFP for the wild-type accelerator and mutant amplifier circuits in the absence (white, black) or presence (red) of TSA. D, Percentage of live cells (by flow cytometry) after 14 days of TSA treatment. TSA treatment has little effect on viability of cells expressing the wild-type accelerator circuit (white) but leads to significantly decreased viability in cells expressing the mutant amplifier cells (black). E, Flow cytometry time-course of the % of GFP expressing cells for the accelerator (white) and amplifier (black) circuits. GFP expression is lost from the cells transduced with the mutant amplifier circuit but is maintained in cells transduced with wild-type accelerator circuit (averages of 3 replicates shown in bold with ±one standard deviation). F, PCR amplification of the MIEP locus from: cellular genomic DNA of cells transduced with either wild-type accelerator circuit or mutant amplifier circuit on day 14 (lanes 1-2); plasmid DNA of wild-type accelerator or mutant amplifier lentiviral vector (lanes 3-4, positive PCR controls); naïve non-transduced cells, negative control (lane 5). At day 14, the mutant amplifier circuit has been lost from the genomic DNA of the transduced population but the wild-type accelerator circuit remains present in the genomic DNA of the transduced population.

Figure 30:
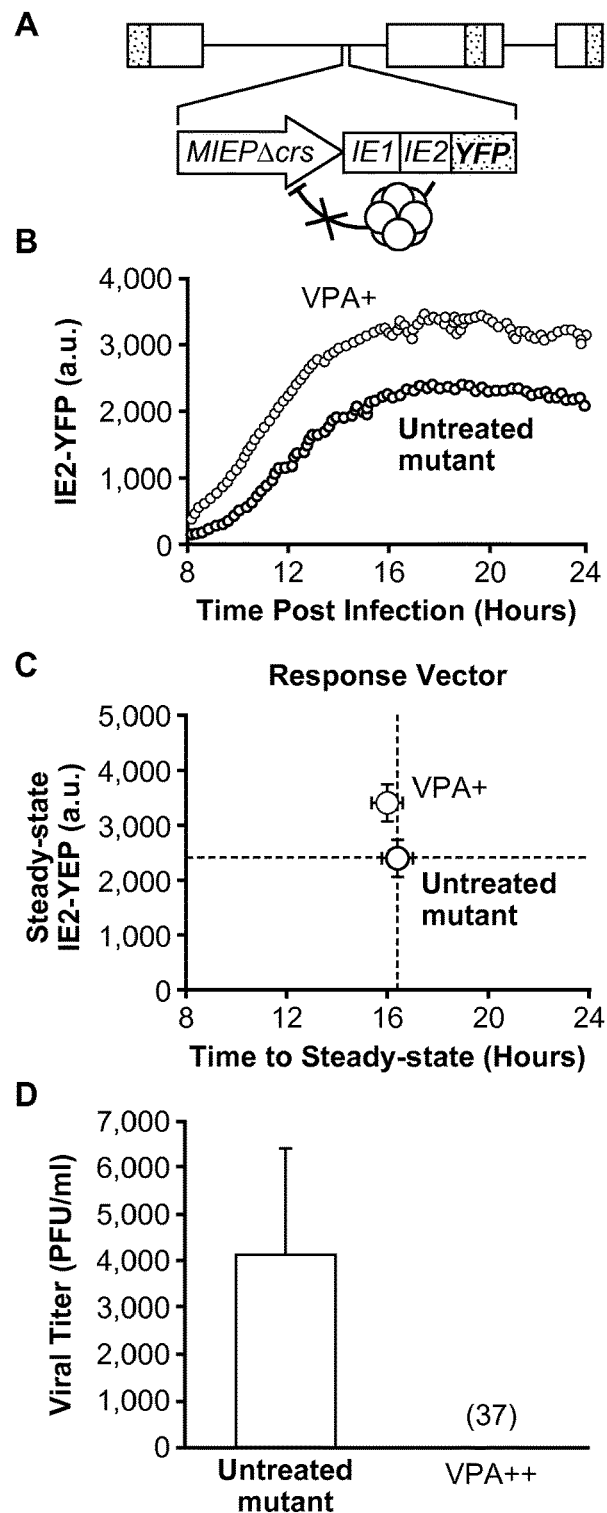
FIGS. 30A-D depict data showing that converting the IE2 accelerator to an amplifier—by eliminating negative feedback—generates a severe fitness cost for the virus.

Converting the Accelerator to an Amplifier Generates a Severe Fitness Cost for the Virus To determine if negative feedback is necessary for the MIE circuit to act as an accelerator in the context of the virus, we constructed a Δcrs virus by BAC mutagenesis of the three nucleotides in the crs binding site (FIG. 30A). In agreement with modeling predictions and the minimal circuit observations (FIG. 29), this Δcrs mutant virus acts as an amplifier generating a ~1.5-fold amplification in single-cell expression levels in the presence of MIEP activators (FIG. 30B) and exhibits virtually no acceleration (FIG. 30C).

Strikingly, replication of this mutant amplifier virus is severely compromised in the presence of activators (FIG. 30D). These data agree with the minimal-circuit data that amplification of IE2 levels is deleterious for the cell, leading to decreased viral output. Potential toxicity of VPA or TSA exposure alone cannot account for reduced viral replication since neither activator reduces replication fitness of the parent virus.

Figure 32:
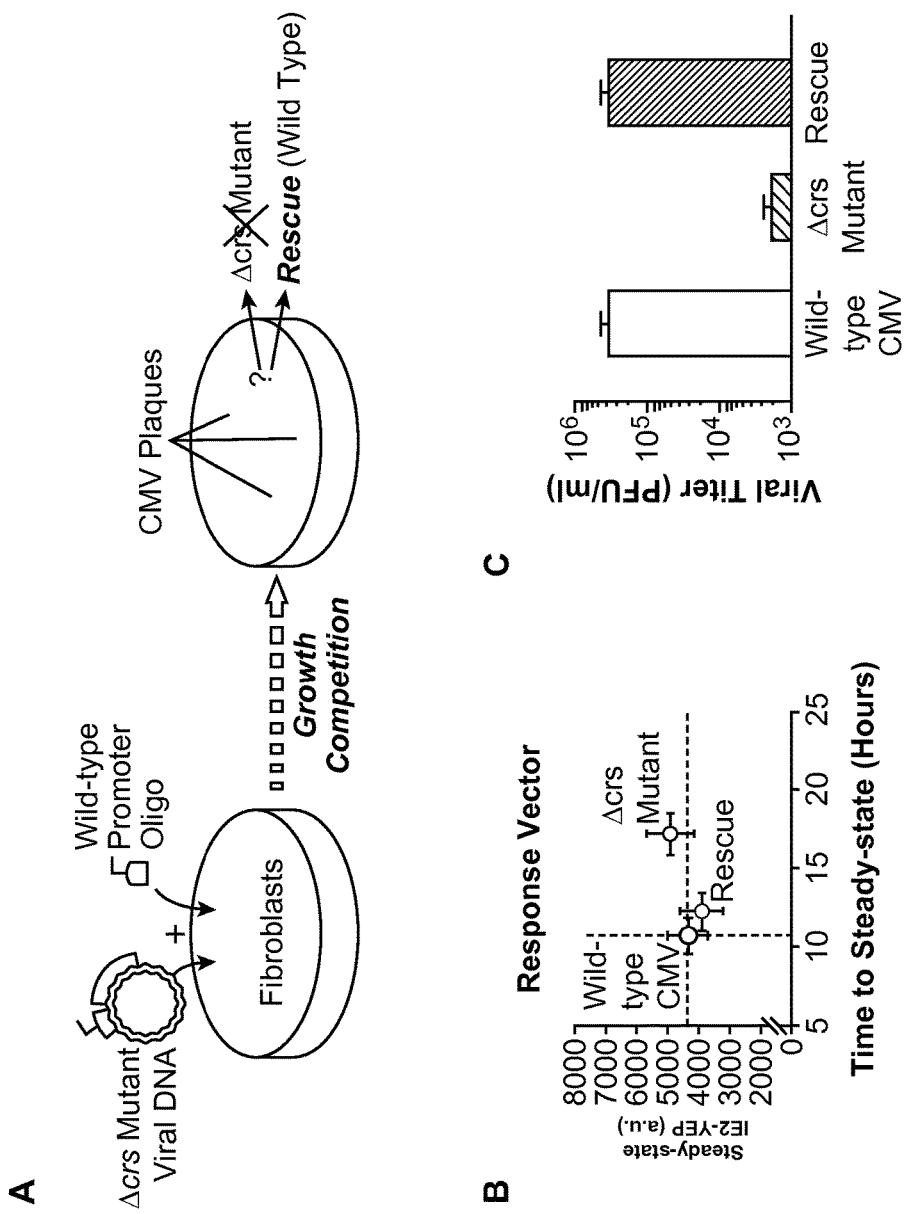
FIGS. 32A-C depict data showing that loss of IE2 acceleration, despite equivalent IE2 levels, carries a heavy fitness cost.

To rule out secondary mutations outside the crs region that could be responsible for amplification, these results were verified in two independently isolated BAC clones, and sequencing 1 kb upstream and downstream of the crs verified the absence of secondary mutations. The generation of a 'rescue' virus with wild-type IE2 expression kinetics (described below and in FIG. 32) independently verifies that secondary mutations do not account for the amplifier phenotype or reduced fitness. This absence of secondary mutations is not unexpected given the reported stability and specificity of BAC mutagenesis for CMV (Reddehase and Lemmermann, 2006).

FIGS. 30A-D: Converting the IE2 accelerator to an amplifier—by eliminating negative feedback—generates a severe fitness cost for the virus. A, Schematic of the mutant CMV Δcrs mutant virus. B, Single-cell time-lapse microscopy of cells undergoing infection with CMV Δcrs mutant in presence of 24-hour pre-treatment of VPA (pink) or absence of VPA (black). Trajectories are averages of 20 cells (bold) together with ±one standard deviation (lighter background). The CMV Δcrs mutant displays an ~1.5-fold amplification in IE2 levels in single cells in response to VPA. C, Response-vector map of single-cell microscopy data showing that the Δcrs mutant virus amplifies steady-state IE2-YFP levels compared to the untreated control (black). Error bars (gray) =±one standard error. D, Replicative fitness of the CMV Δcrs mutant in presence (red) and absence (black) of a 72-hour VPA treatment as measured by PFU/ml on the peak day of viral production (day 10) after infection at MOI=1. Averages are shown in bold gray with ±one standard deviation. Decreased replication is not due to drug toxicity on the infected cells.

Figure 31:
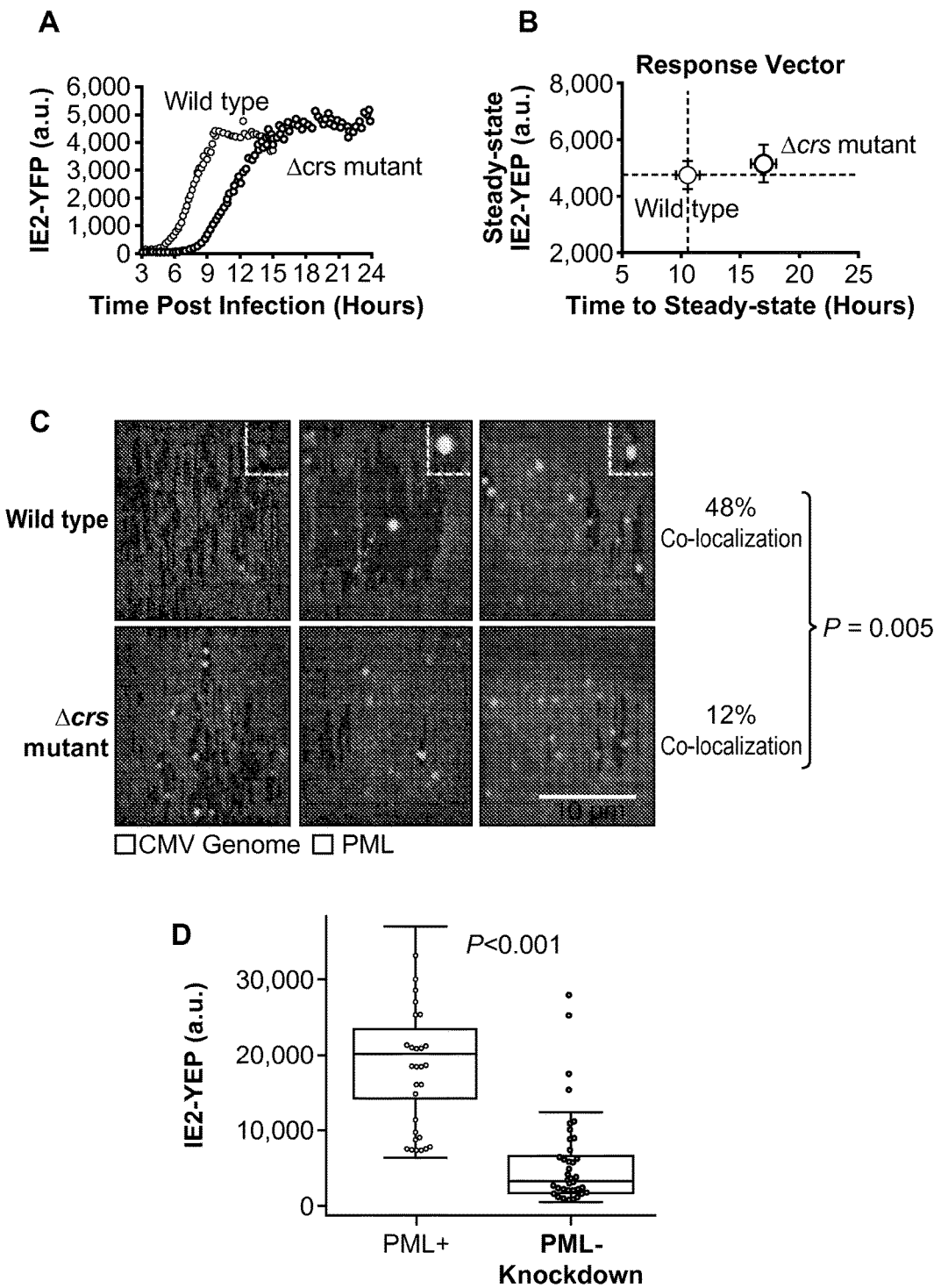
FIGS. 31A-D depict data showing that mutation of the crs in the CMV genome results in inefficient formation of IE transcriptional centers and lower IE2-YFP expression.

The Loss of the Accelerator Circuit in the Δcrs Amplifier Mutant is Buffered by Reduced MIEP Activity through Mislocalization of Incoming Viral Genomes While theory predicts that removal of negative feedback should increase IE2 steady-state levels (as in the minimal circuit), the biology of IE2 cytotoxicity and the presence of the accelerator circuit in the wild-type virus suggests that over the course of viral evolution, there is strong selection for mechanisms to maintain low IE2 levels. Therefore, to determine how the Δcrs amplifier mutant virus was able to maintain any viability even in the absence of activators (FIG. 30D), we tested if IE2 steady-state levels were increased similar to the minimal virus setting or if the mutant virus employed compensatory mechanisms to keep IE2 levels low. Single-cell imaging and flow cytometry analysis reveal that IE2 steady-state levels in the Δcrs mutant amplifier virus (in the absence of activators) are essentially the same as IE2 levels in the wild-type virus (FIG. 31A) but the rate of IE2 expression is significantly slower in the mutant (FIG. 31B). Based on literature indicating that sub-nuclear PML bodies facilitate transcription from the MIEP (Sourvinos et al., 2007), we tested if reduced IE2 levels were the result of decreased MIEP activity due to Δcrs mutation-induced mislocalization of incoming viral genomes away from PML bodies. While the wild-type virus exhibits IE2 localization to PML bodies, the Δcrs mutant virus displays virtually no IE2-positive foci during early infection, and immunofluorescence analysis shows that Δcrs mutant viral genomes do not co-localize with PML bodies (FIG. 31C). To confirm that PML-body mislocalization reduces IE2 levels, we infected a cell line lacking PML bodies (Everett and Chelbi-Alix, 2007) and observed significantly reduced steady-state IE2 levels (FIG. 31D). In summary, the Δcrs mutant amplifier virus appears to compensate for the lack of accelerator circuitry by reducing MIEP transcriptional strength, through misdirecting incoming viral genomes away from sub-nuclear PML bodies.

The minimal circuit is integrated into the genome as a single-copy lentiviral provirus and MIEP does not appear to be influenced by PML body localization in this context.

FIGS. 31A-D: Mutation of the crs in the CMV genome results in inefficient formation of IE transcriptional centers and lower IE2-YFP expression. A, Single-cell time-lapse microscopy analysis comparing CMV IE2-YFP virus, referred to as "wild type" (white), to Δcrs amplifier mutant virus (black); infections imaged in parallel on the same day under the same conditions. Error bars (gray)=±one standard error. B, Response-vector map showing that the Δcrs amplifier mutant virus (black) exhibits decelerated IE2 kinetics but no change in IE2 steady-state level compared to wild-type (white). C, Immunofluorescence micrographs of cells infected with either wild-type CMV (top panels) or the Δcrs mutant virus (bottom panels) and stained for CMV genome (red), PML protein (green), and DNA (blue). CMV genomes and PML bodies appear to co-localize at a significantly higher frequency (P<0.01) in cells infected with wild-type CMV virus compared to Δcrs amplifier mutant virus. Insets: representative co-localization of CMV genomes and PML bodies. D, Steady-state IE2-YFP levels from single-cell microscopy in conventional PML+ cells (green) cells or PML-knockdown cells (black). Both cell types were infected with "wild-type" CMV IE2-YFP virus. Bold black lines in the box plot are the median IE2-YFP levels, boxes represent lower and upper quartile, and whiskers represent 1.5 interquartile range (IQR) of the lower and upper quartiles. PML knockdown significantly reduces IE2-YFP levels (P<0.001).

Reduced MIEP Activity Decelerates IE2 Expression and Carries a Heavy Fitness Cost Since the amplifier mutant and wild-type accelerator viruses exhibit equivalent IE2 steady-state levels but different rates of IE2 expression, we next tested if the mutant's reduced fitness could be rescued by acceleration. To do this, we provided the mutant virus with the opportunity to regain accelerator circuitry through homologous recombination, by co-transfecting cells with the full Δcrs mutant virus genome together with a short 1 kb DNA fragment of the MIEP encoding the wild-type crs sequence. This approach to generate recombinant "rescue" virus (FIG. 32A) creates a "fitness competition" since the mutant must compete with any rescue that arises within the culture. After culturing the co-transfected cells for two weeks (the typical time for growth of CMV IE2-YFP in culture), all observable CMV-positive plaques analyzed were, rescue virus that exhibited accelerated expression kinetics (FIG. 32B) and fitness that was comparable to wild-type virus (FIG. 32C). The fact that high-titer accelerator rescue virus can be isolated from a background Δcrs infection, and that no detectable Δcrs virus can be isolated from this background, indicates that viruses encoding the accelerator circuit directly outcompete viruses encoding the mutant amplifier even in the absence of transcriptional activator drugs. Sequencing results confirm that in the rescue virus the Δcrs locus is restored to the wild-type sequence, and that the rescue virus exhibits a complete recovery of the accelerator phenotype. These results show that a slower rate of IE2 expression is sufficient to generate a heavy fitness cost even when IE2 levels are not elevated.

FIGS. 32A-C: Loss of IE2 acceleration, despite equivalent IE2 levels, carries a heavy fitness cost. A, Schematic of 'rescue' experiment that represents a growth competition between the Δcrs amplifier mutant virus and 'wild-type' CMV IE2-YFP. B, Response-vector map of single-cell microscopy showing that the rescue virus (green) generated from the mutant amplifier virus (black), has regained the accelerated expression kinetics of the wild-type virus (white) and all viruses exhibit equivalent IE2-YFP steady-state levels; all viruses (wild-type, mutant, and rescue) were imaged in parallel on the same day under the same conditions. Error bars (gray)=±one standard error. C, Viral replication titers for the rescue virus (green) compared to Δcrs amplifier mutant (black) and wild-type viruses (white) as measured by PFU/ml on the peak day of viral production in a multi-step assay (MOI=0.1). Despite all viruses exhibiting equivalent IE2-YFP steady-state levels, the rescue virus, which has reacquired the wild-type accelerator, replicates with the same high efficiency as wild-type virus while the Δcrs amplifier mutant virus exhibits a severe fitness disadvantage. Averages are shown in bold gray with ±one standard deviation.

Example 2

Figure 33:
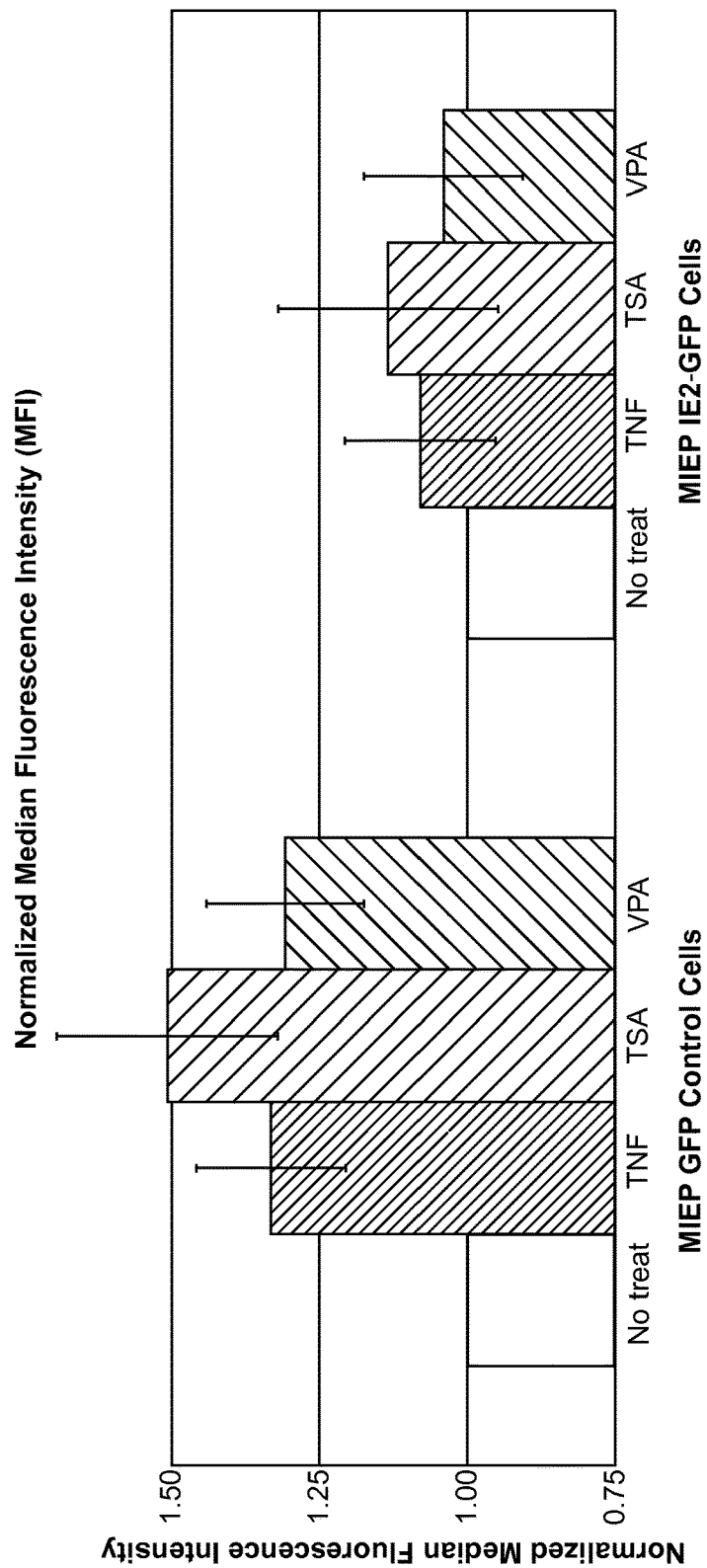
FIG. 33 depicts the response of MIEP-GFP control cells and MIEP-IE2-GFP cells to treatment with 10 ng/ml TNF-α, 400 nM TSA, or 1 mM VPA.

Cell lines (ARPE-19 cells) expressing IE2-GFP from MIE promoter (MIEP) (referred to as "MIEP-IE2-GFP cells") were tested, in comparison to a cell line expressing MIEP-GFP control (referred to as "MIEP-GFP control cells). MIEP-IE2-GFP cells and MIEP-GFP control cells were treated with with 10 ng/ml TNF-α, 400 nM TSA, or 1 mM VPA in MIEP-IE2-GFP cells. The data are depicted in FIG. 33. As summarized in FIG. 33, treatment with 10 ng/ml TNF-α, 400 nM TSA, or 1 mM VPA significantly increased GFP median fluorescence intensity in MIEP-GFP control cells but not in MIEP-IE2-GFP cells.

REFERENCES

Alon, U. (2007). An introduction to systems biology: design principles of biological circuits (Boca Raton, Fla.: Chapman & Hall/CRC).

Barrasa, M. I., Harel, N. Y., and Alwine, J. C. (2005). The phosphorylation status of the serine-rich region of the human cytomegalovirus 86-kilodalton major immediate-early protein IE2/IEP86 affects temporal viral gene expression. J Virol 79, 1428-1437.

Black, H. S. (1999). Stabilized feed-back amplifiers (Reprinted from Electrical Engineering, vol 53, pg 114-120, 1934). Proceedings of the Ieee 87, 379-385.

Bolovan-Fritts, C., and Wiedeman, J. A. (2001). Human cytomegalovirus strain Toledo lacks a virus-encoded tropism factor required for infection of aortic endothelial cells. J Infect Dis 184, 1252-1261.

Bolovan-Fritts, C. A., Trout, R. N., and Spector, S. A. (2004). Human cytomegalovirus-specific CD4+-T-cell cytokine response induces fractalkine in endothelial cells. J Virol 78, 13173-13181.

Bresnahan, W. A., and Shenk, T. E. (2000). UL82 virion protein activates expression of immediate early viral genes in human cytomegalovirus-infected cells. Proc Natl Acad Sci USA 97, 14506-14511.

Cagatay, T., Turcotte, M., Elowitz, M. B., Garcia-Ojalvo, J., and Suel, G. M. (2009). Architecture-dependent noise discriminates functionally analogous differentiation circuits. Cell 139, 512-522.

Carey, M., Peterson, C. L., and Smale, S. T. (2009). Transcriptional regulation in eukaryotes: concepts, strategies, and techniques, 2nd edn (Cold Spring Harbor, N.Y.: Cold Spring Harbor Laboratory Press).

Cauwels, A., and Brouckaert, P. (2007). Survival of TNF toxicity: dependence on caspases and NO. Arch Biochem Biophys 462, 132-139.

Chen, J., Alberti, S., and Matthews, K. S. (1994). Wild-type operator binding and altered cooperativity for inducer binding of lac repressor dimer mutant R3. J Biol Chem 269, 12482-12487.

Chiou, C. J., Zong, J., Waheed, I., and Hayward, G. S. (1993). Identification and mapping of dimerization and DNA-binding domains in the C terminus of the IE2 regulatory protein of human cytomegalovirus. J Virol 67, 6201-6214.

Choi, K. H., Basma, H., Singh, J., and Cheng, P. W. (2005). Activation of CMV promoter-controlled glycosyltransferase and beta-galactosidase glycogenes by butyrate, tricostatin A, and 5-aza-2'-deoxycytidine. Glycoconj J 22, 63-69.

Cuevas-Bennett, C., and Shenk, T. (2008). Dynamic histone H3 acetylation and methylation at human cytomegalovirus promoters during replication in fibroblasts. J Virol 82, 9525-9536.

Deshaies, R. J., and Ferrell, J. E., Jr. (2001). Multisite phosphorylation and the countdown to S phase. Cell 107, 819-822.

Dull, T., Zufferey, R., Kelly, M., Mandel, R. J., Nguyen, M., Trono, D., and Naldini, L. (1998). A third-generation lentivirus vector with a conditional packaging system. J Virol 72, 8463-8471.

Dwarakanath, R. S., Clark, C. L., McElroy, A. K., and Spector, D. H. (2001). The use of recombinant baculoviruses for sustained expression of human cytomegalovirus immediate early proteins in fibroblasts. Virology 284, 297-307.

Everett, R. D., and Chelbi-Alix, M. K. (2007). PML and PML nuclear bodies: implications in antiviral defence. Biochimie 89, 819-830.

Fan, S., Maguire, C. A., Ramirez, S. H., Bradel-Tretheway, B., Sapinoro, R., Sui, Z., Chakraborty-Sett, S., and Dewhurst, S. (2005). Valproic acid enhances gene expression from viral gene transfer vectors. J Virol Methods 125, 23-33.

Flint, S. J., and American Society for Microbiology. (2009). Principles of virology, 3rd edn (Washington, D.C.: ASM Press).

Garcia-Pino, A., Balasubramanian, S., Wyns, L., Gazit, E., De Greve, H., Magnuson, R. D., Charlier, D., van Nuland, N. A., and Loris, R. (2010). Allostery and intrinsic disorder mediate transcription regulation by conditional cooperativity. Cell 142, 101-111.

Gardner, T. S., Cantor, C. R., and Collins, J. J. (2000). Construction of a genetic toggle switch in Escherichia coli. Nature 403, 339-342.

Gautier, I., Tramier, M., Durieux, C., Coppey, J., Pansu, R. B., Nicolas, J. C., Kemnitz, K., and Coppey-Moisan, M. (2001). Homo-FRET microscopy in living cells to measure monomer-dimer transition of GFP-tagged proteins. Biophys J 80, 3000-3008.

Gebert, S., Schmolke, S., Sorg, G., Floss, S., Plachter, B., and Stamminger, T. (1997). The UL84 protein of human cytomegalovirus acts as a transdominant inhibitor of immediate-early-mediated transactivation that is able to prevent viral replication. J Virol 71, 7048-7060.

Haase, A. T. (2010). Targeting early infection to prevent HIV-1 mucosal transmission. Nature 464, 217-223.

Hofmann, H., Floss, S., and Stamminger, T. (2000). Covalent modification of the transactivator protein IE2-p86 of human cytomegalovirus by conjugation to the ubiquitin-homologous proteins SUMO-1 and hSMT3b. J Virol 74, 2510-2524.

Hooshangi, S., Thiberge, S., and Weiss, R. (2005). Ultrasensitivity and noise propagation in a synthetic transcriptional cascade. Proc Natl Acad Sci USA 102, 3581-3586.

Hummel, M., and Abecassis, M. M. (2002). A model for reactivation of CMV from latency. J Clin Virol 25 Suppl 2, S123-136.

Isomura, H., Stinski, M. F., Kudoh, A., Nakayama, S., Murata, T., Sato, Y., Iwahori, S., and Tsurumi, T. (2008). A cis element between the TATA Box and the transcription start site of the major immediate-early promoter of human cytomegalovirus determines efficiency of viral replication. J Virol 82, 849-858.

Kobayashi, H., Kaern, M., Araki, M., Chung, K., Gardner, T. S., Cantor, C. R., and Collins, J. J. (2004). Programmable cells: interfacing natural and engineered gene networks. Proc Natl Acad Sci USA 101, 8414-8419.

Ma, W., Trusina, A., El-Samad, H., Lim, W. A., and Tang, C. (2009). Defining network topologies that can achieve biochemical adaptation. Cell 138, 760-773.

Macias, M. P., and Stinski, M. F. (1993). An in vitro system for human cytomegalovirus immediate early 2 protein (IE2)-mediated site-dependent repression of transcription and direct binding of IE2 to the major immediate early promoter. Proc Natl Acad Sci USA 90, 707-711.

Mocarski, E. S., Shenk, T., and Pass, R. F. (2006). Cytomegaloviruses. In Fields' virology, D. M. Knipe, ed. (Philadelphia: Lippincott Williams & Wilkins), pp. 2708-2772.

Moorman, N.J., Cristea, I. M., Terhune, S. S., Rout, M. P., Chait, B. T., and Shenk, T. (2008). Human cytomegalovirus protein UL38 inhibits host cell stress responses by antagonizing the tuberous sclerosis protein complex. Cell Host Microbe 3, 253-262.

Muzzey, D., Gomez-Uribe, C. A., Mettetal, J. T., and van Oudenaarden, A. (2009). A systems-level analysis of perfect adaptation in yeast osmoregulation. Cell 138, 160-171.

Nevels, M., Brune, W., and Shenk, T. (2004). SUMOylation of the human cytomegalovirus 72-kilodalton IE1 protein facilitates expression of the 86-kilodalton IE2 protein and promotes viral replication. J Virol 78, 7803-7812.

Nowak, M. A., and May, R. M. (2000). Virus dynamics: mathematical principles of immunology and virology (Oxford; New York: Oxford University Press).

Ozbudak, E. M., Thattai, M., Lim, H. N., Shraiman, B. I., and Van Oudenaarden, A. (2004). Multistability in the lactose utilization network of Escherichia coli. Nature 427, 737-740.

Reddehase, M. J., and Lemmermann, N. (2006). Cytomegaloviruses: molecular biology and immunology (Wymondham: Caister Academic Press).

Rosenfeld, N., Elowitz, M. B., and Alon, U. (2002). Negative autoregulation speeds the response times of transcription networks. J Mol Biol 323, 785-793.

Rosenke, K., and Fortunato, E. A. (2004). Bromodeoxyuridine-labeled viral particles as a tool for visualization of the immediate-early events of human cytomegalovirus infection. J Virol 78, 7818-7822.

Roth, J., Rummel, C., Barth, S. W., Gerstberger, R., and Hubschle, T. (2006). Molecular aspects of fever and hyperthermia. Neurol Clin 24, 421-439, v.

Runnels, L. W., and Scarlata, S. F. (1995). Theory and application of fluorescence homotransfer to melittin oligomerization. Biophys J 69, 1569-1583.

Sanders, R. L., Clark, C. L., Morello, C. S., and Spector, D. H. (2008). Development of cell lines that provide tightly controlled temporal translation of the human cytomegalovirus IE2 proteins for complementation and functional analyses of growth-impaired and nonviable IE2 mutant viruses. J Virol 82, 7059-7077.

Savageau, M. A. (1976). Biochemical systems analysis: a study of function and design in molecular biology (Reading, Mass.: Addison-Wesley Pub. Co., Advanced Book Program).

Sourvinos, G., Tavalai, N., Berndt, A., Spandidos, D. A., and Stamminger, T. (2007). Recruitment of human cytomegalovirus immediate-early 2 protein onto parental viral genomes in association with ND10 in live-infected cells. J Virol 81, 10123-10136.

Stinski, M. F., and Isomura, H. (2008). Role of the cytomegalovirus major immediate early enhancer in acute infection and reactivation from latency. Med Microbiol Immunol 197, 223-231.

Stinski, M. F., and Petrik, D. T. (2008). Functional roles of the human cytomegalovirus essential IE86 protein. Curr Top Microbiol Immunol 325, 133-152.

Waheed, I., Chiou, C. J., Ahn, J. H., and Hayward, G. S. (1998). Binding of the human cytomegalovirus 80-kDa immediate-early protein (IE2) to minor groove A/T-rich sequences bounded by CG dinucleotides is regulated by protein oligomerization and phosphorylation. Virology 252, 235-257.

Weinberger, L. S., Dar, R. D., and Simpson, M. L. (2008). Transient-mediated fate determination in a transcriptional circuit of HIV. Nat Genet 40, 466-470.

Weinberger, L. S., and Shenk, T. (2007). An HIV feedback resistor: auto-regulatory circuit deactivator and noise buffer. PLoS Biol 5, e9.

Yu, D., Silva, M. C., and Shenk, T. (2003). Functional map of human cytomegalovirus AD169 defined by global mutational analysis. Proc Natl Acad Sci USA 100, 12396-12401.

Yu, D., Smith, G. A., Enquist, L. W., and Shenk, T. (2002). Construction of a self-excisable bacterial artificial chromosome containing the human cytomegalovirus genome and mutagenesis of the diploid TRL/IRL13 gene. J Virol 76, 2316-2328.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A recombinant expression vector comprising a nucleotide sequence heterologous to the vector, which sequence encodes a negative auto-regulatory (feedback) circuit comprising:
   a) a herpesvirus transactivator;
   b) a herpesvirus transcriptional control element operably linked to the nucleotide sequence encoding the herpesvirus transactivator such that the transactivator negatively auto-regulates its own expression via the herpesvirus transcriptional control element, wherein the herpesvirus transcriptional control element is derived from a naturally occurring herpesvirus transcriptional control element that controls negative auto-regulation of the transactivator in a wild-type herpesvirus, wherein i) the herpesvirus transactivator comprises a cytomegalovirus (CMV) Immediate Early-2 (IE2) polypeptide, and wherein the herpesvirus transcriptional control element is derived from a CMV Major Immediate Early Promoter (MIEP);
   ii) the herpesvirus transactivator comprises a herpes simplex virus-1 (HSV-1) infected cell protein 0 (ICPO) polypeptide, and wherein the herpesvirus transcriptional control element is derived from an HSV-1 ICPO gene promoter;
   iii) the herpesvirus transactivator comprises a herpes simplex virus-1 (HSV-1) infected cell protein 4 (ICP4) polypeptide, and wherein the herpesvirus transcriptional control element is derived from an HSV-1 ICP4 gene promoter;
   iv) the herpesvirus transactivator comprises an Epstein-Barr virus (EBV) Zta polypeptide, and wherein the herpesvirus transcriptional control element is derived from an EBV Zta gene Promoter;

v) the herpesvirus transactivator comprises a varicella zoster virus VZV ORF61 or ORF62 polypeptide, and wherein the herpesvirus transcriptional control element is derived from an VZV ORF61 gene promoter; or vi) the herpesvirus transactivator comprises a human herpesvirus-8 (HHV-8) Orf50 polypeptide, and wherein the herpesvirus transcriptional control element is derived from an HHV-8 Orf50 gene promoter;

c) a reporter, wherein the nucleotide sequence encoding the reporter is operably linked to the herpesvirus transcriptional control element such that expression of the reporter is negatively auto-regulated through the herpesvirus transcriptional control element; and d) a functional nuclear localization signal (NLS), wherein the nucleotide sequence encoding the functional NLS is operably linked to the herpesvirus transcriptional control element such that the transactivator, when expressed in a cell, localizes to the nucleus of the cell and negatively auto-regulates its own expression through the herpesvirus transcriptional control element, the nucleotide sequence heterologous to the vector thereby encoding the negative auto-regulatory (feedback) circuit.

2. The recombinant expression vector of claim 1, wherein the reporter is a polypeptide that provides a detectable signal.

3. The recombinant expression vector of claim 2, wherein the reporter is a fluorescent polypeptide or an enzyme that generates a detectable product upon acting on a substrate.

4. The recombinant expression vector of claim 3, wherein the fluorescent polypeptide is a red fluorescent protein, a green fluorescent protein, a blue fluorescent protein, or a yellow fluorescent protein.

5. The recombinant expression vector of claim 3, wherein the enzyme is luciferase.

6. The recombinant expression vector of claim 1, wherein the reporter is an mRNA.

7. The recombinant expression vector of claim 1, wherein the nucleotide sequence encoding the reporter is 5' of the nucleotide sequence encoding the transactivator.

8. The recombinant expression vector of claim 7, wherein an internal ribosome entry site (IRES) or a p2A element is interposed between the nucleotide sequence encoding the reporter and the nucleotide sequence encoding the transactivator.

9. The recombinant expression vector of claim 1, wherein the nucleotide sequence encoding the reporter is 3' of the nucleotide sequence encoding the transactivator.

10. The recombinant expression vector of claim 9, wherein an internal ribosome entry site (IRES) or a p2A element is interposed between the nucleotide sequence encoding the reporter and the nucleotide sequence encoding the transactivator.

11. The recombinant expression vector of claim 9, wherein the reporter is a polypeptide, and wherein the nucleotide sequence encoding the reporter polypeptide is in frame with the nucleotide sequence encoding the transactivator, such that the reporter polypeptide is fused to the carboxyl-terminus of the transactivator.

12. The recombinant expression vector of claim 1, wherein the recombinant expression vector is a lentivirus vector, a retrovirus vector, an adeno-associated virus vector, or a plasmid.

13. A system comprising:

a) a first recombinant expression vector, wherein the first recombinant expression vector comprises a nucleotide sequence heterologous to the first recombinant expression vector, which sequence encodes:

i) a cytomegalovirus (CMV) transactivator, wherein the CMV transactivator comprises a cytomegalovirus (CMV) Immediate Early-2 (IE2) polypeptide;

ii) a CMV transcriptional control element operably linked to the nucleotide sequence encoding a CMV transactivator such that the transactivator negatively auto-regulates its own expression via the CMV transcriptional control element, wherein the CMV transcriptional control element is derived from a CMV Major Immediate Early Promoter (MIEP);

iii) a first reporter, wherein the nucleotide sequence encoding the first reporter is operably linked to the CMV transcriptional control element such that expression of the first reporter is negatively auto-regulated through the CMV transcriptional control element; and (iv) a functional nuclear localization signal (NLS), wherein the nucleotide sequence encoding the functional NLS is operably linked to the CMV transcriptional control element such that the transactivator, when expressed in a cell, localizes to the nucleus of the cell and negatively auto-regulates its own expression through the CMV transcriptional control element, the nucleotide sequence heterologous to the first recombinant expression vector thereby encoding a negative auto-regulatory (feedback) circuit; and b) a second recombinant expression vector, wherein the second recombinant expression vector comprises a nucleotide sequence heterologous to the second recombinant expression vector, which sequence encodes:

i) a second reporter, ii) a CMV transcriptional control element that is derived from a CMV Major Immediate Early Promoter (MIEP) wherein the nucleotide sequence encoding a second reporter is operably linked to the CMV transcriptional control element of the second recombinant expression vector such that expression of the second reporter is negatively auto-regulated through the CMV transcriptional control element—of the second recombinant expression vector, and iii) a functional nuclear localization signal (NLS), wherein the nucleotide sequence encoding the functional NLS is operably linked to the CMV transcriptional control element of the second recombinant expression vector such that expression of the NLS is negatively auto-regulated by the CMV transcriptional control element of the second recombinant expression vector.

14. A mammalian cell genetically modified with the recombinant expression vector of claim 1, or the system of claim 13.

15. The mammalian cell of claim 14, wherein the cell is a transformed cell line or a primary cell.

16. The recombinant expression vector of claim 1, wherein the herpesvirus transactivator comprises a cytomegalovirus (CMV) Immediate Early-2 (IE2) polypeptide, and wherein the herpesvirus transcriptional control element is derived from a CMV Major Immediate Early Promoter (MIEP).

17. A method of identifying a candidate anti-viral agent, the method comprising:

a) contacting a test agent with a mammalian cell, wherein the mammalian cell is genetically modified with a recombinant expression vector comprising a nucleotide sequence heterologous to the vector, which sequence encodes:
i) a herpesvirus transactivator, wherein the herpesvirus transactivator comprises a cytomegalovirus (CMV) Immediate Early-2 (IE2) polypeptide;
ii) a herpesvirus transcriptional control element operably linked to the nucleotide sequence encoding the herpesvirus transactivator such that the transactivator negatively auto-regulates its own expression via the herpesvirus transcriptional control element, wherein the herpesvirus transcriptional control element is derived from a CMV Major Immediate Early Promoter (MIEP);
iii) a reporter, wherein the nucleotide sequence encoding the reporter is operably linked to the herpesvirus transcriptional control element such that expression of the reporter is negatively auto-regulated through the herpesvirus transcriptional control element; and
iv) a functional nuclear localization signal (NLS), wherein the nucleotide sequence encoding the functional NLS is operably linked to the transcriptional control element such that the transactivator localizes to the nucleus of the mammalian cell and negatively auto-regulates its own expression through the herpesvirus transcriptional control element, the nucleotide sequence heterologous to the vector thereby encoding a negative auto-regulatory (feedback) circuit;
b) determining the effect, if any, of the test agent on transcription of the nucleotide sequence encoding the herpesvirus transactivator, wherein an agent that increases or reduces transcription of the nucleotide sequence encoding the herpesvirus transactivator, compared to a control, is considered a candidate anti-viral agent.

18. The method of claim 17, wherein said determining comprises measuring the level of a reporter in the presence of the test agent and in the absence of the test agent, wherein a level of the reporter in the presence of the test agent that is lower than the level of the reporter in the absence of the test agent indicates that the test agent is a candidate anti-viral agent.

19. The method of claim 18, wherein said measuring is carried out in the intact cell.

20. The method of claim 18, wherein said measuring is carried out on an extract of the cell.

21. A method of identifying a candidate anti-viral agent, the method comprising:
a) contacting a test agent with a mammalian cell, wherein the mammalian cell is genetically modified with a system comprising:
i) a first recombinant expression vector, wherein the first recombinant expression vector comprises a nucleotide sequence heterologous to the first recombinant expression vector, which sequence encodes: a cytomegalovirus (CMV) transactivator, wherein the CMV transactivator comprises a cytomegalovirus (CMV) immediate Early-2(IE2) polypepticie; a CMV transcriptional control element operably linked to the nucleotide sequence encoding a CMV transactivator such that the transactivator negatively auto-regulates its own expression via the CMV transcriptional control element, wherein the CMV transcriptional control element is derived from a CMV Major Immediate Early Promoter (MIEP); a first reporter, wherein the nucleotide sequence encoding the first reporter is operably linked to the CMV transcriptional control element such that expression of the first reporter is negatively auto-regulated by the CMV transcriptional control element; and a functional nuclear localization signal (NLS), wherein the nucleotide sequence encoding the functional NLS is operably linked to the CMV transcriptional control element such that the transactivator localizes to the nucleus of the mammalian cell and negatively auto-regulates its own expression through the CMV transcriptional control element, the nucleotide sequence heterologous to the first recombinant expression vector thereby encoding a negative auto-regulatory (feedback) circuit; and
ii) a second recombinant expression vector, wherein the second recombinant expression vector comprises a nucleotide sequence heterologous to the second recombinant expression vector, which sequence encodes a second reporter, a CMV transcriptional control element that is derived from a CMV Major Immediate Early Promoter (MIEP), wherein the nucleotide sequence encoding a second reporter is operably linked to the CMV transcriptional control element of the second recombinant expression vector such that expression of the second reporter is negatively auto-regulated through the CMV transcriptional control element of the second recombinant expression vector, and a functional nuclear localization signal (NLS), wherein the nucleotide sequence encoding the functional NLS is operably linked to the transcriptional control element of the second recombinant expression vector such that expression of the NLS is negatively regulated by the CMV transcriptional control element of the second recombinant expression vector; and
b) determining the effect, if any, of the test agent on transcription of the nucleotide sequence encoding the CMV transactivator, wherein an agent that increases or reduces transcription of the nucleotide sequence encoding the CMV transactivator, compared to a control, is considered a candidate anti-viral agent.

22. The method of claim 21, wherein said determining comprises measuring the level of a reporter in the presence of the test agent and in the absence of the test agent, wherein a level of the reporter in the presence of the test agent that is lower than the level of the reporter in the absence of the test agent indicates that the test agent is a candidate anti-viral agent.

23. The method of claim 22, wherein said measuring is carried out in the intact cell.

24. The method of claim 22, wherein said measuring is carried out on an extract of the cell.

* * * * *

UNITED STATES PATENT AND TRADEMARK OFFICE
CERTIFICATE OF CORRECTION

PATENT NO.         : 10,106,817 B2
APPLICATION NO.    : 14/767541
DATED              : October 23, 2018
INVENTOR(S)        : Leor S. Weinberger et al.

It is certified that error appears in the above-identified patent and that said Letters Patent is hereby corrected as shown below:

In the Claims

Column 155, Line 57, replace "polypepticie" with --polypeptide--

Signed and Sealed this
Nineteenth Day of March, 2019

Andrei Iancu
*Director of the United States Patent and Trademark Office*

SEQUENCE LISTING

<160> NUMBER OF SEQ ID NOS: 47

<210> SEQ ID NO 1
<211> LENGTH: 580
<212> TYPE: PRT
<213> ORGANISM: Human herpesvirus 5

<400> SEQUENCE: 1

```
Met Glu Ser Ser Ala Lys Arg Lys Met Asp Pro Asp Asn Pro Asp Glu
1               5                   10                  15

Gly Pro Ser Ser Lys Val Pro Arg Pro Glu Thr Pro Val Thr Lys Ala
            20                  25                  30

Thr Thr Phe Leu Gln Thr Met Leu Arg Lys Glu Val Asn Ser Gln Leu
        35                  40                  45

Ser Leu Gly Asp Pro Leu Phe Pro Glu Leu Ala Glu Glu Ser Leu Lys
    50                  55                  60

Thr Phe Glu Gln Val Thr Glu Asp Cys Asn Glu Asn Pro Glu Lys Asp
65                  70                  75                  80

Val Leu Ala Glu Leu Gly Asp Ile Leu Ala Gln Ala Val Asn His Ala
                85                  90                  95

Gly Ile Asp Ser Ser Ser Thr Gly Pro Thr Leu Thr Thr His Ser Cys
            100                 105                 110

Ser Val Ser Ser Ala Pro Leu Asn Lys Pro Thr Pro Thr Ser Val Ala
        115                 120                 125

Val Thr Asn Thr Pro Leu Pro Gly Ala Ser Ala Thr Pro Glu Leu Ser
    130                 135                 140

Pro Arg Lys Lys Pro Arg Lys Thr Thr Arg Pro Phe Lys Val Ile Ile
145                 150                 155                 160

Lys Pro Pro Val Pro Pro Ala Pro Ile Met Leu Pro Leu Ile Lys Gln
                165                 170                 175

Glu Asp Ile Lys Pro Glu Pro Asp Phe Thr Ile Gln Tyr Arg Asn Lys
            180                 185                 190

Ile Ile Asp Thr Ala Gly Cys Ile Val Ile Ser Asp Ser Glu Glu Glu
        195                 200                 205

Gln Gly Glu Glu Val Glu Thr Arg Gly Ala Thr Ala Ser Ser Pro Ser
    210                 215                 220

Thr Gly Ser Gly Thr Pro Arg Val Thr Ser Pro Thr His Pro Leu Ser
225                 230                 235                 240

Gln Met Asn His Pro Pro Leu Pro Asp Pro Leu Gly Arg Pro Asp Glu
                245                 250                 255

Asp Ser Ser Ser Ser Ser Ser Ser Cys Ser Ser Ala Ser Asp Ser
            260                 265                 270

Glu Ser Glu Ser Glu Glu Met Lys Cys Ser Ser Gly Gly Gly Ala Ser
        275                 280                 285
```

```
Val Thr Ser Ser His His Gly Arg Gly Gly Phe Gly Gly Ala Ala Ser
    290                 295                 300

Ser Ser Leu Leu Ser Cys Gly His Gln Ser Ser Gly Gly Ala Ser Thr
305                 310                 315                 320

Gly Pro Arg Lys Lys Lys Ser Lys Arg Ile Ser Glu Leu Asp Asn Glu
                325                 330                 335

Lys Val Arg Asn Ile Met Lys Asp Lys Asn Thr Pro Phe Cys Thr Pro
            340                 345                 350

Asn Val Gln Thr Arg Arg Gly Arg Val Lys Ile Asp Glu Val Ser Arg
        355                 360                 365

Met Phe Arg Asn Thr Asn Arg Ser Leu Glu Tyr Lys Asn Leu Pro Phe
    370                 375                 380

Thr Ile Pro Ser Met His Gln Val Leu Asp Glu Ala Ile Lys Ala Cys
385                 390                 395                 400

Lys Thr Met Gln Val Asn Asn Lys Gly Ile Gln Ile Ile Tyr Thr Arg
                405                 410                 415

Asn His Glu Val Lys Ser Glu Val Asp Ala Val Arg Cys Arg Leu Gly
            420                 425                 430

Thr Met Cys Asn Leu Ala Leu Ser Thr Pro Phe Leu Met Glu His Thr
        435                 440                 445

Met Pro Val Thr His Pro Pro Glu Val Ala Gln Arg Thr Ala Asp Ala
    450                 455                 460

Cys Asn Glu Gly Val Lys Ala Ala Trp Ser Leu Lys Glu Leu His Thr
465                 470                 475                 480

His Gln Leu Cys Pro Arg Ser Ser Asp Tyr Arg Asn Met Ile Ile His
                485                 490                 495

Ala Ala Thr Pro Val Asp Leu Leu Gly Ala Leu Asn Leu Cys Leu Pro
            500                 505                 510

Leu Met Gln Lys Phe Pro Lys Gln Val Met Val Arg Ile Phe Ser Thr
        515                 520                 525

Asn Gln Gly Gly Phe Met Leu Pro Ile Tyr Glu Thr Ala Ala Lys Ala
    530                 535                 540

Tyr Ala Val Gly Gln Phe Glu Gln Pro Thr Glu Thr Pro Pro Glu Asp
545                 550                 555                 560

Leu Asp Thr Leu Ser Leu Ala Ile Glu Ala Ala Ile Gln Asp Leu Arg
                565                 570                 575

Asn Lys Ser Gln
            580

<210> SEQ ID NO 2
<211> LENGTH: 502
<212> TYPE: DNA
<213> ORGANISM: Artificial sequence
<220> FEATURE:
<223> OTHER INFORMATION: Synthetic nucleotide sequence

<400> SEQUENCE: 2
cgcgttacat aacttacggt aaatggcccg cctggctgac cgcccaacga cccccgccca    60
ttgacgtcaa taatgacgta tgttcccata gtaacgccaa tagggacttt ccattgacgt   120
caatgggtgg actatttacg gtaaactgcc cacttggcag tacatcaagt gtatcatatg   180
ccaagtacgc cccctattga cgtcaatgac ggtaaatggc ccgcctggca ttatgcccag   240
tacatgacct tatgggactt tcctacttgg cagtacatct acgtattagt catcgctatt   300
accatggtga tgcggttttg gcagtacatc aatgggcgtg gatagcggtt tgactcacgg   360
```

-continued

```
ggatttccaa gtctccaccc cattgacgtc aatgggagtt tgttttggca ccaaaatcaa      420
cgggactttc caaaatgtcg taacaactcc gccccattga cgcaaatggg cggtaggcgt      480
gtacggtggg aggtctatat aa                                               502
```

<210> SEQ ID NO 3
<211> LENGTH: 776
<212> TYPE: PRT
<213> ORGANISM: Human herpesvirus 1

<400> SEQUENCE: 3

```
Met Glu Pro Arg Pro Gly Ala Ser Thr Arg Arg Pro Glu Gly Arg Pro
1               5                   10                  15

Gln Arg Glu Pro Ala Pro Asp Val Trp Val Phe Pro Cys Asp Arg Asp
            20                  25                  30

Leu Pro Asp Ser Ser Asp Ser Glu Ala Glu Thr Glu Val Gly Gly Arg
        35                  40                  45

Gly Asp Ala Asp His His Asp Asp Ser Ala Ser Glu Ala Asp Ser
    50                  55                  60

Thr Asp Thr Glu Leu Phe Glu Thr Gly Leu Leu Gly Pro Gln Gly Val
65                  70                  75                  80

Asp Gly Gly Ala Val Ser Gly Ser Pro Pro Arg Glu Glu Asp Pro
                85                  90                  95

Gly Ser Cys Gly Gly Ala Pro Pro Arg Glu Asp Gly Ser Asp Glu
            100                 105                 110

Gly Asp Val Cys Ala Val Cys Thr Asp Glu Ile Ala Pro His Leu Arg
        115                 120                 125

Cys Asp Thr Phe Pro Cys Met His Arg Phe Cys Ile Pro Cys Met Lys
    130                 135                 140

Thr Trp Met Gln Leu Arg Asn Thr Cys Pro Leu Cys Asn Ala Lys Leu
145                 150                 155                 160

Val Tyr Leu Ile Val Gly Val Thr Pro Ser Gly Ser Phe Ser Thr Ile
                165                 170                 175

Pro Ile Val Asn Asp Pro Gln Thr Arg Met Glu Ala Glu Ala Val
            180                 185                 190

Arg Ala Gly Thr Ala Val Asp Phe Ile Trp Thr Gly Asn Gln Arg Phe
        195                 200                 205

Ala Pro Arg Tyr Leu Thr Leu Gly Gly His Thr Val Arg Ala Leu Ser
    210                 215                 220

Pro Thr His Pro Glu Pro Thr Thr Asp Glu Asp Asp Asp Leu Asp
225                 230                 235                 240

Asp Ala Asp Tyr Val Pro Pro Ala Pro Arg Arg Thr Pro Arg Ala Pro
                245                 250                 255

Pro Arg Arg Gly Ala Ala Ala Pro Pro Val Thr Gly Gly Ala Ser His
            260                 265                 270

Ala Ala Pro Gln Pro Ala Ala Arg Thr Ala Pro Pro Ser Ala Pro
        275                 280                 285

Ile Gly Pro His Gly Ser Ser Asn Thr Asn Thr Thr Asn Ser Ser
    290                 295                 300

Gly Gly Gly Gly Ser Arg Gln Ser Arg Ala Ala Val Pro Arg Gly Ala
305                 310                 315                 320

Ser Gly Pro Ser Gly Gly Val Gly Val Val Glu Ala Glu Ala Gly Arg
                325                 330                 335

Pro Arg Gly Arg Thr Gly Pro Leu Val Asn Arg Pro Ala Pro Leu Ala
```

```
                340                 345                 350
Asn Asn Arg Asp Pro Ile Val Ile Ser Asp Ser Pro Pro Ala Ser Pro
            355                 360                 365

His Arg Pro Ala Ala Pro Met Pro Gly Ser Ala Pro Arg Pro Gly
        370                 375                 380

Pro Pro Ala Ser Ala Ala Ala Ser Gly Pro Ala Arg Pro Arg Ala Ala
385                 390                 395                 400

Val Ala Pro Cys Val Arg Ala Pro Pro Gly Pro Gly Pro Arg Ala
                405                 410                 415

Pro Ala Pro Gly Ala Glu Pro Ala Arg Pro Ala Asp Ala Arg Arg
            420                 425                 430

Val Pro Gln Ser His Ser Ser Leu Ala Gln Ala Ala Asn Gln Glu Gln
        435                 440                 445

Ser Leu Cys Arg Ala Arg Ala Thr Val Ala Arg Gly Ser Gly Pro
    450                 455                 460

Gly Val Glu Gly Gly His Gly Pro Ser Arg Gly Ala Ala Pro Ser Gly
465                 470                 475                 480

Ala Ala Pro Ser Gly Ala Pro Pro Leu Pro Ser Ala Ala Ser Val Glu
                485                 490                 495

Gln Glu Ala Ala Val Arg Pro Arg Lys Arg Arg Gly Ser Gly Gln Glu
            500                 505                 510

Asn Pro Ser Pro Gln Ser Thr Arg Pro Pro Leu Ala Pro Ala Gly Ala
        515                 520                 525

Lys Arg Ala Ala Thr His Pro Pro Ser Asp Ser Gly Pro Gly Gly Arg
    530                 535                 540

Gly Gln Gly Gly Pro Gly Thr Pro Leu Thr Ser Ser Ala Ala Ser Ala
545                 550                 555                 560

Ser Ser Ser Ser Ala Ser Ser Ser Ala Pro Thr Pro Ala Gly Ala
                565                 570                 575

Thr Ser Ser Ala Thr Gly Ala Ala Ser Ser Ser Ala Ser Ala Ser Ser
            580                 585                 590

Gly Gly Ala Val Gly Ala Leu Gly Gly Arg Gln Glu Glu Thr Ser Leu
        595                 600                 605

Gly Pro Arg Ala Ala Ser Gly Pro Arg Gly Pro Arg Lys Cys Ala Arg
    610                 615                 620

Lys Thr Arg His Ala Glu Thr Ser Gly Ala Val Pro Ala Gly Gly Leu
625                 630                 635                 640

Thr Arg Tyr Leu Pro Ile Ser Gly Val Ser Val Val Ala Leu Ser
                645                 650                 655

Pro Tyr Val Asn Lys Thr Ile Thr Gly Asp Cys Leu Pro Ile Leu Asp
            660                 665                 670

Met Glu Thr Gly Asn Ile Gly Ala Tyr Val Val Leu Val Asp Gln Thr
        675                 680                 685

Gly Asn Met Ala Thr Arg Leu Arg Ala Ala Val Pro Gly Trp Ser Arg
    690                 695                 700

Arg Thr Leu Leu Pro Glu Thr Ala Gly Asn His Val Thr Pro Glu
705                 710                 715                 720

Tyr Pro Thr Ala Pro Ala Ser Glu Trp Asn Ser Leu Trp Met Thr Pro
                725                 730                 735

Val Gly Asn Met Leu Phe Asp Gln Gly Thr Leu Val Gly Ala Leu Asp
            740                 745                 750

Phe Arg Ser Leu Arg Ser Arg His Pro Trp Ser Gly Glu Gln Gly Ala
        755                 760                 765
```

Ser Thr Arg Asp Glu Gly Lys Gln
        770                 775

<210> SEQ ID NO 4
<211> LENGTH: 499
<212> TYPE: DNA
<213> ORGANISM: HSV1 strain F alpha

<400> SEQUENCE: 4
cctggggttc cgggtatggt aatgagtttc ttcgggaagg cgggaagccc cggggcaccg     60
acgcaggcca agcccctgtt gcgtcggtgg gaggggcatg ctaatggggt tctttggggg    120
acaccgggtt ggtcccccaa atcggggggcc gggccgtgca tgctaatgat attctttggg    180
ggcgccgggt tggtccccgg ggacgggccc gccccgcggt gggcctgcct ccccctgggac   240 gcgcggccat tggggggaatc gtcactgccg ccccctttggg gaggggaaag gcgtggggta   300
taagttagcc ctggccccgac agtctggtcg catttgcacc tcggcactcg gagcgagacg   360
cagcagccag gcagactcgg gccgccccct ctccgcatca ccacagaagc cccgcctacg    420
ttgcgacccc cagggaccct ccgtccgcga ccctccagcc gcatacgacc cccatggagc    480
cccgccccgg agcgggtac                                                 499

<210> SEQ ID NO 5
<211> LENGTH: 245
<212> TYPE: PRT
<213> ORGANISM: Human herpesvirus 4

<400> SEQUENCE: 5

Met Met Asp Pro Asn Ser Thr Ser Glu Asp Val Lys Phe Thr Pro Asp
1               5                   10                  15

Pro Tyr Gln Val Pro Phe Val Gln Ala Phe Asp Gln Ala Thr Arg Val
            20                  25                  30

Tyr Gln Asp Leu Gly Gly Pro Ser Gln Ala Pro Leu Pro Cys Val Leu
        35                  40                  45

Trp Pro Val Leu Pro Glu Pro Leu Pro Gln Gly Gln Leu Thr Ala Tyr
    50                  55                  60

His Val Ser Thr Ala Pro Thr Gly Ser Trp Phe Ser Ala Pro Gln Pro
65                  70                  75                  80

Ala Pro Glu Asn Ala Tyr Gln Ala Tyr Ala Ala Pro Gln Leu Phe Pro
                85                  90                  95

Val Ser Asp Ile Thr Gln Asn Gln Gln Thr Asn Gln Ala Gly Gly Glu
            100                 105                 110

Ala Pro Gln Pro Gly Asp Asn Ser Thr Val Gln Thr Ala Ala Ala Val
        115                 120                 125

Val Phe Ala Cys Pro Gly Ala Asn Gln Gly Gln Gln Leu Ala Asp Ile
    130                 135                 140

Gly Val Pro Gln Pro Ala Pro Val Ala Ala Pro Ala Arg Arg Thr Arg
145                 150                 155                 160

Lys Pro Gln Gln Pro Glu Ser Leu Glu Glu Cys Asp Ser Glu Leu Glu
                165                 170                 175

Ile Lys Arg Tyr Lys Asn Arg Val Ala Ser Arg Lys Cys Arg Ala Lys
            180                 185                 190

Phe Lys Gln Leu Leu Gln His Tyr Arg Glu Val Ala Ala Ala Lys Ser
        195                 200                 205

Ser Glu Asn Asp Arg Leu Arg Leu Leu Leu Lys Gln Met Cys Pro Ser
    210                 215                 220

```
Leu Asp Val Asp Ser Ile Ile Pro Arg Thr Pro Asp Val Leu His Glu
225                 230                 235                 240

Asp Leu Leu Asn Phe
            245

<210> SEQ ID NO 6
<211> LENGTH: 222
<212> TYPE: DNA
<213> ORGANISM: Artificial sequence
<220> FEATURE:
<223> OTHER INFORMATION: Synthetic nucleotide sequence

<400> SEQUENCE: 6
gcatatttca actgggctgt ctattttga caccagctta ttttagacac ttctgaaaac     60
tgcctcctcc tcttttggaa actatgcatg agccacaggc attgctaatg tgcctcagag    120
acacacctaa atttagcacg tcccaaacca tgacatcaca gaggaggctg gtgccttggc    180
tttaaagggg agatgttaga caggtaactc actaaacatt gc                      222

<210> SEQ ID NO 7
<211> LENGTH: 691
<212> TYPE: PRT
<213> ORGANISM: Human herpesvirus 8

<400> SEQUENCE: 7

Met Ala Gln Asp Asp Lys Gly Lys Lys Leu Arg Arg Ser Cys Val Glu
1               5                   10                  15

Ser Phe Val Gly Leu Ser Asp Glu Leu Lys Ala Gln Leu Tyr Gln Cys
            20                  25                  30

Val Leu Leu Ile Asn Asp Ala Tyr Glu Thr Ile Tyr Asp Pro Ser Asp
        35                  40                  45

Leu Asn Arg Val Val Glu Asp Val Cys Ile Arg Ile Met Lys Glu Cys
    50                  55                  60

Ser Lys Leu Gly Ala Leu Cys Gly Leu Phe Thr Asp Ile Asn Met Phe
65                  70                  75                  80

Asn Leu Phe Cys Phe Phe Arg Ala Ser Arg Met Arg Thr Lys Gly Ala
                85                  90                  95

Ala Gly Tyr Asn Val Pro Cys Ala Glu Ala Ser Gln Gly Ile Ile Arg
            100                 105                 110

Ile Leu Thr Glu Arg Ile Leu Phe Cys Thr Glu Lys Ala Phe Leu Thr
        115                 120                 125

Ala Ala Cys Ser Gly Val Ser Leu Pro Pro Ala Ile Cys Lys Leu Leu
    130                 135                 140

His Glu Ile Tyr Thr Glu Met Lys Ala Lys Cys Leu Gly Ala Trp Arg
145                 150                 155                 160

Arg Leu Val Cys Asn Arg Arg Pro Ile Met Ile Leu Thr Ser Ser Leu
                165                 170                 175

Leu Lys Leu Tyr Asn Thr Tyr Asp Thr Ala Gly Leu Leu Ser Glu Gln
            180                 185                 190

Ser Arg Ala Leu Cys Leu Leu Val Phe Gln Pro Val Tyr Leu Pro Arg
        195                 200                 205

Ile Met Ala Pro Leu Glu Ile Met Thr Lys Gly Gln Leu Ala Pro Glu
    210                 215                 220

Asn Phe Tyr Ser Ile Thr Gly Ser Ala Glu Lys Arg Arg Pro Ile Thr
225                 230                 235                 240

Thr Gly Lys Val Thr Gly Leu Ser Tyr Pro Gly Ser Gly Leu Met Pro
```

```
                245                 250                 255
Glu Ser Leu Ile Leu Pro Ile Leu Glu Pro Gly Leu Leu Pro Ala Ser
            260                 265                 270

Met Val Asp Leu Ser Asp Val Leu Ala Lys Pro Ala Val Ile Leu Ser
        275                 280                 285

Ala Pro Ala Leu Ser Gln Phe Val Ile Ser Lys Pro His Pro Asn Met
    290                 295                 300

Pro His Thr Val Ser Ile Ile Pro Phe Asn Pro Ser Gly Thr Asp Pro
305                 310                 315                 320

Ala Phe Ile Ser Thr Trp Gln Ala Ser Gln Asn Met Val Tyr Asn
                325                 330                 335

Thr Ser Thr Ala Pro Leu Lys Pro Ala Thr Gly Ser Ser Gln Thr Val
            340                 345                 350

Ser Val Lys Ala Val Ala Gln Gly Ala Val Ile Thr Ala Thr Thr Val
        355                 360                 365

Pro Gln Ala Met Pro Ala Arg Gly Thr Gly Glu Leu Pro Val Met
    370                 375                 380

Ser Ala Ser Thr Pro Ala Arg Asp Gln Val Ala Ala Cys Phe Val Ala
385                 390                 395                 400

Glu Asn Thr Gly Asp Ser Pro Asp Asn Pro Ser Ser Phe Leu Thr Ser
                405                 410                 415

Cys His Pro Cys Asp Pro Asn Thr Val Ile Val Ala Gln Gln Phe Gln
            420                 425                 430

Pro Pro Gln Cys Val Thr Leu Leu Gln Val Thr Cys Ala Pro Ser Ser
        435                 440                 445

Thr Pro Pro Asp Ser Thr Val Arg Ala Pro Val Val Gln Leu Pro
    450                 455                 460

Thr Val Val Pro Leu Pro Ala Ser Ala Phe Leu Pro Ala Leu Ala Gln
465                 470                 475                 480

Pro Glu Ala Ser Gly Glu Glu Leu Pro Gly Gly His Asp Gly Asp Gln
                485                 490                 495

Gly Val Pro Cys Arg Asp Ser Thr Ala Ala Thr Ala Ala Glu Ala
            500                 505                 510

Thr Thr Pro Lys Arg Lys Gln Arg Ser Lys Glu Arg Ser Ser Lys Lys
        515                 520                 525

Arg Lys Ala Leu Thr Val Pro Glu Ala Asp Thr Thr Pro Ser Thr Thr
530                 535                 540

Thr Pro Gly Thr Ser Leu Gly Ser Ile Thr Thr Pro Gln Asp Val His
545                 550                 555                 560

Ala Thr Asp Val Ala Thr Ser Glu Gly Pro Ser Glu Ala Gln Pro Pro
                565                 570                 575

Leu Leu Ser Leu Pro Pro Leu Asp Val Asp Gln Ser Leu Phe Ala
            580                 585                 590

Leu Leu Asp Glu Ala Gly Pro Glu Thr Trp Asp Val Gly Ser Pro Leu
        595                 600                 605

Ser Pro Thr Asp Asp Ala Leu Leu Ser Ser Ile Leu Gln Gly Leu Tyr
    610                 615                 620

Gln Leu Asp Thr Pro Pro Leu Arg Ser Pro Ser Pro Ala Ser Phe
625                 630                 635                 640

Gly Pro Glu Ser Pro Ala Asp Ile Pro Ser Pro Ser Gly Gly Glu Tyr
                645                 650                 655

Thr Gln Leu Gln Pro Val Arg Ala Thr Ser Ala Thr Pro Ala Asn Glu
            660                 665                 670
```

Val Gln Glu Ser Gly Thr Leu Tyr Gln Leu His Gln Trp Arg Asn Tyr
          675                 680                 685

Phe Arg Asp
    690

<210> SEQ ID NO 8
<211> LENGTH: 217
<212> TYPE: DNA
<213> ORGANISM: Artificial sequence
<220> FEATURE:
<223> OTHER INFORMATION: Synthetic nucleotide sequence

<400> SEQUENCE: 8
gttcagtcac atgtacgcta gggtctcccc acccaacccc cataggaccc agctacagct     60
tatcctccac taaataccag gcagctaccg gcgactcatt aagccccgcc cagaaaccag    120
tagctgggtg gcaatgacac gtcccctttta aaaagtcaac cttactccgc aagggggtagt   180 ctgttgtgag aatactgtcc aggcagccac aaaaatg                              217

<210> SEQ ID NO 9
<211> LENGTH: 236
<212> TYPE: PRT
<213> ORGANISM: Artificial sequence
<220> FEATURE:
<223> OTHER INFORMATION: Synthetic amino acid sequence

<400> SEQUENCE: 9

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
        50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
                100                 105                 110

Thr Gln Asp Ser Ser Leu Gln Asp Gly Glu Phe Ile Tyr Lys Val Lys
            115                 120                 125

Leu Arg Gly Thr Asn Phe Pro Ser Asp Gly Pro Val Met Gln Lys Lys
        130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
                180                 185                 190

Gln Leu Pro Gly Ala Tyr Asn Val Asn Ile Lys Leu Asp Ile Thr Ser
            195                 200                 205

His Asn Glu Asp Tyr Thr Ile Val Glu Gln Tyr Glu Arg Ala Glu Gly
        210                 215                 220

Arg His Ser Thr Gly Gly Met Asp Glu Leu Tyr Lys
225                 230                 235

<210> SEQ ID NO 10
<211> LENGTH: 1298
<212> TYPE: PRT
<213> ORGANISM: Artificial sequence
<220> FEATURE:
<223> OTHER INFORMATION: Synthetic amino acid sequence

<400> SEQUENCE: 10

```
Met Ala Ser Glu Asn Lys Gln Arg Pro Gly Ser Pro Gly Pro Thr Asp
1               5                   10                  15

Gly Pro Pro Thr Pro Ser Pro Asp Arg Asp Glu Arg Gly Ala Leu
            20                  25                  30

Gly Trp Gly Ala Glu Thr Glu Glu Gly Gly Asp Asp Pro Asp His Asp
            35                  40                  45

Pro Asp His Pro His Asp Leu Asp Asp Ala Arg Arg Asp Gly Arg Ala
        50                  55                  60

Pro Ala Ala Gly Thr Asp Ala Gly Glu Asp Ala Gly Asp Ala Val Ser
65                  70                  75                  80

Pro Arg Gln Leu Ala Leu Leu Ala Ser Met Val Glu Ala Val Arg
                85                  90                  95

Thr Ile Pro Thr Pro Asp Pro Ala Ala Ser Pro Pro Arg Thr Pro Ala
            100                 105                 110

Phe Arg Ala Asp Asp Asp Gly Asp Glu Tyr Asp Asp Ala Ala Asp
            115                 120                 125

Ala Ala Gly Asp Arg Ala Pro Ala Arg Gly Arg Glu Arg Glu Ala Pro
        130                 135                 140

Leu Arg Gly Ala Tyr Pro Asp Pro Thr Asp Arg Leu Ser Pro Arg Pro
145                 150                 155                 160

Pro Ala Gln Pro Pro Arg Arg Arg His Gly Arg Trp Arg Pro Ser
                165                 170                 175

Ala Ser Ser Thr Ser Ser Asp Ser Gly Ser Ser Ser Ser Ser Ala
            180                 185                 190

Ser Ser Ser Ser Ser Ser Asp Glu Asp Glu Asp Asp Asp Gly Asn
            195                 200                 205

Asp Ala Ala Asp His Ala Arg Glu Ala Arg Ala Val Gly Arg Gly Pro
    210                 215                 220

Ser Ser Ala Ala Pro Ala Ala Pro Gly Arg Thr Pro Pro Pro Gly
225                 230                 235                 240

Pro Pro Pro Leu Ser Glu Ala Ala Pro Lys Pro Arg Ala Ala Ala Arg
                245                 250                 255

Thr Pro Ala Ala Ser Ala Gly Arg Ile Glu Arg Arg Arg Ala Arg Ala
            260                 265                 270

Ala Val Ala Gly Arg Asp Ala Thr Gly Arg Phe Thr Ala Gly Gln Pro
        275                 280                 285

Arg Arg Val Glu Leu Asp Ala Asp Ala Thr Ser Gly Ala Phe Tyr Ala
    290                 295                 300

Arg Tyr Arg Asp Gly Tyr Val Ser Gly Glu Pro Trp Pro Gly Ala Gly
305                 310                 315                 320

Pro Pro Pro Pro Gly Arg Val Leu Tyr Gly Gly Leu Gly Asp Ser Arg
                325                 330                 335

Pro Gly Leu Trp Gly Ala Pro Glu Ala Glu Ala Arg Arg Arg Phe
            340                 345                 350

Glu Ala Ser Gly Ala Pro Ala Val Trp Ala Pro Glu Leu Gly Asp
            355                 360                 365
```

```
Ala Ala Gln Gln Tyr Ala Leu Ile Thr Arg Leu Leu Tyr Thr Pro Asp
    370                 375                 380

Ala Glu Ala Met Gly Trp Leu Gln Asn Pro Arg Val Val Pro Gly Asp
385                 390                 395                 400

Val Ala Leu Asp Gln Ala Cys Phe Arg Ile Ser Gly Ala Ala Arg Asn
                405                 410                 415

Ser Ser Ser Phe Ile Thr Gly Ser Val Ala Arg Ala Val Pro His Leu
            420                 425                 430

Gly Tyr Ala Met Ala Ala Gly Arg Phe Gly Trp Gly Leu Ala His Ala
        435                 440                 445

Ala Ala Ala Val Ala Met Ser Arg Arg Tyr Asp Arg Ala Gln Lys Gly
    450                 455                 460

Phe Leu Leu Thr Ser Leu Arg Arg Ala Tyr Ala Pro Leu Leu Ala Arg
465                 470                 475                 480

Glu Asn Ala Ala Leu Thr Gly Ala Ala Gly Ser Pro Gly Ala Gly Ala
                485                 490                 495

Asp Asp Glu Gly Val Ala Ala Val Ala Ala Ala Pro Gly Glu Arg
            500                 505                 510

Ala Val Pro Ala Gly Tyr Gly Ala Ala Gly Ile Leu Ala Ala Leu Gly
    515                 520                 525

Arg Leu Ser Ala Ala Pro Ala Ser Pro Ala Gly Gly Asp Asp Pro Asp
530                 535                 540

Ala Ala Arg His Ala Asp Ala Asp Asp Ala Gly Arg Arg Ala Gln
545                 550                 555                 560

Ala Gly Arg Val Ala Val Glu Cys Leu Ala Cys Arg Gly Ile Leu
                565                 570                 575

Glu Ala Leu Ala Glu Gly Phe Asp Gly Asp Leu Ala Ala Val Pro Gly
            580                 585                 590

Leu Ala Gly Ala Arg Pro Ala Ser Pro Pro Arg Pro Glu Gly Pro Ala
        595                 600                 605

Gly Pro Ala Ser Pro Pro Pro His Ala Asp Ala Pro Arg Leu Arg
    610                 615                 620

Ala Trp Leu Arg Glu Leu Arg Phe Val Arg Asp Ala Leu Val Leu Met
625                 630                 635                 640

Arg Leu Arg Gly Asp Leu Arg Val Ala Gly Gly Ser Glu Ala Ala Val
                645                 650                 655

Ala Ala Val Arg Ala Val Ser Leu Val Ala Gly Ala Leu Gly Pro Ala
            660                 665                 670

Leu Pro Arg Asp Pro Arg Leu Pro Ser Ser Ala Ala Ala Ala Ala
        675                 680                 685

Asp Leu Leu Phe Asp Asn Gln Ser Leu Arg Pro Leu Leu Ala Ala
    690                 695                 700

Ala Ser Ala Pro Asp Ala Ala Asp Ala Leu Ala Ala Ala Ala Ser
705                 710                 715                 720

Ala Ala Pro Arg Glu Gly Arg Lys Arg Lys Ser Pro Gly Pro Ala Arg
                725                 730                 735

Pro Pro Gly Gly Gly Gly Pro Arg Pro Pro Lys Thr Lys Lys Ser Gly
            740                 745                 750

Ala Asp Ala Pro Gly Ser Asp Ala Arg Ala Pro Leu Pro Ala Pro Ala
        755                 760                 765

Pro Pro Ser Thr Pro Pro Gly Pro Glu Pro Ala Pro Ala Gln Pro Ala
    770                 775                 780
```

```
Ala Pro Arg Ala Ala Ala Gln Ala Arg Pro Arg Pro Val Ala Val
785                 790                 795                 800

Ser Arg Arg Pro Ala Glu Gly Pro Asp Pro Leu Gly Gly Trp Arg Arg
            805                 810                 815

Gln Pro Pro Gly Pro Ser His Thr Ala Ala Pro Ala Ala Ala Ala Leu
            820                 825                 830

Glu Ala Tyr Cys Ser Pro Arg Ala Val Ala Glu Leu Thr Asp His Pro
            835                 840                 845

Leu Phe Pro Val Pro Trp Arg Pro Ala Leu Met Phe Asp Pro Arg Ala
850                 855                 860

Leu Ala Ser Ile Ala Ala Arg Cys Ala Gly Pro Ala Pro Ala Ala Gln
865                 870                 875                 880

Ala Ala Cys Gly Gly Gly Asp Asp Asp Asn Pro His Pro His Gly
            885                 890                 895

Ala Ala Gly Gly Arg Leu Phe Gly Pro Leu Arg Ala Ser Gly Pro Leu
            900                 905                 910

Arg Arg Met Ala Ala Trp Met Arg Gln Ile Pro Asp Pro Glu Asp Val
            915                 920                 925

Arg Val Val Val Leu Tyr Ser Pro Leu Pro Gly Glu Asp Leu Ala Gly
            930                 935                 940

Gly Gly Ala Ser Gly Gly Pro Pro Glu Trp Ser Ala Glu Arg Gly Gly
945                 950                 955                 960

Leu Ser Cys Leu Leu Ala Ala Leu Ala Asn Arg Leu Cys Gly Pro Asp
            965                 970                 975

Thr Ala Ala Trp Ala Gly Asn Trp Thr Gly Ala Pro Asp Val Ser Ala
            980                 985                 990

Leu Gly Ala Gln Gly Val Leu Leu Leu Ser Thr Arg Asp Leu Ala Phe
            995                 1000                1005

Ala Gly Ala Val Glu Phe Leu Gly Leu Leu Ala Ser Ala Gly Asp
    1010                1015                1020

Arg Arg Leu Ile Val Val Asn Thr Val Arg Ala Cys Asp Trp Pro
    1025                1030                1035

Ala Asp Gly Pro Ala Val Ser Arg Gln His Ala Tyr Leu Ala Cys
    1040                1045                1050

Glu Leu Leu Pro Ala Val Gln Cys Ala Val Arg Trp Pro Ala Ala
    1055                1060                1065

Arg Asp Leu Arg Arg Thr Val Leu Ala Ser Gly Arg Val Phe Gly
    1070                1075                1080

Pro Gly Val Phe Ala Arg Val Glu Ala Ala His Ala Arg Leu Tyr
    1085                1090                1095

Pro Asp Ala Pro Pro Leu Arg Leu Cys Arg Gly Gly Asn Val Arg
    1100                1105                1110

Tyr Arg Val Arg Thr Arg Phe Gly Pro Asp Thr Pro Val Pro Met
    1115                1120                1125

Ser Pro Arg Glu Tyr Arg Arg Ala Val Leu Pro Ala Leu Asp Gly
    1130                1135                1140

Arg Ala Ala Ala Ser Gly Thr Thr Asp Ala Met Ala Pro Gly Ala
    1145                1150                1155

Pro Asp Phe Cys Glu Glu Glu Ala His Ser His Ala Ala Cys Ala
    1160                1165                1170

Arg Trp Gly Leu Gly Ala Pro Leu Arg Pro Val Tyr Val Ala Leu
    1175                1180                1185

Gly Arg Glu Ala Val Arg Ala Gly Pro Ala Arg Trp Arg Gly Pro
```

```
                1190                1195                1200
Arg Arg Asp Phe Cys Ala Arg Ala Leu Leu Glu Pro Asp Asp Asp
    1205                1210                1215

Ala Pro Pro Leu Val Leu Arg Gly Asp Asp Gly Pro Gly Ala
    1220                1225                1230

Leu Pro Pro Ala Pro Pro Gly Ile Arg Trp Ala Ser Ala Thr Gly
    1235                1240                1245

Arg Ser Gly Thr Val Leu Ala Ala Ala Gly Ala Val Glu Val Leu
    1250                1255                1260

Gly Ala Glu Ala Gly Leu Ala Thr Pro Pro Arg Arg Glu Val Val
    1265                1270                1275

Asp Trp Glu Gly Ala Trp Asp Glu Asp Gly Gly Ala Phe Glu
    1280                1285                1290

Gly Asp Gly Val Leu
    1295

<210> SEQ ID NO 11
<211> LENGTH: 467
<212> TYPE: PRT
<213> ORGANISM: Human herpesvirus 3

<400> SEQUENCE: 11

Met Asp Thr Ile Leu Ala Gly Gly Ser Gly Thr Ser Asp Ala Ser Asp
1               5                   10                  15

Asn Thr Cys Thr Ile Cys Met Ser Thr Val Ser Asp Leu Gly Lys Thr
                20                  25                  30

Met Pro Cys Leu His Asp Phe Cys Phe Val Cys Ile Arg Ala Trp Thr
            35                  40                  45

Ser Thr Ser Val Gln Cys Pro Leu Cys Arg Cys Pro Val Gln Ser Ile
        50                  55                  60

Leu His Lys Ile Val Ser Asp Thr Ser Tyr Lys Glu Tyr Glu Val His
65                  70                  75                  80

Pro Ser Asp Asp Asp Gly Phe Ser Glu Pro Ser Phe Glu Asp Ser Ile
                85                  90                  95

Asp Ile Leu Pro Gly Asp Val Ile Asp Leu Leu Pro Ser Pro Gly
            100                 105                 110

Pro Ser Arg Glu Ser Ile Gln Gln Pro Thr Ser Arg Ser Ser Arg Glu
        115                 120                 125

Pro Ile Gln Ser Pro Asn Pro Gly Pro Leu Gln Ser Ser Ala Arg Glu
    130                 135                 140

Pro Thr Ala Glu Ser Pro Ser Asp Ser Gln Gln Asp Ser Ile Gln Pro
145                 150                 155                 160

Pro Thr Arg Asp Ser Ser Pro Gly Val Thr Lys Thr Cys Ser Thr Ala
                165                 170                 175

Ser Phe Leu Arg Lys Val Phe Phe Lys Asp Gln Pro Ala Val Arg Ser
            180                 185                 190

Ala Thr Pro Val Val Tyr Gly Ser Ile Glu Ser Ala Gln Pro Arg
        195                 200                 205

Thr Gly Gly Gln Asp Tyr Arg Asp Arg Pro Val Ser Val Gly Ile Asn
    210                 215                 220

Gln Asp Pro Arg Thr Met Asp Arg Leu Pro Phe Arg Ala Thr Asp Arg
225                 230                 235                 240

Gly Thr Glu Gly Asn Ala Arg Phe Pro Cys Tyr Met Gln Pro Leu Leu
                245                 250                 255
```

```
Gly Trp Leu Asp Asp Gln Leu Ala Glu Leu Tyr Gln Pro Glu Ile Val
                260                 265                 270

Glu Pro Thr Lys Met Leu Ile Leu Asn Tyr Ile Gly Ile Tyr Gly Arg
            275                 280                 285

Asp Glu Ala Gly Leu Lys Thr Ser Leu Arg Cys Leu Leu His Asp Ser
        290                 295                 300

Thr Gly Pro Phe Val Thr Asn Met Leu Phe Leu Asp Arg Cys Thr
305                 310                 315                 320

Asp Pro Thr Arg Leu Thr Met Gln Thr Trp Thr Trp Lys Asp Thr Ala
                325                 330                 335

Ile Gln Leu Ile Thr Gly Pro Ile Val Arg Pro Glu Thr Thr Ser Thr
            340                 345                 350

Gly Glu Thr Ser Arg Gly Asp Glu Arg Asp Thr Arg Leu Val Asn Thr
        355                 360                 365

Pro Gln Lys Val Arg Leu Phe Ser Val Leu Pro Gly Ile Lys Pro Gly
    370                 375                 380

Ser Ala Arg Gly Ala Lys Arg Arg Leu Phe His Thr Gly Arg Asp Val
385                 390                 395                 400

Lys Arg Cys Leu Thr Ile Asp Leu Thr Ser Glu Ser Asp Ser Ala Cys
                405                 410                 415

Lys Gly Ser Lys Thr Arg Lys Val Ala Ser Pro Gln Gly Glu Ser Asn
            420                 425                 430

Thr Pro Ser Thr Ser Gly Ser Thr Ser Gly Ser Leu Lys His Leu Thr
        435                 440                 445

Lys Lys Ser Ser Ala Gly Lys Ala Gly Lys Gly Ile Pro Asn Lys Met
    450                 455                 460

Lys Lys Ser
465

<210> SEQ ID NO 12
<211> LENGTH: 1310
<212> TYPE: PRT
<213> ORGANISM: Human herpesvirus 3
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (512)..(512)
<223> OTHER INFORMATION: Xaa can be any naturally occurring amino acid
<220> FEATURE:
<221> NAME/KEY: misc_feature
<222> LOCATION: (1275)..(1275)
<223> OTHER INFORMATION: Xaa can be any naturally occurring amino acid

<400> SEQUENCE: 12

Met Asp Thr Pro Pro Met Gln Arg Ser Thr Pro Gln Arg Ala Gly Ser
1               5                   10                  15

Pro Asp Thr Leu Glu Leu Met Asp Leu Leu Asp Ala Ala Ala Ala
            20                  25                  30

Ala Glu His Arg Ala Arg Val Val Thr Ser Ser Gln Pro Asp Asp Leu
        35                  40                  45

Leu Phe Gly Glu Asn Gly Val Met Val Gly Arg Glu His Glu Ile Val
    50                  55                  60

Ser Ile Pro Ser Val Ser Gly Leu Gln Pro Glu Pro Arg Thr Glu Asp
65                  70                  75                  80

Val Gly Glu Glu Leu Thr Gln Asp Asp Tyr Val Cys Glu Asp Gly Gln
                85                  90                  95
```

```
Asp Leu Xaa Gly Ser Pro Val Ile Pro Leu Ala Glu Val Phe His Thr
            100                 105                 110

Arg Phe Ser Glu Ala Gly Ala Arg Glu Pro Thr Gly Ala Asp Arg Ser
            115                 120                 125

Leu Glu Thr Val Ser Leu Gly Thr Lys Leu Ala Arg Ser Pro Lys Pro
        130                 135                 140

Pro Met Asn Asp Gly Glu Thr Gly Arg Gly Thr Thr Pro Pro Phe Pro
145                 150                 155                 160

Gln Ala Phe Ser Pro Val Ser Pro Ala Ser Pro Val Gly Asp Ala Ala
                165                 170                 175

Gly Asn Asp Gln Arg Glu Asp Gln Arg Ser Ile Pro Arg Gln Thr Thr
            180                 185                 190

Arg Gly Asn Ser Pro Gly Leu Pro Ser Val Val His Arg Asp Arg Gln
        195                 200                 205

Thr Gln Ser Ile Ser Gly Lys Lys Pro Gly Asp Glu Gln Ala Gly His
    210                 215                 220

Ala His Ala Ser Gly Asp Gly Val Val Leu Gln Lys Thr Gln Arg Pro
225                 230                 235                 240

Ala Gln Gly Lys Ser Pro Lys Lys Thr Leu Lys Val Lys Val Pro
                245                 250                 255

Leu Pro Ala Arg Lys Pro Gly Gly Pro Val Pro Gly Pro Val Glu Gln
        260                 265                 270

Leu Tyr His Val Leu Ser Asp Ser Val Pro Ala Lys Gly Ala Lys Ala
    275                 280                 285

Asp Leu Pro Phe Glu Thr Asp Asp Thr Arg Pro Arg Lys His Asp Ala
290                 295                 300

Arg Gly Ile Thr Pro Arg Val Pro Gly Arg Ser Ser Gly Gly Lys Pro
305                 310                 315                 320

Arg Ala Phe Leu Ala Leu Pro Gly Arg Ser His Ala Pro Asp Pro Ile
            325                 330                 335

Glu Asp Asp Ser Pro Val Glu Lys Lys Pro Lys Ser Arg Glu Phe Val
            340                 345                 350

Ser Ser Ser Ser Ser Ser Ser Trp Gly Ser Ser Glu Asp Glu
        355                 360                 365

Asp Asp Glu Pro Arg Arg Val Ser Val Gly Ser Glu Thr Thr Gly Ser
370                 375                 380

Arg Ser Gly Arg Glu His Ala Pro Ser Pro Ser Asn Ser Asp Asp Ser
385                 390                 395                 400

Asp Ser Asn Asp Gly Ser Thr Lys Gln Asn Ile Gln Pro Gly Tyr
                405                 410                 415

Arg Ser Ile Ser Gly Pro Asp Pro Arg Ile Arg Lys Thr Lys Arg Leu
            420                 425                 430

Ala Gly Glu Pro Gly Arg Gln Arg Gln Lys Ser Phe Ser Leu Pro Arg
        435                 440                 445

Ser Arg Thr Pro Ile Ile Pro Pro Val Ser Gly Pro Leu Met Met Pro
    450                 455                 460

Asp Gly Ser Pro Trp Pro Gly Ser Ala Pro Leu Pro Ser Asn Arg Val
465                 470                 475                 480

Arg Phe Gly Pro Ser Gly Glu Thr Arg Glu Gly His Trp Glu Asp Glu
                485                 490                 495

Ala Val Arg Ala Ala Arg Ala Tyr Glu Ala Ser Thr Glu Pro Xaa
                500                 505                 510
```

```
Pro Leu Tyr Val Pro Glu Leu Gly Asp Pro Ala Arg Gln Tyr Arg Ala
            515                 520                 525

Leu Ile Asn Leu Ile Tyr Cys Pro Asp Arg Asp Pro Ile Ala Trp Leu
        530                 535                 540

Gln Asn Pro Lys Leu Thr Gly Val Asn Ser Ala Leu Asn Gln Phe Tyr
545                 550                 555                 560

Gln Lys Leu Leu Pro Pro Gly Arg Ala Gly Thr Ala Val Thr Gly Ser
                565                 570                 575

Val Ala Ser Pro Val Pro His Val Gly Glu Ala Met Ala Thr Gly Glu
            580                 585                 590

Ala Leu Trp Ala Leu Pro His Ala Ala Ala Val Ala Met Ser Arg
        595                 600                 605

Arg Tyr Asp Arg Ala Gln Lys His Phe Ile Leu Gln Ser Leu Arg Arg
        610                 615                 620

Ala Phe Ala Gly Met Ala Tyr Pro Glu Ala Thr Gly Ser Ser Pro Ala
625                 630                 635                 640

Ala Arg Ile Ser Arg Gly His Pro Ser Pro Thr Thr Pro Ala Thr Gln
                645                 650                 655

Thr Pro Asp Pro Gln Pro Ser Ala Ala Ala Arg Ser Leu Ser Val Cys
            660                 665                 670

Pro Pro Asp Asp Arg Leu Arg Thr Pro Arg Lys Arg Lys Ser Gln Pro
        675                 680                 685

Val Glu Ser Arg Ser Leu Leu Asp Lys Ile Arg Glu Thr Pro Val Ala
        690                 695                 700

Asp Ala Arg Val Ala Asp Asp His Val Val Ser Lys Ala Lys Arg Arg
705                 710                 715                 720

Val Ser Glu Pro Val Thr Ile Thr Ser Gly Pro Val Val Asp Pro Pro
                725                 730                 735

Ala Val Ile Thr Met Pro Leu Asp Gly Pro Ala Pro Asn Gly Gly Phe
            740                 745                 750

Arg Arg Ile Pro Arg Gly Ala Leu His Thr Pro Val Pro Ser Asp Gln
        755                 760                 765

Ala Arg Lys Ala Tyr Cys Thr Pro Glu Thr Ile Ala Arg Leu Val Asp
        770                 775                 780

Asp Pro Leu Phe Pro Thr Ala Trp Arg Pro Ala Leu Ser Phe Asp Pro
785                 790                 795                 800

Gly Ala Leu Ala Glu Ile Ala Ala Arg Arg Pro Gly Gly Gly Asp Arg
                805                 810                 815

Arg Phe Gly Pro Pro Ser Gly Val Glu Ala Leu Arg Arg Cys Ala
            820                 825                 830

Trp Met Arg Gln Ile Pro Asp Pro Glu Asp Val Arg Leu Leu Ile Ile
        835                 840                 845

Tyr Asp Pro Leu Pro Gly Glu Asp Ile Asn Gly Pro Leu Glu Ser Thr
        850                 855                 860

Leu Ala Thr Asp Pro Gly Pro Ser Trp Ser Pro Ser Arg Gly Gly Leu
865                 870                 875                 880

Ser Val Val Leu Ala Ala Leu Ser Asn Arg Leu Cys Leu Pro Ser Thr
                885                 890                 895

His Ala Trp Ala Gly Asn Trp Thr Gly Pro Pro Asp Val Ser Ala Leu
            900                 905                 910

Asn Ala Arg Gly Val Leu Leu Leu Ser Thr Arg Asp Leu Ala Phe Ala
        915                 920                 925

Gly Ala Val Glu Tyr Leu Gly Ser Arg Leu Ala Ser Ala Arg Arg Arg
```

```
                930             935             940
Leu Leu Val Leu Asp Ala Val Ala Leu Glu Arg Trp Pro Gly Asp Gly
945             950             955             960
Pro Ala Leu Ser Gln Tyr His Val Tyr Val Arg Ala Pro Ala Arg Pro
            965             970             975
Asp Ala Gln Ala Val Val Arg Trp Pro Asp Ser Ala Val Thr Glu Gly
        980             985             990
Leu Ala Arg Ala Val Phe Ala Ser Ser Arg Thr Phe Gly Pro Ala Ser
    995             1000            1005
Phe Ala Arg Ile Glu Thr Ala Phe Ala Asn Leu Tyr Pro Gly Glu
1010            1015            1020
Gln Pro Leu Cys Leu Cys Arg Gly Gly Asn Val Ala Tyr Thr Val
1025            1030            1035
Cys Thr Arg Ala Gly Pro Lys Thr Arg Val Pro Leu Ser Pro Arg
1040            1045            1050
Glu Tyr Arg Gln Tyr Val Leu Pro Gly Phe Asp Gly Cys Lys Asp
1055            1060            1065
Leu Ala Arg Gln Ser Arg Gly Leu Gly Leu Gly Ala Ala Asp Phe
1070            1075            1080
Val Asp Glu Ala Ala His Ser His Arg Ala Ala Asn Arg Trp Gly
1085            1090            1095
Leu Gly Ala Ala Leu Arg Pro Val Phe Leu Pro Glu Gly Arg Arg
1100            1105            1110
Pro Gly Ala Ala Gly Pro Glu Ala Gly Asp Val Pro Thr Trp Ala
1115            1120            1125
Arg Val Phe Cys Arg His Ala Leu Leu Glu Pro Asp Pro Ala Ala
1130            1135            1140
Glu Pro Leu Val Leu Pro Pro Val Ala Gly Arg Ser Val Ala Leu
1145            1150            1155
Tyr Ala Ser Ala Asp Glu Ala Arg Asn Ala Leu Pro Pro Ile Pro
1160            1165            1170
Arg Val Met Trp Pro Pro Gly Phe Gly Ala Ala Glu Thr Val Leu
1175            1180            1185
Glu Gly Ser Asp Gly Thr Arg Phe Ala Phe Gly His His Gly Gly
1190            1195            1200
Ser Glu Arg Pro Ala Glu Thr Gln Ala Gly Arg Gln Arg Arg Thr
1205            1210            1215
Ala Asp Asp Arg Glu His Ala Leu Glu Pro Asp Trp Glu Val
1220            1225            1230
Gly Cys Glu Asp Ala Trp Asp Ser Glu Glu Gly Gly Asp Asp
1235            1240            1245
Gly Asp Ala Pro Gly Ser Ser Phe Gly Val Ser Val Ser Val
1250            1255            1260
Ala Pro Gly Val Leu Arg Asp Arg Arg Val Gly Xaa Arg Pro Ala
1265            1270            1275
Val Lys Val Glu Leu Leu Ser Ser Ser Ser Ser Glu Asp Glu
1280            1285            1290
Asp Asp Val Trp Gly Gly Arg Gly Gly Arg Ser Pro Pro Gln Ser
1295            1300            1305
Arg Gly
1310

<210> SEQ ID NO 13
```

```
<211> LENGTH: 180
<212> TYPE: DNA
<213> ORGANISM: Artificial sequence
<220> FEATURE:
<223> OTHER INFORMATION: Synthetic nucleotide sequence

<400> SEQUENCE: 13
acattttata cccacgtttt agtgggtggg acttaaaaga aatgggtgga gggatatagg      60
ggtgtgtctt cgttggtacc aattataaaa atgtactcgc cacaactcac aatttagaac     120
gcatggcagt tctgctacgt gtttggatgc ccggacatta aatacagcc agttgttacc      180

<210> SEQ ID NO 14
<211> LENGTH: 11771
<212> TYPE: DNA
<213> ORGANISM: Artificial sequence
<220> FEATURE:
<223> OTHER INFORMATION: Synthetic nucleotide sequence

<400> SEQUENCE: 14
ctagcatgga gtcctctgcc aagagaaaga tggaccctga taatcctgac gagggccctt      60
cctccaaggt gccacggccc gagacacccg tgaccaaggc cacgacgttc ctgcagacta     120
tgttgaggaa ggaggttaac agtcagctga gtctgggaga cccgctgttt ccagagttgg     180
ccgaagaatc cctcaaaact tttgaacaag tgaccgagga ttgcaacgag aaccccgaga     240
aagatgtcct ggcagaactc ggtgacatcc tcgcccaggc tgtcaatcat gccggtatcg     300
attccagtag caccggcccc acgctgacaa cccactcttg cagcgttagc agcgcccctc     360
ttaacaagcc gacccccacc agcgtcgcgg ttactaacac tcctctcccc ggggcatccg     420
ctactcccga gctcagcccg cgtaagaaac gcgcaaaac cacgcgtcct ttcaaggtga     480
ttattaaacc gcccgtgcct cccgcgccta tcatgctgcc cctcatcaaa caggaagaca     540
tcaagcccga gcccgacttt accatccagt accgcaacaa gattatcgat accgccggct     600
gtatcgtgat ctctgatagc gaggaagaac agggtgaaga agtcgaaacc cgcggtgcta     660
ccgcgtcttc cccttccacc ggcagcggca cgccgcgagt gacctctccc acgcacccgc     720
tctcccagat gaaccaccct cctcttcccg atccttggg ccggcccgat gaagatagtt     780
cctcttcgtc ttcctcctcc tgcagttcgg cttcggactc ggagagtgag tccgaggaga     840
tgaaatgcag cagtggcgga ggagcatccg tgacctcgag ccaccatggg cgcggcggtt     900
ttggtggcgc ggcctcctcc tctctgctga gctgcggcca tcagagcagc ggcggggcga     960
gcaccggacc ccgcaagaag aagagcaaac gcatctccga gttggacaac gagaaggtgc    1020
gcaatatcat gaaagataag aacacccct tctgcacacc caacgtgcag actcggcggg    1080
gtcgcgtcaa gattgacgag gtgagccgca tgttccgcaa caccaatcgc tctcttgagt    1140
acaagaacct gccccttcacg attcccagta tgcaccaggt gttagatgag gccatcaaag    1200
cctgcaaaac catgcaggtg aacaacaagg gcatccagat tatctacacc cgcaatcatg    1260
aggtgaagag tgaggtggat gcggtgcggt gtcgcctggg caccatgtgc aacctggccc    1320
tctccactcc cttcctcatg gagcacacca tgcccgtgac acatccaccc gaagtggcgc    1380
agcgcacagc cgatgcttgt aacgaaggcg tcaaggccgc gtggagcctc aaagaattgc    1440
acacccacca attatgcccc cgttcctccg attaccgcaa catgatcatc cacgctgcca    1500
cccccgtgga cctgttgggc gctctcaacc tgtgcctgcc cctgatgcaa agtttccca    1560 aacaggtcat ggtgcgcatc ttctccacca ccaggtgg gttcatgctg cctatctacg     1620
agacggccgc gaaggcctac gccgtggggc agtttgagca gccaccgag acccctcccg    1680
```

```
aagacctgga caccctgagc ctggccatcg aggcagccat ccaggacctg aggaacaagt    1740
ctcagtaagg atccgcccct ctccctcccc ccccctaac gttactggcc gaagccgctt     1800
ggaataaggc cggtgtgcgt ttgtctatat gttattttcc accatattgc cgtcttttgg    1860
caatgtgagg gcccggaaac ctggccctgt cttcttgacg agcattccta ggggtctttc    1920
ccctctcgcc aaaggaatgc aaggtctgtt gaatgtcgtg aaggaagcag ttcctctgga    1980
agcttcttga agacaaacaa cgtctgtagc gaccctttgc aggcagcgga acccccacc     2040 tggcgacagg tgcctctgcg gccaaaagcc acgtgtataa gatacacctg caaaggcggc    2100
acaaccccag tgccacgttg tgagttggat agttgtggaa agagtcaaat ggctctcctc    2160
aagcgtattc aacaaggggc tgaaggatgc ccagaaggta ccccattgta tgggatctga    2220
tctggggcct cggtgcacat gctttacatg tgtttagtcg aggttaaaaa aacgtctagg    2280 cccccgaac cacggggacg tggttttcct ttgaaaaaca cgatgataat atggccacaa     2340
ccatggcctc ctccgaggac gtcatcaagg agttcatgcg cttcaaggtg cgcatggagg    2400
gctccgtgaa cggccacgag ttcgagatcg agggcgaggg cgagggccgc cctacgagg     2460 gcacccagac cgccaagctg aaggtgacca agggcggccc cctgcccttc gcctgggaca    2520
tcctgtcccc ccagttccag tacggctcca aggtgtacgt gaagcacccc gccgacatcc    2580
ccgactacaa gaagctgtcc ttccccgagg gcttcaagtg ggagcgcgtg atgaacttcg    2640
aggacggcgg cgtggtgacc gtgacccagg actcctccct gcaggacggc tccttcatct    2700
acaaggtgaa gttcatcggc gtgaacttcc cctccgacgg ccccgtaatg cagaagaaga    2760
ctatgggctg ggaggcctcc accgagcgcc tgtaccccg cgacgcgtg ctgaagggcg      2820 agatccacaa ggccctgaag ctgaaggacg gcggccacta cctggtggag ttcaagtcca    2880
tctacatggc caagaagccc gtgcagctgc ccggctacta ctacgtggac tccaagctgg    2940
acatcacctc ccacaacgag gactaccacc tcgtggagca gtacgagcgc gccgagggcc    3000
gccaccacct gttcctgtag gcggccgcaa tcaacctctg gattacaaaa tttgtgaaag    3060
attgactggt attcttaact atgttgctcc ttttacgcta tgtggatacg ctgctttaat    3120
gcctttgtat catgctatta cttcccgtac ggctttcatt ttctcctcct tgtataaatc    3180
ctggttgctg tctctttatg aggagttgtg gcccgttgtc aggcaacgtg gcgtggtgtg    3240
cactgtgttt gctgacgcaa ccccactgg ttggggcatt gccaccacct atcaactcct     3300
ttccgggact ttcgctttcc ccctccctat gccacggcg gaactcattg ccgcctgcct     3360 tgcccgctc tggacagggg ctcggctgtt gggcactgac aattccgtgg tgttgtcggg     3420
gaagctgacg tccttccat ggctgctcgc ctgtgttgcc aactggattc tgcgcgggac     3480
gtccttctgc tacgtccctt cggccctcaa tccagcggac cttccttccc gcggcctgct    3540
gccggttctg cggcctcttc cgcgtcttcg ccttcgccct cagacgagtc ggatctccct    3600
ttgggccgcc tccccgcctg cctgcaggtt tgtcagacc tagaaaaaca tggagcaatc     3660
acaagtagca atacagcagc taccaatgct gattgtgcct ggctagaagc acaagaggag    3720
gaggaggtgg ttttccagt cacacctcag gtacctttaa gaccaatgac ttacaaggca     3780
gctgtagatc ttagccactt tttaaaagaa aagggggac tggaagggct aattcactcc     3840
caacgaagac aagatctgct ttttgcttgt actgggtctc tctggttaga ccagatctga    3900
gcctgggagc tctctggcta actagggaac ccactgctta agcctcaata aagcttgcct    3960
tgagtgcttc aagtagtgtg tgcccgtctg ttgtgtgact ctggtaacta gagatccctc    4020
```

```
agacccttttt agtcagtgtg gaaaatctct agcagggccc gtttaaaccc gctgatcagc    4080
ctcgactgtg ccttctagtt gccagccatc tgttgtttgc ccctcccccg tgccttcctt    4140
gaccctggaa ggtgccactc ccactgtcct ttcctaataa aatgaggaaa ttgcatcgca    4200
ttgtctgagt aggtgtcatt ctattctggg gggtggggtg gggcaggaca gcaaggggga    4260
ggattgggaa gacaatagca ggcatgctgg ggatgcggtg ggctctatgg cttctgaggc    4320
ggaaagaacc agctggggct ctaggggta tccccacgcg ccctgtagcg gcgcattaag    4380
cgcggcgggt gtggtggtta cgcgcagcgt gaccgctaca cttgccagcg ccctagcgcc    4440
cgctcctttc gctttcttcc cttcctttct cgccacgttc gccggctttc cccgtcaagc    4500
tctaaatcgg ggcatccctt tagggttccg atttagtgct ttacggcacc tcgaccccaa    4560
aaaacttgat tagggtgatg gttcacgtag tgggccatcg ccctgataga cggttttttcg   4620 ccctttgacg ttggagtcca cgttctttaa tagtggactc ttgttccaaa ctggaacaac    4680
actcaaccct atctcggtct attcttttga ttttataaggg attttgggga tttcggccta    4740
ttggttaaaa aatgagctga tttaacaaaa atttaacgcg aattaattct gtggaatgtg    4800
tgtcagttag ggtgtggaaa gtccccaggc tccccaggca ggcagaagta tgcaaagcat    4860
gcatctcaat tagtcagcaa ccaggtgtgg aaagtcccca ggctccccag caggcagaag    4920
tatgcaaagc atgcatctca attagtcagc aaccatagtc cgcccctaa ctccgcccat    4980 cccgccccta actccgccca gttccgccca ttctccgccc catggctgac taattttttt    5040
tatttatgca gaggccgagg ccgcctctgc ctctgagcta ttccagaagt agtgaggagg    5100
cttttttgga ggcctaggct tttgcaaaaa gctcccggga gcttgtatat ccattttcgg    5160
atctgatcag cacgtgttga caattaatca tcggcatagt atatcggcat agtataatac    5220
gacaaggtga ggaactaaac catggccaag ttgaccagtg ccgttccggt gctcaccgcg    5280
cgcgacgtcg ccggagcggt cgagttctgg accgaccggc tcgggttctc ccgggacttc    5340
gtggaggacg acttcgccgg tgtggtccgg gacgacgtga ccctgttcat cagcgcggtc    5400
caggaccagg tggtgccgga caacaccctg gcctgggtgt gggtgcgcgg cctggacgag    5460
ctgtacgccg agtggtcgga ggtcgtgtcc acgaacttcc gggacgcctc cgggccggcc    5520
atgaccgaga tcggcgagca gccgtggggg cgggagttcg ccctgcgcga cccggccggc    5580
aactgcgtgc acttcgtggc cgaggagcag gactgacacg tgctacgaga tttcgattcc    5640
accgccgcct tctatgaaag gttgggcttc ggaatcgttt tccgggacgc cggctggatg    5700
atcctccagc gcggggatct catgctggag ttcttcgccc accccaactt gtttattgca    5760
gcttataatg gttacaaata aagcaatagc atcacaaatt tcacaaataa agcatttttt    5820
tcactgcatt ctagttgtgg tttgtccaaa ctcatcaatg tatcttatca tgtctgtata    5880
ccgtcgacct ctagctagag cttggcgtaa tcatggtcat agctgtttcc tgtgtgaaat    5940
tgttatccgc tcacaattcc acacaacata cgagccggaa gcataaagtg taaagcctgg    6000
ggtgcctaat gagtgagcta actcacatta attgcgttgc gctcactgcc cgctttccag    6060
tcgggaaacc tgtcgtgcca gctgcattaa tgaatcggcc aacgcgcggg gagaggcggt    6120
ttgcgtattg ggcgctcttc cgcttcctcg ctcactgact cgctgcgctc ggtcgttcgg    6180
ctgcggcgag cggtatcagc tcactcaaag gcggtaatac ggttatccac agaatcaggg    6240
gataacgcag gaaagaacat gtgagcaaaa ggccagcaaa aggccaggaa ccgtaaaaag    6300
gccgcgttgc tggcgttttt ccataggctc cgcccccctg acgagcatca caaaaatcga    6360
cgctcaagtc agaggtggcg aaacccgaca ggactataaa gataccaggc gtttccccct    6420
```

```
ggaagctccc tcgtgcgctc tcctgttccg accctgccgc ttaccggata cctgtccgcc   6480
tttctccctt cgggaagcgt ggcgctttct caatgctcac gctgtaggta tctcagttcg   6540
gtgtaggtcg ttcgctccaa gctgggctgt gtgcacgaac cccccgttca gcccgaccgc   6600
tgcgccttat ccggtaacta tcgtcttgag tccaacccgg taagacacga cttatcgcca   6660
ctggcagcag ccactggtaa caggattagc agagcgaggt atgtaggcgg tgctacagag   6720
ttcttgaagt ggtggcctaa ctacggctac actagaagga cagtatttgg tatctgcgct   6780
ctgctgaagc cagttacctt cggaaaaaga gttggtagct cttgatccgg caaacaaacc   6840
accgctggta gcggtggttt ttttgtttgc aagcagcaga ttacgcgcag aaaaaaagga   6900
tctcaagaag atcctttgat cttttctacg gggtctgacg ctcagtggaa cgaaaactca   6960
cgttaaggga ttttggtcat gagattatca aaaaggatct tcacctagat ccttttaaat   7020
taaaaatgaa gttttaaatc aatctaaagt atatatgagt aaacttggtc tgacagttac   7080
caatgcttaa tcagtgaggc acctatctca gcgatctgtc tatttcgttc atccatagtt   7140
gcctgactcc ccgtcgtgta gataactacg atacgggagg gcttaccatc tggccccagt   7200
gctgcaatga taccgcgaga cccacgctca ccggctccag atttatcagc aataaaccag   7260
ccagccggaa gggccgagcg cagaagtggt cctgcaactt tatccgcctc catccagtct   7320
attaattgtt gccgggaagc tagagtaagt agttcgccag ttaatagttt gcgcaacgtt   7380
gttgccattg ctacaggcat cgtggtgtca cgctcgtcgt ttggtatggc ttcattcagc   7440
tccggttccc aacgatcaag gcgagttaca tgatccccca tgttgtgcaa aaaagcggtt   7500
agctccttcg gtcctccgat cgttgtcaga agtaagttgg ccgcagtgtt atcactcatg   7560
gttatggcag cactgcataa ttctcttact gtcatgccat ccgtaagatg cttttctgtg   7620
actggtgagt actcaaccaa gtcattctga gaatagtgta tgcggcgacc gagttgctct   7680
tgcccggcgt caatacggga taataccgcg ccacatagca gaactttaaa agtgctcatc   7740
attggaaaac gttcttcggg gcgaaaactc tcaaggatct taccgctgtt gagatccagt   7800
tcgatgtaac ccactcgtgc acccaactga tcttcagcat cttttacttt caccagcgtt   7860
tctgggtgag caaaaacagg aaggcaaaat gccgcaaaaa agggaataag ggcgacacgg   7920
aaatgttgaa tactcatact cttcctttttt caatattatt gaagcattta tcagggttat   7980
tgtctcatga gcggatacat atttgaatgt atttagaaaa ataaacaaat aggggttccg   8040
cgcacatttc cccgaaaagt gccacctgac gtcgacggat cgggagatct cccgatcccc   8100
tatggtgcac tctcagtaca atctgctctg atgccgcata gttaagccag tatctgctcc   8160
ctgcttgtgt gttggaggtc gctgagtagt gcgcgagcaa aatttaagct acaacaaggc   8220
aaggcttgac cgacaattgc atgaagaatc tgcttagggt taggcgtttt gcgctgcttc   8280
gcgatgtacg ggccagatat acgcgttgac attgattatt gactagttat taatagtaat   8340
caattacggg gtcattagtt catagcccat atatggagtt ccgcgttaca taacttacgg   8400
taaatggccc gcctggctga ccgcccaacg acccccgccc attgacgtca ataatgacgt   8460
atgttcccat agtaacgcca atagggactt tccattgacg tcaatgggtg gactatttac   8520
ggtaaactgc ccacttggca gtacatcaag tgtatcatat gccaagtacg ccccctattg   8580
acgtcaatga cggtaaatgg cccgcctggc attatgccca gtacatgacc ttatgggact   8640
ttcctacttg gcagtacatc tacgtattag tcatcgctat taccatggtg atgcggtttt   8700
ggcagtacat caatgggcgt ggatagcggt ttgactcacg gggatttcca agtctccacc   8760
```

-continued

| | |
|---|---|
| ccattgacgt caatgggagt ttgttttggc accaaaatca acgggacttt ccaaaatgtc | 8820 |
| gtaacaactc cgccccattg acgcaaatgg gcggtaggcg tgtacggtgg gaggtctata | 8880 |
| taagcagagc tctctggcta actagagaac ccactgctta ctggcttatc gaaattaata | 8940 |
| cgactcacta tagggagacc caagctggtt taaacttaag cttggtaccg agctcactag | 9000 |
| tccagtgtgg tggcagatat ccagcacagt ggcggccgct cgagtctaga gggcccgttt | 9060 |
| tgcctgtact gggtctctct ggttagacca gatctgagcc tgggagctct ctggctaact | 9120 |
| agggaaccca ctgcttaagc ctcaataaag cttgccttga gtgcttcaag tagtgtgtgc | 9180 |
| ccgtctgttg tgtgactctg gtaactagag atccctcaga cccttttagt cagtgtggaa | 9240 |
| aatctctagc agtggcgccc gaacagggac ttgaaagcga aagggaaacc agaggagctc | 9300 |
| tctcgacgca ggactcggct tgctgaagcg cgcacggcaa gaggcgaggg gcggcgactg | 9360 |
| gtgagtacgc caaaaatttt gactagcgga ggctagaagg agagagatgg gtgcgagagc | 9420 |
| gtcagtatta agcgggggag aattagatcg cgatgggaaa aaattcggtt aaggccaggg | 9480 |
| ggaaagaaaa aatataaatt aaaacatata gtatgggcaa gcagggagct agaacgattc | 9540 |
| gcagttaatc ctggcctgtt agaaacatca gaaggctgta gacaaatact gggacagcta | 9600 |
| caaccatccc ttcagacagg atcagaagaa cttagatcat tatataatac agtagcaacc | 9660 |
| ctctattgtg tgcatcaaag gatagagata aagacacca aggaagcttt agacaagata | 9720 |
| gaggaagagc aaaacaaaag taagaccacc gcacagcaag cggccgctga tcttcagacc | 9780 |
| tggaggagga gatatgaggg acaattggag aagtgaatta tataaatata agtagtaaa | 9840 |
| aattgaacca ttaggagtag cacccaccaa ggcaaagaga agtggtgc agagagaaaa | 9900 |
| aagagcagtg ggaataggag ctttgttcct tgggttcttg ggagcagcag gaagcactat | 9960 |
| gggcgcagcg tcaatgacgc tgacggtaca ggccagacaa ttattgtctg gtatagtgca | 10020 |
| gcagcagaac aatttgctga gggctattga ggcgcaacag catctgttgc aactcacagt | 10080 |
| ctggggcatc aagcagctcc aggcaagaat cctggctgtg gaaagatacc taaaggatca | 10140 |
| acagctcctg gggatttggg gttgctctgg aaaactcatt tgcaccactg ctgtgccttg | 10200 |
| gaatgctagt tggagtaata atctctgga acagatttgg aatcacacga cctggatgga | 10260 |
| gtgggacaga gaaattaaca attacacaag cttaatacac tccttaattg aagaatcgca | 10320 |
| aaaccagcaa gaaaagaatg aacaagaatt attggaatta gataaatggg caagtttgtg | 10380 |
| gaattggttt aacataacaa attggctgtg gtatataaaa ttattcataa tgatagtagg | 10440 |
| aggcttggta ggtttaagaa tagttttttgc tgtactttct atagtgaata gagttaggca | 10500 |
| gggatattca ccattatcgt ttcagaccca cctcccaacc ccgagggac ccgacaggcc | 10560 |
| cttaattaat tggctccggt gcccgtcagt gggcagagcg cacatcgccc acagtccccg | 10620 |
| agaagttggg gggaggggtc ggcaattgaa ccggtgccta gagaaggtgg cgcggggtaa | 10680 |
| actgggaaag tgatgtcgtg tactggctcc gccttttttcc cgagggtggg ggagaaccgt | 10740 |
| atataagtgc agtagtcgcc gtgaacgttc tttttcgcaa cgggtttgcc gccagaacac | 10800 |
| aggtaagtgc cgtgtgtggt tcccgcgggc ctggcctctt tacgggttat ggcccttgcg | 10860 |
| tgccttgaat tacttccacc tggctgcagt acgtgattct tgatcccgag cttcggttg | 10920 |
| gaagtgggtg ggagagttcg aggccttgcg cttaaggagc cccttcgcct cgtgcttgag | 10980 |
| ttgaggcctg gcctgggcgc tggggccgcc gcgtgcgaat ctggtggcac cttcgcgcct | 11040 |
| gtctcgctgc tttcgataag tctctagcca tttaaaattt ttgatgacct gctgcgacgc | 11100 |
| tttttttctg gcaagatagt cttgtaaatg cgggccaaga tctgcacact ggtatttcgg | 11160 |

```
tttttgggc  cgcgggcggc  gacggggccc  gtgcgtccca  gcgcacatgt  tcggcgaggc    11220
ggggcctgcg  agcgcggcca  ccgagaatcg  gacggggta   gtctcaagct  ggccggcctg    11280
ctctggtgcc  tggcctcgcg  ccgccgtgta  tcgccccgcc  ctgggcggca  aggctggccc    11340
ggtcggcacc  agttgcgtga  gcggaaagat  ggccgcttcc  cggccctgct  gcaggagagct   11400 caaaatggag  gacgcggcgc  tcgggagagc  gggcgggtga  gtcacccaca  caaggaaaa     11460 gggccttttcc  gtcctcagcc  gtcgcttcat  gtgactccac  ggagtaccgg  gcgccgtcca   11520
ggcacctcga  ttagttctcg  agcttttgga  gtacgtcgtc  tttaggttgg  ggggaggggt    11580
tttatgcgat  ggagttttccc  cacactgagt  gggtggagac  tgaagttagg  ccagcttggc   11640
acttgatgta  attctccttg  gaatttgccc  ttttgagtt   tggatcttgg  ttcattctca    11700
agcctcagac  agtggttcaa  agttttttttc  ttccattttca  ggtgtcgtga  ggaattcggc  11760
cattacggcc  g                                                             11771
```

<210> SEQ ID NO 15
<211> LENGTH: 10760
<212> TYPE: DNA
<213> ORGANISM: Artificial sequence
<220> FEATURE:
<223> OTHER INFORMATION: Synthetic nucleotide sequence

<400> SEQUENCE: 15

```
tcgagaccta  gaaaaacatg  gagcaatcac  aagtagcaat  acagcagcta  ccaatgctga      60
ttgtgcctgg  ctagaagcac  aagaggagga  ggaggtgggt  tttccagtca  cacctcaggt    120
acctttaaga  ccaatgactt  acaaggcagc  tgtagatctt  agccactttt  taaaagaaaa    180
ggggggactg  gaagggctaa  ttcactccca  acgaagacaa  gatctgcttt  ttgcttgtac    240
tgggtctctc  tggttagacc  agatctgagc  ctgggagctc  tctggctaac  tagggaaccc    300
actgcttaag  cctcaataaa  gcttgccttg  agtgcttcaa  gtagtgtgtg  cccgtctgtt    360
gtgtgactct  ggtaactaga  gatccctcag  accctttttag  tcagtgtgga  aaatctctag    420
cagggcccgt  ttaaacccgc  tgatcagcct  cgactgtgcc  ttctagttgc  cagccatctg    480
ttgtttgccc  ctcccccgtg  ccttccttga  ccctggaagg  tgccactccc  actgtccttt    540
cctaataaaa  tgaggaaatt  gcatcgcatt  gtctgagtag  gtgtcattct  attctggggg    600
gtggggtggg  gcaggacagc  aagggggagg  attgggaaga  caatagcagg  catgctgggg    660
atgcggtggg  ctctatggct  tctgaggcgg  aaagaaccag  ctgggctct   agggggtatc    720 cccacgcgcc  ctgtagcggc  gcattaagcg  cggcgggtgt  ggtggttacg  cgcagcgtga    780
ccgctacact  tgccagcgcc  ctagcgcccg  ctcctttcgc  tttcttccct  tcctttctcg    840
ccacgttcgc  cggctttccc  cgtcaagctc  taaatcgggg  catccctttta  gggttccgat    900 ttagtgcttt  acggcacctc  gaccccaaaa  aacttgatta  gggtgatggt  tcacgtagtg    960
ggccatcgcc  ctgatagacg  gttttcgcc   ctttgacgtt  ggagtccacg  ttctttaata   1020
gtggactctt  gttccaaact  ggaacaacac  tcaaccctat  ctcggtctat  tcttttgatt   1080
tataagggat  tttgggggatt  tcggcctatt  ggttaaaaaa  tgagctgatt  taacaaaaat   1140
ttaacgcgaa  ttaattctgt  ggaatgtgtg  tcagttaggg  tgtggaaagt  ccccaggctc   1200
cccaggcagg  cagaagtatg  caaagcatgc  atctcaatta  gtcagcaacc  aggtgtggaa   1260
agtccccagg  ctccccagca  ggcagaagta  tgcaaagcat  gcatctcaat  tagtcagcaa   1320
ccatagtccc  gcccctaact  ccgcccatcc  cgcccctaac  tccgcccagt  tccgcccatt   1380
```

```
ctccgcccca tggctgacta attttttta tttatgcaga ggccgaggcc gcctctgcct      1440
ctgagctatt ccagaagtag tgaggaggct tttttggagg cctaggcttt tgcaaaaagc      1500
tcccgggagc ttgtatatcc attttcggat ctgatcagca cgtgttgaca attaatcatc      1560
ggcatagtat atcggcatag tataatacga caaggtgagg aactaaacca tggccaagtt      1620
gaccagtgcc gttccggtgc tcaccgcgcg cgacgtcgcc ggagcggtcg agttctggac      1680
cgaccggctc gggttctccc gggacttcgt ggaggacgac ttcgccggtg tggtccggga      1740
cgacgtgacc ctgttcatca gcgcggtcca ggaccaggtg gtgccggaca cacccctggc      1800
ctgggtgtgg gtgcgcggcc tggacgagct gtacgccgag tggtcggagg tcgtgtccac      1860
gaacttccgg gacgcctccg ggccggccat gaccgagatc ggcgagcagc cgtgggggcg      1920
ggagttcgcc ctgcgcgacc cggccggcaa ctgcgtgcac ttcgtggccg aggagcagga      1980
ctgacacgtg ctacgagatt tcgattccac cgccgccttc tatgaaaggt tgggcttcgg      2040
aatcgttttc cgggacgccg gctggatgat cctccagcgc ggggatctca tgctggagtt      2100
cttcgcccac cccaacttgt ttattgcagc ttataatggt tacaaataaa gcaatagcat      2160
cacaaatttc acaaataaag cattttttc actgcattct agttgtggtt tgtccaaact      2220
catcaatgta tcttatcatg tctgtatacc gtcgacctct agctagagct tggcgtaatc      2280
atggtcatag ctgttcctg tgtgaaattg ttatccgctc acaattccac acaacatacg      2340
agccggaagc ataaagtgta aagcctgggg tgcctaatga gtgagctaac tcacattaat      2400
tgcgttgcgc tcactgcccg ctttccagtc gggaaacctg tcgtgccagc tgcattaatg      2460
aatcggccaa cgcgcgggga gaggcggttt gcgtattggg cgctcttccg cttcctcgct      2520
cactgactcg ctgcgctcgg tcgttcggct gcggcgagcg gtatcagctc actcaaaggc      2580
ggtaatacgg ttatccacag aatcagggga taacgcagga agaacatgt gagcaaaagg      2640 ccagcaaaag gccaggaacc gtaaaaaggc cgcgttgctg gcgttttcc ataggctccg      2700 ccccctgac gagcatcaca aaatcgacg ctcaagtcag aggtggcgaa acccgacagg      2760
actataaaga taccaggcgt ttccccctgg aagctccctc gtgcgctctc ctgttccgac      2820
cctgccgctt accggatacc tgtccgcctt tctcccttcg ggaagcgtgg cgctttctca      2880
atgctcacgc tgtaggtatc tcagttcggt gtaggtcgtt cgctccaagc tgggctgtgt      2940
gcacgaaccc cccgttcagc ccgaccgctg cgccttatcc ggtaactatc gtcttgagtc      3000
caacccggta agacacgact tatcgccact ggcagcagcc actggtaaca ggattagcag      3060
agcgaggtat gtaggcggtg ctacagagtt cttgaagtgg tggcctaact acggctacac      3120
tagaaggaca gtatttggta tctgcgctct gctgaagcca gttaccttcg gaaaaagagt      3180
tggtagctct tgatccggca acaaaccac cgctggtagc ggtggttttt tgtttgcaa      3240 gcagcagatt acgcgcagaa aaaaggatc tcaagaagat cctttgatct tttctacggg      3300
gtctgacgct cagtggaacg aaaactcacg ttaagggatt ttggtcatga gattatcaaa      3360
aaggatcttc acctagatcc ttttaaatta aaaatgaagt tttaaatcaa tctaaagtat      3420
atatgagtaa acttggtctg acagttacca atgcttaatc agtgaggcac ctatctcagc      3480
gatctgtcta tttcgttcat ccatagttgc ctgactcccc gtcgtgtaga taactacgat      3540
acgggagggc ttaccatctg gccccagtgc tgcaatgata ccgcgagacc cacgctcacc      3600
ggctccagat ttatcagcaa taaaccagcc agcggaagg gccgagcgca gaagtggtcc      3660
tgcaacttta tccgcctcca tccagtctat taattgttgc cgggaagcta gagtaagtag      3720
ttcgccagtt aatagtttgc gcaacgttgt tgccattgct acaggcatcg tggtgtcacg      3780
```

```
ctcgtcgttt ggtatggctt cattcagctc cggttcccaa cgatcaaggc gagttacatg   3840
atcccccatg ttgtgcaaaa aagcggttag ctccttcggt cctccgatcg ttgtcagaag   3900
taagttggcc gcagtgttat cactcatggt tatggcagca ctgcataatt ctcttactgt   3960
catgccatcc gtaagatgct tttctgtgac tggtgagtac tcaaccaagt cattctgaga   4020
atagtgtatg cggcgaccga gttgctcttg cccggcgtca atacgggata ataccgcgcc   4080
acatagcaga actttaaaag tgctcatcat tggaaaacgt tcttcgggc gaaaactctc    4140 aaggatctta ccgctgttga gatccagttc gatgtaaccc actcgtgcac ccaactgatc   4200
ttcagcatct tttactttca ccagcgtttc tgggtgagca aaaacaggaa ggcaaaatgc   4260
cgcaaaaaag ggaataaggg cgacacggaa atgttgaata ctcatactct ccttttttca   4320
atattattga agcatttatc agggttattg tctcatgagc ggatacatat ttgaatgtat   4380
ttagaaaaat aaacaaatag gggttccgcg cacatttccc cgaaaagtgc cacctgacgt   4440
cgacggatcg ggagatctcc cgatcccta tggtgcactc tcagtacaat ctgctctgat    4500
gccgcatagt taagccagta tctgctccct gcttgtgtgt tggaggtcgc tgagtagtgc   4560
gcgagcaaaa tttaagctac aacaaggcaa ggcttaccg acaattgcat gaagaatctg    4620
cttagggtta ggcgttttgc gctgcttcgc gatgtacggg ccagatatac gcgttgacat   4680
tgattattga ctagttatta atagtaatca attacgggt cattagttca tagcccatat    4740
atggagttcc gcgttacata acttacggta aatggcccgc ctggctgacc gcccaacgac   4800
ccccgcccat tgacgtcaat aatgacgtat gttcccatag taacgccaat agggactttc   4860
cattgacgtc aatgggtgga ctatttacgg taaactgccc acttggcagt acatcaagtg   4920
tatcatatgc caagtacgcc ccctattgac gtcaatgacg gtaaatggcc cgcctggcat   4980
tatgcccagt acatgacctt atgggacttt cctacttggc agtacatcta cgtattagtc   5040
atcgctatta ccatggtgat gcggttttgg cagtacatca atgggcgtgg atagcggttt   5100
gactcacggg gatttccaag tctccacccc attgacgtca atgggagttt gttttggcac   5160
caaaatcaac gggactttcc aaaatgtcgt aacaactccg ccccattgac gcaaatgggc   5220
ggtaggcgtg tacggtggga ggtctatata agcagagctc tctggctaac tagagaaccc   5280
actgcttact ggcttatcga aattaatacg actcactata gggagaccca agctggttta   5340
aacttaagct tggtaccgag ctcactagtc cagtgtggtg gcagatatcc agcacagtgg   5400
cggccgctcg agtctagagg gcccgttttg cctgtactgg gtctctctgg ttagaccaga   5460
tctgagcctg ggagctctct ggctaactag gaacccact gcttaagcct caataaagct    5520
tgccttgagt gcttcaagta gtgtgtgccc gtctgttgtg tgactctggt aactagagat   5580
ccctcagacc cttttagtca gtgtggaaaa tctctagcag tggcgcccga acagggactt   5640
gaaagcgaaa gggaaaccag aggagctctc tcgacgcagg actcggcttg ctgaagcgcg   5700
cacggcaaga ggcgaggggc ggcgactggt gagtacgcca aaattttga ctagcggagg    5760 ctagaaggag agagatgggt gcgagagcgt cagtattaag cggggagaa ttagatcgcg    5820 atgggaaaaa attcggttaa ggccaggggg aagaaaaaa tataaattaa aacatatagt    5880
atgggcaagc agggagctag aacgattcgc agttaatcct ggcctgttag aaacatcaga   5940
aggctgtaga caaatactgg gacagctaca accatccctt cagacaggat cagaagaact   6000
tagatcatta tataatacag tagcaaccct ctattgtgtg catttaatta actggaatac   6060
gacaagataa cccggatcgt gggcctggat cagtacctgg agagcgttaa aaaacacaaa   6120
```

```
cggctggatg tgtgccgcgc taaaatgggc tatatgctgc agtgaataat aaaatgtgtg    6180
tttgtccgaa atacgcgttt tgagatttct gtcgccgact aaattcatgt cgcgcgatag    6240
tggtgtttat cgccgataga gatggcgata ttggaaaaat cgatatttga aaatatggca    6300
tattgaaaat gtcgccgatg tgagtttctg tgtaactgat atcgccattt ttccaaaagt    6360
gattttcggg catacgcgat atctggcgat agcgcttata tcgtttacgg gggatggcga    6420
tagacgactt tggtgacttg ggcgattctg tgtgtcgcaa atatcgcagt ttcgatatag    6480
gtgacagacg atatgaggct atatcgccga tagaggcgac atcaagctgg cacatggcca    6540
atgcatatcg atctatacat tgaatcaata ttggccatta gccatattat tcattggtta    6600
tatagcataa atcaatattg gctattggcc attgcatacg ttgtatccat atcataatat    6660
gtacatttat attggctcat gtccaacatt accgccatgt tgacattgat tattgactag    6720
ttattaatag taatcaatta cggggtcatt agttcatagc ccatatatgg agttccgcgt    6780
tacataactt acggtaaatg gcccgcctgg ctgaccgccc aacgacccc gcccattgac    6840 gtcaataatg acgtatgttc ccatagtaac gccaataggg actttccatt gacgtcaatg    6900
ggtggagtat ttacggtaaa ctgcccactt ggcagtacat caagtgtatc atatgccaag    6960 tacgcccct attgacgtca atgacggtaa atggcccgcc tggcattatg cccagtacat    7020
gaccttatgg gactttccta cttggcagta catctacgta ttagtcatcg ctattaccat    7080
ggtgatgcgg ttttggcagt acatcaatgg gcgtggatag cggtttgact cacggggatt    7140
tccaagtctc caccccattg acgtcaatgg gagtttgttt tggcaccaaa atcaacggga    7200
ctttccaaaa tgtcgtaaca actccgcccc attgacgcaa atgggcggta ggcgtgtacg    7260
gtgggaggtc tatataagca gagctcgttt agtgaaccgt cagatcgcct ggagacgcca    7320
tccacgctgt tttgacctcc atagaagaca ccgggaccga tccagcctcc gcggccggga    7380
acggtgcatt ggaacgcgga ttccccgtgc caagagtgac gtaagtaccg cctatagagt    7440
ctataggccc accccttgg cttcttatgc atgctatact gttttttggct ggggtctat    7500 acacccccgc ttcctcatgt tataggtgat ggtatagctt agcctatagg tgtgggttat    7560
tgaccattat tgaccactcc cctattggtg acgatacttt ccattactaa tccataacat    7620
ggctctttgc cacaactctc tttattggct atatgccaat acactgtcct tcagagactg    7680
acacggactc tgtatttta caggatgggg tctcatttat tatttacaaa ttcacatata    7740
caacaccacc gtccccagtg cccgcagttt ttattaaaca taacgtggga tctccacgcg    7800
aatctcgggt acgtgttccg gacatggggct cttctccggt agcggcggag cttctacatc    7860
cgagccctgc tcccatgcct ccagcgactc atggtcgctc ggcagctcct tgctcctaac    7920
agtggaggcc agacttaggc acagcacgat gcccaccacc accagtgtgc cgcacaaggc    7980
cgtggcggta gggtatgtgt ctgaaaatga gctcggggag cgggcttgca ccgctgacgc    8040
atttggaaga cttaaggcag cggcagaaga agatgcaggc agctgagttg ttgtgttctg    8100
ataagagtca gaggtaactc ccgttgcggt gctgttaacg tggagggca gtgtagtctg    8160 agcagtactc gttgctgccg cgcgcgccac cagacataat agctgacaga ctaacagact    8220
gttcctttcc atgggtcttt tctgcagtca ccgtccttga cacggctagc atggagtcct    8280
ctgccaagag aaagatggac cctgataatc ctgacgaggg cccttcctcc aaggtgccac    8340
ggcccgagac acccgtgacc aaggccacga cgttcctgca gactatgttg aggaaggagg    8400
ttaacagtca gctgagtctg ggagaccgc tgtttccaga gttggccgaa gaatccctca    8460
aaacttttga acaagtgacc gaggattgca acagaaccc cgagaaagat gtcctggcag    8520
```

```
aactcggtga catcctcgcc caggctgtca atcatgccgg tatcgattcc agtagcaccg    8580
gccccacgct gacaacccac tcttgcagcg ttagcagcgc ccctcttaac aagccgaccc    8640
ccaccagcgt cgcggttact aacactcctc tccccggggc atccgctact cccgagctca    8700
gcccgcgtaa gaaaccgcgc aaaaccacgc gtcctttcaa ggtgattatt aaaccgcccg    8760
tgcctcccgc gcctatcatg ctgcccctca tcaaacagga agacatcaag cccgagcccg    8820
actttaccat ccagtaccgc aacaagatta tcgataccgc cggctgtatc gtgatctctg    8880
atagcgagga agaacagggt gaagaagtcg aaacccgcgg tgctaccgcg tcttcccctt    8940
ccaccggcag cggcacgccg cgagtgacct ctcccacgca cccgctctcc cagatgaacc    9000
accctcctct tcccgatccc ttgggccggc ccgatgaaga tagttcctct tcgtcttcct    9060
cctcctgcag ttcggcttcg gactcggaga gtgagtccga ggagatgaaa tgcagcagtg    9120
gcggaggagc atccgtgacc tcgagccacc atgggcgcgg cggttttggt ggcgcggcct    9180
cctcctctct gctgagctgc ggccatcaga gcagcgcgg ggcgagcacc ggaccccgca    9240
agaagaagag caaacgcatc tccgagttgg acaacgagaa ggtgcgcaat atcatgaaag    9300
ataagaacac cccctctgc acacccaacg tgcagactcg gcggggtcgc gtcaagattg    9360
acgaggtgag ccgcatgttc cgcaacacca atcgctctct tgagtacaag aacctgccct    9420
tcacgattcc cagtatgcac caggtgttag atgaggccat caaagcctgc aaaaccatgc    9480
aggtgaacaa caagggcatc cagattatct acacccgcaa tcatgaggtg aagagtgagg    9540
tggatgcggt gcggtgtcgc ctgggcacca tgtgcaacct ggccctctcc actccttcc    9600 tcatggagca caccatgccc gtgacacatc caccgaagt ggcgcagcgc acagccgatg    9660
cttgtaacga aggcgtcaag gccgcgtgga gcctcaaaga attgcacacc caccaattat    9720
gcccccgttc ctccgattac cgcaacatga tcatccacgc tgccaccccc gtggacctgt    9780
tgggcgctct caacctgtgc ctgccctga tgcaaaagtt tcccaaacag gtcatggtgc    9840
gcatcttctc caccaaccag ggtgggttca tgctgcctat ctacgagacg gccgcgaagg    9900
cctacgccgt ggggcagttt gagcagccca ccgagacccc tcccgaagac ctggacaccc    9960
tgagcctggc catcgaggca gccatccagg acctgaggaa caagtctcag taaggtgctg    10020
gtgctggtgc tggtgctggt gctgtgagca agggcgagga gctgttcacc ggggtggtgc    10080
ccatcctggt cgagctggac ggcgacgtaa acggccacaa gttcagcgtg tccggcgagg    10140
gcgagggcga tgccacctac ggcaagctga ccctgaagtt catctgcacc accggcaagc    10200
tgcccgtgcc ctggcccacc ctcgtgacca ccctgaccta cggcgtgcag tgcttcagcc    10260
gctaccccga ccacatgaag cagcacgact tcttcaagtc cgccatgccc gaaggctacg    10320
tccaggagcg caccatcttc ttcaaggacg acggcaacta caagacccgc gccgaggtga    10380
agttcgaggg cgacaccctg gtgaaccgca tcgagctgaa gggcatcgac ttcaaggagg    10440
acggcaacat cctggggcac aagctggagt acaactacaa cagccacaac gtctatatca    10500
tggccgacaa gcagaagaac ggcatcaagg tgaacttcaa gatccgccac aacatcgagg    10560
acggcagcgt gcagctcgcc gaccactacc agcagaacac ccccatcggc gacggccccg    10620
tgctgctgcc cgacaaccac tacctgagca cccagtccgc cctgagcaaa gaccccaacg    10680
agaagcgcga tcacatggtc ctgctggagt tcgtgaccgc cgccgggatc actctcggca    10740
tggacgagct gtacaagtaa                                              10760
```

<210> SEQ ID NO 16

<211> LENGTH: 11362
<212> TYPE: DNA
<213> ORGANISM: Artificial sequence
<220> FEATURE:
<223> OTHER INFORMATION: Synthetic nucleotide sequence

<400> SEQUENCE: 16

| | |
|---|---:|
| ggtttgtcga gacctagaaa acatggagc aatcacaagt agcaatacag cagctaccaa | 60 |
| tgctgattgt gcctggctag aagcacaaga ggaggaggag gtgggttttc cagtcacacc | 120 |
| tcaggtacct ttaagaccaa tgacttacaa ggcagctgta gatcttagcc acttttaaa | 180 |
| agaaaagggg ggactggaag ggctaattca ctcccaacga agacaagatc tgcttttgc | 240 |
| ttgtactggg tctctctggt tagaccagat ctgagcctgg gagctctctg gctaactagg | 300 |
| gaacccactg cttaagcctc aataaagctt gccttgagtg cttcaagtag tgtgtgcccg | 360 |
| tctgttgtgt gactctggta actagagatc cctcagaccc ttttagtcag tgtggaaaat | 420 |
| ctctagcagg gcccgtttaa acccgctgat cagcctcgac tgtgccttct agttgccagc | 480 |
| catctgttgt ttgccctcc cccgtgcctt ccttgaccct ggaaggtgcc actcccactg | 540 |
| tccttcccta taaaatgag gaaattgcat cgcattgtct gagtaggtgt cattctattc | 600 |
| tggggggtgg ggtggggcag gacagcaagg gggaggattg gaagacaat agcaggcatg | 660 |
| ctggggatgc ggtgggctct atggcttctg aggcggaaag aaccagctgg ggctctaggg | 720 |
| ggtatcccca cgcgccctgt agcggcgcat taagcgcggc gggtgtggtg gttacgcgca | 780 |
| gcgtgaccgc tacacttgcc agcgccctag cgcccgctcc tttcgctttc ttcccttcct | 840 |
| ttctcgccac gttcgccggc tttccccgtc aagctctaaa tcgggggcatc cctttagggt | 900 |
| tccgatttag tgctttacgg cacctcgacc ccaaaaaact tgattagggt gatggttcac | 960 |
| gtagtgggcc atcgccctga tagacggttt ttcgcccttt gacgttggag tccacgttct | 1020 |
| ttaatagtgg actcttgttc caaactggaa caacactcaa ccctatctcg gtctattctt | 1080 |
| ttgatttata agggattttg gggatttcgg cctattggtt aaaaaatgag ctgatttaac | 1140 |
| aaaaatttaa cgcgaattaa ttctgtggaa tgtgtgtcag ttagggtgtg aaagtcccc | 1200 |
| aggctcccca ggcaggcaga agtatgcaaa gcatgcatct caattagtca gcaaccaggt | 1260 |
| gtggaaagtc cccaggctcc ccagcaggca gaagtatgca aagcatgcat ctcaattagt | 1320 |
| cagcaaccat agtcccgccc ctaactccgc ccatcccgcc cctaactccg cccagttccg | 1380 |
| cccattctcc gccccatggc tgactaattt ttttttattta tgcagaggcc gaggccgcct | 1440 |
| ctgcctctga gctattccag aagtagtgag gaggcttttt tggaggccta ggcttttgca | 1500 |
| aaaagctccc gggagcttgt atatccattt tcggatctga tcagcacgtg ttgacaatta | 1560 |
| atcatcggca tagtatatcg gcatagtata atacgacaag gtgaggaact aaaccatggc | 1620 |
| caagttgacc agtgccgttc cggtgctcac cgcgcgcgac gtcgccggag cggtcgagtt | 1680 |
| ctggaccgac cggctcgggt tctcccggga cttcgtggag gacgacttcg ccggtgtggt | 1740 |
| ccgggacgac gtgaccctgt tcatcagcgc ggtccaggac caggtggtgc cggacaacac | 1800 |
| cctggcctgg gtgtgggtgc gcggcctgga cgagctgtac gccgagtggt cggaggtcgt | 1860 |
| gtccacgaac ttccgggacg cctccggccc ggccatgacc gagatcggcg agcagccgtg | 1920 |
| ggggcgggag ttcgccctgc gcgacccggc cggcaactgc gtgcacttcg tggccgagga | 1980 |
| gcaggactga cacgtgctac gagatttcga ttccaccgcc gccttctatg aaaggttggg | 2040 |
| cttcggaatc gttttccggg acgccggctg gatgatcctc cagcgcgggg atctcatgct | 2100 |
| ggagttcttc gcccaccccca acttgtttat tgcagcttat aatggttaca aataaagcaa | 2160 |

```
tagcatcaca aatttcacaa ataaagcatt tttttcactg cattctagtt gtggtttgtc    2220
caaactcatc aatgtatctt atcatgtctg tataccgtcg acctctagct agagcttggc    2280
gtaatcatgg tcatagctgt ttcctgtgtg aaattgttat ccgctcacaa ttccacacaa    2340
catacgagcc ggaagcataa agtgtaaagc ctggggtgcc taatgagtga gctaactcac    2400
attaattgcg ttgcgctcac tgcccgcttt ccagtcggga aacctgtcgt gccagctgca    2460
ttaatgaatc ggccaacgcg cggggagagg cggtttgcgt attgggcgct cttccgcttc    2520
ctcgctcact gactcgctgc gctcggtcgt tcggctgcgg cgagcggtat cagctcactc    2580
aaaggcggta atacggttat ccacagaatc aggggataac gcaggaaaga acatgtgagc    2640
aaaaggccag caaaaggcca ggaaccgtaa aaaggccgcg ttgctggcgt ttttccatag    2700
gctccgcccc cctgacgagc atcacaaaaa tcgacgctca agtcagaggt ggcgaaaccc    2760
gacaggacta taaagatacc aggcgtttcc ccctggaagc tccctcgtgc gctctcctgt    2820
tccgaccctg ccgcttaccg gatacctgtc cgcctttctc ccttcgggaa gcgtggcgct    2880
ttctcaatgc tcacgctgta ggtatctcag ttcggtgtag tcgttcgct ccaagctggg    2940 ctgtgtgcac gaaccccccg ttcagcccga ccgctgcgcc ttatccggta actatcgtct    3000
tgagtccaac ccggtaagac acgacttatc gccactggca gcagccactg gtaacaggat    3060
tagcagagcg aggtatgtag gcggtgctac agagttcttg aagtggtggc ctaactacgg    3120
ctacactaga aggacagtat ttggtatctg cgctctgctg aagccagtta ccttcggaaa    3180
aagagttggt agctcttgat ccggcaaaca aaccaccgct ggtagcggtg gtttttttgt    3240
ttgcaagcag cagattacgc gcagaaaaaa aggatctcaa gaagatcctt tgatcttttc    3300
tacggggtct gacgctcagt ggaacgaaaa ctcacgttaa gggattttgg tcatgagatt    3360
atcaaaaagg atcttcacct agatcctttt aaattaaaaa tgaagtttta atcaatcta    3420 aagtatatat gagtaaactt ggtctgacag ttaccaatgc ttaatcagtg aggcaccta    3480 ctcagcgatc tgtctatttc gttcatccat agttgcctga ctccccgtcg tgtagataac    3540
tacgatacgg gagggcttac catctggccc cagtgctgca atgataccgc gagacccacg    3600
ctcaccggct ccagatttat cagcaataaa ccagccagcc ggaagggccg agcgcagaag    3660
tggtcctgca actttatccg cctccatcca gtctattaat tgttgccggg aagctagagt    3720
aagtagttcg ccagttaata gtttgcgcaa cgttgttgcc attgctacag gcatcgtggt    3780
gtcacgctcg tcgtttggta tggcttcatt cagctccggt tcccaacgat caaggcgagt    3840
tacatgatcc cccatgttgt gcaaaaaagc ggttagctcc ttcggtcctc cgatcgttgt    3900
cagaagtaag ttggccgcag tgttatcact catggttatg gcagcactgc ataattctct    3960
tactgtcatg ccatccgtaa gatgcttttc tgtgactggt gagtactcaa ccaagtcatt    4020
ctgagaatag tgtatgcggc gaccgagttg ctcttgcccg gcgtcaatac gggataatac    4080
cgcgccacat agcagaactt taaaagtgct catcattgga aaacgttctt cggggcgaaa    4140
actctcaagg atcttaccgc tgttgagatc cagttcgatg taacccactc gtgcacccaa    4200
ctgatcttca gcatctttta ctttcaccag cgtttctggg tgagcaaaaa caggaaggca    4260
aaatgccgca aaaagggaa taaggcgac acgaaatgt tgaatactca tactcttcct    4320
ttttcaatat tattgaagca tttatcaggg ttattgtctc atgagcggat acatatttga    4380
atgtatttag aaaaataaac aaataggggt tccgcgcaca tttccccgaa aagtgccacc    4440
tgacgtcgac ggatcgggag atctcccgat cccctatggt gcactctcag tacaatctgc    4500
```

```
tctgatgccg catagttaag ccagtatctg ctccctgctt gtgtgttgga ggtcgctgag    4560
tagtgcgcga gcaaaattta agctacaaca aggcaaggct tgaccgacaa ttgcatgaag    4620
aatctgctta gggttaggcg ttttgcgctg cttcgcgatg tacgggccag atatacgcgt    4680
tgacattgat tattgactag ttattaatag taatcaatta cggggtcatt agttcatagc    4740
ccatatatgg agttccgcgt tacataactt acggtaaatg gcccgcctgg ctgaccgccc    4800
aacgaccccc gcccattgac gtcaataatg acgtatgttc ccatagtaac gccaataggg    4860
actttccatt gacgtcaatg ggtggactat ttacggtaaa ctgcccactt ggcagtacat    4920
caagtgtatc atatgccaag tacgccccct attgacgtca atgacggtaa atggcccgcc    4980
tggcattatg cccagtacat gaccttatgg gactttccta cttggcagta catctacgta    5040
ttagtcatcg ctattaccat ggtgatgcgg ttttggcagt acatcaatgg gcgtggatag    5100
cggtttgact cacggggatt tccaagtctc cacccccattg acgtcaatgg gagtttgttt    5160
tggcaccaaa atcaacggga ctttccaaaa tgtcgtaaca actccgcccc attgacgcaa    5220
atgggcggta ggcgtgtacg gtgggaggtc tatataagca gagctctctg gctaactaga    5280
gaacccactg cttactggct tatcgaaatt aatacgactc actataggga gacccaagct    5340
ggtttaaact taagcttggt accgagctca ctagtccagt gtggtggcag atatccagca    5400
cagtggcggc cgctcgagtc tagagggccc gttttgcctg tactgggtct ctctggttag    5460
accagatctg agcctgggag ctctctggct aactagggaa cccactgctt aagcctcaat    5520
aaagcttgcc ttgagtgctt caagtagtgt gtgcccgtct gttgtgtgac tctggtaact    5580
agagatccct cagaccettt tagtcagtgt ggaaaatctc tagcagtggc gcccgaacag    5640
ggacttgaaa gcgaaaggga accagagga gctctctcga cgcaggactc ggcttgctga    5700
agcgcgcacg gcaagaggcg aggggcggcg actggtgagt acgccaaaaa ttttgactag    5760
cggaggctag aaggagagag atgggtgcga gagcgtcagt attaagcggg ggagaattag    5820
atcgcgatgg gaaaaaattc ggttaaggcc aggggggaaag aaaaaatata aattaaaaca    5880
tatagtatgg gcaagcaggg agctagaacg attcgcagtt aatcctggcc tgttagaaac    5940
atcagaaggc tgtagacaaa tactgggaca gctacaacca tcccttcaga caggatcaga    6000
agaacttaga tcattatata atacagtagc aaccctctat tgtgtgcatt taattaactg    6060
gaatacgaca agataacccg gatcgtgggc ctggatcagt acctggagag cgttaaaaaa    6120
cacaaacggc tggatgtgtg ccgcgctaaa atgggctata tgctgcagtg aataataaaa    6180
tgtgtgtttg tccgaaatac gcgttttgag atttctgtcg ccgactaaat tcatgtcgcg    6240
cgatagtggt gtttatcgcc gatagagatg gcgatattgg aaaaatcgat atttgaaaat    6300
atggcatatt gaaaatgtcg ccgatgtgag tttctgtgta actgatatcg ccattttttcc    6360 aaaagtgatt tttgggcata cgcgatatct ggcgatagcg cttatatcgt ttacggggga    6420
tggcgataga cgactttggt gacttgggcg attctgtgtg tcgcaaatat cgcagtttcg    6480
atataggtga cagacgatat gaggctatat cgccgataga ggcgacatca agctggcaca    6540
tggccaatgc atatcgatct atacattgaa tcaatattgg ccattagcca tattattcat    6600
tggttatata gcataaatca atattggcta ttggccattg catacgttgt atccatatca    6660
taatatgtac atttatattg gctcatgtcc aacattaccg ccatgttgac attgattatt    6720
gactagttat taatagtaat caattacggg gtcattagtt catagcccat atatggagtt    6780
ccgcgttaca taacttacgg taaatggccc gcctggctga ccgcccaacg acccccgccc    6840
attgacgtca ataatgacgt atgttcccat agtaacgcca atagggactt ccattgacg    6900
```

```
tcaatgggtg gagtatttac ggtaaactgc ccacttggca gtacatcaag tgtatcatat    6960
gccaagtacg ccccctattg acgtcaatga cggtaaatgg cccgcctggc attatgccca    7020
gtacatgacc ttatgggact ttcctacttg gcagtacatc tacgtattag tcatcgctat    7080
taccatggtg atgcggtttt ggcagtacat caatgggcgt ggatagcggt ttgactcacg    7140
gggatttcca agtctccacc ccattgacgt caatgggagt ttgttttggc accaaaatca    7200
acgggacttt ccaaaatgtc gtaacaactc cgccccattg acgcaaatgg gcggtaggcg    7260
tgtacggtgg gaggtctata taagcagagc tcgtttagtg aaccgtcaga tcgcctggag    7320
acgccatcca cgctgttttg acctccatag aagacaccgg gaccgatcca gcctccgcgg    7380
ccgggaacgg tgcattggaa cgcggattcc ccgtgccaag agtgacgtaa gtaccgccta    7440
tagagtctat aggcccaccc ccttggcttc ttatgcatgc tatactgttt ttggcttggg    7500
gtctatacac ccccgcttcc tcatgttata ggtgatggta tagcttagcc tataggtgtg    7560
ggttattgac cattattgac cactccccta ttggtgacga tactttccat tactaatcca    7620
taacatggct ctttgccaca actctcttta ttggctatat gccaatacac tgtccttcag    7680
agactgacac ggactctgta tttttacagg atggggtctc atttattatt tacaaattca    7740
catatacaac accaccgtcc ccagtgcccg cagtttttat taaacataac gtgggatctc    7800
cacgcgaatc tcgggtacgt gttccggaca tgggctcttc tccggtagcg gcggagcttc    7860
tacatccgag ccctgctccc atgcctccag cgactcatgg tcgctcggca gctccttgct    7920
cctaacagtg gaggccagac ttaggcacag cacgatgccc accaccacca gtgtgccgca    7980
caaggccgtg gcggtagggt atgtgtctga aaatgagctc ggggagcggg cttgcaccgc    8040
tgacgcattt ggaagactta aggcagcggc agaagaagat gcaggcagct gagttgttgt    8100
gttctgataa gagtcagagg taactcccgt tgcggtgctg ttaacggtgg agggcagtgt    8160
agtctgagca gtactcgttg ctgccgcgcg cgccaccaga cataatagct gacagactaa    8220
cagactgttc cttttccatgg gtcttttctg cagtcaccgt ccttgacacg gctagcatgg    8280
agtcctctgc caagagaaag atggaccctg ataatcctga cgagggccct tcctccaagg    8340
tgccacggcc cgagacaccc gtgaccaagg ccacgacgtt cctgcagact atgttgagga    8400
aggaggttaa cagtcagctg agtctgggag acccgctgtt tccagagttg gccgaagaat    8460
ccctcaaaac ttttgaacga gtgaccgagg attgcaacga gaaccccgag aaagatgtcc    8520
tggcagaact cggtgacatc ctcgcccagg ctgtcaatca tgccggtatc gattccagta    8580
gcaccggccc cacgctgaca acccactctt gcagcgttag cagcgcccct cttaacaagc    8640 cgaccccac cagcgtcgcg gttactaaca ctcctctccc cggggcatcc gctactcccg    8700
agctcagccc gcgtaagaaa ccgcgcaaaa ccacgcgtcc tttcaaggtg attattaaac    8760
cgcccgtgcc tcccgcgcct atcatgctgc ccctcatcaa acaggaagac atcaagcccg    8820
agcccgactt taccatccag taccgcaaca gattatcga taccgccggc tgtatcgtga    8880
tctctgatag cgaggaagaa cagggtgaag aagtcgaaac ccgcggtgct accgcgtctt    8940 cccccttccac cggcagcggc acgcgcgag tgacctctcc cacgcacccg ctctcccaga    9000
taaaccaccc tcctcttccc gatcccttgg gccggcccga tgaagatagt tcctcttcgt    9060
cttcctcctg cagttcggct tcggactcgg agagtgagtc cgaggagatg aaatgcagca    9120
gtggcggagg agcatccgtg acctcgagcc accatgggcg cggcggtttt ggtgcgcgg    9180 cctcctcctc tctgctgagc tgcggccatc agagcagcgg cggggcgagc accggacccc    9240
```

```
gcaagaagaa gagcaaacgc atctccgagt tggacaacga gaaggtgcgc aatatcatga    9300
aagataagaa cacccccttc tgcacaccca acgtgcagac tcggcggggt cgcgtcaaga    9360
ttgacgaggt gagccgcatg ttccgcaaca ccaatcgctc tcttgagtac aagaacctgc    9420
ccttcacgat tcccagtatg caccaggtgt tagatgaggc catcaaagcc tgcaaaacca    9480
tgcaggtgaa caacaagggc atccagatta tctacacccg caatcatgag gtgaagagtg    9540
aggtggatgc ggtgcggtgt cgcctgggca ccatgtgcaa cctggccctc tccactccct    9600
tcctcatgga gcacaccatg cccgtgacac atccacccga agtggcgcag cgcacagccg    9660
atacttgtaa cgaaggcgtc aaggccgcgt ggagcctcaa agaattgcac acccaccaat    9720 tatgccccg ttcctccgat taccgcaaca tgatcatcca cgctgccacc cccgtggacc     9780
tgttgggcgc tctcaacctg tgcctgcccc tgatgcaaaa gtttcccaaa caggtcatgg    9840
tgcgcatctt ctccaccaac cagggtgggt tcatgctgcc tatctacgag acggccgcga    9900
aggcctacgc cgtggggcag tttgagcagc ccaccgagac ccctcccgaa gacctggaca    9960
ccctgagcct ggccatcgag gcagccatcc aggacctgag gaacaagtct cagtaaggat   10020
ccgcccctct ccctccccccc ccctaacgt tactggccga agccgcttgg aataaggccg   10080
gtgtgcgttt gtctatatgt tatttttccac catattgccg tcttttggca atgtgagggc   10140
ccggaaacct ggccctgtct tcttgacgag cattcctagg ggtctttccc ctctcgccaa   10200
aggaatgcaa ggtctgttga atgtcgtgaa ggaagcagtt cctctggaag cttcttgaag   10260
acaaacaacg tctgtagcga cccttttgcag gcagcggaac ccccacctg gcgacaggtg   10320 cctctgcggc caaaagccac gtgtataaga tacacctgca aaggcggcac aaccccagtg   10380
ccacgttgtg agttggatag ttgtggaaag agtcaaatgg ctctcctcaa gcgtattcaa   10440
caaggggctg aaggatgccc agaaggtacc ccattgtatg ggatctgatc tggggcctcg   10500
gtacacatgc tttacatgtg tttagtcgag gttaaaaaaa cgtctaggcc ccccgaacca   10560
cggggacgtg gttttccttt gaaaaacacg atgataatat ggccacaacc atggtgagca   10620
agggcgagga ggataacatg gccatcatca aggagttcat gcgcttcaag gtgcacatgg   10680
agggctccgt gaacggccac gagttcgaga tcgaggcga gggcgagggc cgcccctacg   10740
agggcaccca gaccgccaag ctgaaggtga ccaagggtgg ccccctgccc ttcgcctggg   10800
acatcctgtc ccctcagttc atgtacggct ccaaggccta cgtgaagcac cccgccgaca   10860
tccccgacta cttgaagctg tccttccccg agggcttcaa gtgggagcgc gtgatgaact   10920
tcgaggacgg cggcgtggtg accgtgaccc aggactcctc cctgcaggac ggcgagttca   10980
tctacaaggt gaagctgcgc ggcaccaact tcccctccga cggccccgta atgcagaaga   11040
agaccatggg ctgggaggcc tcctccgagc ggatgtaccc cgaggacggc gccctgaagg   11100
gcgagatcaa gcagaggctg aagctgaagg acggcggcca ctacgacgct gaggtcaaga   11160
ccacctacaa ggccaagaag cccgtgcagc tgccggcgc ctacaacgtc aacatcaagt   11220
tggacatcac ctcccacaac gaggactaca ccatcgtgga acagtacgaa cgcgccgagg   11280
gccgccactc caccggcggc atggacgagc tgtacaagag cagcctgagg cctcctaaga   11340
agaagaggaa ggtttgaatg ca                                            11362
```

<210> SEQ ID NO 17
<211> LENGTH: 11375
<212> TYPE: DNA
<213> ORGANISM: Artificial sequence
<220> FEATURE:
<223> OTHER INFORMATION: Synthetic nucleotide sequence

<400> SEQUENCE: 17

```
gatccgcccc tctccctccc ccccccctaa cgttactggc cgaagccgct tggaataagg      60
ccggtgtgcg tttgtctata tgttattttc caccatattg ccgtcttttg gcaatgtgag     120
ggcccggaaa cctggccctg tcttcttgac gagcattcct aggggtcttt ccctctcgc     180
caaaggaatg caaggtctgt tgaatgtcgt gaaggaagca gttcctctgg aagcttcttg     240
aagacaaaca acgtctgtag cgacccttg caggcagcgg aacccccac ctggcgacag      300
gtgcctctgc ggccaaaagc cacgtgtata agatacacct gcaaaggcgg cacaacccca    360
gtgccacgtt gtgagttgga tagttgtgga aagagtcaaa tggctctcct caagcgtatt    420
caacaagggg ctgaaggatg cccagaaggt accccattgt atgggatctg atctggggcc    480
tcggtgcaca tgctttacat gtgtttagtc gaggttaaaa aaacgtctag gccccccgaa    540
ccacggggac gtggttttcc tttgaaaaac acgatgataa tatggccaca accatggtga    600
gcaagggcga ggagctgttc accggggtgg tgcccatcct ggtcgagctg gacggcgacg    660
taaacggcca caagttcagc gtgtccggcg agggcgaggg cgatgccacc tacggcaagc    720
tgaccctgaa gttcatctgc accaccggca agctgcccgt gccctggccc accctcgtga    780
ccaccctgac ctacggcgtg cagtgcttca gccgctaccc cgaccacatg aagcagcacg    840
acttcttcaa gtccgccatg cccgaaggct acgtccagga gcgcaccatc ttcttcaagg    900
acgacggcaa ctacaagacc cgcgccgagg tgaagttcga gggcgacacc ctggtgaacc    960
gcatcgagct gaagggcatc gacttcaagg aggacggcaa catcctgggg cacaagctgg   1020
agtacaacta caacagccac aacgtctata tcatggccga caagcagaag aacggcatca   1080
aggtgaactt caagatccgc cacaacatcg aggacggcag cgtgcagctc gccgaccact   1140
accagcagaa cacccccatc ggcgacggcc ccgtgctgct gcccgacaac cactacctga   1200
gcacccagtc cgccctgagc aaagacccca acgagaagcg cgatcacatg gtcctgctgg   1260
agttcgtgac cgccgccggg atcactctcg gcatggacga gctgtacaag agcagcctga   1320
ggcctcctaa gaagaagagg aaggtttgac ctgcaggttt gtcgagacct agaaaaacat   1380
ggagcaatca caagtagcaa tacagcagct accaatgctg attgtgcctg gctagaagca   1440
caagaggagg aggaggtggg ttttccagtc acacctcagg tacctttaag accaatgact   1500
tacaaggcag ctgtagatct tagccacttt ttaaaagaaa aggggggact ggaagggcta   1560
attcactccc aacgaagaca agatctgctt tttgcttgta ctgggtctct ctggttagac   1620
cagatctgag cctgggagct ctctggctaa ctagggaacc cactgcttaa gcctcaataa   1680
agcttgcctt gagtgcttca agtagtgtgt gcccgtctgt tgtgtgactc tggtaactag   1740
agatccctca gaccctttta gtcagtgtgg aaaatctcta gcagggcccg tttaaacccg   1800
ctgatcagcc tcgactgtgc cttctagttg ccagccatct gttgtttgcc cctcccccgt   1860
gccttccttg accctggaag gtgccactcc cactgtcctt tcctaataaa atgaggaaat   1920
tgcatcgcat tgtctgagta ggtgtcattc tattctgggg ggtggggtgg ggcaggacag   1980
caagggggag gattgggaag acaatagcag gcatgctggg gatgcggtgg gctctatggc   2040
ttctgaggcg gaaagaacca gctggggctc taggggtat cccacgcgc cctgtagcgg     2100
cgcattaagc gcggcgggtg tggtggttac gcgcagcgtg accgctacac ttgccagcgc   2160
cctagcgccc gctcctttcg ctttcttccc ttcctttctc gccacgttcg ccggctttcc   2220
ccgtcaagct ctaaatcggg gcatcccttt agggttccga tttagtgctt tacggcacct   2280
```

```
cgaccccaaa aaacttgatt agggtgatgg ttcacgtagt gggccatcgc cctgatagac    2340 ggttttcgc cctttgacgt tggagtccac gttctttaat agtggactct tgttccaaac     2400
tggaacaaca ctcaaccta tctcggtcta ttcttttgat ttataaggga ttttggggat     2460
ttcggcctat tggttaaaaa atgagctgat ttaacaaaaa tttaacgcga attaattctg    2520
tggaatgtgt gtcagttagg gtgtggaaag tccccaggct ccccaggcag gcagaagtat    2580
gcaaagcatg catctcaatt agtcagcaac caggtgtgga aagtcccag gctccccagc     2640 aggcagaagt atgcaaagca tgcatctcaa ttagtcagca accatagtcc cgcccctaac    2700
tccgcccatc ccgcccctaa ctccgcccag ttccgcccat tctccgcccc atggctgact    2760
aatttttttt atttatgcag aggccgaggc cgcctctgcc tctgagctat tccagaagta    2820
gtgaggaggc ttttttggag gcctaggctt ttgcaaaaag ctcccgggag cttgtatatc    2880 catttcgga tctgatcagc acgtgttgac aattaatcat cggcatagta tatcggcata    2940
gtataatacg acaaggtgag gaactaaacc atggccaagt tgaccagtgc cgttccggtg    3000
ctcaccgcgc gcgacgtcgc cggagcggtc gagttctgga ccgaccggct cgggttctcc    3060
cgggacttcg tggaggacga cttcgccggt gtggtccggg acgacgtgac cctgttcatc    3120
agcgcggtcc aggaccaggt ggtgccggac aacaccctgg cctgggtgtg ggtgcgcggc    3180
ctggacgagc tgtacgccga gtggtcggag gtcgtgtcca cgaacttccg ggacgcctcc    3240
gggccggcca tgaccgagat cggcgagcag ccgtgggggc gggagttcgc cctgcgcgac    3300
ccggccggca actgcgtgca cttcgtggcc gaggagcagg actgacacgt gctacgagat    3360
ttcgattcca ccgccgcctt ctatgaaagg ttgggcttcg gaatcgtttt ccgggacgcc    3420
ggctggatga tcctccagcg cggggatctc atgctggagt tcttcgccca ccccaacttg    3480
tttattgcag cttataatgg ttacaaataa agcaatagca tcacaaattt cacaaataaa    3540
gcattttttt cactgcattc tagttgtggt ttgtccaaac tcatcaatgt atcttatcat    3600
gtctgtatac cgtcgacctc tagctagagc ttggcgtaat catggtcata gctgtttcct    3660
gtgtgaaatt gttatccgct cacaattcca cacaacatac gagccggaag cataaagtgt    3720
aaagcctggg gtgcctaatg agtgagctaa ctcacattaa ttgcgttgcg ctcactgccc    3780
gctttccagt cgggaaacct gtcgtgccag ctgcattaat gaatcggcca acgcgcgggg    3840
agaggcggtt tgcgtattgg gcgctcttcc gcttcctcgc tcactgactc gctgcgctcg    3900
gtcgttcggc tgcggcgagc ggtatcagct cactcaaagg cggtaatacg ttatccaca    3960 gaatcagggg ataacgcagg aaagaacatg tgagcaaaag gccagcaaaa ggccaggaac    4020
cgtaaaaagg ccgcgttgct ggcgtttttc cataggctcc gcccccctga cgagcatcac    4080
aaaaatcgac gctcaagtca gaggtggcga aacccgacag gactataaag ataccaggcg    4140
tttccccctg gaagctccct cgtgcgctct cctgttccga ccctgccgct taccggatac    4200
ctgtccgcct ttctcccttc gggaagcgtg gcgctttctc aatgctcacg ctgtaggtat    4260
ctcagttcgg tgtaggtcgt tcgctccaag ctgggctgtg tgcacgaacc ccccgttcag    4320
cccgaccgct gcgccttatc cggtaactat cgtcttgagt ccaacccggt aagacacgac    4380
ttatcgccac tggcagcagc cactggtaac aggattagca gagcgaggta tgtaggcggt    4440
gctacagagt tcttgaagtg gtggcctaac tacggctaca ctagaaggac agtatttggt    4500
atctgcgctc tgctgaagcc agttaccttc ggaaaaagag ttggtagctc ttgatccggc    4560
aaacaaacca ccgctggtag cggtggtttt tttgttgca agcagcagat tacgcgcaga    4620
aaaaaaggat ctcaagaaga tccttgatc ttttctacgg ggtctgacgc tcagtggaac    4680
```

```
gaaaactcac gttaagggat tttggtcatg agattatcaa aaaggatctt cacctagatc   4740
cttttaaatt aaaaatgaag ttttaaatca atctaaagta tatatgagta aacttggtct   4800
gacagttacc aatgcttaat cagtgaggca cctatctcag cgatctgtct atttcgttca   4860
tccatagttg cctgactccc cgtcgtgtag ataactacga tacgggaggg cttaccatct   4920
ggccccagtg ctgcaatgat accgcgagac ccacgctcac cggctccaga tttatcagca   4980
ataaccagc cagccggaag ggccgagcgc agaagtggtc ctgcaacttt atccgcctcc   5040
atccagtcta ttaattgttg ccgggaagct agagtaagta gttcgccagt taatagtttg   5100
cgcaacgttg ttgccattgc tacaggcatc gtggtgtcac gctcgtcgtt tggtatggct   5160
tcattcagct ccggttccca acgatcaagg cgagttacat gatcccccat gttgtgcaaa   5220
aaagcggtta gctccttcgg tcctccgatc gttgtcagaa gtaagttggc cgcagtgtta   5280
tcactcatgg ttatggcagc actgcataat tctcttactg tcatgccatc cgtaagatgc   5340
ttttctgtga ctggtgagta ctcaaccaag tcattctgag aatagtgtat gcggcgaccg   5400
agttgctctt gcccggcgtc aatacgggat aataccgcgc cacatagcag aactttaaaa   5460
gtgctcatca ttggaaaacg ttcttcgggg cgaaaactct caaggatctt accgctgttg   5520
agatccagtt cgatgtaacc cactcgtgca cccaactgat cttcagcatc ttttactttc   5580
accagcgttt ctgggtgagc aaaaacagga aggcaaaatg ccgcaaaaaa gggaataagg   5640
gcgacacgga aatgttgaat actcatactc ttcctttttc aatattattg aagcatttat   5700
cagggttatt gtctcatgag cggatacata tttgaatgta tttagaaaaa taaacaaata   5760
ggggttccgc gcacatttcc ccgaaaagtg ccacctgacg tcgacggatc gggagatctc   5820
ccgatcccct atggtgcact ctcagtacaa tctgctctga tgccgcatag ttaagccagt   5880
atctgctccc tgcttgtgtg ttggaggtcg ctgagtagtg cgcgagcaaa atttaagcta   5940
caacaaggca aggcttgacc gacaattgca tgaagaatct gcttagggtt aggcgttttg   6000
cgctgcttcg cgatgtacgg gccagatata cgcgttgaca ttgattattg actagttatt   6060
aatagtaatc aattacgggg tcattagttc atagcccata tatggagttc cgcgttacat   6120
aacttacggt aaatggcccg cctggctgac cgcccaacga cccccgccca ttgacgtcaa   6180
taatgacgta tgttcccata gtaacgccaa tagggacttt ccattgacgt caatgggtgg   6240
actatttacg gtaaactgcc cacttggcag tacatcaagt gtatcatatg ccaagtacgc   6300
cccctattga cgtcaatgac ggtaaatggc ccgcctggca ttatgcccag tacatgacct   6360
tatgggactt tcctacttgg cagtacatct acgtattagt catcgctatt accatggtga   6420
tgcggttttg gcagtacatc aatgggcgtg gatagcggtt tgactcacgg ggatttccaa   6480
gtctccaccc cattgacgtc aatgggagtt tgttttggca ccaaaatcaa cgggactttc   6540
caaaatgtcg taacaactcc gccccattga cgcaaatggg cggtaggcgt gtacggtggg   6600
aggtctatat aagcagagct ctctggctaa ctagagaacc cactgcttac tggcttatcg   6660
aaattaatac gactcactat agggagaccc aagctggttt aaacttaagc ttggtaccga   6720
gctcactagt ccagtgtggt ggcagatatc cagcacagtg gcggccgctc gagtctagag   6780
ggcccgtttt gcctgtactg gtctctctg gttagaccag atctgagcct gggagctctc   6840
tggctaacta gggaacccac tgcttaagcc tcaataaagc ttgccttgag tgcttcaagt   6900
agtgtgtgcc cgtctgttgt gtgactctgg taactagaga tccctcagac ccttttagtc   6960
agtgtggaaa atctctagca gtggcgcccg aacagggact tgaaagcgaa agggaaacca   7020
```

```
gaggagctct ctcgacgcag gactcggctt gctgaagcgc gcacggcaag aggcgagggg      7080
cggcgactgg tgagtacgcc aaaaattttg actagcggag gctagaagga gagagatggg      7140
tgcgagagcg tcagtattaa gcgggggaga attagatcgc gatgggaaaa aattcggtta      7200
aggccagggg gaaagaaaaa atataaatta aaacatatag tatgggcaag cagggagcta      7260
gaacgattcg cagttaatcc tggcctgtta gaaacatcag aaggctgtag acaaatactg      7320
ggacagctac aaccatccct tcagacagga tcagaagaac ttagatcatt atataataca      7380
gtagcaaccc tctattgtgt gcatttaatt aactggaata cgacaagata acccggatcg      7440
tgggcctgga tcagtacctg gagagcgtta aaaacacaa acggctggat gtgtgccgcg      7500
ctaaaatggg ctatatgctg cagtgaataa taaaatgtgt gtttgtccga aatacgcgtt      7560
ttgagatttc tgtcgccgac taaattcatg tcgcgcgata gtggtgttta tcgccgatag      7620
agatggcgat attggaaaaa tcgatatttg aaaatatggc atattgaaaa tgtcgccgat      7680
gtgagtttct gtgtaactga tatcgccatt ttccaaaag tgattttggg gcatacgcga      7740
tatctggcga tagcgcttat atcgtttacg ggggatggcg atagacgact ttggtgactt      7800
gggcgattct gtgtgtcgca aatatcgcag tttcgatata ggtgacagac gatatgaggc      7860
tatatcgccg atagaggcga catcaagctg gcacatggcc aatgcatatc gatctataca      7920
ttgaatcaat attggccatt agccatatta ttcattggtt atatagcata aatcaatatt      7980
ggctattggc cattgcatac gttgtatcca tatcataata tgtacattta tattggctca      8040
tgtccaacat taccgccatg ttgacattga ttattgacta gttattaata gtaatcaatt      8100
acggggtcat tagttcatag cccatatatg gagttccgcg ttacataact tacggtaaat      8160
ggcccgcctg gctgaccgcc caacgacccc cgcccattga cgtcaataat gacgtatgtt      8220
cccatagtaa cgccaatagg gactttccat tgacgtcaat gggtggagta tttacggtaa      8280
actgcccact tggcagtaca tcaagtgtat catatgccaa gtacgccccc tattgacgtc      8340
aatgacggta aatggcccgc ctggcattat gcccagtaca tgaccttatg gactttcct      8400 acttggcagt acatctacgt attagtcatc gctattacca tggtgatgcg gttttggcag      8460
tacatcaatg ggcgtggata gcggtttgac tcacggggat ttccaagtct ccaccccatt      8520
gacgtcaatg ggagtttgtt ttggcaccaa aatcaacggg actttccaaa atgtcgtaac      8580
aactccgccc cattgacgca aatgggcggt aggcgtgtac ggtgggaggt ctatataagc      8640
agagctcgtt tagtgaaccg tcagatcgcc tggagacgcc atccacgctg ttttgacctc      8700
catagaagac accgggaccg atccagcctc cgcggccggg aacggtgcat tggaacgcgg      8760
attccccgtg ccaagagtga cgtaagtacc gcctatagag tctataggcc cacccccttg      8820
gcttcttatg catgctatac tgttttggc ttggggtcta tacacccccg cttcctcatg      8880
ttataggtga tggtatagct tagcctatag gtgtgggtta ttgaccatta ttgaccactc      8940
ccctattggt gacgatactt tccattacta atccataaca tggctctttg ccacaactct      9000
ctttattggc tatatgccaa tacactgtcc ttcagagact gacacggact ctgtattttt      9060
acaggatggg gtctcatta ttatttacaa attcacatat acaacaccac cgtccccagt      9120
gcccgcagtt tttattaaac ataacgtggg atctccacgc gaatctcggg tacgtgttcc      9180
ggacatgggc tcttctccgg tagcggcgga gcttctacat ccgagccctg ctcccatgcc      9240
tccagcgact catggtcgct cggcagctcc ttgctcctaa cagtggaggc cagacttagg      9300
cacagcacga tgcccaccac caccagtgtg ccgcacaagg ccgtggcggt agggtatgtg      9360
tctgaaaatg agctcgggga gcgggcttgc accgctgacg catttggaag acttaaggca      9420
```

```
gcggcagaag aagatgcagg cagctgagtt gttgtgttct gataagagtc agaggtaact    9480
cccgttgcgg tgctgttaac ggtggagggc agtgtagtct gagcagtact cgttgctgcc    9540
gcgcgcgcca ccagacataa tagctgacag actaacagac tgttcctttc catgggtctt    9600
ttctgcagtc accgtccttg acacggctag catggagtcc tctgccaaga gaaagatgga    9660
ccctgataat cctgacgagg gcccttcctc caaggtgcca cggcccgaga cacccgtgac    9720
caaggccacg acgttcctgc agactatgtt gaggaaggag gttaacagtc agctgagtct    9780
gggagacccg ctgtttccag agttggccga agaatccctc aaaacttttg aacaagtgac    9840
cgaggattgc aacgagaacc ccgagaaaga tgtcctggca gaactcggtg acatcctcgc    9900
ccaggctgtc aatcatgccg gtatcgattc cagtagcacc ggccccacgc tgacaaccca    9960
ctcttgcagc gttagcagcg cccctcttaa caagccgacc cccaccagcg tcgcggttac   10020
taacactcct ctccccgggg catccgctac tcccgagctc agcccgcgta agaaaccgcg   10080
caaaaccacg cgtcctttca aggtgattat taaaccgccc gtgcctcccg cgcctatcat   10140
gctgcccctc atcaaacagg aagacatcaa gcccgagccc gactttacca tccagtaccg   10200
caacaagatt atcgataccg ccggctgtat cgtgatctct gatagcgagg aagaacaggg   10260
tgaagaagtc gaaacccgcg gtgctaccgc gtcttcccct tccaccggca gcggcacgcc   10320
gcgagtgacc tctcccacgc acccgctctc ccagatgaac caccctcctc ttcccgatcc   10380
cttgggccgg cccgatgaag atagttcctc ttcgtcttcc tcctcctgca gttcggcttc   10440
ggactcggag agtgagtccg aggagatgaa atgcagcagt ggcggaggag catccgtgac   10500
ctcgagccac catgggcgcg gcggttttgg tggcgcggcc tcctcctctc tgctgagctg   10560
cggccatcag agcagcggcg gggcgagcac cggaccccgc aagaagaaga gcaaacgcat   10620
ctccgagttg gacaacgaga aggtgcgcaa tatcatgaaa gataagaaca ccccttctg   10680 cacacccaac gtgcagactc ggcggggtcg cgtcaagatt gacgaggtga gccgcatgtt   10740
ccgcaacacc aatcgctctc ttgagtacaa gaacctgccc ttcacgattc ccagtatgca   10800
ccaggtgtta gatgaggcca tcaaagcctg caaaaccatg caggtgaaca caagggcat   10860 ccagattatc tacacccgca atcatgaggt gaagagtgag gtggatgcgg tgcggtgtcg   10920
cctgggcacc atgtgcaacc tggccctctc cactcccttc ctcatggagc acaccatgcc   10980
cgtgacacat ccaccgaag tggcgcagcg cacagccgat gcttgtaacg aaggcgtcaa   11040
ggccgcgtgg agcctcaaag aattgcacac ccaccaatta tgccccgtt cctccgatta   11100 ccgcaacatg atcatccacg ctgccacccc cgtggacctg ttgggcgctc tcaacctgtg   11160 cctgccctg atgcaaaagt tcccaaaca ggtcatggtg cgcatcttct ccaccaacca   11220
gggtgggttc atgctgccta tctacgagac ggccgcgaag gcctacgccg tggggcagtt   11280
tgagcagccc accgagaccc ctcccgaaga cctggacacc ctgagcctgg ccatcgaggc   11340
agccatccag gacctgagga acaagtctca gtaag                              11375
```

<210> SEQ ID NO 18
<211> LENGTH: 11939
<212> TYPE: DNA
<213> ORGANISM: Artificial sequence
<220> FEATURE:
<223> OTHER INFORMATION: Synthetic nucleotide sequence

<400> SEQUENCE: 18

```
gatccgcccc tctccctccc cccccctaa cgttactggc cgaagccgct tggaataagg      60
```

-continued

| | |
|---|---|
| ccggtgtgcg tttgtctata tgttattttc caccatattg ccgtcttttg gcaatgtgag | 120 |
| ggcccggaaa cctggccctg tcttcttgac gagcattcct aggggtcttt ccctctcgc | 180 |
| caaaggaatg caaggtctgt tgaatgtcgt gaaggaagca gttcctctgg aagcttcttg | 240 |
| aagacaaaca acgtctgtag cgacccttg caggcagcgg aaccccccac ctggcgacag | 300 |
| gtgcctctgc ggccaaaagc cacgtgtata agatacacct gcaaaggcgg cacaacccca | 360 |
| gtgccacgtt gtgagttgga tagttgtgga aagagtcaaa tggctctcct caagcgtatt | 420 |
| caacaagggg ctgaaggatg cccagaaggt accccattgt atgggatctg atctggggcc | 480 |
| tcggtgcaca tgctttacat gtgtttagtc gaggttaaaa aaacgtctag gccccccgaa | 540 |
| ccacggggac gtggttttcc tttgaaaaac acgatgataa tatggccaca accatggtga | 600 |
| gcaagggcga ggagctgttc accggggtgg tgcccatcct ggtcgagctg gacggcgacg | 660 |
| taaacggcca caagttcagc gtgtccggcg agggcgaggg cgatgccacc tacggcaagc | 720 |
| tgaccctgaa gttcatctgc accaccggca agctgcccgt gccctggccc accctcgtga | 780 |
| ccaccctgac ctacggcgtg cagtgcttca gccgctaccc cgaccacatg aagcagcacg | 840 |
| acttcttcaa gtccgccatg cccgaaggct acgtccagga gcgcaccatc ttcttcaagg | 900 |
| acgacggcaa ctacaagacc cgcgccgagg tgaagttcga gggcgacacc ctggtgaacc | 960 |
| gcatcgagct gaagggcatc gacttcaagg aggacggcaa catcctgggg cacaagctgg | 1020 |
| agtacaacta caacagccac aacgtctata tcatggccga caagcagaag aacggcatca | 1080 |
| aggtgaactt caagatccgc cacaacatcg aggacggcag cgtgcagctc gccgaccact | 1140 |
| accagcagaa caccccatc ggcgacggcc ccgtgctgct gcccgacaac cactacctga | 1200 |
| gcacccagtc cgccctgagc aaagacccca acgagaagcg cgatcacatg gtcctgctgg | 1260 |
| agttcgtgac cgccgccggg atcactctcg gcatggacga gctgtacaag taagcggccg | 1320 |
| caatcaacct ctggattaca aaatttgtga aagattgact ggtattctta actatgttgc | 1380 |
| tcctttacg ctatgtggat acgctgcttt aatgcctttg tatcatgcta ttacttcccg | 1440 |
| tacggctttc atttctcct ccttgtataa atcctggttg ctgtctcttt atgaggagtt | 1500 |
| gtggcccgtt gtcaggcaac gtggcgtggt gtgcactgtg tttgctgacg caaccccac | 1560 |
| tggttgggc attgccacca cctatcaact cctttccggg actttcgctt tccccctccc | 1620 |
| tattgccacg gcggaactca ttgccgcctg ccttgcccgc tgctggacag ggctcggct | 1680 |
| gttgggcact gacaattccg tggtgttgtc ggggaagctg acgtccttc catggctgct | 1740 |
| cgcctgtgtt gccaactgga ttctgcgcgg gacgtcctc tgctacgtcc cttcggccct | 1800 |
| caatccagcg gaccttcctt cccgcggcct gctgccggtt ctgcggcctc ttccgcgtct | 1860 |
| tcgccttcgc cctcagacga gtcggatctc ccttgggcc gctcccgc ctgcctgcag | 1920 |
| gtttgtcgag acctagaaaa acatggagca atcacaagta gcaatacagc agctaccaat | 1980 |
| gctgattgtg cctggctaga agcacaagag gaggaggagg tgggttttcc agtcacacct | 2040 |
| caggtaccttt aagaccaat gacttacaag gcagctgtag atcttagcca cttttaaaa | 2100 |
| gaaaaggggg gactggaagg gctaattcac tcccaacgaa gacaagatct gcttttgct | 2160 |
| tgtactgggt ctctctggtt agaccagatc tgagcctggg agctctctgg ctaactaggg | 2220 |
| aacccactgc ttaagcctca ataaagcttg ccttgagtgc ttcaagtagt gtgtgcccgt | 2280 |
| ctgttgtgtg actctggtaa ctagagatcc ctcagaccct tttagtcagt gtggaaaatc | 2340 |
| tctagcaggg cccgttttaaa cccgctgatc agcctcgact gtgccttcta gttgccagcc | 2400 |
| atctgttgtt tgcccctccc ccgtgccttc cttgaccctg gaaggtgcca ctcccactgt | 2460 |

```
cctttcctaa taaaatgagg aaattgcatc gcattgtctg agtaggtgtc attctattct    2520
gggggtgggg gtggggcagg acagcaaggg ggaggattgg gaagacaata gcaggcatgc    2580
tggggatgcg gtgggctcta tggcttctga ggcggaaaga accagctggg gctctagggg    2640
gtatccccac gcgccctgta gcggcgcatt aagcgcggcg ggtgtggtgg ttacgcgcag    2700
cgtgaccgct acacttgcca gcgccctagc gcccgctcct ttcgctttct tcccttcctt    2760
tctcgccacg ttcgccggct ttccccgtca agctctaaat cggggcatcc ctttagggtt    2820
ccgatttagt gctttacggc acctcgaccc caaaaaactt gattagggtg atggttcacg    2880
tagtgggcca tcgccctgat agacggtttt tcgccctttg acgttggagt ccacgttctt    2940
taatagtgga ctcttgttcc aaactggaac aacactcaac cctatctcgg tctattcttt    3000
tgatttataa gggattttgg ggatttcggc ctattggtta aaaaatgagc tgatttaaca    3060
aaaatttaac gcgaattaat tctgtggaat gtgtgtcagt tagggtgtgg aaagtcccca    3120
ggctccccag gcaggcagaa gtatgcaaag catgcatctc aattagtcag caaccaggtg    3180
tggaaagtcc ccaggctccc cagcaggcag aagtatgcaa agcatgcatc tcaattagtc    3240
agcaaccata gtcccgcccc taactccgcc catcccgccc ctaactccgc ccagttccgc    3300
ccattctccg ccccatggct gactaatttt ttttatttat gcagaggccg aggccgcctc    3360
tgcctctgag ctattccaga agtagtgagg aggcttttt ggaggcctag gcttttgcaa    3420
aaagctcccg ggagcttgta tatccatttt cggatctgat cagcacgtgt tgacaattaa    3480
tcatcggcat agtatatcgg catagtataa tacgacaagg tgaggaacta aaccatggcc    3540
aagttgacca gtgccgttcc ggtgctcacc gcgcgcgacg tcgccggagc ggtcgagttc    3600
tggaccgacc ggctcgggtt ctcccgggac ttcgtggagg acgacttcgc cggtgtggtc    3660
cgggacgacg tgaccctgtt catcagcgcg gtccaggacc aggtggtgcc ggacaacacc    3720
ctggcctggg tgtgggtgcg cggcctggac gagctgtacg ccgagtggtc ggaggtcgtg    3780
tccacgaact tccgggacgc ctccgggccg gccatgaccg agatcggcga gcagccgtgg    3840
gggcgggagt tcgccctgcg cgacccggcc ggcaactgcg tgcacttcgt ggccgaggag    3900
caggactgac acgtgctacg agatttcgat tccaccgccg ccttctatga aaggttgggc    3960
ttcggaatcg ttttccggga cgccggctgg atgatcctcc agcgcgggga tctcatgctg    4020
gagttcttcg cccacccccaa cttgtttatt gcagcttata atggttacaa ataaagcaat    4080
agcatcacaa atttcacaaa taaagcattt ttttcactgc attctagttg tggtttgtcc    4140
aaactcatca atgtatctta tcatgtctgt ataccgtcga cctctagcta gagcttggcg    4200
taatcatggt catagctgtt tcctgtgtga aattgttatc cgctcacaat tccacacaac    4260
atacgagccg gaagcataaa gtgtaaagcc tggggtgcct aatgagtgag ctaactcaca    4320
ttaattgcgt tgcgctcact gcccgctttc cagtcgggaa acctgtcgtg ccagctgcat    4380
taatgaatcg gccaacgcgc ggggagaggc ggtttgcgta ttgggcgctc ttccgcttcc    4440
tcgctcactg actcgctgcg ctcggtcgtt cggctgcggc gagcggtatc agctcactca    4500
aaggcggtaa tacggttatc cacagaatca ggggataacg caggaaagaa catgtgagca    4560
aaaggccagc aaaaggccag gaaccgtaaa aaggccgcgt tgctggcgtt tttccatagg    4620
ctccgccccc ctgacgagca tcacaaaaat cgacgctcaa gtcagaggtg gcgaaacccg    4680
acaggactat aaagatacca ggcgtttccc cctggaagct ccctcgtgcg ctctcctgtt    4740
ccgaccctgc cgcttaccgg atacctgtcc gcctttctcc cttcgggaag cgtggcgctt    4800
```

-continued

```
tctcaatgct cacgctgtag gtatctcagt tcggtgtagg tcgttcgctc caagctgggc    4860
tgtgtgcacg aaccccccgt tcagcccgac cgctgcgcct tatccggtaa ctatcgtctt    4920
gagtccaacc cggtaagaca cgacttatcg ccactggcag cagccactgg taacaggatt    4980
agcagagcga ggtatgtagg cggtgctaca gagttcttga agtggtggcc taactacggc    5040
tacactagaa ggacagtatt tggtatctgc gctctgctga agccagttac cttcggaaaa    5100
agagttggta gctcttgatc cggcaaacaa accaccgctg gtagcggtgg ttttttttgtt   5160
tgcaagcagc agattacgcg cagaaaaaaa ggatctcaag aagatccttt gatcttttct    5220
acggggtctg acgctcagtg gaacgaaaac tcacgttaag gattttggt catgagatta     5280
tcaaaaagga tcttcaccta gatcctttta aattaaaaat gaagttttaa atcaatctaa    5340
agtatatatg agtaaacttg gtctgacagt taccaatgct taatcagtga ggcacctatc    5400
tcagcgatct gtctatttcg ttcatccata gttgcctgac tccccgtcgt gtagataact    5460
acgatacggg agggcttacc atctggcccc agtgctgcaa tgataccgcg agacccacgc    5520
tcaccggctc cagatttatc agcaataaac cagccagccg aagggccga gcgcagaagt     5580
ggtcctgcaa ctttatccgc ctccatccag tctattaatt gttgccggga agctagagta    5640
agtagttcgc cagttaatag tttgcgcaac gttgttgcca ttgctacagg catcgtggtg    5700
tcacgctcgt cgtttggtat ggcttcattc agctccggtt cccaacgatc aaggcgagtt    5760
acatgatccc ccatgttgtg caaaaaagcg gttagctcct tcggtcctcc gatcgttgtc    5820
agaagtaagt tggccgcagt gttatcactc atggttatgg cagcactgca taattctctt    5880
actgtcatgc catccgtaag atgcttttct gtgactggtg agtactcaac caagtcattc    5940
tgagaatagt gtatgcggcg accgagttgc tcttgcccgg cgtcaatacg ggataatacc    6000
gcgccacata gcagaacttt aaaagtgctc atcattggaa aacgttcttc ggggcgaaaa    6060
ctctcaagga tcttaccgct gttgagatcc agttcgatgt aacccactcg tgcacccaac    6120
tgatcttcag catcttttac tttcaccagc gtttctgggt gagcaaaaac aggaaggcaa    6180
aatgccgcaa aaaagggaat aagggcgaca cggaaatgtt gaatactcat actcttcctt    6240
tttcaatatt attgaagcat ttatcagggt tattgtctca tgagcggata catatttgaa    6300
tgtatttaga aaaataaaca ataggggtt ccgcgcacat ttccccgaaa agtgccacct     6360
gacgtcgacg gatcgggaga tctcccgatc ccctatggtg cactctcagt acaatctgct    6420
ctgatgccgc atagttaagc cagtatctgc tccctgcttg tgtgttggag gtcgctgagt    6480
agtgcgcgag caaaatttaa gctacaacaa ggcaaggctt gaccgacaat tgcatgaaga    6540
atctgcttag ggttaggcgt tttgcgctgc ttcgcgatgt acgggccaga tatacgcgtt    6600
gacattgatt attgactagt tattaatagt aatcaattac gggtcatta gttcatagcc     6660
catatatgga gttccgcgtt acataactta cggtaaatgg cccgcctggc tgaccgccca    6720
acgacccccg cccattgacg tcaataatga cgtatgttcc catagtaacg ccaatagga     6780
ctttccattg acgtcaatgg gtggactatt tacggtaaac tgcccacttg gcagtacatc    6840
aagtgtatca tatgccaagt acgccccta ttgacgtcaa tgacggtaaa tggcccgcct     6900
ggcattatgc ccagtacatg acctatggg actttcctac ttggcagtac atctacgtat     6960
tagtcatcgc tattaccatg gtgatgcggt tttggcagta catcaatggg cgtggatagc    7020
ggtttgactc acggggattt ccaagtctcc accccattga cgtcaatggg agtttgtttt    7080
ggcaccaaaa tcaacgggac tttccaaaat gtcgtaacaa ctccgcccca ttgacgcaaa    7140
tgggcggtag gcgtgtacgg tgggaggtct atataagcag agctctctgg ctaactagag    7200
```

```
aacccactgc ttactggctt atcgaaatta atacgactca ctatagggag acccaagctg   7260
gtttaaactt aagcttggta ccgagctcac tagtccagtg tggtggcaga tatccagcac   7320
agtggcggcc gctcgagtct agagggcccg ttttgcctgt actgggtctc tctggttaga   7380
ccagatctga gcctgggagc tctctggcta actagggaac ccactgctta agcctcaata   7440
aagcttgcct tgagtgcttc aagtagtgtg tgcccgtctg ttgtgtgact ctggtaacta   7500
gagatccctc agacccttt t agtcagtgtg gaaaatctct agcagtggcg cccgaacagg   7560
gacttgaaag cgaaagggaa accagaggag ctctctcgac gcaggactcg gcttgctgaa   7620
gcgcgcacgg caagaggcga ggggcggcga ctggtgagta cgccaaaaat tttgactagc   7680
ggaggctaga aggagagaga tgggtgcgag agcgtcagta ttaagcgggg gagaattaga   7740
tcgcgatggg aaaaaattcg gttaaggcca gggggaaaga aaaatataaa attaaaacat   7800
atagtatggg caagcaggga gctagaacga ttcgcagtta atcctggcct gttagaaaca   7860
tcagaaggct gtagacaaat actgggacag ctacaaccat cccttcagac aggatcagaa   7920
gaacttagat cattatataa tacagtagca accctctatt gtgtgcattt aattaactgg   7980
aatacgacaa gataacccgg atcgtgggcc tggatcagta cctggagagc gttaaaaaac   8040
acaaacggct ggatgtgtgc cgcgctaaaa tgggctatat gctgcagtga ataataaaat   8100
gtgtgtttgt ccgaaatacg cgttttgaga tttctgtcgc cgactaaatt catgtcgcgc   8160
gatagtggtg tttatcgccg atagagatgg cgatattgga aaaatcgata tttgaaaata   8220
tggcatattg aaaatgtcgc cgatgtgagt ttctgtgtaa ctgatatcgc catttttcca   8280
aaagtgattt ttgggcatac gcgatatctg gcgatagcgc ttatatcgtt tacgggggat   8340
ggcgatagac gactttggtg acttgggcga ttctgtgtgt cgcaaatatc gcagtttcga   8400
tataggtgac agacgatatg aggctatatc gccgatagag gcgacatcaa gctggcacat   8460
ggccaatgca tatcgatcta tacattgaat caatattggc cattagccat attattcatt   8520
ggttatatag cataaatcaa tattggctat tggccattgc atacgttgta tccatatcat   8580
aatatgtaca tttatattgg ctcatgtcca acattaccgc catgttgaca ttgattattg   8640
actagttatt aatagtaatc aattacgggg tcattagttc atagcccata tatggagttc   8700
cgcgttacat aacttacggt aaatggcccg cctggctgac cgcccaacga cccccgccca   8760
ttgacgtcaa taatgacgta tgttcccata gtaacgccaa tagggacttt ccattgacgt   8820
caatgggtgg agtatttacg gtaaactgcc cacttggcag tacatcaagt gtatcatatg   8880
ccaagtacgc cccctattga cgtcaatgac ggtaaatggc ccgcctggca ttatgcccag   8940
tacatgacct tatgggactt tcctacttgg cagtacatct acgtattagt catcgctatt   9000
accatggtga tgcggttttg gcagtacatc aatgggcgtg gatagcggtt tgactcacgg   9060
ggatttccaa gtctccaccc cattgacgtc aatgggagtt tgttttggca ccaaaatcaa   9120
cgggactttc caaaatgtcg taacaactcc gccccattga cgcaaatggg cggtaggcgt   9180
gtacggtggg aggtctatat aagcagagct cgtttagtga accgtcagat cgcctggaga   9240
cgccatccac gctgttttga cctccataga agacaccggg accgatccag cctccgcggc   9300
cgggaacggt gcattggaac gcggattccc cgtgccaaga gtgacgtaag taccgcctat   9360
agagtctata ggcccacccc cttggcttct tatgcatgct atactgtttt tggcttgggg   9420
tctatacacc cccgcttcct catgttatag gtgatggtat agcttagcct ataggtgtgg   9480
gttattgacc attattgacc actcccctat tggtgacgat actttccatt actaatccat   9540
```

```
aacatggctc tttgccacaa ctctctttat tggctatatg ccaatacact gtccttcaga    9600
gactgacacg gactctgtat ttttacagga tggggtctca tttattattt acaaattcac    9660
atatacaaca ccaccgtccc cagtgcccgc agttttatt aaacataacg tgggatctcc     9720
acgcgaatct cgggtacgtg ttccggacat gggctcttct ccggtagcgg cggagcttct    9780
acatccgagc cctgctccca tgcctccagc gactcatggt cgctcggcag ctccttgctc    9840
ctaacagtgg aggccagact taggcacagc acgatgccca ccaccaccag tgtgccgcac    9900
aaggccgtgg cggtagggta tgtgtctgaa aatgagctcg gggagcgggc ttgcaccgct    9960
gacgcatttg aaagacttaa ggcagcggca gaagaagatg caggcagctg agttgttgtg    10020
ttctgataag agtcagaggt aactcccgtt gcggtgctgt taacggtgga gggcagtgta    10080
gtctgagcag tactcgttgc tgccgcgcgc gccaccagac ataatagctg acagactaac    10140
agactgttcc tttccatggg tcttttctgc agtcaccgtc cttgacacgg ctagcatgga    10200
gtcctctgcc aagagaaaga tggaccctga taatcctgac gagggccctt cctccaaggt    10260
gccacggccc gagacacccg tgaccaaggc cacgacgttc ctgcagacta tgttgaggaa    10320
ggaggttaac agtcagctga gtctgggaga cccgctgttt ccagagttgg ccgaagaatc    10380
cctcaaaact tttgaacaag tgaccgagga ttgcaacgaa aaccccgaga aagatgtcct    10440
ggcagaactc ggtgacatcc tcgcccaggc tgtcaatcat gccggtatcg attccagtag    10500
caccggcccc acgctgacaa cccactcttg cagcgttagc agcgccctc ttaacaagcc      10560 gacccccacc agcgtcgcgg ttactaacac tcctctcccc ggggcatccg ctactcccga    10620
gctcagcccg cgtaagaaac cgcgcaaaac cacgcgtcct ttcaaggtga ttattaaacc    10680
gcccgtgcct cccgcgccta tcatgctgcc cctcatcaaa caggaagaca tcaagcccga    10740
gcccgacttt accatccagt accgcaacaa gattatcgat accgccggct gtatcgtgat    10800
ctctgatagc gaggaagaac agggtgaaga agtcgaaacc cgcggtgcta ccgcgtcttc    10860 ccccttccacc ggcagcggca cgccgcgagt gacctctccc acgcaccccgc tctcccagat  10920 gaaccaccct cctcttcccg atcccttggg ccggcccgat gaagatagtt cctcttcgtc    10980
ttcctcctcc tgcagttcgg cttcggactc ggagagtgag tccgaggaga tgaaatgcag    11040
cagtggcgga ggagcatccg tgacctcgag ccaccatggg cgcggcggtt ttggtggcgc    11100
ggcctcctcc tctctgctga gctgcggcca tcagagcagc ggcggggcga gcaccggacc    11160
ccgcaagaag aagagcaaac gcatctccga gttggacaac gagaaggtgc gcaatatcat    11220
gaaagataag aacaccccct tctgcacacc caacgtgcag actcggcggg tcgcgtcaa     11280 gattgacgag gtgagccgca tgttccgcaa caccaatcgc tctcttgagt acaagaacct    11340 gccctcacg attcccagta tgcaccaggt gttagatgag gccatcaaag cctgcaaaac     11400
catgcaggtg aacaacaagg gcatccagat tatctacacc cgcaatcatg aggtgaagag    11460
tgaggtggat gcggtgcggt gtcgcctggg caccatgtgc aacctggccc tctccactcc    11520
cttcctcatg gagcacacca tgcccgtgac acatccaccc gaagtggcgc agcgcacagc    11580
cgatgcttgt aacgaaggcg tcaaggccgc gtggagcctc aaagaattgc cacccacca    11640 attatgcccc cgttcctccg attaccgcaa catgatcatc cacgctgcca ccccgtgga     11700 cctgttgggc gctctcaacc tgtgcctgcc cctgatgcaa aagtttccca aacaggtcat    11760
ggtgcgcatc ttctccacca accagggtgg gttcatgctg cctatctacg agacggccgc    11820
gaaggcctac gccgtggggc agtttgagca gcccaccgag acccctcccg aagacctgga    11880
caccctgagc ctggccatcg aggcagccat ccaggacctg aggaacaagt ctcagtaag    11939
```

<210> SEQ ID NO 19
<211> LENGTH: 10343
<212> TYPE: DNA
<213> ORGANISM: Artificial sequence
<220> FEATURE:
<223> OTHER INFORMATION: Synthetic nucleotide sequence

<400> SEQUENCE: 19

| | | | | | |
|---|---|---|---|---|---|
| ttaattaact | ggaatacgac | aagataaccc | ggatcgtggg | cctggatcag | tacctggaga | 60 |
| gcgttaaaaa | acacaaacgg | ctggatgtgt | gccgcgctaa | aatgggctat | atgctgcagt | 120 |
| gaataataaa | atgtgtgttt | gtccgaaata | cgcgttttga | gatttctgtc | gccgactaaa | 180 |
| ttcatgtcgc | gcgatagtgg | tgtttatcgc | cgatagagat | ggcgatattg | gaaaaatcga | 240 |
| tatttgaaaa | tatggcatat | tgaaaatgtc | gccgatgtga | gtttctgtgt | aactgatatc | 300 |
| gccattttc | caaaagtgat | ttttgggcat | acgcgatatc | tggcgatagc | gcttatatcg | 360 |
| tttacggggg | atggcgatag | acgactttgg | tgacttgggc | gattctgtgt | gtcgcaaata | 420 |
| tcgcagtttc | gatataggtg | acagacgata | tgaggctata | tcgccgatag | aggcgacatc | 480 |
| aagctggcac | atgccaatg | catatcgatc | tatacattga | atcaatattg | gccattagcc | 540 |
| atattattca | ttggttatat | agcataaatc | aatattggct | attggccatt | gcatacgttg | 600 |
| tatccatatc | ataatatgta | catttatatt | ggctcatgtc | caacattacc | gccatgttga | 660 |
| cattgattat | tgactagtta | ttaatagtaa | tcaattacgg | ggtcattagt | tcatagccca | 720 |
| tatatggagt | tccgcgttac | ataacttacg | gtaaatggcc | cgcctggctg | accgcccaac | 780 |
| gacccccgcc | cattgacgtc | aataatgacg | tatgttccca | tagtaacgcc | aatagggact | 840 |
| ttccattgac | gtcaatgggt | ggagtattta | cggtaaactg | cccacttggc | agtacatcaa | 900 |
| gtgtatcata | tgccaagtac | gccccctatt | gacgtcaatg | acggtaaatg | gcccgcctgg | 960 |
| cattatgccc | agtacatgac | cttatgggac | tttcctactt | ggcagtacat | ctacgtatta | 1020 |
| gtcatcgcta | ttaccatggt | gatgcggttt | tggcagtaca | tcaatgggcg | tggatagcgg | 1080 |
| tttgactcac | ggggatttcc | aagtctccac | cccattgacg | tcaatgggag | tttgttttgg | 1140 |
| caccaaaatc | aacgggactt | tccaaaatgt | cgtaacaact | ccgccccatt | gacgcaaatg | 1200 |
| ggcggtaggc | gtgtacggtg | ggaggtctat | ataagcagag | ctcgtttagt | gaaccgtcag | 1260 |
| atcgcctgga | gacgccatcc | acgctgtttt | gacctccata | gaagacaccg | ggaccgatcc | 1320 |
| agcctccgcg | gccgggaacg | gtgcattgga | acgcggattc | cccgtgccaa | gagtgacgta | 1380 |
| agtaccgcct | atagagtcta | taggcccacc | cccttggctt | cttatgcatg | ctatactgtt | 1440 |
| tttggcttgg | ggtctataca | cccccgcttc | ctcatgttat | aggtgatggt | atagcttagc | 1500 |
| ctataggtgt | gggttattga | ccattattga | ccactcccct | attggtgacg | atactttcca | 1560 |
| ttactaatcc | ataacatggc | tctttgccac | aactctcttt | attggctata | tgccaataca | 1620 |
| ctgtccttca | gagactgaca | cggactctgt | atttttacag | gatggggtct | catttattat | 1680 |
| ttacaaattc | acatatacaa | caccaccgtc | cccagtgccc | gcagttttta | ttaaacataa | 1740 |
| cgtgggatct | ccacgcgaat | ctcgggtacg | tgttccggac | atgggctctt | ctccggtagc | 1800 |
| ggcggagctt | ctacatccga | gccctgctcc | catgcctcca | gcgactcatg | gtcgctcggc | 1860 |
| agctccttgc | tcctaacagt | ggaggccaga | cttaggcaca | gcacgatgcc | caccaccacc | 1920 |
| agtgtgccgc | acaaggccgt | ggcggtaggg | tatgtgtctg | aaaatgagct | cggggagcgg | 1980 |
| gcttgcaccg | ctgacgcatt | tggaagactt | aaggcagcgg | cagaagaaga | tgcaggcagc | 2040 |

```
tgagttgttg tgttctgata agagtcagag gtaactcccg ttgcggtgct gttaacggtg    2100
gagggcagtg tagtctgagc agtactcgtt gctgccgcgc gcgccaccag acataatagc    2160
tgacagacta acagactgtt cctttccatg ggtcttttct gcagtcaccg tccttgacac    2220
ggctagcatg gtgagcaagg gcgaggagga taacatggcc atcatcaagg agttcatgcg    2280
cttcaaggtg cacatggagg gctccgtgaa cggccacgag ttcgagatcg agggcgaggg    2340
cgagggccgc ccctacgagg gcacccagac cgccaagctg aaggtgacca agggtggccc    2400
cctgcccttc gcctgggaca tcctgtcccc tcagttcatg tacggctcca aggcctacgt    2460
gaagcacccc gccgacatcc ccgactactt gaagctgtcc ttccccgagg gcttcaagtg    2520
ggagcgcgtg atgaacttcg aggacggcgg cgtggtgacc gtgacccagg actcctccct    2580
gcaggacggc gagttcatct acaaggtgaa gctgcgcggc accaacttcc cctccgacgg    2640 cccegtaatg cagaagaaga ccatgggctg ggaggcctcc tccgagcgga tgtaccccga    2700
ggacggcgcc ctgaagggcg agatcaagca gaggctgaag ctgaaggacg gcggccacta    2760
cgacgctgag gtcaagacca cctacaaggc caagaagccc gtgcagctgc ccggcgccta    2820
caacgtcaac atcaagttgg acatcaccte cacaacgag gactacacca tcgtggaaca    2880
gtacgaacgc gccgagggcc gccactccac cggcggcatg gacgagctgt acaagtaagg    2940
atccgcccct ctccctcccc cccccctaac gttactggcc gaagccgctt ggaataaggc    3000
cggtgtgcgt ttgtctatat gttatttttcc accatattgc cgtcttttgg caatgtgagg    3060
gcccggaaac ctggccctgt cttcttgacg agcattccta ggggtctttc cctctcgcc    3120 aaaggaatgc aaggtctgtt gaatgtcgtg aaggaagcag ttcctctgga agcttcttga    3180
agacaaacaa cgtctgtagc gacccttgc aggcagcgga accccccacc tggcgacagg    3240
tgcctctgcg gccaaaagcc acgtgtataa gatacacctg caaaggcggc acaaccccag    3300
tgccacgttg tgagttggat agttgtggaa agagtcaaat ggctctcctc aagcgtattc    3360
aacaaggggc tgaaggatgc ccagaaggta cccccattgta tgggatctga tctgggcct    3420 cggtgcacat gctttacatg tgtttagtcg aggttaaaaa aacgtctagg cccccgaac    3480 cacggggacg tggttttcct ttgaaaaaca cgatgataat atggccacaa ccatggtgag    3540
caagggcgag gagctgttca ccggggtggt gcccatcctg gtcgagctgg acggcgacgt    3600
aaacggccac aagttcagcg tgtccggcga gggcgagggc gatgccacct acggcaagct    3660
gaccctgaag ttcatctgca ccaccggcaa gctgcccgtg ccctggccca ccctcgtgac    3720
caccctgacc tacggcgtgc agtgcttcag ccgctacccc gaccacatga agcagcacga    3780
cttcttcaag tccgccatgc ccgaaggcta cgtccaggag cgcaccatct tcttcaagga    3840
cgacggcaac tacaagaccc gcgccgaggt gaagttcgag ggcgacaccc tggtgaaccg    3900
catcgagctg aagggcatcg acttcaagga ggacggcaac atcctggggc acaagctgga    3960
gtacaactac aacagccaca acgtctatat catggccgac aagcagaaga acggcatcaa    4020
ggtgaacttc aagatccgcc acaacatcga ggacggcagc gtgcagctcg ccgaccacta    4080
ccagcagaac accccatcg gcgacggccc cgtgctgctg cccgacaacc actacctgag    4140
cacccagtcc gccctgagca agacccaa cgagaagcgc gatcacatgg tcctgctgga    4200
gttcgtgacc gccgccggga tcactctcgg catggacgag ctgtacaaga gcagcctgag    4260
gcctcctaag aagaagagga aggtttgacc tgcaggtttg tcgagaccta gaaaaacatg    4320
gagcaatcac aagtagcaat acagcagcta ccaatgctga ttgtgcctgg ctagaagcac    4380
aagaggagga ggaggtgggt tttccagtca cacctcaggt acctttaaga ccaatgactt    4440
```

```
acaaggcagc tgtagatctt agccactttt taaaagaaaa gggggactg aagggctaa    4500 ttcactccca acgaagacaa gatctgcttt ttgcttgtac tgggtctctc tggttagacc    4560
agatctgagc ctgggagctc tctggctaac tagggaaccc actgcttaag cctcaataaa    4620
gcttgccttg agtgcttcaa gtagtgtgtg cccgtctgtt gtgtgactct ggtaactaga    4680
gatccctcag acccttttag tcagtgtgga aaatctctag cagggcccgt ttaaacccgc    4740
tgatcagcct cgactgtgcc ttctagttgc cagccatctg ttgtttgccc ctcccccgtg    4800
ccttccttga ccctggaagg tgccactccc actgtccttt cctaataaaa tgaggaaatt    4860
gcatcgcatt gtctgagtag gtgtcattct attctggggg gtggggtggg caggacagc     4920 aagggggagg attgggaaga caatagcagg catgctgggg atgcggtggg ctctatggct    4980
tctgaggcga aaagaaccag ctggggctct aggggtatc cccacgcgcc ctgtagcggc     5040
gcattaagcg cggcgggtgt ggtggttacg cgcagcgtga ccgctacact tgccagcgcc    5100
ctagcgcccg ctcctttcgc tttcttccct cctttctcg ccacgttcgc cggctttccc     5160
cgtcaagctc taaatcgggg catcccttta gggttccgat ttagtgcttt acggcacctc    5220
gaccccaaaa aacttgatta gggtgatggt tcacgtagtg ggccatcgcc ctgatagacg    5280 gttttttcgcc ctttgacgtt ggagtccacg ttctttaata gtggactctt gttccaaact    5340
ggaacaacac tcaaccctat ctcggtctat tctttgatt tataagggat ttggggatt      5400 tcggcctatt ggttaaaaaa tgagctgatt taacaaaaat ttaacgcgaa ttaattctgt    5460
ggaatgtgtg tcagttaggg tgtggaaagt ccccaggctc cccaggcagg cagaagtatg    5520
caaagcatgc atctcaatta gtcagcaacc aggtgtggaa agtccccagg ctccccagca    5580
ggcagaagta tgcaaagcat gcatctcaat tagtcagcaa ccatagtccc gcccctaact    5640
ccgcccatcc cgcccctaac tccgcccagt tccgcccatt ctccgcccca tggctgacta    5700
atttttttta tttatgcaga ggccgaggcc gcctctgcct ctgagctatt ccagaagtag    5760
tgaggaggct ttttggagg cctaggcttt tgcaaaaagc tcccgggagc ttgtatatcc     5820
attttcggat ctgatcagca cgtgttgaca attaatcatc ggcatagtat atcggcatag    5880
tataatacga caaggtgagg aactaaacca tggccaagtt gaccagtgcc gttccggtgc    5940
tcaccgcgcg cgacgtcgcc ggagcggtcg agttctggac cgaccggctc gggttctccc    6000
gggacttcgt ggaggacgac ttcgccggtg tggtccggga cgacgtgacc ctgttcatca    6060
gcgcggtcca ggaccaggtg gtgccggaca cacccctggc ctgggtgtgg gtgcgcggcc    6120
tggacgagct gtacgccgag tggtcggagg tcgtgtccac gaacttccgg gacgcctccg    6180
ggccggccat gaccgagatc ggcgagcagc cgtggggggcg ggagttcgcc ctgcgcgacc    6240
cggccggcaa ctgcgtgcac ttcgtggccg aggagcagga ctgacacgtg ctacgagatt    6300
tcgattccac cgccgccttc tatgaaaggt tgggcttcgg aatcgttttc cgggacgccg    6360
gctggatgat cctccagcgc ggggatctca tgctggagtt cttcgcccac cccaacttgt    6420
ttattgcagc ttataatggt tacaaataaa gcaatagcat cacaaatttc acaaataaag    6480 cattttttc actgcattct agttgtggtt tgtccaaact catcaatgta tcttatcatg     6540
tctgtatacc gtcgacctct agctagagct tggcgtaatc atggtcatag ctgtttcctg    6600
tgtgaaattg ttatccgctc acaattccac acaacatacg agccggaagc ataaagtgta    6660
aagcctgggg tgcctaatga gtgagctaac tcacattaat tgcgttgcgc tcactgcccg    6720 cttttccagtc gggaaacctg tcgtgccagc tgcattaatg aatcggccaa cgcgcgggga    6780
```

```
gaggcggttt gcgtattggg cgctcttccg cttcctcgct cactgactcg ctgcgctcgg      6840
tcgttcggct gcggcgagcg gtatcagctc actcaaaggc ggtaatacgg ttatccacag      6900
aatcagggga taacgcagga agaacatgt gagcaaaagg ccagcaaaag gccaggaacc       6960
gtaaaaaggc cgcgttgctg gcgttttttcc ataggctccg ccccctgac gagcatcaca      7020 aaaatcgacg ctcaagtcag aggtggcgaa acccgacagg actataaaga taccaggcgt      7080
ttccccctgg aagctccctc gtgcgctctc ctgttccgac cctgccgctt accggatacc      7140
tgtccgcctt tctcccttcg ggaagcgtgg cgctttctca atgctcacgc tgtaggtatc      7200
tcagttcggt gtaggtcgtt cgctccaagc tgggctgtgt gcacgaaccc cccgttcagc      7260
ccgaccgctg cgccttatcc ggtaactatc gtcttgagtc caacccggta agacacgact      7320
tatcgccact ggcagcagcc actggtaaca ggattagcag agcgaggtat gtaggcggtg      7380
ctacagagtt cttgaagtgg tggcctaact acggctacac tagaaggaca gtatttggta      7440
tctgcgctct gctgaagcca gttaccttcg gaaaaagagt tggtagctct tgatccggca      7500
aacaaaccac cgctggtagc ggtggttttt ttgtttgcaa gcagcagatt acgcgcagaa      7560
aaaaaggatc tcaagaagat cctttgatct tttctacggg gtctgacgct cagtggaacg      7620
aaaactcacg ttaagggatt ttggtcatga gattatcaaa aaggatcttc acctagatcc      7680
ttttaaatta aaaatgaagt tttaaatcaa tctaaagtat atatgagtaa acttggtctg      7740
acagttacca atgcttaatc agtgaggcac ctatctcagc gatctgtcta tttcgttcat      7800
ccatagttgc ctgactcccc gtcgtgtaga taactacgat acgggagggc ttaccatctg      7860
gccccagtgc tgcaatgata ccgcgagacc cacgctcacc ggctccagat ttatcagcaa      7920
taaaccagcc agccggaagg gccgagcgca gaagtggtcc tgcaacttta tccgcctcca      7980
tccagtctat taattgttgc cgggaagcta gagtaagtag ttcgccagtt aatagtttgc      8040
gcaacgttgt tgccattgct acaggcatcg tggtgtcacg ctcgtcgttt ggtatggctt      8100
cattcagctc cggttcccaa cgatcaaggc gagttacatg atcccccatg ttgtgcaaaa      8160
aagcggttag ctccttcggt cctccgatcg ttgtcagaag taagttggcc gcagtgttat      8220
cactcatggt tatggcagca ctgcataatt ctcttactgt catgccatcc gtaagatgct      8280
tttctgtgac tggtgagtac tcaaccaagt cattctgaga atagtgtatg cggcgaccga      8340
gttgctcttg cccggcgtca atacgggata ataccgcgcc acatagcaga actttaaaag      8400
tgctcatcat tggaaaacgt tcttcgggc gaaaactctc aaggatctta ccgctgttga      8460
gatccagttc gatgtaaccc actcgtgcac ccaactgatc ttcagcatct tttactttca      8520
ccagcgtttc tgggtgagca aaaacaggaa ggcaaaatgc cgcaaaaaag gaataagggg      8580
cgacacggaa atgttgaata ctcatactct ccttttttca atattattga agcatttatc      8640
agggttattg tctcatgagc ggatacatat ttgaatgtat ttagaaaaat aaacaaatag      8700
gggttccgcg cacatttccc cgaaaagtgc cacctgacgt cgacggatcg ggagatctcc      8760
cgatccccta tggtgcactc tcagtacaat ctgctctgat gccgcatagt taagccagta      8820
tctgctccct gcttgtgtgt tggaggtcgc tgagtagtgc gcgagcaaaa tttaagctac      8880
aacaaggcaa ggcttgaccg acaattgcat gaagaatctg cttagggtta ggcgttttgc      8940
gctgcttcgc gatgtacggg ccagatatac gcgttgacat tgattattga ctagttatta      9000
atagtaatca attacggggt cattagttca tagcccatat atggagttcc gcgttacata      9060
acttacggta aatggcccgc ctggctgacc gcccaacgac ccccgccat tgacgtcaat       9120 aatgacgtat gttcccatag taacgccaat agggactttc cattgacgtc aatgggtgga      9180
```

```
ctatttacgg taaactgccc acttggcagt acatcaagtg tatcatatgc caagtacgcc    9240
ccctattgac gtcaatgacg gtaaatggcc cgcctggcat tatgcccagt acatgacctt    9300
atgggacttt cctacttggc agtacatcta cgtattagtc atcgctatta ccatggtgat    9360
gcggttttgg cagtacatca atgggcgtgg atagcggttt gactcacggg gatttccaag    9420
tctccacccc attgacgtca atgggagttt gttttggcac caaaatcaac gggactttcc    9480
aaaatgtcgt aacaactccg ccccattgac gcaaatgggc ggtaggcgtg tacggtggga    9540
ggtctatata agcagagctc tctggctaac tagagaaccc actgcttact ggcttatcga    9600
aattaatacg actcactata gggagaccca agctggttta aacttaagct tggtaccgag    9660
ctcactagtc cagtgtggtg gcagatatcc agcacagtgg cggccgctcg agtctagagg    9720
gcccgttttg cctgtactgg gtctctctgg ttagaccaga tctgagcctg ggagctctct    9780
ggctaactag ggaacccact gcttaagcct caataaagct tgccttgagt gcttcaagta    9840
gtgtgtgccc gtctgttgtg tgactctggt aactagagat ccctcagacc cttttagtca    9900
gtgtggaaaa tctctagcag tggcgcccga acagggactt gaaagcgaaa gggaaaccag    9960
aggagctctc tcgacgcagg actcggcttg ctgaagcgcg cacggcaaga ggcgaggggc    10020
ggcgactggt gagtacgcca aaaattttga ctagcggagg ctagaaggag agagatgggt    10080
gcgagagcgt cagtattaag cgggggagaa ttagatcgcg atgggaaaaa attcggttaa    10140
ggccaggggg aaagaaaaaa tataaattaa acatatagt atgggcaagc agggagctag    10200
aacgattcgc agttaatcct ggcctgttag aaacatcaga aggctgtaga caaatactgg    10260
gacagctaca accatcccct cagacaggat cagaagaact tagatcatta tataatacag    10320
tagcaaccct ctattgtgtg cat                                            10343

<210> SEQ ID NO 20
<211> LENGTH: 11369
<212> TYPE: DNA
<213> ORGANISM: Artificial sequence
<220> FEATURE:
<223> OTHER INFORMATION: Synthetic nucleotide sequence

<400> SEQUENCE: 20
gatccagcag cctgaggcct cctaagaaga agaggaaggt ttgagaattc gcccctctcc      60 ctccccccc cctaacgtta ctggccgaag ccgcttggaa taaggccggt gtgcgtttgt     120
ctatatgtta ttttccacca tattgccgtc ttttggcaat gtgagggccc ggaaacctgg     180
ccctgtcttc ttgacgagca ttcctagggg tctttcccct ctcgccaaag gaatgcaagg     240
tctgttgaat gtcgtgaagg aagcagttcc tctggaagct tcttgaagac aaacaacgtc     300
tgtagcgacc ctttgcaggc agcggaaccc cccacctggc gacaggtgcc tctgcggcca     360
aaagccacgt gtataagata cacctgcaaa ggcggcacaa ccccagtgcc acgttgtgag     420
ttggatagtt gtggaaagag tcaaatggct ctcctcaagc gtattcaaca aggggctgaa     480
ggatgcccag aaggtacccc attgtatggg atctgatctg gggcctcggt acacatgctt     540
tacatgtgtt tagtcgaggt taaaaaaacg tctaggcccc ccgaaccacg ggacgtggt     600 tttcctttga aaaacacgat gataatatgg ccacaaccat ggagtcctct gccaagagaa     660
agatggaccc tgataatcct gacgagggcc cttcctccaa ggtgccacgg cccgagacac     720
ccgtgaccaa ggccacgacg ttcctgcaga ctatgttgag gaaggaggtt aacagtcagc     780
tgagtctggg agacccgctg tttccagagt tggccgaaga atccctcaaa acttttgaac     840
```

```
gagtgaccga ggattgcaac gagaacccccg agaaagatgt cctggcagaa ctcggtgaca    900
tcctcgccca ggctgtcaat catgccggta tcgattccag tagcaccggc cccacgctga    960
caacccactc ttgcagcgtt agcagcgccc ctcttaacaa gccgaccccc accagcgtcg   1020
cggttactaa cactcctctc cccgggggcat ccgctactcc cgagctcagc ccgcgtaaga   1080
aaccgcgcaa aaccacgcgt cctttcaagg tgattattaa accgcccgtg cctcccgcgc   1140
ctatcatgct gcccctcatc aaacaggaag acatcaagcc cgagcccgac tttaccatcc   1200
agtaccgcaa caagattatc gataccgccg gctgtatcgt gatctctgat agcgaggaag   1260
aacagggtga agaagtcgaa acccgcggtg ctaccgcgtc ttccccttcc accggcagcg   1320
gcacgccgcg agtgacctct cccacgcacc cgctctccca gataaaccac cctcctcttc   1380
ccgatccctt gggccggccc gatgaagata gttcctcttc gtcttcctcc tgcagttcgg   1440
cttcggactc ggagagtgag tccgaggaga tgaaatgcag cagtggcgga ggagcatccg   1500
tgacctcgag ccaccatggg cgcggcggtt ttggtggcgc ggcctcctcc tctctgctga   1560
gctgcggcca tcagagcagc ggcggggcga gcaccggacc ccgcaagaag aagagcaaac   1620
gcatctccga gttggacaac gagaaggtgc gcaatatcat gaaagataag aacacccccct  1680
tctgcacacc caacgtgcag actcggcggg gtcgcgtcaa gattgacgag gtgagccgca   1740
tgttccgcaa caccaatcgc tctcttgagt acaagaacct gcccttcacg attcccagta   1800
tgcaccaggt gttagatgag gccatcaaag cctgcaaaac catgcaggtg aacaacaagg   1860
gcatccagat tatctacacc cgcaatcatg aggtgaagag tgaggtggat gcggtgcggt   1920
gtcgcctggg caccatgtgc aacctggccc tctccactcc cttcctcatg gagcacacca   1980
tgcccgtgac acatccaccc gaagtggcgc agcgcacagc cgatacttgt aacgaaggcg   2040
tcaaggccgt gtggagcctc aaagaattgc acacccacca attatgcccc cgttcctccg   2100
attaccgcaa catgatcatc cacgctgcca cccccgtgga cctgttgggc gctctcaacc   2160
tgtgcctgcc cctgatgcaa aagtttccca acaggtcat ggtgcgcatc ttctccacca   2220
accagggtgg gttcatgctg cctatctacg agacggccgc gaaggcctac gccgtggggc   2280
agtttgagca gccaccgag acccctcccg aagacctgga cacctgagc ctggccatcg   2340
aggcagccat ccaggacctg aggaacaagt ctcagtaacc tgcaggtttg tcgagaccta   2400
gaaaaacatg gagcaatcac aagtagcaat acagcagcta ccaatgctga ttgtgcctgg   2460
ctagaagcac aagaggagga ggaggtgggt tttccagtca cacctcaggt accttttaagaa  2520
ccaatgactt acaaggcagc tgtagatctt agccactttt taaaagaaaa ggggggactg   2580
gaagggctaa ttcactccca acgaagacaa gatctgcttt ttgcttgtac tgggtctctc   2640
tggttagacc agatctgagc ctgggagctc tctggctaac tagggaaccc actgcttaag   2700
cctcaataaa gcttgccttg agtgcttcaa gtagtgtgtg cccgtctgtt gtgtgactct   2760
ggtaactaga gatccctcag acccttttag tcagtgtgga aaatctctag cagggcccgt   2820
ttaaacccgc tgatcagcct cgactgtgcc ttctagttgc cagccatctg ttgtttgccc   2880
ctcccccgtg ccttccttga ccctggaagg tgccactccc actgtccttt cctaataaaa   2940
tgaggaaatt gcatcgcatt gtctgagtag gtgtcattct attctggggg gtggggtggg   3000
gcaggacagc aagggggagg attgggaaga caatagcagg catgctgggg atgcggtggg   3060
ctctatggct tctgaggcgg aaagaaccag ctggggctct aggggggtatc cccacgcgcc   3120
ctgtagcggc gcattaagcg cggcgggtgt ggtggttacg cgcagcgtga ccgctacact   3180
tgccagcgcc ctagcgcccg ctcctttcgc tttcttccct tcctttctcg ccacgttcgc   3240
```

```
cggctttccc cgtcaagctc taaatcgggg catcccttta gggttccgat ttagtgcttt    3300
acggcacctc gaccccaaaa aacttgatta gggtgatggt tcacgtagtg ggccatcgcc    3360
ctgatagacg ttttttcgcc ctttgacgtt ggagtccacg ttctttaata gtggactctt    3420
gttccaaact ggaacaacac tcaaccctat ctcggtctat tcttttgatt tataagggat    3480
tttggggatt tcggcctatt ggttaaaaaa tgagctgatt taacaaaaat ttaacgcgaa    3540
ttaattctgt ggaatgtgtg tcagttaggg tgtggaaagt ccccaggctc cccaggcagg    3600
cagaagtatg caaagcatgc atctcaatta gtcagcaacc aggtgtggaa agtccccagg    3660
ctccccagca ggcagaagta tgcaaagcat gcatctcaat tagtcagcaa ccatagtccc    3720
gcccctaact ccgcccatcc cgcccctaac tccgcccagt tccgcccatt ctccgcccca    3780
tggctgacta ttttttttta tttatgcaga ggccgaggcc gcctctgcct ctgagctatt    3840
ccagaagtag tgaggaggct ttttggagg cctaggcttt tgcaaaaagc tcccgggagc    3900
ttgtatatcc attttcggat ctgatcagca cgtgttgaca attaatcatc ggcatagtat    3960
atcggcatag tataatacga caaggtgagg aactaaacca tggccaagtt gaccagtgcc    4020
gttccggtgc tcaccgcgcg cgacgtcgcc ggagcggtcg agttctggac cgaccggctc    4080
gggttctccc gggacttcgt ggaggacgac ttcgccggtg tggtccggga cgacgtgacc    4140
ctgttcatca gcgcggtcca ggaccaggtg gtgccggaca cacccctggc ctgggtgtgg    4200
gtgcgcggcc tggacgagct gtacgccgag tggtcggagg tcgtgtccac gaacttccgg    4260
gacgcctccg ggccggccat gaccgagatc ggcgagcagc cgtggggcg ggagttcgcc    4320 ctgcgcgacc cggccggcaa ctgcgtgcac ttcgtggccg aggagcagga ctgacacgtg    4380
ctacgagatt tcgattccac cgccgccttc tatgaaaggt tgggcttcgg aatcgttttc    4440
cgggacgccg gctggatgat cctccagcgc ggggatctca tgctggagtt cttcgcccac    4500
cccaacttgt ttattgcagc ttataatggt tacaaataaa gcaatagcat cacaaatttc    4560
acaaataaag catttttttc actgcattct agttgtggtt tgtccaaact catcaatgta    4620
tcttatcatg tctgtatacc gtcgacctct agctagagct tggcgtaatc atggtcatag    4680
ctgtttcctg tgtgaaattg ttatccgctc acaattccac acaacatacg agccggaagc    4740
ataaagtgta aagcctgggg tgcctaatga gtgagctaac tcacattaat tgcgttgcgc    4800
tcactgcccg ctttccagtc gggaaacctg tcgtgccagc tgcattaatg aatcggccaa    4860
cgcgcgggga gaggcggttt gcgtattggg cgctcttccg cttcctcgct cactgactcg    4920
ctgcgctcgg tcgttcggct gcggcgagcg gtatcagctc actcaaaggc ggtaatacgg    4980
ttatccacag aatcagggga taacgcagga agaacatgt gagcaaaagg ccagcaaaag    5040
gccaggaacc gtaaaaaggc cgcgttgctg gcgtttttcc ataggctccg cccccctgac    5100
gagcatcaca aaaatcgacg ctcaagtcag aggtggcgaa acccgacagg actataaaga    5160
taccaggcgt ttccccctgg aagctccctc gtgcgctctc ctgttccgac cctgccgctt    5220
accggatacc tgtccgcctt tctcccttcg ggaagcgtgg cgctttctca atgctcacgc    5280
tgtaggtatc tcagttcggt gtaggtcgtt cgctccaagc tgggctgtgt gcacgaaccc    5340
cccgttcagc ccgaccgctg cgccttatcc ggtaactatc gtcttgagtc aacccggta    5400 agacacgact tatcgccact ggcagcagcc actggtaaca ggattagcag agcgaggtat    5460
gtaggcggtg ctacagagtt cttgaagtgg tggcctaact acggctacac tagaaggaca    5520
gtatttggta tctgcgctct gctgaagcca gttaccttcg aaaaagagt tggtagctct    5580
```

```
tgatccggca aacaaaccac cgctggtagc ggtggttttt ttgtttgcaa gcagcagatt    5640
acgcgcagaa aaaaggatc tcaagaagat cctttgatct tttctacggg gtctgacgct    5700
cagtggaacg aaaactcacg ttaagggatt ttggtcatga gattatcaaa aaggatcttc    5760
acctagatcc ttttaaatta aaaatgaagt tttaaatcaa tctaaagtat atatgagtaa    5820
acttggtctg acagttacca atgcttaatc agtgaggcac ctatctcagc gatctgtcta    5880
tttcgttcat ccatagttgc ctgactcccc gtcgtgtaga taactacgat acgggagggc    5940
ttaccatctg gccccagtgc tgcaatgata ccgcgagacc cacgctcacc ggctccagat    6000
ttatcagcaa taaaccagcc agccggaagg gccgagcgca gaagtggtcc tgcaacttta    6060
tccgcctcca tccagtctat taattgttgc cgggaagcta gagtaagtag ttcgccagtt    6120
aatagtttgc gcaacgttgt tgccattgct acaggcatcg tggtgtcacg ctcgtcgttt    6180
ggtatggctt cattcagctc cggttcccaa cgatcaaggc gagttacatg atcccccatg    6240
ttgtgcaaaa aagcggttag ctccttcggt cctccgatcg ttgtcagaag taagttggcc    6300
gcagtgttat cactcatggt tatggcagca ctgcataatt ctcttactgt catgccatcc    6360
gtaagatgct tttctgtgac tggtgagtac tcaaccaagt cattctgaga atagtgtatg    6420
cggcgaccga gttgctcttg cccggcgtca atacgggata ataccgcgcc acatagcaga    6480
actttaaaag tgctcatcat tggaaaacgt tcttcggggc gaaaactctc aaggatctta    6540
ccgctgttga tccagttc gatgtaaccc actcgtgcac ccaactgatc ttcagcatct    6600
tttactttca ccagcgtttc tgggtgagca aaaacaggaa ggcaaaatgc cgcaaaaaag    6660
ggaataaggg cgacacggaa atgttgaata ctcatactct ccttttttca atattattga    6720
agcatttatc agggttattg tctcatgagc ggatacatat ttgaatgtat ttagaaaaat    6780
aaacaaatag gggttccgcg cacatttccc cgaaaagtgc cacctgacgt cgacggatcg    6840
ggagatctcc cgatcccta tggtgcactc tcagtacaat ctgctctgat gccgcatagt    6900
taagccagta tctgctccct gcttgtgtgt tggaggtcgc tgagtagtgc gcgagcaaaa    6960
tttaagctac aacaaggcaa ggcttgaccg acaattgcat gaagaatctg cttagggtta    7020
ggcgttttgc gctgcttcgc gatgtacggg ccagatatac gcgttgacat tgattattga    7080
ctagttatta atagtaatca attacggggt cattagttca tagcccatat atggagttcc    7140
gcgttacata acttacggta atggcccgc ctggctgacc gcccaacgac ccccgcccat    7200
tgacgtcaat aatgacgtat gttcccatag taacgccaat agggactttc cattgacgtc    7260
aatgggtgga ctatttacgg taaactgccc acttggcagt acatcaagtg tatcatatgc    7320
caagtacgcc ccctattgac gtcaatgacg gtaaatggcc cgcctggcat tatgcccagt    7380
acatgacctt atgggacttt cctacttggc agtacatcta cgtattagtc atcgctatta    7440
ccatggtgat gcggttttgg cagtacatca atgggcgtgg atagcggttt gactcacggg    7500
gatttccaag tctccacccc attgacgtca atgggagttt gttttggcac caaaatcaac    7560
gggactttcc aaaatgtcgt aacaactccg ccccattgac gcaaatgggc ggtaggcgtg    7620
tacggtggga ggtctatata agcagagctc tctggctaac tagagaaccc actgcttact    7680
ggcttatcga aattaatacg actcactata gggagaccca agctggttta aacttaagct    7740
tggtaccgag ctcactagtc cagtgtggtg gcagatatcc agcacagtgg cggccgctcg    7800
agtctagagg gcccgttttg cctgtactgg gtctctctgg ttagaccaga tctgagcctg    7860
ggagctctct ggctaactag ggaacccact gcttaagcct caataaagct tgccttgagt    7920
gcttcaagta gtgtgtgccc gtctgttgtg tgactctggt aactagagat ccctcagacc    7980
```

```
cttttagtca gtgtggaaaa tctctagcag tggcgcccga acagggactt gaaagcgaaa    8040
gggaaaccag aggagctctc tcgacgcagg actcggcttg ctgaagcgcg cacggcaaga    8100
ggcgaggggc ggcgactggt gagtacgcca aaattttga ctagcggagg ctagaaggag     8160
agagatgggt gcgagagcgt cagtattaag cgggggagaa ttagatcgcg atgggaaaaa    8220
attcggttaa ggccaggggg aaagaaaaaa tataaattaa acatatagt atgggcaagc     8280 agggagctag aacgattcgc agttaatcct ggcctgttag aaacatcaga aggctgtaga    8340
caaatactgg gacagctaca accatccctt cagacaggat cagaagaact tagatcatta    8400
tataatacag tagcaaccct ctattgtgtg catttaatta actggaatac gacaagataa    8460
cccggatcgt gggcctggat cagtacctgg agagcgttaa aaaacacaaa cggctggatg    8520
tgtgccgcgc taaaatgggc tatatgctgc agtgaataat aaaatgtgtg tttgtccgaa    8580
atacgcgttt tgagatttct gtcgccgact aaattcatgt cgcgcgatag tggtgtttat    8640
cgccgataga gatggcgata ttggaaaaat cgatatttga aaatatggca tattgaaaat    8700
gtcgccgatg tgagtttctg tgtaactgat atcgccattt ttccaaaagt gattttttggg   8760 catacgcgat atctggcgat agcgcttata tcgtttacgg gggatggcga tagacgactt    8820
tggtgacttg ggcgattctg tgtgtcgcaa atatcgcagt ttcgatatag gtgacagacg    8880
atatgaggct atatcgccga tagaggcgac atcaagctgg cacatggcca atgcatatcg    8940
atctatacat tgaatcaata ttggccatta gccatattat tcattggtta tatagcataa    9000
atcaatattg gctattggcc attgcatacg ttgtatccat atcataatat gtacattttat   9060 attggctcat gtccaacatt accgccatgt tgacattgat tattgactag ttattaatag    9120
taatcaatta cggggtcatt agttcatagc ccatatatgg agttccgcgt tacataactt    9180
acggtaaatg gcccgcctgg ctgaccgccc aacgaccccc gcccattgac gtcaataatg    9240
acgtatgttc ccatagtaac gccaataggg actttccatt gacgtcaatg ggtggagtat    9300
ttacggtaaa ctgcccactt ggcagtacat caagtgtatc atatgccaag tacgcccccct  9360 attgacgtca atgacggtaa atggcccgcc tggcattatg cccagtacat gaccttatgg    9420
gactttccta cttggcagta catctacgta ttagtcatcg ctattaccat ggtgatgcgg    9480
ttttggcagt acatcaatgg gcgtggatag cggtttgact cacggggatt tccaagtctc    9540
caccccattg acgtcaatgg gagtttgttt tggcaccaaa atcaacggga ctttccaaaa    9600
tgtcgtaaca actccgcccc attgacgcaa atgggcggta ggcgtgtacg gtgggaggtc    9660
tatataagca gagctcgttt agtgaaccgt cagatcgcct ggagacgcca tccacgctgt    9720
tttgacctcc atagaagaca ccgggaccga tccagcctcc gcggccggga acggtgcatt    9780
ggaacgcgga ttccccgtgc caagagtgac gtaagtaccg cctatagagt ctataggccc    9840 accccccttgg cttcttatgc atgctatact gttttttggct tggggtctat acacccccgc   9900
ttcctcatgt tataggtgat ggtatagctt agcctatagg tgtgggttat tgaccattat    9960
tgaccactcc cctattggtg acgatacttt ccattactaa tccataacat ggctctttgc    10020
cacaactctc tttattggct atatgccaat acactgtcct tcagagactg acacggactc    10080 tgtatttta caggatgggg tctcatttat tatttacaaa ttcacatata caacaccacc     10140
gtccccagtg cccgcagttt ttattaaaca taacgtggga tctccacgcg aatctcgggt    10200
acgtgttccg gacatgggct cttctccggt agcggcggag cttctacatc cgagccctgc    10260
tcccatgcct ccagcgactc atggtcgctc ggcagctcct tgctcctaac agtggaggcc    10320
```

```
agacttaggc acagcacgat gcccaccacc accagtgtgc cgcacaaggc cgtggcggta   10380
gggtatgtgt ctgaaaatga gctcggggag cgggcttgca ccgctgacgc atttggaaga   10440
cttaaggcag cggcagaaga agatgcaggc agctgagttg ttgtgttctg ataagagtca   10500
gaggtaactc ccgttgcggt gctgttaacg gtggagggca gtgtagtctg agcagtactc   10560
gttgctgccg cgcgcgccac cagacataat agctgacaga ctaacagact gttcctttcc   10620
atgggtcttt tctgcagtca ccgtccttga cacggctagc atggtgagca agggcgagga   10680
ggataacatg gccatcatca aggagttcat gcgcttcaag gtgcacatgg agggctccgt   10740
gaacggccac gagttcgaga tcgagggcga gggcgagggc cgcccctacg agggcaccca   10800
gaccgccaag ctgaaggtga ccaagggtgg ccccctgccc ttcgcctggg acatcctgtc   10860
ccctcagttc atgtacggct ccaaggccta cgtgaagcac cccgccgaca tccccgacta   10920
cttgaagctg tccttccccg agggcttcaa gtgggagcgc gtgatgaact tcgaggacgg   10980
cggcgtggtg accgtgaccc aggactcctc cctgcaggac ggcgagttca tctacaaggt   11040
gaagctgcgc ggcaccaact tcccctccga cggccccgta atgcagaaga agaccatggg   11100
ctgggaggcc tcctccgagc ggatgtaccc cgaggacggc gccctgaagg gcgagatcaa   11160
gcagaggctg aagctgaagg acggcggcca ctacgacgct gaggtcaaga ccacctacaa   11220
ggccaagaag cccgtgcagc tgcccggcgc ctacaacgtc aacatcaagt tggacatcac   11280
ctcccacaac gaggactaca ccatcgtgga acagtacgaa cgcgccgagg ccgccactc   11340 caccggcggc atggacgagc tgtacaagg                                     11369
```

<210> SEQ ID NO 21
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 21

Tyr Gly Arg Lys Lys Arg Arg Gln Arg Arg Arg
1               5                   10

<210> SEQ ID NO 22
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 22

Arg Arg Gln Arg Arg Thr Ser Lys Leu Met Lys Arg
1               5                   10

<210> SEQ ID NO 23
<211> LENGTH: 27
<212> TYPE: PRT
<213> ORGANISM: Artificial sequence
<220> FEATURE:
<223> OTHER INFORMATION: Synthetic amino acid sequence

<400> SEQUENCE: 23

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

```
<210> SEQ ID NO 24
<211> LENGTH: 33
<212> TYPE: PRT
<213> ORGANISM: Artificial sequence
<220> FEATURE:
<223> OTHER INFORMATION: Synthetic amino acid sequence

<400> SEQUENCE: 24

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 25
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 25

Arg Gln Ile Lys Ile Trp Phe Gln Asn Arg Arg Met Lys Trp Lys Lys
1               5                   10                  15

<210> SEQ ID NO 26
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 26

Arg Lys Lys Arg Arg Gln Arg Arg Arg
1               5

<210> SEQ ID NO 27
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 27

Tyr Ala Arg Ala Ala Ala Arg Gln Ala Arg Ala
1               5                   10

<210> SEQ ID NO 28
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 28

Thr His Arg Leu Pro Arg Arg Arg Arg Arg
1               5                   10

<210> SEQ ID NO 29
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 29
```

Gly Gly Arg Arg Ala Arg Arg Arg Arg Arg
1               5                   10

<210> SEQ ID NO 30
<211> LENGTH: 580
<212> TYPE: PRT
<213> ORGANISM: Artificial sequence
<220> FEATURE:
<223> OTHER INFORMATION: Synthetic amino acid sequence

<400> SEQUENCE: 30

Met Glu Ser Ser Ala Lys Arg Lys Met Asp Pro Asp Asn Pro Asp Glu
1               5                   10                  15

Gly Pro Ser Ser Lys Val Pro Arg Pro Glu Thr Pro Val Thr Lys Ala
                20                  25                  30

Thr Thr Phe Leu Gln Thr Met Leu Arg Lys Glu Val Asn Ser Gln Leu
            35                  40                  45

Ser Leu Gly Asp Pro Leu Phe Pro Glu Leu Ala Glu Glu Ser Leu Lys
        50                  55                  60

Thr Phe Glu Gln Val Thr Glu Asp Cys Asn Glu Asn Pro Glu Lys Asp
65                  70                  75                  80

Val Leu Ala Glu Leu Gly Asp Ile Leu Ala Gln Ala Val Asn His Ala
                85                  90                  95

Gly Ile Asp Ser Ser Ser Thr Gly Pro Thr Leu Thr Thr His Ser Cys
                100                 105                 110

Ser Val Ser Ser Ala Pro Leu Asn Lys Pro Thr Pro Thr Ser Val Ala
            115                 120                 125

Val Thr Asn Thr Pro Leu Pro Gly Ala Ser Ala Thr Pro Glu Leu Ser
        130                 135                 140

Pro Arg Lys Lys Pro Arg Lys Thr Thr Arg Pro Phe Lys Val Ile Ile
145                 150                 155                 160

Lys Pro Pro Val Pro Pro Ala Pro Ile Met Leu Pro Leu Ile Lys Gln
                165                 170                 175

Glu Asp Ile Lys Pro Glu Pro Asp Phe Thr Ile Gln Tyr Arg Asn Lys
                180                 185                 190

Ile Ile Asp Thr Ala Gly Cys Ile Val Ile Ser Asp Ser Glu Glu Glu
            195                 200                 205

Gln Gly Glu Glu Val Glu Thr Arg Gly Ala Thr Ala Ser Ser Pro Ser
        210                 215                 220

Thr Gly Ser Gly Thr Pro Arg Val Thr Ser Pro Thr His Pro Leu Ser
225                 230                 235                 240

Gln Met Asn His Pro Pro Leu Pro Asp Pro Leu Gly Arg Pro Asp Glu
                245                 250                 255

Asp Ser Ser Ser Ser Ser Ser Ser Cys Ser Ser Ala Ser Asp Ser
                260                 265                 270

Glu Ser Glu Ser Glu Glu Met Lys Cys Ser Ser Gly Gly Gly Ala Ser
            275                 280                 285

Val Thr Ser Ser His His Gly Arg Gly Phe Gly Gly Ala Ala Ser
        290                 295                 300

Ser Ser Leu Leu Ser Cys Gly His Gln Ser Ser Gly Gly Ala Ser Thr
305                 310                 315                 320

Gly Pro Arg Lys Lys Ser Lys Arg Ile Ser Glu Leu Asp Asn Glu
                325                 330                 335

Lys Val Arg Asn Ile Met Lys Asp Lys Asn Thr Pro Phe Cys Thr Pro
                340                 345                 350

-continued

```
Asn Val Gln Thr Arg Arg Gly Arg Val Lys Ile Asp Glu Val Ser Arg
            355                 360                 365

Met Phe Arg Asn Thr Asn Arg Ser Leu Glu Tyr Lys Asn Leu Pro Phe
370                 375                 380

Thr Ile Pro Ser Met His Gln Val Leu Asp Glu Ala Ile Lys Ala Cys
385                 390                 395                 400

Lys Thr Met Gln Val Asn Asn Lys Gly Ile Gln Ile Tyr Thr Arg
            405                 410                 415

Asn His Glu Val Lys Ser Glu Val Asp Ala Val Arg Cys Arg Leu Gly
                420                 425                 430

Thr Met Cys Asn Leu Ala Leu Ser Thr Pro Phe Leu Met Glu His Thr
            435                 440                 445

Met Pro Val Thr His Pro Pro Glu Val Ala Gln Arg Thr Ala Asp Ala
            450                 455                 460

Cys Asn Glu Gly Val Lys Ala Ala Trp Ser Leu Lys Glu Leu His Thr
465                 470                 475                 480

His Gln Leu Cys Pro Arg Ser Ser Asp Tyr Arg Asn Met Ile Ile His
                485                 490                 495

Ala Ala Thr Pro Val Asp Leu Leu Gly Ala Leu Asn Leu Cys Leu Pro
            500                 505                 510

Leu Met Gln Lys Phe Pro Lys Gln Val Met Val Arg Ile Phe Ser Thr
            515                 520                 525

Asn Gln Gly Gly Phe Met Leu Pro Ile Tyr Glu Thr Ala Ala Lys Ala
            530                 535                 540

Tyr Ala Val Gly Gln Phe Glu Gln Pro Thr Thr Pro Pro Glu Asp
545                 550                 555                 560

Leu Asp Thr Leu Ser Leu Ala Ile Glu Ala Ile Gln Asp Leu Arg
                565                 570                 575

Asn Lys Ser Gln
            580

<210> SEQ ID NO 31
<211> LENGTH: 131
<212> TYPE: PRT
<213> ORGANISM: Artificial sequence
<220> FEATURE:
<223> OTHER INFORMATION: Synthetic amino acid sequence

<400> SEQUENCE: 31

Met Cys Gln Leu Asp Val Ala Ser Ile Gly Asp Ile Ala Ser Tyr Arg
1               5                   10                  15

Leu Ser Pro Ile Ser Lys Leu Arg Tyr Leu Arg His Thr Glu Ser Pro
            20                  25                  30

Lys Ser Pro Lys Ser Ser Ile Ala Ile Pro Arg Lys Arg Tyr Lys Arg
        35                  40                  45

Tyr Arg Gln Ile Ser Arg Met Pro Lys Asn His Phe Trp Lys Asn Gly
50                  55                  60

Asp Ile Ser Tyr Thr Glu Thr His Ile Gly Asp Ile Phe Asn Met Pro
65                  70                  75                  80

Tyr Phe Gln Ile Ser Ile Phe Pro Ile Ser Pro Ser Leu Ser Ala Ile
                85                  90                  95

Asn Thr Thr Ile Ala Arg His Glu Phe Ser Arg Arg Gln Lys Ser Gln
            100                 105                 110

Asn Ala Tyr Phe Gly Gln Thr His Ile Leu Leu Phe Thr Ala Ala Tyr
        115                 120                 125
```

```
Ser Pro Phe
    130
```

<210> SEQ ID NO 32
<211> LENGTH: 124
<212> TYPE: PRT
<213> ORGANISM: Artificial sequence
<220> FEATURE:
<223> OTHER INFORMATION: Synthetic amino acid sequence

<400> SEQUENCE: 32

```
Met Ala Lys Leu Thr Ser Ala Val Pro Val Leu Thr Ala Arg Asp Val
1               5                   10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
        115                 120
```

<210> SEQ ID NO 33
<211> LENGTH: 286
<212> TYPE: PRT
<213> ORGANISM: Artificial sequence
<220> FEATURE:
<223> OTHER INFORMATION: Synthetic amino acid sequence

<400> SEQUENCE: 33

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175
```

```
Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285

<210> SEQ ID NO 34
<211> LENGTH: 225
<212> TYPE: PRT
<213> ORGANISM: Artificial sequence
<220> FEATURE:
<223> OTHER INFORMATION: Synthetic amino acid sequence

<400> SEQUENCE: 34

Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Ser Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Ala Glu Gly Arg His His Leu Phe
    210                 215                 220

Leu
225

<210> SEQ ID NO 35
```

```
<211> LENGTH: 239
<212> TYPE: PRT
<213> ORGANISM: Artificial sequence
<220> FEATURE:
<223> OTHER INFORMATION: Synthetic amino acid sequence

<400> SEQUENCE: 35

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 36
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 36

Pro Lys Lys Lys Arg Lys Val
1               5

<210> SEQ ID NO 37
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 37

Lys Arg Pro Ala Ala Thr Lys Lys Ala Gly Gln Ala Lys Lys Lys Lys
1               5                   10                  15
```

<210> SEQ ID NO 38
<211> LENGTH: 40
<212> TYPE: PRT
<213> ORGANISM: Artificial sequence
<220> FEATURE:
<223> OTHER INFORMATION: Synthetic amino acid sequence

<400> SEQUENCE: 38

Ser Val Gly Arg Ala Thr Ser Thr Ala Glu Leu Leu Val Gln Gly Glu
1               5                   10                  15

Glu Glu Val Pro Ala Lys Lys Thr Lys Thr Ile Val Ser Thr Ala Gln
            20                  25                  30

Ile Ser Glu Ser Arg Gln Thr Arg
        35                  40

<210> SEQ ID NO 39
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 39

Val Gln Gly Glu Glu Glu Val Pro Ala Lys Lys Thr Lys Thr Ile Val
1               5                   10                  15

<210> SEQ ID NO 40
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 40

Val Pro Ala Lys Lys Thr Lys Thr Ile Val
1               5                   10

<210> SEQ ID NO 41
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 41

Pro Ala Lys Lys Thr Lys Thr
1               5

<210> SEQ ID NO 42
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 42

Ser Ser Leu Arg Pro Pro Lys Lys Arg Lys Val
1               5                   10

<210> SEQ ID NO 43
<211> LENGTH: 12
<212> TYPE: PRT
<213> ORGANISM: Artificial sequence
<220> FEATURE:
<223> OTHER INFORMATION: Synthetic amino acid sequence

```
<400> SEQUENCE: 43

Ser Ser Leu Arg Pro Pro Lys Lys Arg Gly Arg Phe
1               5                   10

<210> SEQ ID NO 44
<211> LENGTH: 19
<212> TYPE: DNA
<213> ORGANISM: Artificial Sequence
<220> FEATURE:
<223> OTHER INFORMATION: Synthetic nucleotide sequence

<400> SEQUENCE: 44
tgcatgagcc acaggcatt                                              19

<210> SEQ ID NO 45
<211> LENGTH: 27
<212> TYPE: DNA
<213> ORGANISM: Artificial sequence
<220> FEATURE:
<223> OTHER INFORMATION: Synthetic nucleotide sequence

<400> SEQUENCE: 45
gctgtctatt tttgacacca gcttatt                                     27

<210> SEQ ID NO 46
<211> LENGTH: 50
<212> TYPE: DNA
<213> ORGANISM: Artificial sequence
<220> FEATURE:
<223> OTHER INFORMATION: Synthetic nucleic acid sequence

<400> SEQUENCE: 46
agtgggtggg acttaaaaga aatgggtgga gggatatagg ggtgtgtctt             50

<210> SEQ ID NO 47
<211> LENGTH: 16
<212> TYPE: PRT
<213> ORGANISM: Artificial Sequence
<220> FEATURE:
<223> OTHER INFORMATION: Synthetic amino acid sequence
<220> FEATURE:
<221> NAME/KEY: misc_feature
<222> LOCATION: (3)..(12)
<223> OTHER INFORMATION: Xaa can be any amino acid

<400> SEQUENCE: 47

Lys Arg Xaa Xaa Xaa Xaa Xaa Xaa Xaa Xaa Xaa Xaa Lys Lys Lys Leu
1               5                   10                  15
```